US012442021B2

(12) United States Patent
Adair et al.

(10) Patent No.: US 12,442,021 B2
(45) Date of Patent: *Oct. 14, 2025

(54) GENOMIC SAFE HARBORS FOR GENETIC THERAPIES IN HUMAN STEM CELLS AND ENGINEERED NANOPARTICLES TO PROVIDE TARGETED GENETIC THERAPIES

(71) Applicant: Fred Hutchinson Cancer Center, Seattle, WA (US)

(72) Inventors: Jennifer E. Adair, Seattle, WA (US); Reza Shahbazi, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 162 days.

This patent is subject to a terminal disclaimer.

(21) Appl. No.: 18/063,511

(22) Filed: Dec. 8, 2022

(65) Prior Publication Data

US 2023/0279441 A1 Sep. 7, 2023

Related U.S. Application Data

(63) Continuation of application No. 16/619,211, filed as application No. PCT/US2018/036154 on Jun. 5, 2018, now Pat. No. 11,603,544.

(60) Provisional application No. 62/664,045, filed on Apr. 27, 2018, provisional application No. 62/564,129, filed on Sep. 27, 2017, provisional application No. 62/515,474, filed on Jun. 5, 2017.

(51) Int. Cl.

*C07H 21/02* (2006.01)
*A61K 40/10* (2025.01)
*A61K 40/40* (2025.01)
*A61K 47/69* (2017.01)
*C07H 21/04* (2006.01)
*C12N 5/078* (2010.01)
*C12N 9/22* (2006.01)
*C12N 15/113* (2010.01)
*C12N 15/90* (2006.01)

(52) U.S. Cl.

CPC ............ *C12N 15/907* (2013.01); *A61K 40/10* (2025.01); *A61K 40/40* (2025.01); *A61K 47/6929* (2017.08); *C12N 5/0634* (2013.01); *C12N 9/22* (2013.01); *C12N 15/113* (2013.01); *A61K 2239/31* (2023.05); *A61K 2239/38* (2023.05); *C12N 2510/00* (2013.01)

(58) Field of Classification Search

CPC .......................... C12N 15/111; C12N 2310/20
See application file for complete search history.

(56) References Cited

U.S. PATENT DOCUMENTS 8,697,359 B1 4/2014 Zhang
8,771,945 B1 7/2014 Zhang
8,795,965 B2 8/2014 Zhang
8,865,406 B2 10/2014 Zhang et al.
8,871,445 B2 10/2014 Cong et al.
8,889,356 B2 11/2014 Zhang
8,889,418 B2 11/2014 Zhang et al.
8,895,308 B1 11/2014 Zhang et al.
8,906,616 B2 12/2014 Zhang et al.
8,932,814 B2 1/2015 Cong et al.
8,945,839 B2 2/2015 Zhang
8,993,233 B2 3/2015 Zhang et al.
8,999,641 B2 4/2015 Zhang et al.
9,580,701 B2 2/2017 May et al.
2001/0005581 A1 6/2001 Grant et al.
2003/0053983 A1 3/2003 Tamarkin et al.
2003/0118657 A1 6/2003 West et al.
2008/0050774 A1 2/2008 Berka et al.
2016/0208243 A1 7/2016 Zhang et al.
2017/0058272 A1 3/2017 Carter et al.
2017/0106025 A1 4/2017 Kovarik
2018/0030425 A1 2/2018 Joung et al.
2019/0345450 A1 11/2019 Radtke et al.
2021/0171983 A1 6/2021 Adair et al.

FOREIGN PATENT DOCUMENTS

WO WO2014018423 1/2014
WO WO2014093595 A1 6/2014
WO WO2014093622 A2 6/2014
WO WO2014093635 A1 6/2014
WO WO2014093655 A2 6/2014
WO WO2014093661 A2 6/2014
WO WO2014093694 A1 6/2014
WO WO2014093701 A1 6/2014
WO WO2014093709 A1 6/2014
WO WO2014093712 A1 6/2014
WO WO2014093718 A1 6/2014
WO WO2014145599 A2 9/2014
WO WO2014204723 A1 12/2014
(Continued)

OTHER PUBLICATIONS

Yan, et al., "BLISS is a versatile and quantitative method for genome-wide profiling of DNA double-strand breaks." Nat. Commun., vol. 8, 2017, 9 pages.
(Continued)

*Primary Examiner* — Amy Rose Hudson
(74) *Attorney, Agent, or Firm* — Lee & Hayes, P.C.

(57) ABSTRACT

Genomic safe harbors (GSH) for genetic therapies in human stem cells and engineered nanoparticles to provide targeted genetic therapies are described. The GSH and/or associated nanoparticles can be used to safely and efficiently treat a variety of genetic, infectious, and malignant diseases.

20 Claims, 72 Drawing Sheets

Specification includes a Sequence Listing.

(56) References Cited

FOREIGN PATENT DOCUMENTS

| | | | |
|---|---|---|---|
| WO | WO2014204724 | A1 | 12/2014 |
| WO | WO2014204725 | A1 | 12/2014 |
| WO | WO2014204726 | A1 | 12/2014 |
| WO | WO2014204727 | A1 | 12/2014 |
| WO | WO2014204728 | A1 | 12/2014 |
| WO | WO2014204729 | A1 | 12/2014 |
| WO | WO2015048577 | A2 | 4/2015 |
| WO | WO2015065964 | A1 | 5/2015 |
| WO | WO2015089351 | A1 | 6/2015 |
| WO | WO2015089354 | A1 | 6/2015 |
| WO | WO2015089364 | A1 | 6/2015 |
| WO | WO2015089419 | A2 | 6/2015 |
| WO | WO2015089427 | A1 | 6/2015 |
| WO | WO2015089462 | A1 | 6/2015 |
| WO | WO2015089465 | A1 | 6/2015 |
| WO | WO2015089473 | A1 | 6/2015 |
| WO | WO2015089486 | A2 | 6/2015 |
| WO | WO2016094874 | A1 | 6/2016 |
| WO | WO2016118780 | A1 | 7/2016 |
| WO | WO2016205711 | A1 | 12/2016 |
| WO | WO2017004261 | A1 | 1/2017 |
| WO | WO2017015015 | A1 | 1/2017 |
| WO | 2017053312 | A1 | 3/2017 |
| WO | WO2017053713 | A1 | 3/2017 |
| WO | WO2016115179 | A1 | 4/2017 |
| WO | WO2017062983 | A1 | 4/2017 |
| WO | WO2017066588 | A2 | 4/2017 |
| WO | WO2017106657 | A1 | 6/2017 |
| WO | WO2017127807 | A1 | 7/2017 |
| WO | WO2017184768 | A1 | 10/2017 |
| WO | WO2017218948 | A2 | 12/2017 |

OTHER PUBLICATIONS

Yin, et al., "CRISPR-Cas9 and CRISPR-Cpf1 mediated targeting of a stomatal developmental gene EPFL9 in rice," Plant Cell Rep., vol. 36, No. 5, 2017, pp. 745-757.

Yin, et al., "Delivery technologies for genome editing," Nat. Rev., vol. 16, 2017, pp. 387-399.

Zaidi, et al., "CRISPR-Cpf1: A New Tool for PLant Genome Editing," Cell Press, vol. 22, No. 7, 2017, pp. 550-553.

Zetsche, et al., "Cpf1 Is a Single RNA-Guided Endonuclease of a Class 2 CRISPR-Cas System," Cell, vol. 163, No. 3, 2015, pp. 795-771.

Zetsche, et al., "Multiplex gene editing by CRISPR-Cpf1 through autonomous processing of a single crRNA array," Nat. Biotechnol., vol. 35, No. 1, 2017, pp. 31-34.

Zhang, et al., "CRISPR-Cpf1 correction of muscular dystrophy mutations in human cardiomycocytes and mice," Sci. Adv., vol. 3, No. 4, 2017, pp. 1-10.

Zhang, et al., "Instantaneous and Quantitative Functionalization of Gold Nanoparticles With Thiolated DNA Using a pH-assisted and Surfactant-Free Route," J. Am. Chem. Soc., vol. 134. No. 17, 2012, pp. 7266-7269.

Zhang, et al., "Multiplex gene regulation by CRISPR-ddCpf1," Cell Discovery, vol. 3, 2017, pp. 1-9.

Zhong, et al., "Cpf1 proteins excise CRISPR RNAs from mRNA transcripts in mammalian cells," Nat. Chem. Biol., vol. 13, No. 8, 2017, pp. 834-841.

Office Action for Canadian Application No. 3,102,054, Dated Jul. 31, 2024, 6 pages.

Bedel, et al., "Metabolic Correction of Congenital Erythropoietic Porphyria with iPSCs Free of Reprogramming Factors", The American Journal of Human Genetics, vol. 91, No. 1, May 31, 2012, pp. 109-121.

Bibikova, et al., "Enhancing Gene Targeting with Designed Zinc Finger Nucleases," Science, vol. 300, 2003, 1 page.

Bibikova, et al., "Targeted Chromosomal Cleavage and Mutagenesis in Drosophila Using Zinc-Finger Nucleases," Genetics, vol. 161, 2002, pp. 1169-1175.

Boch, et al., "Breaking the Code of DNA Binding Specificity of TAL-Type III Effectors," Science, vol. 326, 2009, pp. 1509-1512.

Bonifant, et al., "Toxicity and management in CAR T-cell therapy," Mol. Ther. Oncolytics, vol. 3, 2016, 7 pages.

Chang & Wilson, "Modification of DNA ends can decrease end joining relative to homologous recombination in mammalian cells," PNAS, vol. 84, No. 14, 1987, pp. 4959-4963.

Choudhary, et al., "Knockdown of HPRT for Selection of Genetically Modified Human Hematopoietic Progenitor Cells," PLoS One, vol. 8, No. 3, 2013, 9 pages.

Christian, et al., "Targeting DNA Double-Strand Breaks with TAL Effector Nucleases," Genetics, vol. 186, 2010, pp. 757-761.

Corrigan-Curay, et al., "Genome Editing Technologies: Defining a Path to Clinic", Molecular Therapy, vol. 23, No. 5, May 1, 2015, pp. 796-806.

De Ravin et al., "CRISPR-Cas9 Gene Repair of Hematopoietic Stem Cells From Patients With X-linked Chronic Granulomatous Disease," Sci. Transl. Med., vol. 9, No. 372, 2017, 10 pages.

Ding et al., "Gold Nanoparticles for Nucleic Acid Delivery," Molecular Therapy, vol. 22, No. 6, 2014, pp. 1075-1083.

Dong, et al., "The Crystal Structure of Cpf1 in Complex With Crispr RNA," Nature, vol. 532, No. 7600, 2016, pp. 522-526.

Extended European Search Report mailed Feb. 11, 2021 for European Patent Application No. 18812653.6, 9 pages.

Genbank, "*Homo sapiens* genomic DNA, chromosome 11q clone:RP11-655M14, complete sequences", retrieved on Sep. 27, 20 18 at <<https://www.ncbi.nlm.nih.gov/nuccore/AP003385.2/>>, GenBank Accession No. AP003385.2, 2 pages.

Gori, et al., "In vivo Selection of Autologous MGMT Gene-Modified Cells Following Reduced Intensity Conditioning with BCNU and Temozolomide in the Dog Model," Cancer Gene. Ther., vol. 19, No. 8, 2012, pp. 523-529.

Hakkinen, "The Gold-Sulfur Interface at the Nanoscale," Nat. Chem., vol. 4, No. 6, 2012, pp. 443-455.

Huang, et al., "Cancer Cell Targeting Using Multiple Aptamers Conjugated on Nanorods," Anal. Chem., vol. 80, No. 3, 2008, pp. 567-572.

Jiang, et al., "CRISPR-Cpf1 assisted genome editing of Corynebacterium glutamicum," Nat. Commun., vol. 8, No. 15179, 2017, pp. 1-11.

Kennedy, et al., "Ex Vivo y-Retroviral Gene Therapy of Dogs with X-linked Severe Combined Immunodeficiency and the Development of a Thymic T Cell Lymphoma," Vet. Immunol. Immunopathol., vol. 142, No. 1-2, 2011, pp. 36-48.

Kim, et al., "CRISPR/Cpf1-mediated DNA-free plant genome editing," Nat. Comm., vol. 8, No. 14406, 2017, pp. 1-7.

Kim, et al., "Efficient Transcriptional Gene Repression by Type V-A CRISPR-Cpf1 from Eubacterium eligens," ACS. Synth. Biol., vol. 6, No. 7, 2017, pp. 1273-1282.

Kim, et al., "Genome-wide Analysis Reveals Specificities of Cpf1 Endonucleases in Human Cells," Nat. Biotechnol., vol. 34, No. 8, 2016, pp. 863-868.

Kim, et al., "Hybrid restriction enzymes Zinc finger fusion to Fok I cleavage domain," PNAS, vol. 93, 1996, pp. 1156-1160.

Lee, et al., "Nanoparticle delivery of Cas9 ribonucleoprotein and donor DNA in vivo induces homology-directed DNA repair," Nat. Biomed. Eng., vol. 1, 2017, pp. 889-901.

Li, et al., "Engineering CRISPR-Cpf1 crRNAs and mRNAs to maximize genome editing efficiency," Nat. Biomed. Eng., vol. 1, No. 5, 2017, 21 pages.

Miller, et al., "A TALE nuclease architecture for efficient genome editing," Nat. Biotechl., vol. 29, No. 2, 2011, pp. 143-150.

Miller, et al., "An improved zinc-finger nuclease architecture for highly specific genome editing," Nat. Biotechnol., vol. 25, No. 7, 2007, pp. 778-785.

Miller, et al., "Repetitive Zinc-Binding Domains in the Protein Transcription Factor IIIA From Xenopus Oocytes," EMBO J., vol. 4, No. 6, 1985, pp. 1609-1614.

Mirkin, et al., "A DNA-based Method for Rationally Assembling Nanoparticles Into Macroscopic Materials," Nature, vol. 382, No. 6592, 1996, pp. 607-609.

Moscou & Bogdanove, "A Simple Cipher Governs DNA Recognition by TAL Effectors," Science, vol. 326, 2009, pp. 1501.

(56) References Cited

OTHER PUBLICATIONS

Nehls, et al., "Two Genetically Separable Steps in the Differentiation of Thymic Epithelium," Science, vol. 272, No. 5263, 1996, pp. 886-889.
Papapetrou & Schambach, "Gene Insertion Into Genomic Safe Harbors for Human Gene Therapy," Mol. Ther., vol. 24, No. 4, 2016. pp. 678-684.
Papapetrou, et al., "Genomic safe harbors permit high beta-globin transgene expression in thalassemia induced pluripotent stem cells," Nat. Biotechnol., vol. 29, No. 1, 2011, pp. 73-78.
Invitation to Pay Additional Fees Dated Aug. 14, 2018 in International Application No. PCT/US18/36154, 3 pages.
Search Report and Written Opinion Dated Oct. 26, 2018 for International Application No. PCT/US18/36154, 17 pages.
Pellenz, et al., "New Human Chromosomal Sites with Safe Harbor Potential for Targeted Transgene Insertion", Human Gene Therapy, vol. 30, No. 7, 2019, 15 pages.
Perrault & Chan, "Synthesis and Surface Modification of Highly Monodispersed, Spherical Gold Nanoparticles of 50-200 Nm," J. Am. Chem. Soc., vol. 131, No. 47, 2009, pp. 17042-17043.
Radtke, et al., "A distinct hematopoietic stem cell population for rapid multilineage engraftment in nonhuman primates," Sci. Transl. Med., vol. 9, No. 414, 2017, 22 pages.
Ran, et al., "Double Nicking by RNA-guided CRISPR Cas9 for Enhanced Genome Editing Specificity," Cell, vol. 154, No. 6, 2013, pp. 1380-1389.
Richardson, et al., "Enhancing homology-directed genome editing by catalytically active and inactive CRISPR-Cas9 using asymmetric donor DNA," Nat. Biotechnol., vol. 34, No. 3, 2016, pp. 339-344.
Sadelain, et al., "Safe Harbours for the Integration of New DNA in the Human Genome", Nature Reviews Cancer, vol. 12, No. 1, Jan. 1, 2011, pp. 51-58.
Sayandip, et al., "Gene Therapy for PIDs: Progress, Pitfalls and Prospects", Gene, vol. 525, No. 2, Apr. 6, 2013, pp. 174-181.
Shahbazi, et al., "Functionalized Gold Nanoparticles Manifested as Potent Carriers for Nucleolar Targeting," Nanotechnology, vol. 28, No. 2, 2017, 12 pages.
Shahbazi, et al., "Modified Gold-Based siRNA Nanotherapeutics for Targeted Therapy of Triple-Negative Breast Cancer," Nanomedicine, vol. 12, No. 16, 2017, pp. 1961-1973.
Supplementary Table XP55767862, "Nucleotide Sequence Variants in mCrel Genomic Target Sites, Together with Predicted Effect on mCrel Cleavage Sensitivity", retrieved on Jan. 22, 2021 from https://www.ncbi.nlm.nih.gov/pmc/articles/PMC6648220/ , Jul. 16, 2019, 8 pages.
Tang, et al., "A CRISP-Cpf1 system for efficient genome editing and transcriptional repression in plants," Nat. Plants., vol. 3, No. 17018, 2017, 21 pages.
Turkevich, et al., "A study of the nucleation and growth processes in the synthesis of colloidal gold," Discussions of the Faraday Society, vol. 11, No. 0, 1951, pp. 55-75.
Wisniewski, et al., "Further phenotypic characterization of the primitive lineage—CD34+CD38-CD90+CD45RA-hematopoietic stem cell/progenitor cell sub-population isolated from cord blood, mobilized peripheral blood and patients with chronic myelogenous leukemia," Blood Cancer Journal, vol. 1, No. 9, 2011, pp. 1-11.
Wolfe, et al., "DNA Recognition by Cys2His2 Zinc Finger Proteins," Ann. Rev. Biophy. Biomol., vol. 29, 2000, pp. 183-212.
Xu, et al., "Generation of targeted mutant rice using a CRISPR-Cpf1 system," Plant Biotechnol. J., vol. 15, No. 6, 2017, pp. 713-717.

FIG. 3

Targeting Second Safe Harbor Chromosomal Location: chr11:67839126-67839150

PAM

5' TTGTTGTTTATCCAAACCTCCTAAATGATACGTGTTT 3' Non-target strand (SEQ ID NO: 251)

3' AACAACAAATAGGTTTGGAGGATTTACTATGCACAAA5' Target strand (SEQ ID NO: 252)

Target

Modified crRNA sequence

5'-handle

5' UAAUUUCUACUCUUGUAGAUUCCAAACCUCCUAAAUGAUAC 3'/iSp18//3ThioMC3-D/ (SEQ ID NO: 253)

Guide segment

Genomic locus

Cut

5' GCTTAGTGCTTATTTATTTTAGGTTGTTGTTTATCCAAACCTCCTAAATGATACGTGTTTGGAACAAGTAACAGCATTGTTCCTTGATGTTG 3' (SEQ ID NO: 254)

3' CGAATCACGAATAAATAAAATCCAACAACAAATAGGTTTGGAGGATTTACTATGCACAAACCTTGTTCATTGTCGTAACAAGGAACTACAAC 5' (SEQ ID NO: 255)

Cut ssDNA homology template

PAM mutation

NotI

5' GCTTAGTGCTTATTTATTTTAGGTTGTTGTTCATCCAAACCTCCTAAATGGCGGCCGCATACGTGTTTGGAACAAGTAACAGCATTGTTCCTTGATGTTG 3' (SEQ ID NO: 256)

/3ThioMC3-D//iSp18 3' CGAATCACGAATAAATAAAATCCAACAACAAGTAGGTTTGGAGGATTTACCGCCGGCGTATGCACAAACCTTGTTCATTGTCGTAACAAGGAACTACAAC 5' (SEQ ID NO: 257)

FIG. 4

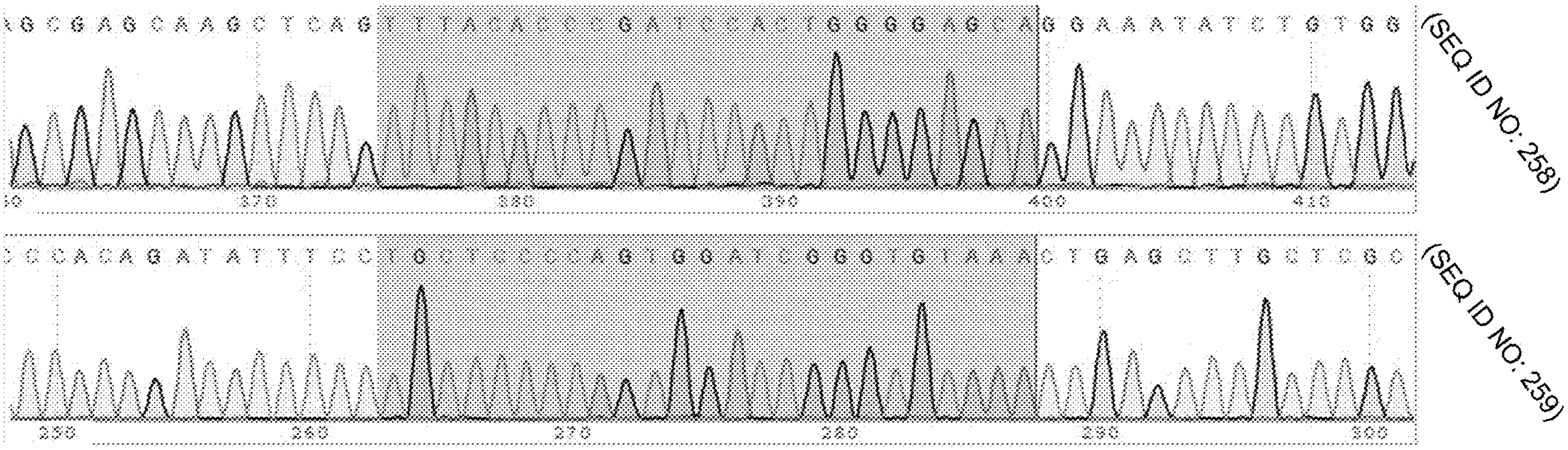

(SEQ ID NO: 258)

(SEQ ID NO: 259)

crRNA:

5'-/AltR1/rUrA rArUrU rUrCrU rArCrU rCrUrU rGrUrA rGrArU rCrArC rCrCrG rArUrC rCrArC rUrGrG rGrGrA rGrCrA /iSp18//3ThioMC3-D/-3' (SEQ ID NO: 260)

Homology template for non-target strand:

CCACTTGAGTCCGTGTCACAAGCCCACAGATATTTCCTGCGCGGCCGCTCCCCAGTGGATCGGGTGTAAACTGAGCTTGC TCGCTCGG (SEQ ID NO: 261)

Homology template for target strand:

NotI restriction site (bold, underline

CGAGCAAGCTCAGTTCACACCCGATCCACTGGGGAGCAGGGCGGCCGCAAATATCTGTGGGCTTGTGACACGGACTCAAG TGGGCTGG (SEQ ID NO: 262)

FIG. 10A
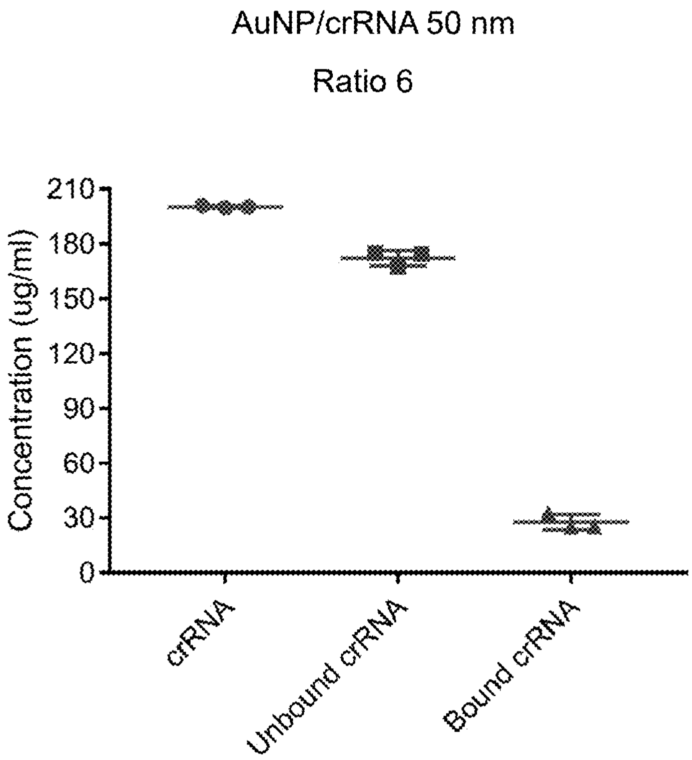
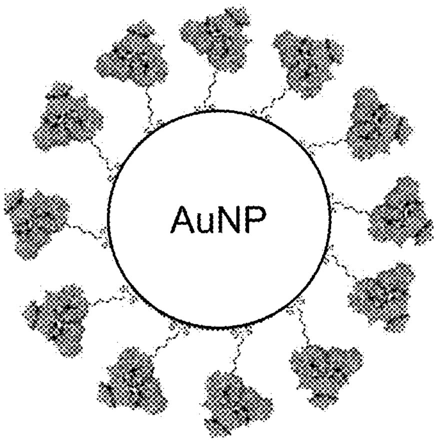

FIG. 10A cont'd
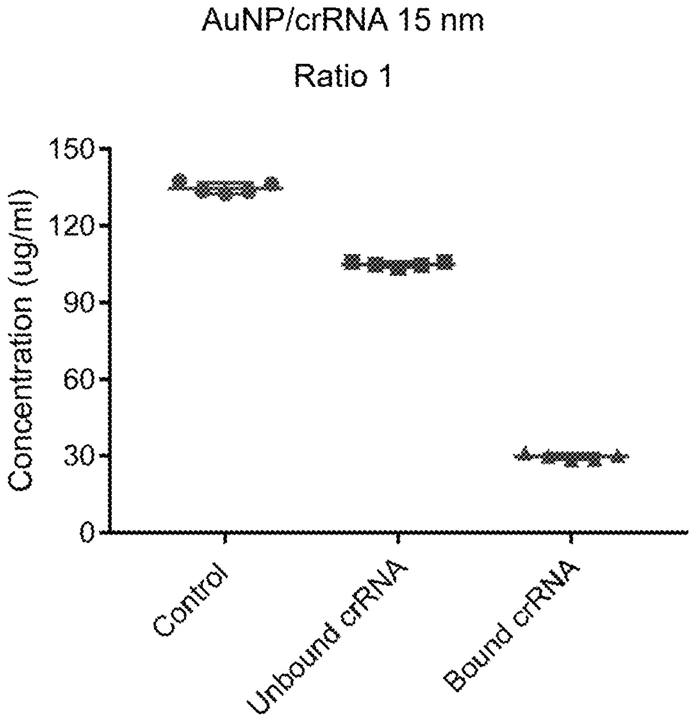
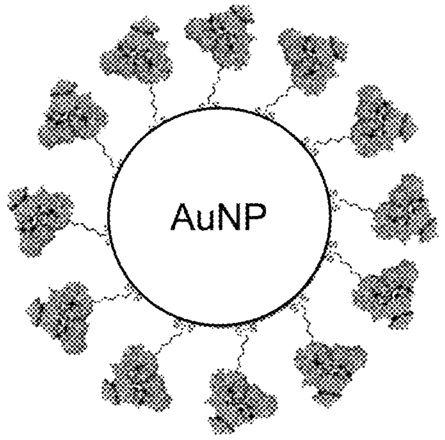

FIG. 10A cont'd
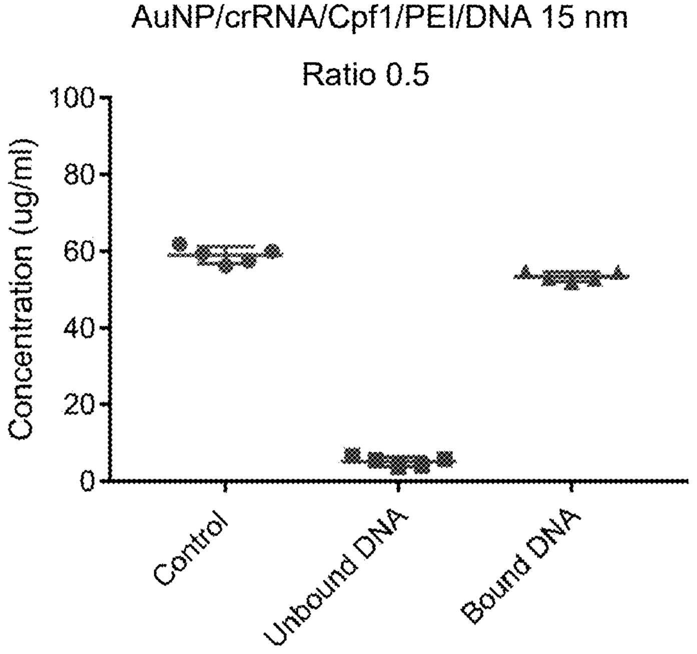
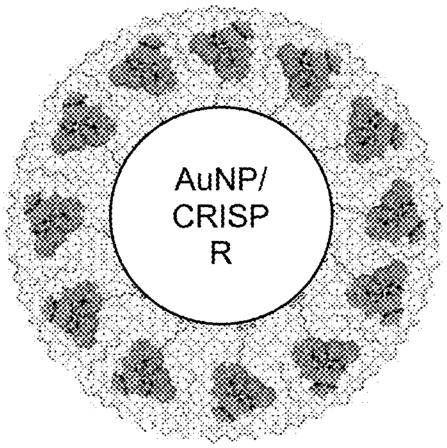

| Concentration (ug/mL) | Number of Particles | Surface area ($nm^2$) |
|---|---|---|
| 50 | $1.46 \times 10^{12}$ | $1.032 \times 10^{15}$ |
| 50 | $3.95 \times 10^{10}$ | $3.10 \times 10^{14}$ |

3.33 x

FIG. 12A
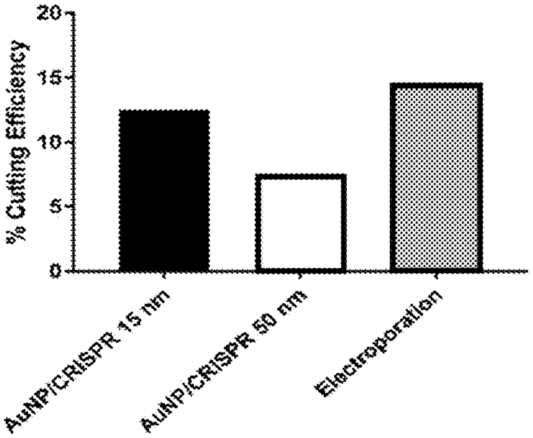
FIG. 12B
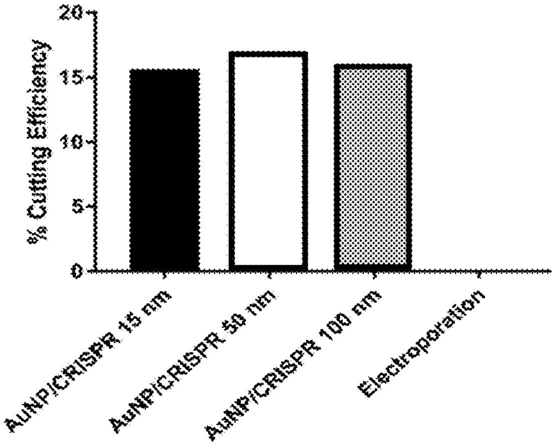
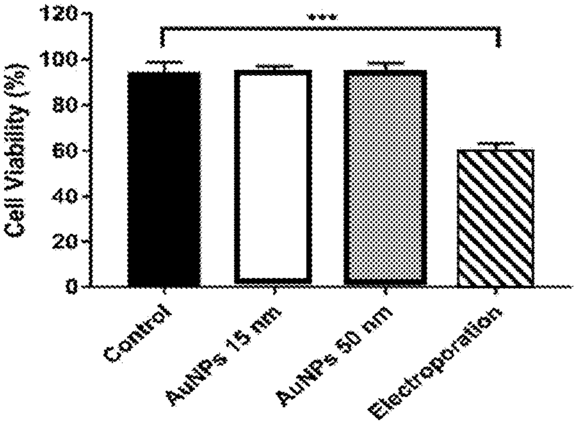
FIG. 12C
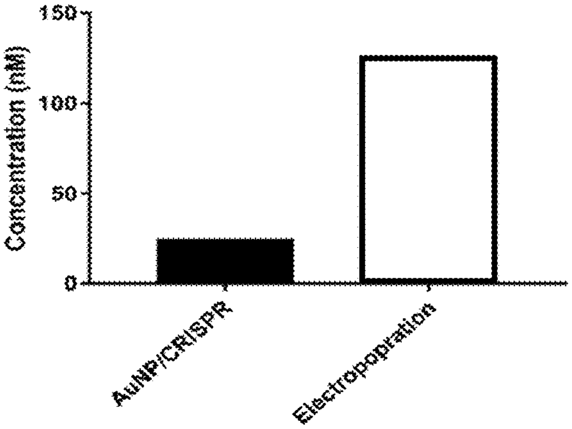
FIG. 12D

Analysis:

Flow cytometry (CD45, CD3, CD4, CD8, CD20, CD14)

Gene editing analysis by TIDE and restriction enzyme digestion

CFU potential

| Groups | Cell dose | Number of mice |
|---|---|---|
| AuNP/CRISPR-HDT | $1\times10^6$ | 10 |
| AuNP | $1\times10^6$ | 10 |
| Mock | $1\times10^6$ | 5 |
| Uninjected | - | 5 |

FIG. 23

>PGK promoter
GGGGTTGGGGTTGCGCCTTTTCCAAGGCAGCCCTGGGTTTGCGCAGGGACGCGGCTGCT
CTGGGCGTGGTTCCGGGAAACGCAGCGGCGCCGACCCTGGGTCTCGCACATTCTTCACG
TCCGTTCGCAGCGTCACCCGGATCTTCGCCGCTACCCTTGTGGGCCCCCCGGCGACGCTT
CCTGCTCCGCCCCTAAGTCGGGAAGGTTCCTTGCGGTTCGCGGCGTGCCGGACGTGACA
AACGGAAGCCGCACGTCTCACTAGTACCCTCGCAGACGGACAGCGCCAGGGAGCAATGG
CAGCGCGCCGACCGCGATGGGCTGTGGCCAATAGCGGCTGCTCAGCGGGGCGCGCCGA
GAGCAGCGGCCGGGAAGGGGCGGTGCGGGAGGCGGGGTGTGGGGCGGTAGTGTGGGC
CCTGTTCCTGCCCGCGCGGTGTTCCGCATTCTGCAAGCCTCCGGAGCGCACGTCGGCAG
TCGGCTCCCTCGTTGACCGAATCACCGACCTCTCTCCCCAG (SEQ ID NO: 214)

>Streptococcus pyogenes serotype M1 Cas9 cds (nucleotides 854751-858857 of NCBI Reference Sequence: NC_002737.2)
ATGGATAAGAAATACTCAATAGGCTTAGATATCGGCACAAATAGCGTCGGATGGGCGGTGA
TCACTGATGAATATAAGGTTCCGTCTAAAAAGTTCAAGGTTCTGGGAAATACAGACCGCCA
CAGTATCAAAAAAAATCTTATAGGGGCTCTTTTATTTGACAGTGGAGAGACAGCGGAAGCG
ACTCGTCTCAAACGGACAGCTCGTAGAAGGTATACACGTCGGAAGAATCGTATTTGTTATC
TACAGGAGATTTTTTCAAATGAGATGGCGAAAGTAGATGATAGTTTCTTTCATCGACTTGAA
GAGTCTTTTTTGGTGGAAGAAGACAAGAAGCATGAACGTCATCCTATTTTTGGAAATATAGT
AGATGAAGTTGCTTATCATGAGAAATATCCAACTATCTATCATCTGCGAAAAAAATTGGTAG
ATTCTACTGATAAAGCGGATTTGCGCTTAATCTATTTGGCCTTAGCGCATATGATTAAGTTT
CGTGGTCATTTTTTGATTGAGGGAGATTTAAATCCTGATAATAGTGATGTGGACAAACTATT
TATCCAGTTGGTACAAACCTACAATCAATTATTTGAAGAAAACCCTATTAACGCAAGTGGAG
TAGATGCTAAAGCGATTCTTTCTGCACGATTGAGTAAATCAAGACGATTAGAAAATCTCATT
GCTCAGCTCCCCGGTGAGAAGAAAAATGGCTTATTTGGGAATCTCATTGCTTTGTCATTGG
GTTTGACCCCTAATTTTAAATCAAATTTTGATTTGGCAGAAGATGCTAAATTACAGCTTTCAA
AAGATACTTACGATGATGATTTAGATAATTTATTGGCGCAAATTGGAGATCAATATGCTGAT
TTGTTTTTGGCAGCTAAGAATTTATCAGATGCTATTTTACTTTCAGATATCCTAAGAGTAAAT
ACTGAAATAACTAAGGCTCCCCTATCAGCTTCAATGATTAAACGCTACGATGAACATCATCA
AGACTTGACTCTTTTAAAAGCTTTAGTTCGACAACAACTTCCAGAAAAGTATAAAGAAATCTT
TTTTGATCAATCAAAAAACGGATATGCAGGTTATATTGATGGGGGAGCTAGCCAAGAAGAA
TTTTATAAATTTATCAAACCAATTTTAGAAAAAATGGATGGTACTGAGGAATTATTGGTGAAA
CTAAATCGTGAAGATTTGCTGCGCAAGCAACGGACCTTTGACAACGGCTCTATTCCCCATC
AAATTCACTTGGGTGAGCTGCATGCTATTTTGAGAAGACAAGAAGACTTTTATCCATTTTTA
AAAGACAATCGTGAGAAGATTGAAAAAATCTTGACTTTTCGAATTCCTTATTATGTTGGTCC
ATTGGCGCGTGGCAATAGTCGTTTTGCATGGATGACTCGGAAGTCTGAAGAAACAATTACC
CCATGGAATTTTGAAGAAGTTGTCGATAAAGGTGCTTCAGCTCAATCATTTATTGAACGCAT
GACAAACTTTGATAAAAATCTTCCAAATGAAAAAGTACTACCAAAACATAGTTTGCTTTATGA
GTATTTTACGGTTTATAACGAATTGACAAAGGTCAAATATGTTACTGAAGGAATGCGAAAAC
CAGCATTTCTTTCAGGTGAACAGAAGAAAGCCATTGTTGATTTACTCTTCAAAACAAATCGA
AAAGTAACCGTTAAGCAATTAAAAGAAGATTATTTCAAAAAAATAGAATGTTTTGATAGTGTT
GAAATTTCAGGAGTTGAAGATAGATTTAATGCTTCATTAGGTACCTACCATGATTTGCTAAA
AATTATTAAAGATAAAGATTTTTTGGATAATGAAGAAAATGAAGATATCTTAGAGGATATTGT
TTTAACATTGACCTTATTTGAAGATAGGGAGATGATTGAGGAAAGACTTAAAACATATGCTC
ACCTCTTTGATGATAAGGTGATGAAACAGCTTAAACGTCGCCGTTATACTGGTTGGGGACG
TTTGTCTCGAAAATTGATTAATGGTATTAGGGATAAGCAATCTGGCAAAACAATATTAGATTT
TTTGAAATCAGATGGTTTTGCCAATCGCAATTTTATGCAGCTGATCCATGATGATAGTTTGA
CATTTAAAGAAGACATTCAAAAAGCACAAGTGTCTGGACAAGGCGATAGTTTACATGAACAT
ATTGCAAATTTAGCTGGTAGCCCTGCTATTAAAAAAGGTATTTTACAGACTGTAAAAGTTGT

FIG. 23 cont'd.

TGATGAATTGGTCAAAGTAATGGGGCGGCATAAGCCAGAAAATATCGTTATTGAAATGGCA
CGTGAAAATCAGACAACTCAAAAGGGCCAGAAAAATTCGCGAGAGCGTATGAAACGAATC
GAAGAAGGTATCAAAGAATTAGGAAGTCAGATTCTTAAAGAGCATCCTGTTGAAAATACTCA
ATTGCAAAATGAAAAGCTCTATCTCTATTATCTCCAAAATGGAAGAGACATGTATGTGGACC
AAGAATTAGATATTAATCGTTTAAGTGATTATGATGTCGATCACATTGTTCCACAAAGTTTCC
TTAAAGACGATTCAATAGACAATAAGGTCTTAACGCGTTCTGATAAAAATCGTGGTAAATCG
GATAACGTTCCAAGTGAAGAAGTAGTCAAAAAGATGAAAAACTATTGGAGACAACTTCTAAA
CGCCAAGTTAATCACTCAACGTAAGTTTGATAATTTAACGAAAGCTGAACGTGGAGGTTTGA
GTGAACTTGATAAAGCTGGTTTTATCAAACGCCAATTGGTTGAAACTCGCCAAATCACTAAG
CATGTGGCACAAATTTTGGATAGTCGCATGAATACTAAATACGATGAAAATGATAAACTTAT
TCGAGAGGTTAAAGTGATTACCTTAAAATCTAAATTAGTTTCTGACTTCCGAAAAGATTTCCA
ATTCTATAAAGTACGTGAGATTAACAATTACCATCATGCCCATGATGCGTATCTAAATGCCG
TCGTTGGAACTGCTTTGATTAAGAAATATCCAAAACTTGAATCGGAGTTTGTCTATGGTGAT
TATAAAGTTTATGATGTTCGTAAAATGATTGCTAAGTCTGAGCAAGAAATAGGCAAAGCAAC
CGCAAAATATTTCTTTTACTCTAATATCATGAACTTCTTCAAAACAGAAATTACACTTGCAAA
TGGAGAGATTCGCAAACGCCCTCTAATCGAAACTAATGGGGAAACTGGAGAAATTGTCTGG
GATAAAGGGCGAGATTTTGCCACAGTGCGCAAAGTATTGTCCATGCCCCAAGTCAATATTG
TCAAGAAAACAGAAGTACAGACAGGCGGATTCTCCAAGGAGTCAATTTTACCAAAAAGAAA
TTCGGACAAGCTTATTGCTCGTAAAAAAGACTGGGATCCAAAAAAATATGGTGGTTTTGATA
GTCCAACGGTAGCTTATTCAGTCCTAGTGGTTGCTAAGGTGGAAAAAGGGAAATCGAAGAA
GTTAAAATCCGTTAAAGAGTTACTAGGGATCACAATTATGGAAAGAAGTTCCTTTGAAAAAA
ATCCGATTGACTTTTTAGAAGCTAAAGGATATAAGGAAGTTAAAAAAGACTTAATCATTAAAC
TACCTAAATATAGTCTTTTTGAGTTAGAAAACGGTCGTAAACGGATGCTGGCTAGTGCCGG
AGAATTACAAAAAGGAAATGAGCTGGCTCTGCCAAGCAAATATGTGAATTTTTTATATTTAG
CTAGTCATTATGAAAAGTTGAAGGGTAGTCCAGAAGATAACGAACAAAAACAATTGTTTGTG
GAGCAGCATAAGCATTATTTAGATGAGATTATTGAGCAAATCAGTGAATTTTCTAAGCGTGT
TATTTTAGCAGATGCCAATTTAGATAAAGTTCTTAGTGCATATAACAAACATAGAGACAAAC
CAATACGTGAACAAGCAGAAAATATTATTCATTTATTTACGTTGACGAATCTTGGAGCTCCC
GCTGCTTTTAAATATTTTGATACAACAATTGATCGTAAACGATATACGTCTACAAAAGAAGTT
TTAGATGCCACTCTTATCCATCAATCCATCACTGGTCTTTATGAAACACGCATTGATTTGAG
TCAGCTAGGAGGTGACTGA (SEQ ID NO: 215)

FIG. 23 cont'd.

>Francisella tularensis type V CRISPR-associated Cpf1 cds (nucleotides 652838-656740 of NCBI Reference Sequence: NZ_CP009633.1)
ATGTCAATTTATCAAGAATTTGTTAATAAATATAGTTTAAGTAAAACTCTAAGATTTGAGTTAA
TCCCACAGGGTAAAACACTTGAAAACATAAAAGCAAGAGGTTTGATTTTAGATGATGAGAAA
AGAGCTAAAGACTACAAAAAGGCTAAACAAATAATTGATAAATATCATCAGTTTTTTATAGAG
GAGATATTAAGTTCGGTTTGTATTAGCGAAGATTTATTACAAAACTATTCTGATGTTTATTTT
AAACTTAAAAAGAGTGATGATGATAATCTACAAAAAGATTTTAAAAGTGCAAAAGATACGAT
AAAGAAACAAATATCTGAATATATAAAGGACTCAGAGAAATTTAAGAATTTGTTTAATCAAAA
CCTTATCGATGCTAAAAAAGGGCAAGAGTCAGATTTAATTCTATGGCTAAAGCAATCTAAGG
ATAATGGTATAGAACTATTTAAAGCCAATAGTGATATCACAGATATAGATGAGGCGTTAGAA
ATAATCAAATCTTTTAAAGGTTGGACAACTTATTTTAAGGGTTTTCATGAAAATAGAAAAAAT
GTTTATAGTAGCAATGATATTCCTACATCTATTATTTATAGGATAGTAGATGATAATTTGCCT
AAATTTCTAGAAAATAAAGCTAAGTATGAGAGTTTAAAAGACAAAGCTCCAGAAGCTATAAA
CTATGAACAAATTAAAAAAGATTTGGCAGAAGAGCTAACCTTTGATATTGACTACAAAACAT
CTGAAGTTAATCAAAGAGTTTTTTCACTTGATGAAGTTTTTGAGATAGCAAACTTTAATAATT
ATCTAAATCAAAGTGGTATTACTAAATTTAATACTATTATTGGTGGTAAATTTGTAAATGGTG
AAAATACAAAGAGAAAAGGTATAAATGAATATATAAATCTATACTCACAGCAAATAAATGATA
AAACACTCAAAAAATATAAAATGAGTGTTTTATTTAAGCAAATTTTAAGTGATACAGAATCTA
AATCTTTTGTAATTGATAAGTTAGAAGATGATAGTGATGTAGTTACAACGATGCAAAGTTTTT
ATGAGCAAATAGCAGCTTTTAAAACAGTAGAAGAAAAATCTATTAAAGAAACACTATCTTTAT
TATTTGATGATTTAAAAGCTCAAAAACTTGATTTGAGTAAAATTTATTTTAAAAATGATAAATC
TCTTACTGATCTATCACAACAAGTTTTTGATGATTATAGTGTTATTGGTACAGCGGTACTAGA
ATATATAACTCAACAAATAGCACCTAAAAATCTTGATAACCCTAGTAAGAAAGAGCAAGAAT
TAATAGCCAAAAAAACTGAAAAAGCAAAATACTTATCTCTAGAAACTATAAAGCTTGCCTTA
GAAGAATTTAATAAGCATAGAGATATAGATAAACAGTGTAGGTTTGAAGAAATACTTGCAAA
CTTTGCGGCTATTCCGATGATATTTGATGAAATAGCTCAAAACAAAGACAATTTGGCACAGA
TATCTATCAAATATCAAAATCAAGGTAAAAAAGACCTACTTCAAGCTAGTGCGGAAGATGAT
GTTAAAGCTATCAAGGATCTTTTAGATCAAACTAATAATCTCTTACATAAACTAAAAATATTT
CATATTAGTCAGTCAGAAGATAAGGCAAATATTTTAGACAAGGATGAGCATTTTTATCTAGT
ATTTGAGGAGTGCTACTTTGAGCTAGCGAATATAGTGCCTCTTTATAACAAAATTAGAAACT
ATATAACTCAAAAGCCATATAGTGATGAGAAATTTAAGCTCAATTTTGAGAACTCGACTTTG
GCTAATGGTTGGGATAAAAATAAAGAGCCTGACAATACGGCAATTTTATTTATCAAAGATGA
TAAATATTATCTGGGTGTGATGAATAAGAAAAATAACAAAATATTTGATGATAAAGCTATCAA
AGAAAATAAAGGCGAGGGTTATAAAAAAATTGTTTATAAACTTTTACCTGGCGCAAATAAAA
TGTTACCTAAGGTTTTCTTTTCTGCTAAATCTATAAAATTTTATAATCCTAGTGAAGATATACT
TAGAATAAGAAATCATTCCACACATACAAAAAATGGTAGTCCTCAAAAAGGATATGAAAAAT
TTGAGTTTAATATTGAAGATTGCCGAAAATTTATAGATTTTTATAAACAGTCTATAAGTAAGC
ATCCGGAGTGGAAAGATTTTGGATTTAGATTTTCTGATACTCAAAGATATAATTCTATAGATG
AATTTTATAGAGAAGTTGAAAATCAAGGCTACAAACTAACTTTTGAAAATATATCAGAGAGCT
ATATTGATAGCGTAGTTAATCAGGGTAAATTGTACCTATTCCAAATCTATAATAAAGATTTTT
CAGCTTATAGCAAAGGGCGACCAAATCTACATACTTTATATTGGAAAGCGCTGTTTGATGA
GAGAAATCTTCAAGATGTGGTTTATAAGCTAAATGGTGAGGCAGAGCTTTTTTATCGTAAAC
AATCAATACCTAAAAAAATCACTCACCCAGCTAAAGAGGCAATAGCTAATAAAAACAAAGAT
AATCCTAAAAAAGAGAGTGTTTTTGAATATGATTTAATCAAAGATAAACGCTTTACTGAAGAT
AAGTTTTTCTTTCACTGTCCTATTACAATCAATTTTAAATCTAGTGGAGCTAATAAGTTTAAT
GATGAAATCAATTTATTGCTAAAAGAAAAAGCAAATGATGTTCATATATTAAGTATAGATAGA
GGTGAAAGACATTTAGCTTACTATACTTTGGTAGATGGTAAAGGCAATATCATCAAACAAGA
TACTTTCAACATCATTGGTAATGATAGAATGAAAACAAACTACCATGATAAGCTTGCTGCAA
TAGAGAAAGATAGGGATTCAGCTAGGAAAGACTGGAAAAAGATAAATAACATCAAAGAGAT

FIG. 23 cont'd.

GAAAGAGGGCTATCTATCTCAGGTAGTTCATGAAATAGCTAAGCTAGTTATAGAGTATAATG
CTATTGTGGTTTTTGAGGATTTAAATTTTGGATTTAAAAGAGGGCGTTTCAAGGTAGAGAAG
CAGGTCTATCAAAAGTTAGAAAAAATGCTAATTGAGAAACTAAACTATCTAGTTTTCAAAGAT
AATGAGTTTGATAAAACTGGGGGAGTGCTTAGAGCTTATCAGCTAACAGCACCTTTTGAGA
CTTTTAAAAAGATGGGTAAACAAACAGGTATTATCTACTATGTACCAGCTGGTTTTACTTCAA
AAATTTGTCCTGTAACTGGTTTTGTAAATCAGTTATATCCTAAGTATGAAAGTGTCAGCAAAT
CTCAAGAGTTCTTTAGTAAGTTTGACAAGATTTGTTATAACCTTGATAAGGGCTATTTTGAGT
TTAGTTTTGATTATAAAAACTTTGGTGACAAGGCTGCCAAAGGCAAGTGGACTATAGCTAGC
TTTGGGAGTAGATTGATTAACTTTAGAAATTCAGATAAAAATCATAATTGGGATACTCGAGA
AGTTTATCCAACTAAAGAGTTGGAGAAATTGCTAAAAGATTATTCTATCGAATATGGGCATG
GCGAATGTATCAAAGCAGCTATTTGCGGTGAGAGCGACAAAAAGTTTTTTGCTAAGCTAAC
TAGTGTCCTAAATACTATCTTACAAATGCGTAACTCAAAAACAGGTACTGAGTTAGATTATCT
AATTTCACCAGTAGCAGATGTAAATGGCAATTTCTTTGATTCGCGACAGGCGCCAAAAAATA
TGCCTCAAGATGCTGATGCCAATGGTGCTTATCATATTGGGCTAAAAGGTCTGATGCTACT
AGGTAGGATCAAAAATAATCAAGAGGGCAAAAAACTCAATTTGGTTATCAAAAATGAAGAGT
ATTTTGAGTTCGTGCAGAATAGGAATAACTAA (SEQ ID NO: 216)

FIG. 23 cont'd.

>Acidaminococcus sp. BV3L6 Cpf1 (AsCpf1) cds from Zetsche 2015
ATGACACAGTTCGAGGGCTTTACCAACCTGTATCAGGTGAGCAAGACACTGCGGTTTGAG
CTGATCCCACAGGGCAAGACCCTGAAGCACATCCAGGAGCAGGGCTTCATCGAGGAGGA
CAAGGCCCGCAATGATCACTACAAGGAGCTGAAGCCCATCATCGATCGGATCTACAAGAC
CTATGCCGACCAGTGCCTGCAGCTGGTGCAGCTGGATTGGGAGAACCTGAGCGCCGCCA
TCGACTCCTATAGAAAGGAGAAAACCGAGGAGACAAGGAACGCCCTGATCGAGGAGCAGG
CCACATATCGCAATGCCATCCACGACTACTTCATCGGCCGGACAGACAACCTGACCGATG
CCATCAATAAGAGACACGCCGAGATCTACAAGGGCCTGTTCAAGGCCGAGCTGTTTAATG
GCAAGGTGCTGAAGCAGCTGGGCACCGTGACCACAACCGAGCACGAGAACGCCCTGCTG
CGGAGCTTCGACAAGTTTACAACCTACTTCTCCGGCTTTTATGAGAACAGGAAGAACGTGT
TCAGCGCCGAGGATATCAGCACAGCCATCCCACACCGCATCGTGCAGGACAACTTCCCCA
AGTTTAAGGAGAATTGTCACATCTTCACACGCCTGATCACCGCCGTGCCCAGCCTGCGGG
AGCACTTTGAGAACGTGAAGAAGGCCATCGGCATCTTCGTGAGCACCTCCATCGAGGAGG
TGTTTTCCTTCCCTTTTTATAACCAGCTGCTGACACAGACCCAGATCGACCTGTATAACCAG
CTGCTGGGAGGAATCTCTCGGGAGGCAGGCACCGAGAAGATCAAGGGCCTGAACGAGGT
GCTGAATCTGGCCATCCAGAAGAATGATGAGACAGCCCACATCATCGCCTCCCTGCCACA
CAGATTCATCCCCCTGTTTAAGCAGATCCTGTCCGATAGGAACACCCTGTCTTTCATCCTG
GAGGAGTTTAAGAGCGACGAGGAAGTGATCCAGTCCTTCTGCAAGTACAAGACACTGCTG
AGAAACGAGAACGTGCTGGAGACAGCCGAGGCCCTGTTTAACGAGCTGAACAGCATCGAC
CTGACACACATCTTCATCAGCCACAAGAAGCTGGAGACAATCAGCAGCGCCCTGTGCGAC
CACTGGGATACACTGAGGAATGCCCTGTATGAGCGGAGAATCTCCGAGCTGACAGGCAAG
ATCACCAAGTCTGCCAAGGAGAAGGTGCAGCGCAGCCTGAAGCACGAGGATATCAACCTG
CAGGAGATCATCTCTGCCGCAGGCAAGGAGCTGAGCGAGGCCTTCAAGCAGAAAACCAG
CGAGATCCTGTCCCACGCACACGCCGCCCTGGATCAGCCACTGCCTACAACCCTGAAGAA
GCAGGAGGAGAAGGAGATCCTGAAGTCTCAGCTGGACAGCCTGCTGGGCCTGTACCACC
TGCTGGACTGGTTTGCCGTGGATGAGTCCAACGAGGTGGACCCCGAGTTCTCTGCCCGGC
TGACCGGCATCAAGCTGGAGATGGAGCCTTCTCTGAGCTTCTACAACAAGGCCAGAAATTA
TGCCACCAAGAAGCCCTACTCCGTGGAGAAGTTCAAGCTGAACTTTCAGATGCCTACACTG
GCCTCTGGCTGGGACGTGAATAAGGAGAAGAACAATGGCGCCATCCTGTTTGTGAAGAAC
GGCCTGTACTATCTGGGCATCATGCCAAAGCAGAAGGGCAGGTATAAGGCCCTGAGCTTC
GAGCCCACAGAGAAAACCAGCGAGGGCTTTGATAAGATGTACTATGACTACTTCCCTGATG
CCGCCAAGATGATCCCAAAGTGCAGCACCCAGCTGAAGGCCGTGACAGCCCACTTTCAGA
CCCACACAACCCCCATCCTGCTGTCCAACAATTTCATCGAGCCTCTGGAGATCACAAAGGA
GATCTACGACCTGAACAATCCTGAGAAGGAGCCAAAGAAGTTTCAGACAGCCTACGCCAA
GAAAACCGGCGACCAGAAGGGCTACAGAGAGGCCCTGTGCAAGTGGATCGACTTCACAA
GGGATTTTCTGTCCAAGTATACCAAGACAACCTCTATCGATCTGTCTAGCCTGCGGCCATC
CTCTCAGTATAAGGACCTGGGCGAGTACTATGCCGAGCTGAATCCCCTGCTGTACCACATC
AGCTTCCAGAGAATCGCCGAGAAGGAGATCATGGATGCCGTGGAGACAGGCAAGCTGTAC
CTGTTCCAGATCTATAACAAGGACTTTGCCAAGGGCCACCACGGCAAGCCTAATCTGCACA
CACTGTATTGGACCGGCCTGTTTTCTCCAGAGAACCTGGCCAAGACAAGCATCAAGCTGAA
TGGCCAGGCCGAGCTGTTCTACCGCCCTAAGTCCAGGATGAAGAGGATGGCACACCGGC
TGGGAGAGAAGATGCTGAACAAGAAGCTGAAGGATCAGAAAACCCCAATCCCCGACACCC
TGTACCAGGAGCTGTACGACTATGTGAATCACAGACTGTCCCACGACCTGTCTGATGAGG
CCAGGGCCCTGCTGCCCAACGTGATCACCAAGGAGGTGTCTCACGAGATCATCAAGGATA
GGCGCTTTACCAGCGACAAGTTCTTTTTCCACGTGCCTATCACACTGAACTATCAGGCCGC
CAATTCCCCATCTAAGTTCAACCAGAGGGTGAATGCCTACCTGAAGGAGCACCCCGAGAC
ACCTATCATCGGCATCGATCGGGGCGAGAGAAACCTGATCTATATCACAGTGATCGACTCC
ACCGGCAAGATCCTGGAGCAGCGGAGCCTGAACACCATCCAGCAGTTTGATTACCAGAAG
AAGCTGGACAACAGGGAGAAGGAGAGGGTGGCAGCAAGGCAGGCCTGGTCTGTGGTGG

FIG. 23 cont'd.

GCACAATCAAGGATCTGAAGCAGGGCTATCTGAGCCAGGTCATCCACGAGATCGTGGACC
TGATGATCCACTACCAGGCCGTGGTGGTGCTGGAGAACCTGAATTTCGGCTTTAAGAGCA
AGAGGACCGGCATCGCCGAGAAGGCCGTGTACCAGCAGTTCGAGAAGATGCTGATCGATA
AGCTGAATTGCCTGGTGCTGAAGGACTATCCAGCAGAGAAAGTGGGAGGCGTGCTGAACC
CATACCAGCTGACAGACCAGTTCACCTCCTTTGCCAAGATGGGCACCCAGTCTGGCTTCCT
GTTTTACGTGCCTGCCCCATATACATCTAAGATCGATCCCCTGACCGGCTTCGTGGACCCC
TTCGTGTGGAAAACCATCAAGAATCACGAGAGCCGCAAGCACTTCCTGGAGGGCTTCGAC
TTTCTGCACTACGACGTGAAAACCGGCGACTTCATCCTGCACTTTAAGATGAACAGAAATC
TGTCCTTCCAGAGGGGCCTGCCCGGCTTTATGCCTGCATGGGATATCGTGTTCGAGAAGA
ACGAGACACAGTTTGACGCCAAGGGCACCCCTTTCATCGCCGGCAAGAGAATCGTGCCAG
TGATCGAGAATCACAGATTCACCGGCAGATACCGGGACCTGTATCCTGCCAACGAGCTGA
TCGCCCTGCTGGAGGAGAAGGGCATCGTGTTCAGGGATGGCTCCAACATCCTGCCAAAGC
TGCTGGAGAATGACGATTCTCACGCCATCGACACCATGGTGGCCCTGATCCGCAGCGTGC
TGCAGATGCGGAACTCCAATGCCGCCACAGGCGAGGACTATATCAACAGCCCCGTGCGC
GATCTGAATGGCGTGTGCTTCGACTCCCGGTTTCAGAACCCAGAGTGGCCCATGGACGCC
GATGCCAATGGCGCCTACCACATCGCCCTGAAGGGCCAGCTGCTGCTGAATCACCTGAAG
GAGAGCAAGGATCTGAAGCTGCAGAACGGCATCTCCAATCAGGACTGGCTGGCCTACATC
CAGGAGCTGCGCAAC (SEQ ID NO: 217)

FIG. 23 cont'd.

>Lachnospiraceae bacterium MC2017 Cpf1 (Lb3Cpf1) cds from Zetsche 2015
ATGGATTACGGCAACGGCCAGTTTGAGCGGAGAGCCCCCCTGACCAAGACAATCACCCTG
CGCCTGAAGCCTATCGGCGAGACACGGGAGACAATCCGCGAGCAGAAGCTGCTGGAGCA
GGACGCCGCCTTCAGAAAGCTGGTGGAGACAGTGACCCCTATCGTGGACGATTGTATCAG
GAAGATCGCCGATAACGCCCTGTGCCACTTTGGCACCGAGTATGACTTCAGCTGTCTGGG
CAACGCCATCTCTAAGAATGACAGCAAGGCCATCAAGAAGGAGACAGAGAAGGTGGAGAA
GCTGCTGGCCAAGGTGCTGACCGAGAATCTGCCAGATGGCCTGCGCAAGGTGAACGACA
TCAATTCCGCCGCCTTTATCCAGGATACACTGACCTCTTTCGTGCAGGACGATGCCGACAA
GCGGGTGCTGATCCAGGAGCTGAAGGGCAAGACCGTGCTGATGCAGCGGTTCCTGACCA
CACGGATCACAGCCCTGACCGTGTGGCTGCCCGACAGAGTGTTCGAGAACTTTAATATCTT
CATCGAGAACGCCGAGAAGATGAGAATCCTGCTGGACTCCCCTCTGAATGAGAAGATCAT
GAAGTTTGACCCAGATGCCGAGCAGTACGCCTCTCTGGAGTTCTATGGCCAGTGCCTGTC
TCAGAAGGACATCGATAGCTACAACCTGATCATCTCCGGCATCTATGCCGACGATGAGGTG
AAGAACCCTGGCATCAATGAGATCGTGAAGGAGTACAATCAGCAGATCCGGGGCGACAAG
GATGAGTCCCCACTGCCCAAGCTGAAGAAGCTGCACAAGCAGATCCTGATGCCAGTGGAG
AAGGCCTTCTTTGTGCGCGTGCTGTCTAACGACAGCGATGCCCGGAGCATCCTGGAGAAG
ATCCTGAAGGACACAGAGATGCTGCCCTCCAAGATCATCGAGGCCATGAAGGAGGCAGAT
GCAGGCGACATCGCCGTGTACGGCAGCCGGCTGCACGAGCTGAGCCACGTGATCTACGG
CGATCACGGCAAGCTGTCCCAGATCATCTATGACAAGGAGTCCAAGAGGATCTCTGAGCT
GATGGAGACACTGTCTCCAAAGGAGCGCAAGGAGAGCAAGAAGCGGCTGGAGGGCCTGG
AGGAGCACATCAGAAAGTCTACATACACCTTCGACGAGCTGAACAGGTATGCCGAGAAGA
ATGTGATGGCAGCATACATCGCAGCAGTGGAGGAGTCTTGTGCCGAGATCATGAGAAAGG
AGAAGGATCTGAGGACCCTGCTGAGCAAGGAGGACGTGAAGATCCGGGGCAACAGACAC
AATACACTGATCGTGAAGAACTACTTTAATGCCTGGACCGTGTTCCGGAACCTGATCAGAA
TCCTGAGGCGCAAGTCCGAGGCCGAGATCGACTCTGACTTCTACGATGTGCTGGACGATT
CCGTGGAGGTGCTGTCTCTGACATACAAGGGCGAGAATCTGTGCCGCAGCTATATCACCA
AGAAGATCGGCTCCGACCTGAAGCCCGAGATCGCCACATACGGCAGCGCCCTGAGGCCT
AACAGCCGCTGGTGGTCCCCAGGAGAGAAGTTTAATGTGAAGTTCCACACCATCGTGCGG
AGAGATGGCCGGCTGTACTATTTCATCCTGCCCAAGGGCGCCAAGCCTGTGGAGCTGGAG
GACATGGATGGCGACATCGAGTGTCTGCAGATGAGAAAGATCCCTAACCCAACAATCTTTC
TGCCCAAGCTGGTGTTCAAGGACCCTGAGGCCTTCTTTAGGGATAATCCAGAGGCCGACG
AGTTCGTGTTTCTGAGCGGCATGAAGGCCCCCGTGACAATCACCAGAGAGACATACGAGG
CCTACAGGTATAAGCTGTATACCGTGGGCAAGCTGCGCGATGGCGAGGTGTCCGAAGAG
GAGTACAAGCGGGCCCTGCTGCAGGTGCTGACCGCCTACAAGGAGTTTCTGGAGAACAGA
ATGATCTATGCCGACCTGAATTTCGGCTTTAAGGATCTGGAGGAGTATAAGGACAGCTCCG
AGTTTATCAAGCAGGTGGAGACACACAACACCTTCATGTGCTGGGCCAAGGTGTCTAGCTC
CCAGCTGGACGATCTGGTGAAGTCTGGCAACGGCCTGCTGTTCGAGATCTGGAGCGAGC
GCCTGGAGTCCTACTATAAGTACGGCAATGAGAAGGTGCTGCGGGGCTATGAGGGCGTG
CTGCTGAGCATCCTGAAGGATGAGAACCTGGTGTCCATGCGGACCCTGCTGAACAGCCGG
CCCATGCTGGTGTACCGGCCAAAGGAGTCTAGCAAGCCTATGGTGGTGCACCGGGATGG
CAGCAGAGTGGTGGACAGGTTTGATAAGGACGGCAAGTACATCCCCCCTGAGGTGCACGA
CGAGCTGTATCGCTTCTTTAACAATCTGCTGATCAAGGAGAAGCTGGGCGAGAAGGCCCG
GAAGATCCTGGACAACAAGAAGGTGAAGGTGAAGGTGCTGGAGAGCGAGAGAGTGAAGT
GGTCCAAGTTCTACGATGAGCAGTTTGCCGTGACCTTCAGCGTGAAGAAGAACGCCGATT
GTCTGGACACCACAAAGGACCTGAATGCCGAAGTGATGGAGCAGTATAGCGAGTCCAACA
GACTGATCCTGATCAGGAATACCACAGATATCCTGTACTATCTGGTGCTGGACAAGAATGG
CAAGGTGCTGAAGCAGAGATCCCTGAACATCATCAATGACGGCGCCAGGGATGTGGACTG
GAAGGAGAGGTTCCGCCAGGTGACAAAGGATAGAAACGAGGGCTACAATGAGTGGGATTA
TTCCAGGACCTCTAACGACCTGAAGGAGGTGTACCTGAATTATGCCCTGAAGGAGATCGC

FIG. 23 cont'd.

CGAGGCCGTGATCGAGTACAACGCCATCCTGATCATCGAGAAGATGTCTAATGCCTTTAAG
GACAAGTATAGCTTCCTGGACGACGTGACCTTCAAGGGCTTCGAGACAAAGCTGCTGGCC
AAGCTGAGCGATCTGCACTTTAGGGGCATCAAGGACGGCGAGCCATGTTCCTTCACAAAC
CCCCTGCAGCTGTGCCAGAACGATTCTAATAAGATCCTGCAGGACGGCGTGATCTTTATGG
TGCCAAATTCTATGACACGGAGCCTGGACCCCGACACCGGCTTCATCTTTGCCATCAACGA
CCACAATATCAGGACCAAGAAGGCCAAGCTGAACTTTCTGAGCAAGTTCGATCAGCTGAAG
GTGTCCTCTGAGGGCTGCCTGATCATGAAGTACAGCGGCGATTCCCTGCCTACACACAAC
ACCGACAATCGCGTGTGGAACTGCTGTTGCAATCACCCAATCACAAACTATGACCGGGAG
ACAAAGAAGGTGGAGTTCATCGAGGAGCCCGTGGAGGAGCTGTCCCGCGTGCTGGAGGA
GAATGGCATCGAGACAGACACCGAGCTGAACAAGCTGAATGAGCGGGAGAACGTGCCTG
GCAAGGTGGTGGATGCCATCTACTCTCTGGTGCTGAATTATCTGCGCGGCACAGTGAGCG
GAGTGGCAGGACAGAGGGCCGTGTACTATAGCCCTGTGACCGGCAAGAAGTACGATATCT
CCTTTATCCAGGCCATGAACCTGAATAGGAAGTGTGACTACTATAGGATCGGCTCCAAGGA
GAGGGGAGAGTGGACCGATTTCGTGGCCCAGCTGATCAAC (SEQ ID NO: 218)

>Lachnospiraceae bacterium ND2006 type V CRISPR-associated protein Cpf1 coding
ATGAGCAAGCTGGAGAAGTTTACAAACTGCTACTCCCTGTCTAAGACCCTGAGGTTCAAGG
CCATCCCTGTGGGCAAGACCCAGGAGAACATCGACAATAAGCGGCTGCTGGTGGAGGAC
GAGAAGAGAGCCGAGGATTATAAGGGCGTGAAGAAGCTGCTGGATCGCTACTATCTGTCT
TTTATCAACGACGTGCTGCACAGCATCAAGCTGAAGAATCTGAACAATTACATCAGCCTGTT
CCGGAAGAAAACCAGAACCGAGAAGGAGAATAAGGAGCTGGAGAACCTGGAGATCAATCT
GCGGAAGGAGATCGCCAAGGCCTTCAAGGGCAACGAGGGCTACAAGTCCCTGTTTAAGAA
GGATATCATCGAGACAATCCTGCCAGAGTTCCTGGACGATAAGGACGAGATCGCCCTGGT
GAACAGCTTCAATGGCTTTACCACAGCCTTCACCGGCTTCTTTGATAACAGAGAGAATATG
TTTTCCGAGGAGGCCAAGAGCACATCCATCGCCTTCAGGTGTATCAACGAGAATCTGACCC
GCTACATCTCTAATATGGACATCTTCGAGAAGGTGGACGCCATCTTTGATAAGCACGAGGT
GCAGGAGATCAAGGAGAAGATCCTGAACAGCGACTATGATGTGGAGGATTTCTTTGAGGG
CGAGTTCTTTAACTTTGTGCTGACACAGGAGGGCATCGACGTGTATAACGCCATCATCGGC
GGCTTCGTGACCGAGAGCGGCGAGAAGATCAAGGGCCTGAACGAGTACATCAACCTGTAT
AATCAGAAAACCAAGCAGAAGCTGCCTAAGTTTAAGCCACTGTATAAGCAGGTGCTGAGCG
ATCGGGAGTCTCTGAGCTTCTACGGCGAGGGCTATACATCCGATGAGGAGGTGCTGGAGG
TGTTTAGAAACACCCTGAACAAGAACAGCGAGATCTTCAGCTCCATCAAGAAGCTGGAGAA
GCTGTTCAAGAATTTTGACGAGTACTCTAGCGCCGGCATCTTTGTGAAGAACGGCCCCGC
CATCAGCACAATCTCCAAGGATATCTTCGGCGAGTGGAACGTGATCCGGGACAAGTGGAA
TGCCGAGTATGACGATATCCACCTGAAGAAGAAGGCCGTGGTGACCGAGAAGTACGAGGA
CGATCGGAGAAAGTCCTTCAAGAAGATCGGCTCCTTTTCTCTGGAGCAGCTGCAGGAGTA
CGCCGACGCCGATCTGTCTGTGGTGGAGAAGCTGAAGGAGATCATCATCCAGAAGGTGGA
TGAGATCTACAAGGTGTATGGCTCCTCTGAGAAGCTGTTCGACGCCGATTTTGTGCTGGAG
AAGAGCCTGAAGAAGAACGACGCCGTGGTGGCCATCATGAAGGACCTGCTGGATTCTGTG
AAGAGCTTCGAGAATTACATCAAGGCCTTCTTTGGCGAGGGCAAGGAGACAAACAGGGAC
GAGTCCTTCTATGGCGATTTTGTGCTGGCCTACGACATCCTGCTGAAGGTGGACCACATCT
ACGATGCCATCCGCAATTATGTGACCCAGAAGCCCTACTCTAAGGATAAGTTCAAGCTGTA
TTTTCAGAACCCTCAGTTCATGGGCGGCTGGGACAAGGATAAGGAGACAGACTATCGGGC
CACCATCCTGAGATACGGCTCCAAGTACTATCTGGCCATCATGGATAAGAAGTACGCCAAG
TGCCTGCAGAAGATCGACAAGGACGATGTGAACGGCAATTACGAGAAGATCAACTATAAG
CTGCTGCCCGGCCCTAATAAGATGCTGCCAAAGGTGTTCTTTTCTAAGAAGTGGATGGCCT
ACTATAACCCCAGCGAGGACATCCAGAAGATCTACAAGAATGGCACATTCAAGAAGGGCG
ATATGTTTAACCTGAATGACTGTCACAAGCTGATCGACTTCTTTAAGGATAGCATCTCCCGG

FIG. 23 cont'd.

TATCCAAAGTGGTCCAATGCCTACGATTTCAACTTTTCTGAGACAGAGAAGTATAAGGACAT
CGCCGGCTTTTACAGAGAGGTGGAGGAGCAGGGCTATAAGGTGAGCTTCGAGTCTGCCA
GCAAGAAGGAGGTGGATAAGCTGGTGGAGGAGGGCAAGCTGTATATGTTCCAGATCTATA
ACAAGGACTTTTCCGATAAGTCTCACGGCACACCCAATCTGCACACCATGTACTTCAAGCT
GCTGTTTGACGAGAACAATCACGGACAGATCAGGCTGAGCGGAGGAGCAGAGCTGTTCAT
GAGGCGCGCCTCCCTGAAGAAGGAGGAGCTGGTGGTGCACCCAGCCAACTCCCCTATCG
CCAACAAGAATCCAGATAATCCCAAGAAAACCACAACCCTGTCCTACGACGTGTATAAGGA
TAAGAGGTTTTCTGAGGACCAGTACGAGCTGCACATCCCAATCGCCATCAATAAGTGCCCC
AAGAACATCTTCAAGATCAATACAGAGGTGCGCGTGCTGCTGAAGCACGACGATAACCCCT
ATGTGATCGGCATCGATAGGGGCGAGCGCAATCTGCTGTATATCGTGGTGGTGGACGGCA
AGGGCAACATCGTGGAGCAGTATTCCCTGAACGAGATCATCAACAACTTCAACGGCATCAG
GATCAAGACAGATTACCACTCTCTGCTGGACAAGAAGGAGAAGGAGAGGTTCGAGGCCCG
CCAGAACTGGACCTCCATCGAGAATATCAAGGAGCTGAAGGCCGGCTATATCTCTCAGGT
GGTGCACAAGATCTGCGAGCTGGTGGAGAAGTACGATGCCGTGATCGCCCTGGAGGACC
TGAACTCTGGCTTTAAGAATAGCCGCGTGAAGGTGGAGAAGCAGGTGTATCAGAAGTTCG
AGAAGATGCTGATCGATAAGCTGAACTACATGGTGGACAAGAAGTCTAATCCTTGTGCAAC
AGGCGGCGCCCTGAAGGGCTATCAGATCACCAATAAGTTCGAGAGCTTTAAGTCCATGTCT
ACCCAGAACGGCTTCATCTTTTACATCCCTGCCTGGCTGACATCCAAGATCGATCCATCTA
CCGGCTTTGTGAACCTGCTGAAAACCAAGTATACCAGCATCGCCGATTCCAAGAAGTTCAT
CAGCTCCTTTGACAGGATCATGTACGTGCCCGAGGAGGATCTGTTCGAGTTTGCCCTGGA
CTATAAGAACTTCTCTCGCACAGACGCCGATTACATCAAGAAGTGGAAGCTGTACTCCTAC
GGCAACCGGATCAGAATCTTCCGGAATCCTAAGAAGAACAACGTGTTCGACTGGGAGGAG
GTGTGCCTGACCAGCGCCTATAAGGAGCTGTTCAACAAGTACGGCATCAATTATCAGCAG
GGCGATATCAGAGCCCTGCTGTGCGAGCAGTCCGACAAGGCCTTCTACTCTAGCTTTATG
GCCCTGATGAGCCTGATGCTGCAGATGCGGAACAGCATCACAGGCCGCACCGACGTGGA
TTTTCTGATCAGCCCTGTGAAGAACTCCGACGGCATCTTCTACGATAGCCGGAACTATGAG
GCCCAGGAGAATGCCATCCTGCCAAAGAACGCCGACGCCAATGGCGCCTATAACATCGCC
AGAAAGGTGCTGTGGGCCATCGGCCAGTTCAAGAAGGCCGAGGACGAGAAGCTGGATAA
GGTGAAGATCGCCATCTCTAACAAGGAGTGGCTGGAGTACGCCCAGACCAGCGTGAAGCA
C (SEQ ID NO: 219)

>Francisella tularensis subsp. Novicida U112 Cpf1 (FnCpf1) coding
ATGAGCATCTACCAGGAGTTCGTCAACAAGTATTCACTGAGTAAGACACTGCGGTTCGAGC
TGATCCCACAGGGCAAGACACTGGAGAACATCAAGGCCCGAGGCCTGATTCTGGACGATG
AGAAGCGGGCAAAAGACTATAAGAAAGCCAAGCAGATCATTGATAAATACCACCAGTTCTT
TATCGAGGAAATTCTGAGCTCCGTGTGCATCAGTGAGGATCTGCTGCAGAATTACTCAGAC
GTGTACTTCAAGCTGAAGAAGAGCGACGATGACAACCTGCAGAAGGACTTCAAGTCCGCC
AAGGACACCATCAAGAAACAGATTAGCGAGTACATCAAGGACTCCGAAAAGTTTAAAAATC
TGTTCAACCAGAATCTGATCGATGCTAAGAAAGGCCAGGAGTCCGACCTGATCCTGTGGCT
GAAACAGTCTAAGGACAATGGGATTGAACTGTTCAAGGCTAACTCCGATATCACTGATATT
GACGAGGCACTGGAAATCATCAAGAGCTTCAAGGGATGGACCACATACTTTAAAGGCTTCC
ACGAGAACCGCAAGAACGTGTACTCCAGCAACGACATTCCTACCTCCATCATCTACCGAAT
CGTCGATGACAATCTGCCAAAGTTCCTGGAGAACAAGGCCAAATATGAATCTCTGAAGGAC
AAAGCTCCCGAGGCAATTAATTACGAACAGATCAAGAAAGATCTGGCTGAGGAACTGACAT
TCGATATCGACTATAAGACTAGCGAGGTGAACCAGAGGGTCTTTTCCCTGGACGAGGTGTT
TGAAATCGCCAATTTCAACAATTACCTGAACCAGTCCGGCATTACTAAATTCAATACCATCA
TTGGCGGGAAGTTTGTGAACGGGGAGAATACCAAGCGCAAGGGAATTAACGAATACATCA
ATCTGTATAGCCAGCAGATCAACGACAAAACTCTGAAGAAATACAAGATGTCTGTGCTGTT
CAAACAGATCCTGAGTGATACCGAGTCCAAGTCTTTTGTCATTGATAAACTGGAAGATGACT

FIG. 23 cont'd.

CAGACGTGGTCACTACCATGCAGAGCTTTTATGAGCAGATCGCCGCTTTCAAGACAGTGGA
GGAAAAATCTATTAAGGAAACTCTGAGTCTGCTGTTCGATGACCTGAAAGCCCAGAAGCTG
GACCTGAGTAAGATCTACTTCAAAAACGATAAGAGTCTGACAGACCTGTCACAGCAGGTGT
TTGATGACTATTCCGTGATTGGGACCGCCGTCCTGGAGTACATTACACAGCAGATCGCTCC
AAAGAACCTGGATAATCCCTCTAAGAAAGAGCAGGAACTGATCGCTAAGAAAACCGAGAAG
GCAAAATATCTGAGTCTGGAAACAATTAAGCTGGCACTGGAGGAGTTCAACAAGCACAGG
GATATTGACAAACAGTGCCGCTTTGAGGAAATCCTGGCCAACTTCGCAGCCATCCCCATGA
TTTTTGATGAGATCGCCCAGAACAAAGACAATCTGGCTCAGATCAGTATTAAGTACCAGAA
CCAGGGCAAGAAAGACCTGCTGCAGGCTTCAGCAGAAGATGACGTGAAAGCCATCAAGGA
TCTGCTGGACCAGACCAACAATCTGCTGCACAAGCTGAAAATCTTCCATATTAGTCAGTCA
GAGGATAAGGCTAATATCCTGGATAAAGACGAACACTTCTACCTGGTGTTCGAGGAATGTT
ACTTCGAGCTGGCAAACATTGTCCCCCTGTATAACAAGATTAGGAACTACATCACACAGAA
GCCTTACTCTGACGAGAAGTTTAAACTGAACTTCGAAAATAGTACCCTGGCCAACGGGTGG
GATAAGAACAAGGAGCCTGACAACACAGCTATCCTGTTCATCAAGGATGACAAGTACTATC
TGGGAGTGATGAATAAGAAAAACAATAAGATCTTCGATGACAAAGCCATTAAGGAGAACAA
AGGGGAAGGATACAAGAAAATCGTGTATAAGCTGCTGCCCGGCGCAAATAAGATGCTGCC
TAAGGTGTTCTTCAGCGCCAAGAGTATCAAATTCTACAACCCATCCGAGGACATCCTGCGG
ATTAGAAATCACTCAACACATACTAAGAACGGGAGCCCCCAGAAGGGATATGAGAAATTTG
AGTTCAACATCGAGGATTGCAGGAAGTTTATTGACTTCTACAAGCAGAGCATCTCCAAACA
CCCTGAATGGAAGGATTTTGGCTTCCGGTTTTCCGACACACAGAGATATAACTCTATCGAC
GAGTTCTACCGCGAGGTGGAAAATCAGGGGTATAAGCTGACTTTTGAGAACATTTCTGAAA
GTTACATCGACAGCGTGGTCAATCAGGGAAAGCTGTACCTGTTCCAGATCTATAACAAAGA
TTTTTCAGCATACAGCAAGGGCAGACCAAACCTGCATACACTGTACTGGAAGGCCCTGTTC
GATGAGAGGAATCTGCAGGACGTGGTCTATAAACTGAACGGAGAGGCCGAACTGTTTTAC
CGGAAGCAGTCTATTCCTAAGAAAATCACTCACCCAGCTAAGGAGGCCATCGCTAACAAGA
ACAAGGACAATCCTAAGAAAGAGAGCGTGTTCGAATACGATCTGATTAAGGACAAGCGGTT
CACCGAAGATAAGTTCTTTTTCCATTGTCCAATCACCATTAACTTCAAGTCAAGCGGCGCTA
ACAAGTTCAACGACGAGATCAATCTGCTGCTGAAGGAAAAAGCAAACGATGTGCACATCCT
GAGCATTGACCGAGGAGAGCGGCATCTGGCCTACTATACCCTGGTGGATGGCAAAGGGAA
TATCATTAAGCAGGATACATTCAACATCATTGGCAATGACCGGATGAAAACCAACTACCAC
GATAAACTGGCTGCAATCGAGAAGGATAGAGACTCAGCTAGGAAGGACTGGAAGAAAATC
AACAACATTAAGGAGATGAAGGAAGGCTATCTGAGCCAGGTGGTCCATGAGATTGCAAAG
CTGGTCATCGAATACAATGCCATTGTGGTGTTCGAGGATCTGAACTTCGGCTTTAAGAGGG
GGCGCTTTAAGGTGGAAAAACAGGTCTATCAGAAGCTGGAGAAAATGCTGATCGAAAAGCT
GAATTACCTGGTGTTTAAAGATAACGAGTTCGACAAGACCGGAGGCGTCCTGAGAGCCTA
CCAGCTGACAGCTCCCTTTGAAACTTTCAAGAAAATGGGAAAACAGACAGGCATCATCTAC
TATGTGCCAGCCGGATTCACTTCCAAGATCTGCCCCGTGACCGGCTTTGTCAACCAGCTGT
ACCCTAAATATGAGTCAGTGAGCAAGTCCCAGGAATTTTTCAGCAAGTTCGATAAGATCTGT
TATAATCTGGACAAGGGGTACTTCGAGTTTTCCTTCGATTACAAGAACTTCGGCGACAAGG
CCGCTAAGGGGAAATGGACCATTGCCTCCTTCGGATCTCGCCTGATCAACTTTCGAAATTC
CGATAAAAACCACAATTGGGACACTAGGGAGGTGTACCCAACCAAGGAGCTGGAAAAGCT
GCTGAAAGACTACTCTATCGAGTATGGACATGGCGAATGCATCAAGGCAGCCATCTGTGG
CGAGAGTGATAAGAAATTTTTCGCCAAGCTGACCTCAGTGCTGAATACAATCCTGCAGATG
CGGAACTCAAAGACCGGGACAGAACTGGACTATCTGATTAGCCCCGTGGCTGATGTCAAC
GGAAACTTCTTCGACAGCAGACAGGCACCCAAAAATATGCCTCAGGATGCAGACGCCAAC
GGGGCCTACCACATCGGGCTGAAGGGACTGATGCTGCTGGGCCGGATCAAGAACAATCA
GGAGGGGAAGAAGCTGAACCTGGTCATTAAGAACGAGGAATACTTCGAGTTTGTCCAGAA
TAGAAATAAC (SEQ ID NO: 220)

FIG. 23 cont'd.

>Peregrinibacteria bacterium GW2011_GWA_33_10 Cpf1 (PeCpf1) coding
ATGTCCAACTTCTTTAAGAATTTCACCAACCTGTATGAGCTGTCCAAGACACTGAGGTTTGA
GCTGAAGCCCGTGGGCGACACCCTGACAAACATGAAGGACCACCTGGAGTACGATGAGAA
GCTGCAGACCTTCCTGAAGGATCAGAATATCGACGATGCCTATCAGGCCCTGAAGCCTCA
GTTCGACGAGATCCACGAGGAGTTTATCACAGATTCTCTGGAGAGCAAGAAGGCCAAGGA
GATCGACTTCTCCGAGTACCTGGATCTGTTTCAGGAGAAGAAGGAGCTGAACGACTCTGA
GAAGAAGCTGCGCAACAAGATCGGCGAGACATTCAACAAGGCCGGCGAGAAGTGGAAGA
AGGAGAAGTACCCTCAGTATGAGTGGAAGAAGGGCTCCAAGATCGCCAATGGCGCCGACA
TCCTGTCTTGCCAGGATATGCTGCAGTTTATCAAGTATAAGAACCCAGAGGATGAGAAGAT
CAAGAATTACATCGACGATACACTGAAGGGCTTCTTTACCTATTTCGGCGGCTTTAATCAGA
ACAGGGCCAACTACTATGAGACAAAGAAGGAGGCCTCCACCGCAGTGGCAACAAGGATCG
TGCACGAGAACCTGCCAAAGTTCTGTGACAATGTGATCCAGTTTAAGCACATCATCAAGCG
GAAGAAGGATGGCACCGTGGAGAAAACCGAGAGAAAGACCGAGTACCTGAACGCCTACCA
GTATCTGAAGAACAATAACAAGATCACACAGATCAAGGACGCCGAGACAGAGAAGATGATC
GAGTCTACACCCATCGCCGAGAAGATCTTCGACGTGTACTACTTCAGCAGCTGCCTGAGC
CAGAAGCAGATCGAGGAGTACAACCGGATCATCGGCCACTATAATCTGCTGATCAACCTGT
ATAACCAGGCCAAGAGATCTGAGGGCAAGCACCTGAGCGCCAACGAGAAGAAGTATAAGG
ACCTGCCTAAGTTCAAGACCCTGTATAAGCAGATCGGCTGCGGCAAGAAGAAGGACCTGT
TTTACACAATCAAGTGTGATACCGAGGAGGAGGCCAATAAGTCCCGGAACGAGGGCAAGG
AGTCCCACTCTGTGGAGGAGATCATCAACAAGGCCCAGGAGGCCATCAATAAGTACTTCAA
GTCTAATAACGACTGTGAGAATATCAACACCGTGCCCGACTTCATCAACTATATCCTGACAA
AGGAGAATTACGAGGGCGTGTATTGGAGCAAGGCCGCCATGAACACCATCTCCGACAAGT
ACTTCGCCAATTATCACGACCTGCAGGATAGACTGAAGGAGGCCAAGGTGTTTCAGAAGG
CCGATAAGAAGTCCGAGGACGATATCAAGATCCCAGAGGCCATCGAGCTGTCTGGCCTGT
TCGGCGTGCTGGACAGCCTGGCCGATTGGCAGACCACACTGTTTAAGTCTAGCATCCTGA
GCAACGAGGACAAGCTGAAGATCATCACAGATTCCCAGACCCCCTCTGAGGCCCTGCTGA
AGATGATCTTCAATGACATCGAGAAGAACATGGAGTCCTTTCTGAAGGAGACAAACGATAT
CATCACCCTGAAGAAGTATAAGGGCAATAAGGAGGGCACCGAGAAGATCAAGCAGTGGTT
CGACTATACACTGGCCATCAACCGGATGCTGAAGTACTTTCTGGTGAAGGAGAATAAGATC
AAGGGCAACTCCCTGGATACCAATATCTCTGAGGCCCTGAAAACCCTGATCTACAGCGAC
GATGCCGAGTGGTTCAAGTGGTACGACGCCCTGAGAAACTATCTGACCCAGAAGCCTCAG
GATGAGGCCAAGGAGAATAAGCTGAAGCTGAATTTCGACAACCCATCTCTGGCCGGCGGC
TGGGATGTGAACAAGGAGTGCAGCAATTTTTGCGTGATCCTGAAGGACAAGAACGAGAAG
AAGTACCTGGCCATCATGAAGAAGGGCGAGAATACCCTGTTCCAGAAGGAGTGGACAGAG
GGCCGGGGCAAGAACCTGACAAAGAAGTCTAATCCACTGTTCGAGATCAATAACTGCGAG
ATCCTGAGCAAGATGGAGTATGACTTTTGGGCCGACGTGAGCAAGATGATCCCCAAGTGT
AGCACCCAGCTGAAGGCCGTGGTGAACCACTTCAAGCAGTCCGACAATGAGTTCATCTTTC
CTATCGGCTACAAGGTGACAAGCGGCGAGAAGTTTAGGGAGGAGTGCAAGATCTCCAAGC
AGGACTTCGAGCTGAATAACAAGGTGTTTAATAAGAACGAGCTGAGCGTGACCGCCATGC
GCTACGATCTGTCCTCTACACAGGAGAAGCAGTATATCAAGGCCTTCCAGAAGGAGTACTG
GGAGCTGCTGTTTAAGCAGGAGAAGCGGGACACCAAGCTGACAAATAACGAGATCTTCAA
CGAGTGGATCAATTTTTGCAACAAGAAGTATAGCGAGCTGCTGTCCTGGGAGAGAAAGTAC
AAGGATGCCCTGACCAATTGGATCAACTTCTGTAAGTACTTTCTGAGCAAGTATCCCAAGA
CCACACTGTTCAACTACTCTTTTAAGGAGAGCGAGAATTATAACTCCCTGGACGAGTTCTAC
CGGGACGTGGATATCTGTTCTTACAAGCTGAATATCAACACCACAATCAATAAGAGCATCC
TGGATAGACTGGTGGAGGAGGGCAAGCTGTACCTGTTTGAGATCAAGAATCAGGACAGCA
ACGATGGCAAGTCCATCGGCCACAAGAATAACCTGCACACCATCTACTGGAACGCCATCTT
CGAGAATTTTGACAACAGGCCTAAGCTGAATGGCGAGGCCGAGATCTTCTATCGCAAGGC

FIG. 23 cont'd.

CATCTCCAAGGATAAGCTGGGCATCGTGAAGGGCAAGAAAACCAAGAACGGCACCGAGAT
CATCAAGAATTACAGATTCAGCAAGGAGAAGTTTATCCTGCACGTGCCAATCACCCTGAAC
TTCTGCTCCAATAACGAGTATGTGAATGACATCGTGAACACAAAGTTCTACAATTTTTCCAA
CCTGCACTTTCTGGGCATCGATAGGGGCGAGAAGCACCTGGCCTACTATTCTCTGGTGAA
TAAGAACGGCGAGATCGTGGACCAGGGCACACTGAACCTGCCTTTCACCGACAAGGATGG
CAATCAGCGCAGCATCAAGAAGGAGAAGTACTTTTATAACAAGCAGGAGGACAAGTGGGA
GGCCAAGGAGGTGGATTGTTGGAATTATAACGACCTGCTGGATGCCATGGCCTCTAACCG
GGACATGGCCAGAAAGAATTGGCAGAGGATCGGCACCATCAAGGAGGCCAAGAACGGCT
ACGTGAGCCTGGTCATCAGGAAGATCGCCGATCTGGCCGTGAATAACGAGCGCCCCGCCT
TCATCGTGCTGGAGGACCTGAATACAGGCTTTAAGCGGTCCAGACAGAAGATCGATAAGA
GCGTGTACCAGAAGTTCGAGCTGGCCCTGGCCAAGAAGCTGAACTTTCTGGTGGACAAGA
ATGCCAAGCGCGATGAGATCGGCTCCCCTACAAAGGCCCTGCAGCTGACCCCCCCTGTGA
ATAACTACGGCGACATTGAGAACAAGAAGCAGGCCGGCATCATGCTGTATACCCGGGCCA
ATTATACCTCTCAGACAGATCCAGCCACAGGCTGGAGAAAGACCATCTATCTGAAGGCCG
GCCCCGAGGAGACAACATACAAGAAGGACGGCAAGATCAAGAACAAGAGCGTGAAGGAC
CAGATCATCGAGACATTCACCGATATCGGCTTTGACGGCAAGGATTACTATTTCGAGTACG
ACAAGGGCGAGTTTGTGGATGAGAAAACCGGCGAGATCAAGCCCAAGAAGTGGCGGCTG
TACTCCGGCGAGAATGGCAAGTCCCTGGACAGGTTCCGCGGAGAGAGGGAGAAGGATAA
GTATGAGTGGAAGATCGACAAGATCGATATCGTGAAGATCCTGGACGATCTGTTCGTGAAT
TTTGACAAGAACATCAGCCTGCTGAAGCAGCTGAAGGAGGGCGTGGAGCTGACCCGGAAT
AACGAGCACGGCACAGGCGAGTCCCTGAGATTCGCCATCAACCTGATCCAGCAGATCCGG
AATACCGGCAATAACGAGAGAGACAACGATTTCATCCTGTCCCCAGTGAGGGACGAGAAT
GGCAAGCACTTTGACTCTCGCGAGTACTGGGATAAGGAGACAAAGGGCGAGAAGATCAGC
ATGCCCAGCTCCGGCGATGCCAATGGCGCCTTCAACATCGCCCGGAAGGGCATCATCATG
AACGCCCACATCCTGGCCAATAGCGACTCCAAGGATCTGTCCCTGTTCGTGTCTGACGAG
GAGTGGGATCTGCACCTGAATAACAAGACCGAGTGGAAGAAGCAGCTGAACATCTTTTCTA
GCAGGAAGGCCATGGCCAAGCGCAAGAAG (SEQ ID NO: 221)

>Parcubacteria bacterium GWC2011_GWC2_44_17 Cpf1 (PbCpf1) coding
ATGGAGAACATCTTCGACCAGTTTATCGGCAAGTACAGCCTGTCCAAGACCCTGAGATTCG
AGCTGAAGCCCGTGGGCAAGACAGAGGACTTCCTGAAGATCAACAAGGTGTTTGAGAAGG
ATCAGACCATCGACGATAGCTACAATCAGGCCAAGTTCTATTTTGATTCCCTGCACCAGAA
GTTTATCGACGCCGCCCTGGCCTCCGATAAGACATCCGAGCTGTCTTTCCAGAACTTTGCC
GACGTGCTGGAGAAGCAGAATAAGATCATCCTGGATAAGAAGAGAGAGATGGGCGCCCTG
AGGAAGCGCGACAAGAACGCCGTGGGCATCGATAGGCTGCAGAAGGAGATCAATGACGC
CGAGGATATCATCCAGAAGGAGAAGGAGAAGATCTACAAGGACGTGCGCACCCTGTTCGA
TAACGAGGCCGAGTCTTGGAAAACCTACTATCAGGAGCGGGAGGTGGACGGCAAGAAGAT
CACCTTCAGCAAGGCCGACCTGAAGCAGAAGGGCGCCGATTTTCTGACAGCCGCCGGCAT
CCTGAAGGTGCTGAAGTATGAGTTCCCCGAGGAGAAGGAGAAGGAGTTTCAGGCCAAGAA
CCAGCCCTCCCTGTTCGTGGAGGAGAAGGAGAATCCTGGCCAGAAGAGGTACATCTTCGA
CTCTTTTGATAAGTTCGCCGGCTATCTGACCAAGTTTCAGCAGACAAAGAAGAATCTGTAC
GCAGCAGACGGCACCAGCACAGCAGTGGCCACCCGCATCGCCGATAACTTTATCATCTTC
CACCAGAATACCAAGGTGTTCCGGGACAAGTACAAGAACAATCACACAGACCTGGGCTTC
GATGAGGAGAACATCTTTGAGATCGAGAGGTATAAGAATTGCCTGCTGCAGCGCGAGATC
GAGCACATCAAGAATGAGAATAGCTACAACAAGATCATCGGCCGGATCAATAAGAAGATCA
AGGAGTATCGGGACCAGAAGGCCAAGGATACCAAGCTGACAAAGTCCGACTTCCCTTTCT
TTAAGAACCTGGATAAGCAGATCCTGGGCGAGGTGGAGAAGGAGAAGCAGCTGATCGAGA
AAACCCGGGAGAAAACCGAGGAGGACGTGCTGATCGAGCGGTTCAAGGAGTTCATCGAG
AACAATGAGGAGAGGTTCACCGCCGCCAAGAAGCTGATGAATGCCTTCTGTAACGGCGAG

FIG. 23 cont'd.

TTTGAGTCCGAGTACGAGGGCATCTATCTGAAGAATAAGGCCATCAACACAATCTCCCGGA
GATGGTTCGTGTCTGACAGAGATTTTGAGCTGAAGCTGCCTCAGCAGAAGTCCAAGAACAA
GTCTGAGAAGAATGAGCCAAAGGTGAAGAAGTTCATCTCCATCGCCGAGATCAAGAACGC
CGTGGAGGAGCTGGACGGCGATATCTTTAAGGCCGTGTTCTACGACAAGAAGATCATCGC
CCAGGGCGGCTCTAAGCTGGAGCAGTTCCTGGTCATCTGGAAGTACGAGTTTGAGTATCT
GTTCCGGGACATCGAGAGAGAGAACGGCGAGAAGCTGCTGGGCTATGATAGCTGCCTGA
AGATCGCCAAGCAGCTGGGCATCTTCCCACAGGAGAAGGAGGCCCGCGAGAAGGCAACC
GCCGTGATCAAGAATTACGCCGACGCCGGCCTGGGCATCTTCCAGATGATGAAGTATTTTT
CTCTGGACGATAAGGATCGGAAGAACACCCCCGGCCAGCTGAGCACAAATTTCTACGCCG
AGTATGACGGCTACTACAAGGATTTCGAGTTTATCAAGTACTACAACGAGTTTAGGAACTTC
ATCACCAAGAAGCCTTTCGACGAGGATAAGATCAAGCTGAACTTTGAGAATGGCGCCCTGC
TGAAGGGCTGGGACGAGAACAAGGAGTACGATTTCATGGGCGTGATCCTGAAGAAGGAG
GGCCGCCTGTATCTGGGCATCATGCACAAGAACCACCGGAAGCTGTTTCAGTCCATGGGC
AATGCCAAGGGCGACAACGCCAATAGATACCAGAAGATGATCTATAAGCAGATCGCCGAC
GCCTCTAAGGATGTGCCCAGGCTGCTGCTGACCAGCAAGAAGGCCATGGAGAAGTTCAAG
CCTTCCCAGGAGATCCTGAGAATCAAGAAGGAGAAAACCTTCAAGCGGGAGAGCAAGAAC
TTTTCCCTGAGAGATCTGCACGCCCTGATCGAGTACTATAGGAACTGCATCCCTCAGTACA
GCAATTGGTCCTTTTATGACTTCCAGTTTCAGGATACCGGCAAGTACCAGAATATCAAGGA
GTTCACAGACGATGTGCAGAAGTACGGCTATAAGATCTCCTTTCGCGACATCGACGATGAG
TATATCAATCAGGCCCTGAACGAGGGCAAGATGTACCTGTTCGAGGTGGTGAACAAGGAT
ATCTATAACACCAAGAATGGCTCCAAGAATCTGCACACACTGTACTTTGAGCACATCCTGTC
TGCCGAGAACCTGAATGACCCAGTGTTCAAGCTGTCTGGCATGGCCGAGATCTTTCAGCG
GCAGCCCAGCGTGAACGAAAGAGAGAAGATCACCCACACAGAAGAATCAGTGTATCCTGGA
CAAGGGCGATAGAGCCTACAAGTATAGGCGCTACACCGAGAAGAAGATCATGTTCCACAT
GAGCCTGGTGCTGAACACAGGCAAGGGCGAGATCAAGCAGGTGCAGTTTAATAAGATCAT
CAACCAGAGGATCAGCTCCTCTGACAACGAGATGAGGGTGAATGTGATCGGCATCGATCG
CGGCGAGAAGAACCTGCTGTACTATAGCGTGGTGAAGCAGAATGGCGAGATCATCGAGCA
GGCCTCCCTGAACGAGATCAATGGCGTGAACTACCGGGACAAGCTGATCGAGAGGGAGA
AGGAGCGCCTGAAGAACCGGCAGAGCTGGAAGCCTGTGGTGAAGATCAAGGATCTGAAG
AAGGGCTACATCTCCCACGTGATCCACAAGATCTGCCAGCTGATCGAGAAGTATTCTGCCA
TCGTGGTGCTGGAGGACCTGAATATGAGATTCAAGCAGATCAGGGGAGGAATCGAGCGGA
GCGTGTACCAGCAGTTCGAGAAGGCCCTGATCGATAAGCTGGGCTATCTGGTGTTTAAGG
ACAACAGGGATCTGAGGGCACCAGGAGGCGTGCTGAATGGCTACCAGCTGTCTGCCCCC
TTTGTGAGCTTCGAGAAGATGCGCAAGCAGACCGGCATCCTGTTCTACACACAGGCCGAG
TATACCAGCAAGACAGACCCAATCACCGGCTTTCGGAAGAACGTGTATATCTCTAATAGCG
CCTCCCTGGATAAGATCAAGGAGGCCGTGAAGAAGTTCGACGCCATCGGCTGGGATGGCA
AGGAGCAGTCTTACTTCTTTAAGTACAACCCTTACAACCTGGCCGACGAGAAGTATAAGAA
CTCTACCGTGAGCAAGGAGTGGGCCATCTTTGCCAGCGCCCCAAGAATCCGGAGACAGAA
GGGCGAGGACGGCTACTGGAAGTATGATAGGGTGAAAGTGAATGAGGAGTTCGAGAAGCT
GCTGAAGGTCTGGAATTTTGTGAACCCAAAGGCCACAGATATCAAGCAGGAGATCATCAAG
AAGGAGAAGGCAGGCGACCTGCAGGGAGAGAAGGAGCTGGATGGCCGGCTGAGAAACTT
TTGGCACTCTTTCATCTACCTGTTTAACCTGGTGCTGGAGCTGCGCAATTCTTTCAGCCTG
CAGATCAAGATCAAGGCAGGAGAAGTGATCGCAGTGGACGAGGGCGTGGACTTCATCGC
CAGCCCAGTGAAGCCCTTCTTTACCACACCCAACCCTTACATCCCCTCCAACCTGTGCTGG
CTGGCCGTGGAGAATGCAGACGCAAACGGAGCCTATAATATCGCCAGGAAGGGCGTGAT
GATCCTGAAGAAGATCCGCGAGCACGCCAAGAAGGACCCCGAGTTCAAGAAGCTGCCAAA
CCTGTTTATCAGCAATGCAGAGTGGGACGAGGCAGCCCGGGATTGGGGCAAGTACGCAG
GCACCACAGCCCTGAACCTGGACCAC (SEQ ID NO: 222)

FIG. 23 cont'd.

>Lachnospiraceae bacterium MA2020 (Lb2Cpf1) coding
ATGTACTATGAGTCCCTGACCAAGCAGTACCCCGTGTCTAAGACAATCCGGAATGAGCTGA
TCCCTATCGGCAAGACACTGGATAACATCCGCCAGAACAATATCCTGGAGAGCGACGTGA
AGCGGAAGCAGAACTACGAGCACGTGAAGGGCATCCTGGATGAGTATCACAAGCAGCTGA
TCAACGAGGCCCTGGACAATTGCACCCTGCCATCCCTGAAGATCGCCGCCGAGATCTACC
TGAAGAATCAGAAGGAGGTGTCTGACAGAGAGGATTTCAACAAGACACAGGACCTGCTGA
GGAAGGAGGTGGTGGAGAAGCTGAAGGCCCACGAGAACTTTACCAAGATCGGCAAGAAG
GACATCCTGGATCTGCTGGAGAAGCTGCCTTCCATCTCTGAGGACGATTACAATGCCCTG
GAGAGCTTCCGCAACTTTTACACCTATTTCACATCCTACAACAAGGTGCGGGAGAATCTGT
ATTCTGATAAGGAGAAGAGCTCCACAGTGGCCTACAGACTGATCAACGAGAATTTCCCAAA
GTTTCTGGACAATGTGAAGAGCTATAGGTTTGTGAAAACCGCAGGCATCCTGGCAGATGG
CCTGGGAGAGGAGGAGCAGGACTCCCTGTTCATCGTGGAGACATTCAACAAGACCCTGAC
ACAGGACGGCATCGATACCTACAATTCTCAAGTGGGCAAGATCAACTCTAGCATCAATCTG
TATAACCAGAAGAATCAGAAGGCCAATGGCTTCAGAAAGATCCCCAAGATGAAGATGCTGT
ATAAGCAGATCCTGTCCGATAGGGAGGAGTCTTTCATCGACGAGTTTCAGAGCGATGAGG
TGCTGATCGACAACGTGGAGTCTTATGGCAGCGTGCTGATCGAGTCTCTGAAGTCCTCTAA
GGTGAGCGCCTTCTTTGATGCCCTGAGAGAGTCTAAGGGCAAGAACGTGTACGTGAAGAA
TGACCTGGCCAAGACAGCCATGAGCAACATCGTGTTCGAGAATTGGAGGACCTTTGACGA
TCTGCTGAACCAGGAGTACGACCTGGCCAACGAGAACAAGAAGAAGGACGATAAGTATTT
CGAGAAGCGCCAGAAGGAGCTGAAGAAGAATAAGAGCTACTCCCTGGAGCACCTGTGCAA
CCTGTCCGAGGATTCTTGTAACCTGATCGAGAATTATATCCACCAGATCTCCGACGATATC
GAGAATATCATCATCAACAATGAGACATTCCTGCGCATCGTGATCAATGAGCACGACAGGT
CCCGCAAGCTGGCCAAGAACCGGAAGGCCGTGAAGGCCATCAAGGACTTTCTGGATTCTA
TCAAGGTGCTGGAGCGGGAGCTGAAGCTGATCAACAGCTCCGGCCAGGAGCTGGAGAAG
GATCTGATCGTGTACTCTGCCCACGAGGAGCTGCTGGTGGAGCTGAAGCAGGTGGACAG
CCTGTATAACATGACCAGAAATTATCTGACAAAGAAGCCTTTCTCTACCGAGAAGGTGAAG
CTGAACTTTAATCGCAGCACACTGCTGAACGGCTGGGATCGGAATAAGGAGACAGACAAC
CTGGGCGTGCTGCTGCTGAAGGACGGCAAGTACTATCTGGGCATCATGAACACAAGCGCC
AATAAGGCCTTCGTGAATCCCCCTGTGGCCAAGACCGAGAAGGTGTTTAAGAAGGTGGAT
TACAAGCTGCTGCCAGTGCCCAACCAGATGCTGCCAAAGGTGTTCTTTGCCAAGAGCAATA
TCGACTTCTATAACCCCTCTAGCGAGATCTACTCCAATTATAAGAAGGGCACCCACAAGAA
GGGCAATATGTTTTCCCTGGAGGATTGTCACAACCTGATCGACTTCTTTAAGGAGTCTATCA
GCAAGCACGAGGACTGGAGCAAGTTCGGCTTTAAGTTCAGCGATACAGCCTCCTACAACG
ACATCTCCGAGTTCTATCGCGAGGTGGAGAAGCAGGGCTACAAGCTGACCTATACAGACA
TCGATGAGACATACATCAATGATCTGATCGAGCGGAACGAGCTGTACCTGTTCCAGATCTA
TAATAAGGACTTTAGCATGTACTCCAAGGGCAAGCTGAACCTGCACACACTGTATTTCATG
ATGCTGTTTGATCAGCGCAATATCGACGACGTGGTGTATAAGCTGAACGGAGAGGCAGAG
GTGTTCTATAGGCCAGCCTCCATCTCTGAGGACGAGCTGATCATCCACAAGGCCGGCGAG
GAGATCAAGAACAAGAATCCTAACCGGGCCAGAACCAAGGAGACAAGCACCTTCAGCTAC
GACATCGTGAAGGATAAGCGGTATAGCAAGGATAAGTTTACCCTGCACATCCCCATCACAA
TGAACTTCGGCGTGGATGAGGTGAAGCGGTTCAACGACGCCGTGAACAGCGCCATCCGG
ATCGATGAGAATGTGAACGTGATCGGCATCGACCGGGGCGAGAGAAATCTGCTGTACGTG
GTGGTCATCGACTCTAAGGGCAACATCCTGGAGCAGATCTCCCTGAACTCTATCATCAATA
AGGAGTACGACATCGAGACAGATTATCACGCACTGCTGGATGAGAGGGAGGGCGGCAGA
GATAAGGCCCGGAAGGACTGGAACACCGTGGAGAATATCAGGGACCTGAAGGCCGGCTA
CCTGAGCCAGGTGGTGAACGTGGTGGCCAAGCTGGTGCTGAAGTATAATGCCATCATCTG
CCTGGAGGACCTGAACTTTGGCTTCAAGAGGGGCCGCCAGAAGGTGGAGAAGCAGGTGT
ACCAGAAGTTCGAGAAGATGCTGATCGATAAGCTGAATTACCTGGTCATCGACAAGAGCCG
CGAGCAGACATCCCCTAAGGAGCTGGGAGGCGCCCTGAACGCACTGCAGCTGACCTCTA

FIG. 23 cont'd.

AGTTCAAGAGCTTTAAGGAGCTGGGCAAGCAGTCCGGCGTGATCTACTATGTGCCTGCCT
ACCTGACCTCTAAGATCGATCCAACCACAGGCTTCGCCAATCTGTTTTATATGAAGTGTGA
GAACGTGGAGAAGTCCAAGAGATTCTTTGACGGCTTTGATTTCATCAGGTTCAACGCCCTG
GAGAACGTGTTCGAGTTCGGCTTTGACTACCGGAGCTTCACCCAGAGGGCCTGCGGCATC
AATTCCAAGTGGACCGTGTGCACCAACGGCGAGCGCATCATCAAGTATCGGAATCCAGAT
AAGAACAATATGTTCGACGAGAAGGTGGTGGTGGTGACCGATGAGATGAAGAACCTGTTT
GAGCAGTACAAGATCCCCTATGAGGATGGCAGAAATGTGAAGGACATGATCATCAGCAAC
GAGGAGGCCGAGTTCTACCGGAGACTGTATAGGCTGCTGCAGCAGACCCTGCAGATGAG
AAACAGCACCTCCGACGGCACAAGGGATTACATCATCTCCCCTGTGAAGAATAAGAGAGA
GGCCTACTTCAACAGCGAGCTGTCCGACGGCTCTGTGCCAAAGGACGCCGATGCCAACG
GCGCCTACAATATCGCCAGAAAGGGCCTGTGGGTGCTGGAGCAGATCAGGCAGAAGAGC
GAGGGCGAGAAGATCAATCTGGCCATGACCAACGCCGAGTGGCTGGAGTATGCCCAGAC
ACACCTGCTG (SEQ ID NO: 223)

>Candidatus Methanoplasma termitum Cpf1 (CMtCpf1) coding
ATGAACAATTACGACGAGTTCACCAAGCTGTATCCTATCCAGAAAACCATCCGGTTTGAGC
TGAAGCCACAGGGCAGAACCATGGAGCACCTGGAGACATTCAACTTCTTTGAGGAGGACC
GGGATAGAGCCGAGAAGTATAAGATCCTGAAGGAGGCCATCGACGAGTACCACAAGAAGT
TTATCGATGAGCACCTGACCAATATGTCCCTGGATTGGAACTCTCTGAAGCAGATCAGCGA
GAAGTACTATAAGAGCAGGGAGGAGAAGGACAAGAAGGTGTTCCTGTCCGAGCAGAAGAG
GATGCGCCAGGAGATCGTGTCTGAGTTTAAGAAGGACGATCGCTTCAAGGACCTGTTTTCC
AAGAAGCTGTTCTCTGAGCTGCTGAAGGAGGAGATCTACAAGAAGGGCAACCACCAGGAG
ATCGACGCCCTGAAGAGCTTCGATAAGTTTTCCGGCTATTTCATCGGCCTGCACGAGAATA
GGAAGAACATGTACTCCGACGGCGATGAGATCACCGCCATCTCCAATCGCATCGTGAATG
AGAACTTCCCCAAGTTTCTGGATAACCTGCAGAAGTACCAGGAGGCCAGGAAGAAGTATC
CTGAGTGGATCATCAAGGCCGAGAGCGCCCTGGTGGCCCACAATATCAAGATGGACGAG
GTGTTCTCCCTGGAGTACTTTAATAAGGTGCTGAACCAGGAGGGCATCCAGCGGTACAAC
CTGGCCCTGGGCGGCTATGTGACCAAGAGCGGCGAGAAGATGATGGGCCTGAATGATGC
CCTGAACCTGGCCCACCAGTCCGAGAAGAGCTCCAAGGGCAGAATCCACATGACCCCCCT
GTTCAAGCAGATCCTGTCCGAGAAGGAGTCCTTCTCTTACATCCCCGACGTGTTTACAGAG
GATTCTCAGCTGCTGCCTAGCATCGGCGGCTTCTTTGCCCAGATCGAGAATGACAAGGAT
GGCAACATCTTCGACCGGGCCCTGGAGCTGATCTCTAGCTACGCCGAGTATGATACCGAG
CGGATCTATATCAGACAGGCCGACATCAATAGAGTGTCCAACGTGATCTTTGGAGAGTGG
GGCACCCTGGGAGGCCTGATGAGGGAGTACAAGGCCGACTCTATCAATGATATCAACCTG
GAGCGCACATGCAAGAAGGTGGACAAGTGGCTGGATTCTAAGGAGTTTGCCCTGAGCGAT
GTGCTGGAGGCCATCAAGAGGACCGGCAACAATGACGCCTTCAACGAGTATATCTCCAAG
ATGCGGACAGCCAGAGAGAAGATCGATGCCGCCCGCAAGGAGATGAAGTTCATCAGCGA
GAAGATCTCCGGCGATGAGGAGTCTATCCACATCATCAAGACCCTGCTGGACAGCGTGCA
GCAGTTCCTGCACTTCTTTAATCTGTTTAAGGCAAGGCAGGACATCCCACTGGATGGAGCC
TTCTACGCCGAGTTTGACGAGGTGCACAGCAAGCTGTTTGCCATCGTGCCCCTGTATAACA
AGGTGCGGAACTATCTGACCAAGAACAATCTGAACACAAAGAAGATCAAGCTGAATTTCAA
GAACCCTACACTGGCCAATGGCTGGGACCAGAACAAGGTGTACGATTATGCCTCCCTGAT
CTTTCTGCGGGACGGCAATTACTATCTGGGCATCATCAATCCTAAGAGAAAGAAGAACATC
AAGTTCGAGCAGGGCTCTGGCAACGGCCCCTTCTACCGGAAGATGGTGTATAAGCAGATC
CCCGGCCCTAATAAGAACCTGCCAAGAGTGTTCCTGACCTCCACAAAGGGCAAGAAGGAG
TATAAGCCCTCTAAGGAGATCATCGAGGGCTACGAGGCCGACAAGCACATCAGGGGCGAT
AAGTTCGACCTGGATTTTTGTCACAAGCTGATCGATTTCTTTAAGGAGTCCATCGAGAAGCA
CAAGGACTGGTCTAAGTTCAACTTCTACTTCAGCCCAACCGAGAGCTATGGCGACATCTCT
GAGTTCTACCTGGATGTGGAGAAGCAGGGCTATCGCATGCACTTTGAGAATATCAGCGCC

FIG. 23 cont'd.

GAGACAATCGACGAGTATGTGGAGAAGGGCGATCTGTTTCTGTTCCAGATCTACAACAAGG
ATTTTGTGAAGGCCGCCACCGGCAAGAAGGACATGCACACAATCTACTGGAATGCCGCCT
TCAGCCCCGAGAACCTGCAGGACGTGGTGGTGAAGCTGAACGGCGAGGCCGAGCTGTTT
TATAGGGACAAGTCCGATATCAAGGAGATCGTGCACCGCGAGGGCGAGATCCTGGTGAAT
AGGACCTACAACGGCCGCACACCAGTGCCCGACAAGATCCACAAGAAGCTGACCGATTAT
CACAATGGCCGGACAAAGGACCTGGGCGAGGCCAAGGAGTACCTGGATAAGGTGAGATA
CTTCAAGGCCCACTATGACATCACCAAGGATCGGAGATACCTGAACGACAAGATCTATTTC
CACGTGCCTCTGACCCTGAACTTCAAGGCCAACGGCAAGAAGAATCTGAACAAGATGGTC
ATCGAGAAGTTCCTGTCCGATGAGAAGGCCCACATCATCGGCATCGACAGGGGCGAGCG
CAATCTGCTGTACTATTCCATCATCGACAGGTCTGGCAAGATCATCGATCAGCAGAGCCTG
AATGTGATCGACGGCTTTGATTATCGGGAGAAGCTGAACCAGAGAGAGATCGAGATGAAG
GATGCCCGCCAGTCTTGGAACGCCATCGGCAAGATCAAGGACCTGAAGGAGGGCTACCT
GAGCAAGGCCGTGCACGAGATCACCAAGATGGCCATCCAGTATAATGCCATCGTGGTCAT
GGAGGAGCTGAACTACGGCTTCAAGCGGGGCCGGTTCAAGGTGGAGAAGCAGATCTATC
AGAAGTTCGAGAATATGCTGATCGATAAGATGAACTACCTGGTGTTTAAGGACGCACCTGA
TGAGTCCCCAGGAGGCGTGCTGAATGCCTACCAGCTGACAAACCCACTGGAGTCTTTCGC
CAAGCTGGGCAAGCAGACCGGCATCCTGTTTTACGTGCCAGCCGCCTATACATCCAAGAT
CGACCCCACCACAGGCTTCGTGAATCTGTTTAACACCTCCTCTAAGACAAACGCCCAGGAG
CGGAAGGAGTTCCTGCAGAAGTTTGAGAGCATCTCCTATTCTGCCAAGGATGGCGGCATC
TTTGCCTTCGCCTTTGACTACAGAAAGTTCGGCACCAGCAAGACAGATCACAAGAACGTGT
GGACCGCCTATACAAACGGCGAGAGGATGCGCTACATCAAGGAGAAGAAGCGGAATGAG
CTGTTTGACCCTTCTAAGGAGATCAAGGAGGCCCTGACCAGCTCCGGCATCAAGTACGAT
GGCGGCCAGAACATCCTGCCAGACATCCTGAGGAGCAACAATAACGGCCTGATCTACACA
ATGTATTCTAGCTTCATCGCCGCCATCCAGATGCGCGTGTACGACGGCAAGGAGGATTATA
TCATCAGCCCCATCAAGAACTCCAAGGGCGAGTTCTTTAGGACCGACCCCAAGAGGCGCG
AGCTGCCTATCGACGCCGATGCCAATGGCGCCTACAACATCGCCCTGAGGGGAGAGCTG
ACAATGAGGGCAATCGCAGAGAAGTTCGACCCTGATAGCGAGAAGATGGCCAAGCTGGAG
CTGAAGCACAAGGATTGGTTCGAGTTTATGCAGACCAGAGGCGAC (SEQ ID NO: 224)

>Eubacterium eligens Cpf1 (EeCpf1) coding
ATGAACGGCAATAGGTCCATCGTGTACCGCGAGTTCGTGGGCGTGATCCCCGTGGCCAAG
ACCCTGAGGAATGAGCTGCGCCCTGTGGGCCACACACAGGAGCACATCATCCAGAACGG
CCTGATCCAGGAGGACGAGCTGCGGCAGGAGAAGAGCACCGAGCTGAAGAACATCATGG
ACGATTACTATAGAGAGTACATCGATAAGTCTCTGAGCGGCGTGACCGACCTGGACTTCAC
CCTGCTGTTCGAGCTGATGAACCTGGTGCAGAGCTCCCCCTCCAAGGACAATAAGAAGGC
CCTGGAGAAGGAGCAGTCTAAGATGAGGGAGCAGATCTGCACCCACCTGCAGTCCGACTC
TAACTACAAGAATATCTTTAACGCCAAGCTGCTGAAGGAGATCCTGCCTGATTTCATCAAGA
ACTACAATCAGTATGACGTGAAGGATAAGGCCGGCAAGCTGGAGACACTGGCCCTGTTTA
ATGGCTTCAGCACATACTTTACCGACTTCTTTGAGAAGAGGAAGAACGTGTTCACCAAGGA
GGCCGTGAGCACATCCATCGCCTACCGCATCGTGCACGAGAACTCCCTGATCTTCCTGGC
CAATATGACCTCTTATAAGAAGATCAGCGAGAAGGCCCTGGATGAGATCGAAGTGATCGAG
AAGAACAATCAGGACAAGATGGGCGATTGGGAGCTGAATCAGATCTTTAACCCTGACTTCT
ACAATATGGTGCTGATCCAGTCCGGCATCGACTTCTACAACGAGATCTGCGGCGTGGTGA
ATGCCCACATGAACCTGTACTGTCAGCAGACCAAGAACAATTATAACCTGTTCAAGATGCG
GAAGCTGCACAAGCAGATCCTGGCCTACACCAGCACCAGCTTCGAGGTGCCCAAGATGTT
CGAGGACGATATGAGCGTGTATAACGCCGTGAACGCCTTCATCGACGAGACAGAGAAGGG
CAACATCATCGGCAAGCTGAAGGATATCGTGAATAAGTACGACGAGCTGGATGAGAAGAG
AATCTATATCAGCAAGGACTTTTACGAGACACTGAGCTGCTTCATGTCCGGCAACTGGAAT
CTGATCACAGGCTGCGTGGAGAACTTCTACGATGAGAACATCCACGCCAAGGGCAAGTCC

FIG. 23 cont'd.

AAGGAGGAGAAGGTGAAGAAGGCCGTGAAGGAGGACAAGTACAAGTCTATCAATGACGTG
AACGATCTGGTGGAGAAGTATATCGATGAGAAGGAGAGGAATGAGTTCAAGAACAGCAAT
GCCAAGCAGTACATCCGCGAGATCTCCAACATCATCACCGACACAGAGACAGCCCACCTG
GAGTATGACGATCACATCTCTCTGATCGAGAGCGAGGAGAAGGCCGACGAGATGAAGAAG
CGGCTGGATATGTATATGAACATGTACCACTGGGCCAAGGCCTTTATCGTGGACGAGGTG
CTGGACAGAGATGAGATGTTCTACAGCGATATCGACGATATCTATAATATCCTGGAGAACA
TCGTGCCACTGTATAATCGGGTGAGAAACTACGTGACCCAGAAGCCCTACAACTCTAAGAA
GATCAAGCTGAATTTCCAGAGCCCTACACTGGCCAATGGCTGGTCCCAGTCTAAGGAGTTC
GACAACAATGCCATCATCCTGATCAGAGATAACAAGTACTATCTGGCCATCTTCAATGCCAA
GAACAAGCCAGACAAGAAGATCATCCAGGGCAACTCCGATAAGAAGAACGACAACGATTA
CAAGAAGATGGTGTATAACCTGCTGCCAGGCGCCAACAAGATGCTGCCCAAGGTGTTTCT
GTCTAAGAAGGGCATCGAGACATTCAAGCCCTCCGACTATATCATCTCTGGCTACAACGCC
CACAAGCACATCAAGACAAGCGAGAATTTTGATATCTCCTTCTGTCGGGACCTGATCGATT
ACTTCAAGAACAGCATCGAGAAGCACGCCGAGTGGAGAAAGTATGAGTTCAAGTTTTCCGC
CACCGACAGCTACTCCGATATCTCTGAGTTCTATCGGGAGGTGGAGATGCAGGGCTACAG
AATCGACTGGACATATATCAGCGAGGCCGACATCAACAAGCTGGATGAGGAGGGCAAGAT
CTATCTGTTTCAGATCTACAATAAGGATTTCGCCGAGAACAGCACCGGCAAGGAGAATCTG
CACACAATGTACTTTAAGAACATCTTCTCCGAGGAGAATCTGAAGGACATCATCATCAAGCT
GAACGGCCAGGCCGAGCTGTTTTATCGGAGAGCCTCTGTGAAGAATCCCGTGAAGCACAA
GAAGGATAGCGTGCTGGTGAACAAGACCTACAAGAATCAGCTGGACAACGGCGACGTGGT
GAGAATCCCCATCCCTGACGATATCTATAACGAGATCTACAAGATGTATAATGGCTACATCA
AGGAGTCCGACCTGTCTGAGGCCGCCAAGGAGTACCTGGATAAGGTGGAGGTGAGGACC
GCCCAGAAGGACATCGTGAAGGATTACCGCTATACAGTGGACAAGTACTTCATCCACACAC
CTATCACCATCAACTATAAGGTGACCGCCCGCAACAATGTGAATGATATGGTGGTGAAGTA
CATCGCCCAGAACGACGATATCCACGTGATCGGCATCGACCGGGGCGAGAGAAACCTGAT
CTACATCTCCGTGATCGATTCTCACGGCAACATCGTGAAGCAGAAATCCTACAACATCCTG
AACAACTACGACTACAAGAAGAAGCTGGTGGAGAAGGAGAAAACCCGGGAGTACGCCAGA
AAGAACTGGAAGAGCATCGGCAATATCAAGGAGCTGAAGGAGGGCTATATCTCCGGCGTG
GTGCACGAGATCGCCATGCTGATCGTGGAGTACAACGCCATCATCGCCATGGAGGACCTG
AATTATGGCTTTAAGAGGGGCCGCTTCAAGGTGGAGCGGCAGGTGTACCAGAAGTTTGAG
AGCATGCTGATCAATAAGCTGAACTATTTCGCCAGCAAGGAGAAGTCCGTGGACGAGCCA
GGAGGCCTGCTGAAGGGCTATCAGCTGACCTACGTGCCCGATAATATCAAGAACCTGGGC
AAGCAGTGCGGCGTGATCTTTTACGTGCCTGCCGCCTTCACCAGCAAGATCGACCCATCC
ACAGGCTTTATCTCTGCCTTCAACTTTAAGTCTATCAGCACAAATGCCTCTCGGAAGCAGTT
CTTTATGCAGTTTGACGAGATCAGATACTGTGCCGAGAAGGATATGTTCAGCTTTGGCTTC
GACTACAACAACTTCGATACCTACAACATCACAATGGGCAAGACACAGTGGACCGTGTATA
CAAACGGCGAGAGACTGCAGTCTGAGTTCAACAATGCCAGGCGCACCGGCAAGACAAAGA
GCATCAATCTGACAGAGACAATCAAGCTGCTGCTGGAGGACAATGAGATCAACTACGCCG
ACGGCCACGATATCAGGATCGATATGGAGAAGATGGACGAGGATAAGAAGAGCGAGTTCT
TTGCCCAGCTGCTGAGCCTGTATAAGCTGACCGTGCAGATGCGCAATTCCTATACAGAGG
CCGAGGAGCAGGAGAACGGCATCTCTTACGACAAGATCATCAGCCCTGTGATCAATGATG
AGGGCGAGTTCTTTGACTCCGATAACTATAAGGAGTCTGACGATAAGGAGTGCAAGATGCC
AAAGGACGCCGATGCCAACGGCGCCTACTGTATCGCCCTGAAGGGCCTGTATGAGGTGCT
GAAGATCAAGAGCGAGTGGACCGAGGACGGCTTTGATAGGAATTGCCTGAAGCTGCCACA
CGCAGAGTGGCTGGACTTCATCCAGAACAAGCGGTACGAG (SEQ ID NO: 225)

FIG. 23 cont'd.

>Moraxella bovoculi 237 Cpf1 (MbCpf1) coding
ATGCTGTTCCAGGACTTTACCCACCTGTATCCACTGTCCAAGACAGTGAGATTTGAGCTGA
AGCCCATCGATAGGACCCTGGAGCACATCCACGCCAAGAACTTCCTGTCTCAGGACGAGA
CAATGGCCGATATGCACCAGAAGGTGAAAGTGATCCTGGACGATTACCACCGCGACTTCA
TCGCCGATATGATGGGCGAGGTGAAGCTGACCAAGCTGGCCGAGTTCTATGACGTGTACC
TGAAGTTTCGGAAGAACCCAAAGGACGATGAGCTGCAGAAGCAGCTGAAGGATCTGCAGG
CCGTGCTGAGAAAGGAGATCGTGAAGCCCATCGGCAATGGCGGCAAGTATAAGGCCGGC
TACGACAGGCTGTTCGGCGCCAAGCTGTTTAAGGACGGCAAGGAGCTGGGCGATCTGGC
CAAGTTCGTGATCGCACAGGAGGGAGAGAGCTCCCCAAAGCTGGCCCACCTGGCCCACTT
CGAGAAGTTTTCCACCTATTTCACAGGCTTTCACGATAACCGGAAGAATATGTATTCTGACG
AGGATAAGCACACCGCCATCGCCTACCGCCTGATCCACGAGAACCTGCCCCGGTTTATCG
ACAATCTGCAGATCCTGACCACAATCAAGCAGAAGCACTCTGCCCTGTACGATCAGATCAT
CAACGAGCTGACCGCCAGCGGCCTGGACGTGTCTCTGGCCAGCCACCTGGATGGCTATC
ACAAGCTGCTGACACAGGAGGGCATCACCGCCTACAATACACTGCTGGGAGGAATCTCCG
GAGAGGCAGGCTCTCCTAAGATCCAGGGCATCAACGAGCTGATCAATTCTCACCACAACC
AGCACTGCCACAAGAGCGAGAGAATCGCCAAGCTGAGGCCACTGCACAAGCAGATCCTGT
CCGACGGCATGAGCGTGTCCTTCCTGCCCTCTAAGTTTGCCGACGATAGCGAGATGTGCC
AGGCCGTGAACGAGTTCTATCGCCACTACGCCGACGTGTTCGCCAAGGTGCAGAGCCTGT
TCGACGGCTTTGACGATCACCAGAAGGATGGCATCTACGTGGAGCACAAGAACCTGAATG
AGCTGTCCAAGCAGGCCTTCGGCGACTTTGCACTGCTGGGACGCGTGCTGGACGGATACT
ATGTGGATGTGGTGAATCCAGAGTTCAACGAGCGGTTTGCCAAGGCCAAGACCGACAATG
CCAAGGCCAAGCTGACAAAGGAGAAGGATAAGTTCATCAAGGGCGTGCACTCCCTGGCCT
CTCTGGAGCAGGCCATCGAGCACTATACCGCAAGGCACGACGATGAGAGCGTGCAGGCA
GGCAAGCTGGGACAGTACTTCAAGCACGGCCTGGCCGGAGTGGACAACCCCATCCAGAA
GATCCACAACAATCACAGCACCATCAAGGGCTTTCTGGAGAGGGAGCGCCCTGCAGGAGA
GAGAGCCCTGCCAAAGATCAAGTCCGGCAAGAATCCTGAGATGACACAGCTGAGGCAGCT
GAAGGAGCTGCTGGATAACGCCCTGAATGTGGCCCACTTCGCCAAGCTGCTGACCACAAA
GACCACACTGGACAATCAGGATGGCAACTTCTATGGCGAGTTTGGCGTGCTGTACGACGA
GCTGGCCAAGATCCCCACCCTGTATAACAAGGTGAGAGATTACCTGAGCCAGAAGCCTTT
CTCCACCGAGAAGTACAAGCTGAACTTTGGCAATCCAACACTGCTGAATGGCTGGGACCT
GAACAAGGAGAAGGATAATTTCGGCGTGATCCTGCAGAAGGACGGCTGCTACTATCTGGC
CCTGCTGGACAAGGCCCACAAGAAGGTGTTTGATAACGCCCCTAATACAGGCAAGAGCAT
CTATCAGAAGATGATCTATAAGTACCTGGAGGTGAGGAAGCAGTTCCCCAAGGTGTTCTTT
TCCAAGGAGGCCATCGCCATCAACTACCACCCTTCTAAGGAGCTGGTGGAGATCAAGGAC
AAGGGCCGGCAGAGATCCGACGATGAGCGCCTGAAGCTGTATCGGTTTATCCTGGAGTGT
CTGAAGATCCACCCTAAGTACGATAAGAAGTTCGAGGGCGCCATCGGCGACATCCAGCTG
TTTAAGAAGGATAAGAAGGGCAGAGAGGTGCCAATCAGCGAGAAGGACCTGTTCGATAAG
ATCAACGGCATCTTTTCTAGCAAGCCTAAGCTGGAGATGGAGGACTTCTTTATCGGCGAGT
TCAAGAGGTATAACCCAAGCCAGGACCTGGTGGATCAGTATAATATCTACAAGAAGATCGA
CTCCAACGATAATCGCAAGAAGGAGAATTTCTACAACAATCACCCCAAGTTTAAGAAGGAT
CTGGTGCGGTACTATTACGAGTCTATGTGCAAGCACGAGGAGTGGGAGGAGAGCTTCGAG
TTTTCCAAGAAGCTGCAGGACATCGGCTGTTACGTGGATGTGAACGAGCTGTTTACCGAGA
TCGAGACACGGAGACTGAATTATAAGATCTCCTTCTGCAACATCAATGCCGACTACATCGA
TGAGCTGGTGGAGCAGGGCCAGCTGTATCTGTTCCAGATCTACAACAAGGACTTTTCCCCA
AAGGCCCACGGCAAGCCCAATCTGCACACCCTGTACTTCAAGGCCCTGTTTTCTGAGGAC
AACCTGGCCGATCCTATCTATAAGCTGAATGGCGAGGCCCAGATCTTCTACAGAAAGGCCT
CCCTGGACATGAACGAGACAACAATCCACAGGGCCGGCGAGGTGCTGGAGAACAAGAAT
CCCGATAATCCTAAGAAGAGACAGTTCGTGTACGACATCATCAAGGATAAGAGGTACACAC
AGGACAAGTTCATGCTGCACGTGCCAATCACCATGAACTTTGGCGTGCAGGGCATGACAA

FIG. 23 cont'd.

TCAAGGAGTTCAATAAGAAGGTGAACCAGTCTATCCAGCAGTATGACGAGGTGAACGTGAT
CGGCATCGATCGGGGCGAGAGACACCTGCTGTACCTGACCGTGATCAATAGCAAGGGCG
AGATCCTGGAGCAGTGTTCCCTGAACGACATCACCACAGCCTCTGCCAATGGCACACAGA
TGACCACACCTTACCACAAGATCCTGGATAAGAGGGAGATCGAGCGCCTGAACGCCCGGG
TGGGATGGGGCGAGATCGAGACAATCAAGGAGCTGAAGTCTGGCTATCTGAGCCACGTG
GTGCACCAGATCAGCCAGCTGATGCTGAAGTACAACGCCATCGTGGTGCTGGAGGACCTG
AATTTCGGCTTTAAGAGGGGCCGCTTTAAGGTGGAGAAGCAGATCTATCAGAACTTCGAGA
ATGCCCTGATCAAGAAGCTGAACCACCTGGTGCTGAAGGACAAGGCCGACGATGAGATCG
GCTCTTACAAGAATGCCCTGCAGCTGACCAACAATTTCACAGATCTGAAGAGCATCGGCAA
GCAGACCGGCTTCCTGTTTTATGTGCCCGCCTGGAACACCTCTAAGATCGACCCTGAGAC
AGGCTTTGTGGATCTGCTGAAGCCAAGATACGAGAACATCGCCCAGAGCCAGGCCTTCTT
TGGCAAGTTCGACAAGATCTGCTATAATGCCGACAAGGATTACTTCGAGTTTCACATCGAC
TACGCCAAGTTTACCGATAAGGCCAAGAATAGCCGCCAGATCTGGACAATCTGTTCCCACG
GCGACAAGCGGTACGTGTACGATAAGACAGCCAACCAGAATAAGGGCGCCGCCAAGGGC
ATCAACGTGAATGATGAGCTGAAGTCCCTGTTCGCCCGCCACCACATCAACGAGAAGCAG
CCCAACCTGGTCATGGACATCTGCCAGAACAATGATAAGGAGTTTCACAAGTCTCTGATGT
ACCTGCTGAAAACCCTGCTGGCCCTGCGGTACAGCAACGCCTCCTCTGACGAGGATTTCA
TCCTGTCCCCCGTGGCAAACGACGAGGGCGTGTTCTTTAATAGCGCCCTGGCCGACGATA
CACAGCCTCAGAATGCCGATGCCAACGGCGCCTACCACATCGCCCTGAAGGGCCTGTGG
CTGCTGAATGAGCTGAAGAACTCCGACGATCTGAACAAGGTGAAGCTGGCCATCGACAAT
CAGACCTGGCTGAATTTCGCCCAGAACAGG (SEQ ID NO: 226)

>Prevotella disiens Cpf1 (PdCpf1) coding
ATGGAGAACTATCAGGAGTTCACCAACCTGTTTCAGCTGAATAAGACACTGAGATTCGAGC
TGAAGCCCATCGGCAAGACCTGCGAGCTGCTGGAGGAGGGCAAGATCTTCGCCAGCGGC
TCCTTTCTGGAGAAGGACAAGGTGAGGGCCGATAACGTGAGCTACGTGAAGAAGGAGATC
GACAAGAAGCACAAGATCTTTATCGAGGAGACACTGAGCTCCTTCTCTATCAGCAACGATC
TGCTGAAGCAGTACTTTGACTGCTATAATGAGCTGAAGGCCTTCAAGAAGGACTGTAAGAG
CGATGAGGAGGAGGTGAAGAAAACCGCCCTGCGCAACAAGTGTACCTCCATCCAGAGGG
CCATGCGCGAGGCCATCTCTCAGGCCTTTCTGAAGAGCCCCCAGAAGAAGCTGCTGGCCA
TCAAGAACCTGATCGAGAACGTGTTCAAGGCCGACGAGAATGTGCAGCACTTCTCCGAGT
TTACCAGCTATTTCTCCGGCTTTGAGACAAACAGAGAGAATTTCTACTCTGACGAGGAGAA
GTCCACATCTATCGCCTATAGGCTGGTGCACGATAACCTGCCTATCTTCATCAAGAACATC
TACATCTTCGAGAAGCTGAAGGAGCAGTTCGACGCCAAGACCCTGAGCGAGATCTTCGAG
AACTACAAGCTGTATGTGGCCGGCTCTAGCCTGGATGAGGTGTTCTCCCTGGAGTACTTTA
ACAATACCCTGACACAGAAGGGCATCGACAACTATAATGCCGTGATCGGCAAGATCGTGAA
GGAGGATAAGCAGGAGATCCAGGGCCTGAACGAGCACATCAACCTGTATAATCAGAAGCA
CAAGGACCGGAGACTGCCCTTCTTTATCTCCCTGAAGAAGCAGATCCTGTCCGATCGGGA
GGCCCTGTCTTGGCTGCCTGACATGTTCAAGAATGATTCTGAAGTGATCAAGGCCCTGAAG
GGCTTCTACATCGAGGACGGCTTTGAGAACAATGTGCTGACACCTCTGGCCACCCTGCTG
TCCTCTCTGGATAAGTACAACCTGAATGGCATCTTTATCCGCAACAATGAGGCCCTGAGCT
CCCTGTCCCAGAACGTGTATCGGAATTTTTCTATCGACGAGGCCATCGATGCCAACGCCGA
GCTGCAGACCTTCAACAATTACGAGCTGATCGCCAATGCCCTGCGCGCCAAGATCAAGAA
GGAGACAAAGCAGGGCCGGAAGTCTTTCGAGAAGTACGAGGAGTATATCGATAAGAAGGT
GAAGGCCATCGACAGCCTGTCCATCCAGGAGATCAACGAGCTGGTGGAGAATTACGTGAG
CGAGTTTAACTCTAATAGCGGCAACATGCCAAGAAAGGTGGAGGACTACTTCAGCCTGATG
AGGAAGGGCGACTTCGGCTCCAACGATCTGATCGAAAATATCAAGACCAAGCTGAGCGCC
GCAGAGAAGCTGCTGGGCACAAAGTACCAGGAGACAGCCAAGGACATCTTCAAGAAGGAT
GAGAACTCCAAGCTGATCAAGGAGCTGCTGGACGCCACCAAGCAGTTCCAGCACTTTATC

FIG. 23 cont'd.

AAGCCACTGCTGGGCACAGGCGAGGAGGCAGATCGGGACCTGGTGTTCTACGGCGATTT
TCTGCCCCTGTATGAGAAGTTTGAGGAGCTGACCCTGCTGTATAACAAGGTGCGGAATAGA
CTGACACAGAAGCCCTATTCCAAGGACAAGATCCGCCTGTGCTTCAACAAGCCTAAGCTGA
TGACAGGCTGGGTGGATTCCAAGACCGAGAAGTCTGACAACGGCACACAGTACGGCGGC
TATCTGTTTCGGAAGAAGAATGAGATCGGCGAGTACGATTATTTTCTGGGCATCTCTAGCA
AGGCCCAGCTGTTCAGAAAGAACGAGGCCGTGATCGGCGACTACGAGAGGCTGGATTACT
ATCAGCCAAAGGCCAATACCATCTACGGCTCTGCCTATGAGGGCGAGAACAGCTACAAGG
AGGACAAGAAGCGGCTGAACAAAGTGATCATCGCCTATATCGAGCAGATCAAGCAGACAA
ACATCAAGAAGTCTATCATCGAGTCCATCTCTAAGTATCCTAATATCAGCGACGATGACAAG
GTGACCCCATCCTCTCTGCTGGAGAAGATCAAGAAGGTGTCTATCGACAGCTACAACGGC
ATCCTGTCCTTCAAGTCTTTTCAGAGCGTGAACAAGGAAGTGATCGATAACCTGCTGAAAA
CCATCAGCCCCCTGAAGAACAAGGCCGAGTTTCTGGACCTGATCAATAAGGATTATCAGAT
CTTCACCGAGGTGCAGGCCGTGATCGACGAGATCTGCAAGCAGAAAACCTTCATCTACTTT
CCAATCTCCAACGTGGAGCTGGAGAAGGAGATGGGCGATAAGGACAAGCCCCTGTGCCT
GTTCCAGATCAGCAATAAGGATCTGTCCTTCGCCAAGACCTTTAGCGCCAACCTGCGGAAG
AAGAGAGGCGCCGAGAATCTGCACACAATGCTGTTTAAGGCCCTGATGGAGGGCAACCAG
GATAATCTGGACCTGGGCTCTGGCGCCATCTTCTACAGAGCCAAGAGCCTGGACGGCAAC
AAGCCCACACACCCTGCCAATGAGGCCATCAAGTGTAGGAACGTGGCCAATAAGGATAAG
GTGTCCCTGTTCACCTACGACATCTATAAGAACAGGCGCTACATGGAGAATAAGTTCCTGT
TTCACCTGAGCATCGTGCAGAACTATAAGGCCGCCAATGACTCCGCCCAGCTGAACAGCT
CCGCCACCGAGTATATCAGAAAGGCCGATGACCTGCACATCATCGGCATCGATAGGGGCG
AGCGCAATCTGCTGTACTATTCCGTGATCGATATGAAGGGCAACATCGTGGAGCAGGACT
CTCTGAATATCATCAGGAACAATGACCTGGAGACAGATTACCACGACCTGCTGGATAAGAG
GGAGAAGGAGCGCAAGGCCAACCGGCAGAATTGGGAGGCCGTGGAGGGCATCAAGGAC
CTGAAGAAGGGCTACCTGAGCCAGGCCGTGCACCAGATCGCCCAGCTGATGCTGAAGTAT
AACGCCATCATCGCCCTGGAGGATCTGGGCCAGATGTTTGTGACCCGCGGCCAGAAGATC
GAGAAGGCCGTGTACCAGCAGTTCGAGAAGAGCCTGGTGGATAAGCTGTCCTACCTGGTG
GACAAGAAGCGGCCTTATAATGAGCTGGGCGGCATCCTGAAGGCCTACCAGCTGGCCTCT
AGCATCACCAAGAACAATTCTGACAAGCAGAACGGCTTCCTGTTTTATGTGCCAGCCTGGA
ATACAAGCAAGATCGATCCCGTGACCGGCTTTACAGACCTGCTGCGGCCCAAGGCCATGA
CCATCAAGGAGGCCCAGGACTTCTTTGGCGCCTTCGATAACATCTCTTACAATGACAAGGG
CTATTTCGAGTTTGAGACAAACTACGACAAGTTTAAGATCAGAATGAAGAGCGCCCAGACC
AGGTGGACAATCTGCACCTTCGGCAATCGGATCAAGAGAAAGAAGGATAAGAACTACTGG
AATTATGAGGAGGTGGAGCTGACCGAGGAGTTCAAGAAGCTGTTTAAGGACAGCAACATC
GATTACGAGAACTGTAATCTGAAGGAGGAGATCCAGAACAAGGACAATCGCAAGTTCTTTG
ATGACCTGATCAAGCTGCTGCAGCTGACACTGCAGATGCGGAACTCCGATGACAAGGGCA
ATGATTATATCATCTCTCCTGTGGCCAACGCCGAGGGCCAGTTCTTTGACTCCCGCAATGG
CGATAAGAAGCTGCCACTGGATGCAGACGCAAACGGAGCCTACAATATCGCCCGCAAGGG
CCTGTGGAACATCCGGCAGATCAAGCAGACCAAGAACGACAAGAAGCTGAATCTGAGCAT
CTCCTCTACAGAGTGGCTGGATTTCGTGCGGGAGAAGCCTTACCTGAAG (SEQ ID NO: 227)

>Streptococcus pyogenes serotype M1 Cas9 protein (UniProt Accession Q99ZW2)
MDKKYSIGLDIGTNSVGWAVITDEYKVPSKKFKVLGNTDRHSIKKNLIGALLFDSGETAEATRLK
RTARRRYTRRKNRICYLQEIFSNEMAKVDDSFFHRLEESFLVEEDKKHERHPIFGNIVDEVAYH
EKYPTIYHLRKKLVDSTDKADLRLIYLALAHMIKFRGHFLIEGDLNPDNSDVDKLFIQLVQTYNQL
FEENPINASGVDAKAILSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGTEELLVK

FIG. 23 cont'd.

LNREDLLRKQRTFDNGSIPHQIHLGELHAILRRQEDFYPFLKDNREKIEKILTFRIPYYVGPLARG
NSRFAWMTRKSEETITPWNFEEVVDKGASAQSFIERMTNFDKNLPNEKVLPKHSLLYEYFTVY
NELTKVKYVTEGMRKPAFLSGEQKKAIVDLLFKTNRKVTVKQLKEDYFKKIECFDSVEISGVEDR
FNASLGTYHDLLKIIKDKDFLDNEENEDILEDIVLTLTLFEDREMIEERLKTYAHLFDDKVMKQLK
RRRYTGWGRLSRKLINGIRDKQSGKTILDFLKSDGFANRNFMQLIHDDSLTFKEDIQKAQVSGQ
GDSLHEHIANLAGSPAIKKGILQTVKVVDELVKVMGRHKPENIVIEMARENQTTQKGQKNSRER
MKRIEEGIKELGSQILKEHPVENTQLQNEKLYLYYLQNGRDMYVDQELDINRLSDYDVDHIVPQ
SFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFY
KVREINNYHHAHDAYLNAVVGTALIKKYPKLESEFVYGDYKVYDVRKMIAKSEQEIGKATAKYFF
YSNIMNFFKTEITLANGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGKSKKLKSVKELLGITI
MERSSFEKNPIDFLEAKGYKEVKKDLIIKLPKYSLFELENGRKRMLASAGELQKGNELALPSKYV
NFLYLASHYEKLKGSPEDNEQKQLFVEQHKHYLDEIIEQISEFSKRVILADANLDKVLSAYNKHR
DKPIREQAENIIHLFTLTNLGAPAAFKYFDTTIDRKRYTSTKEVLDATLIHQSITGLYETRIDLSQLG
GD (SEQ ID NO: 228)

>Francisella tularensis type V CRISPR-associated protein Cpf1 (NCBI Reference Sequence: WP_003040289.1)
MSIYQEFVNKYSLSKTLRFELIPQGKTLENIKARGLILDDEKRAKDYKKAKQIIDKYHQFFIEEILSS
VCISEDLLQNYSDVYFKLKKSDDDNLQKDFKSAKDTIKKQISEYIKDSEKFKNLFNQNLIDAKKG
QESDLILWLKQSKDNGIELFKANSDITDIDEALEIIKSFKGWTTYFKGFHENRKNVYSSNDIPTSII
YRIVDDNLPKFLENKAKYESLKDKAPEAINYEQIKKDLAEELTFDIDYKTSEVNQRVFSLDEVFEI
ANFNNYLNQSGITKFNTIIGGKFVNGENTKRKGINEYINLYSQQINDKTLKKYKMSVLFKQILSDT
ESKSFVIDKLEDDSDVVTTMQSFYEQIAAFKTVEEKSIKETLSLLFDDLKAQKLDLSKIYFKNDKS
LTDLSQQVFDDYSVIGTAVLEYITQQIAPKNLDNPSKKEQELIAKKTEKAKYLSLETIKLALEEFNK
HRDIDKQCRFEEILANFAAIPMIFDEIAQNKDNLAQISIKYQNQGKKDLLQASAEDDVKAIKDLLD
QTNNLLHKLKIFHISQSEDKANILDKDEHFYLVFEECYFELANIVPLYNKIRNYITQKPYSDEKFKL
NFENSTLANGWDKNKEPDNTAILFIKDDKYYLGVMNKKNNKIFDDKAIKENKGEGYKKIVYKLLP
GANKMLPKVFFSAKSIKFYNPSEDILRIRNHSTHTKNGSPQKGYEKFEFNIEDCRKFIDFYKQSIS
KHPEWKDFGFRFSDTQRYNSIDEFYREVENQGYKLTFENISESYIDSVVNQGKLYLFQIYNKDF
SAYSKGRPNLHTLYWKALFDERNLQDVVYKLNGEAELFYRKQSIPKKITHPAKEAIANKNKDNP
KKESVFEYDLIKDKRFTEDKFFFHCPITINFKSSGANKFNDEINLLLKEKANDVHILSIDRGERHLA
YYTLVDGKGNIIKQDTFNIIGNDRMKTNYHDKLAAIEKDRDSARKDWKKINNIKEMKEGYLSQVV
HEIAKLVIEYNAIVVFEDLNFGFKRGRFKVEKQVYQKLEKMLIEKLNYLVFKDNEFDKTGGVLRA
YQLTAPFETFKKMGKQTGIIYYVPAGFTSKICPVTGFVNQLYPKYESVSKSQEFFSKFDKICYNL
DKGYFEFSFDYKNFGDKAAKGKWTIASFGSRLINFRNSDKNHNWDTREVYPTKELEKLLKDYSI
EYGHGECIKAAICGESDKKFFAKLTSVLNTILQMRNSKTGTELDYLISPVADVNGNFFDSRQAPK
NMPQDADANGAYHIGLKGLMLLGRIKNNQEGKKLNLVIKNEEYFEFVQNRNN (SEQ ID NO: 229)

>Acidaminococcus sp. BV3L6 type V CRISPR-associated protein Cpf1 (AsCpf1) (NCBI Reference Sequence: WP_021736722.1)
MTQFEGFTNLYQVSKTLRFELIPQGKTLKHIQEQGFIEEDKARNDHYKELKPIIDRIYKTYADQCL
QLVQLDWENLSAAIDSYRKEKTEETRNALIEEQATYRNAIHDYFIGRTDNLTDAINKRHAEIYKGL
FKAELFNGKVLKQLGTVTTTEHENALLRSFDKFTTYFSGFYENRKNVFSAEDISTAIPHRIVQDN
FPKFKENCHIFTRLITAVPSLREHFENVKKAIGIFVSTSIEEVFSFPFYNQLLTQTQIDLYNQLLGGI
SREAGTEKIKGLNEVLNLAIQKNDETAHIIASLPHRFIPLFKQILSDRNTLSFILEEFKSDEEVIQSF
CKYKTLLRNENVLETAEALFNELNSIDLTHIFISHKKLETISSALCDHWDTLRNALYERRISELTGK

FIG. 23 cont'd.

ITKSAKEKVQRSLKHEDINLQEIISAAGKELSEAFKQKTSEILSHAHAALDQPLPTTLKKQEEKEIL
KSQLDSLLGLYHLLDWFAVDESNEVDPEFSARLTGIKLEMEPSLSFYNKARNYATKKPYSVEKF
KLNFQMPTLASGWDVNKEKNNGAILFVKNGLYYLGIMPKQKGRYKALSFEPTEKTSEGFDKMY
YDYFPDAAKMIPKCSTQLKAVTAHFQTHTTPILLSNNFIEPLEITKEIYDLNNPEKEPKKFQTAYA
KKTGDQKGYREALCKWIDFTRDFLSKYTKTTSIDLSSLRPSSQYKDLGEYYAELNPLLYHISFQR
IAEKEIMDAVETGKLYLFQIYNKDFAKGHHGKPNLHTLYWTGLFSPENLAKTSIKLNGQAELFYR
PKSRMKRMAHRLGEKMLNKKLKDQKTPIPDTLYQELYDYVNHRLSHDLSDEARALLPNVITKEV
SHEIIKDRRFTSDKFFFHVPITLNYQAANSPSKFNQRVNAYLKEHPETPIIGIDRGERNLIYITVIDS
TGKILEQRSLNTIQQFDYQKKLDNREKERVAARQAWSVVGTIKDLKQGYLSQVIHEIVDLMIHYQ
AVVVLENLNFGFKSKRTGIAEKAVYQQFEKMLIDKLNCLVLKDYPAEKVGGVLNPYQLTDQFTS
FAKMGTQSGFLFYVPAPYTSKIDPLTGFVDPFVWKTIKNHESRKHFLEGFDFLHYDVKTGDFIL
HFKMNRNLSFQRGLPGFMPAWDIVFEKNETQFDAKGTPFIAGKRIVPVIENHRFTGRYRDLYPA
NELIALLEEKGIVFRDGSNILPKLLENDDSHAIDTMVALIRSVLQMRNSNAATGEDYINSPVRDLN
GVCFDSRFQNPEWPMDADANGAYHIALKGQLLLNHLKESKDLKLQNGISNQDWLAYIQELRN
(SEQ ID NO: 230)

>Lachnospiraceae bacterium MC2017 type V CRISPR-associated protein Cpf1 (NCBI Reference Sequence: WP_044910712.1)
MDYGNGQFERRAPLTKTITLRLKPIGETRETIREQKLLEQDAAFRKLVETVTPIVDDCIRKIADNA
LCHFGTEYDFSCLGNAISKNDSKAIKKETEKVEKLLAKVLTENLPDGLRKVNDINSAAFIQDTLTS
FVQDDADKRVLIQELKGKTVLMQRFLTTRITALTVWLPDRVFENFNIFIENAEKMRILLDSPLNEK
IMKFDPDAEQYASLEFYGQCLSQKDIDSYNLIISGIYADDEVKNPGINEIVKEYNQQIRGDKDESP
LPKLKKLHKQILMPVEKAFFVRVLSNDSDARSILEKILKDTEMLPSKIIEAMKEADAGDIAVYGSR
LHELSHVIYGDHGKLSQIIYDKESKRISELMETLSPKERKESKKRLEGLEEHIRKSTYTFDELNRY
AEKNVMAAYIAAVEESCAEIMRKEKDLRTLLSKEDVKIRGNRHNTLIVKNYFNAWTVFRNLIRILR
RKSEAEIDSDFYDVLDDSVEVLSLTYKGENLCRSYITKKIGSDLKPEIATYGSALRPNSRWWSP
GEKFNVKFHTIVRRDGRLYYFILPKGAKPVELEDMDGDIECLQMRKIPNPTIFLPKLVFKDPEAFF
RDNPEADEFVFLSGMKAPVTITRETYEAYRYKLYTVGKLRDGEVSEEEYKRALLQVLTAYKEFL
ENRMIYADLNFGFKDLEEYKDSSEFIKQVETHNTFMCWAKVSSSQLDDLVKSGNGLLFEIWSE
RLESYYKYGNEKVLRGYEGVLLSILKDENLVSMRTLLNSRPMLVYRPKESSKPMVVHRDGSRV
VDRFDKDGKYIPPEVHDELYRFFNNLLIKEKLGEKARKILDNKKVKVKVLESERVKWSKFYDEQ
FAVTFSVKKNADCLDTTKDLNAEVMEQYSESNRLILIRNTTDILYYLVLDKNGKVLKQRSLNIIND
GARDVDWKERFRQVTKDRNEGYNEWDYSRTSNDLKEVYLNYALKEIAEAVIEYNAILIIEKMSN
AFKDKYSFLDDVTFKGFETKLLAKLSDLHFRGIKDGEPCSFTNPLQLCQNDSNKILQDGVIFMVP
NSMTRSLDPDTGFIFAINDHNIRTKKAKLNFLSKFDQLKVSSEGCLIMKYSGDSLPTHNTDNRV
WNCCCNHPITNYDRETKKVEFIEEPVEELSRVLEENGIETDTELNKLNERENVPGKVVDAIYSLV
LNYLRGTVSGVAGQRAVYYSPVTGKKYDISFIQAMNLNRKCDYYRIGSKERGEWTDFVAQLIN
(SEQ ID NO: 231)

>Lachnospiraceae bacterium ND2006 type V CRISPR-associated protein Cpf1 (NCBI Reference Sequence: WP_051666128.1)
MLKNVGIDRLDVEKGRKNMSKLEKFTNCYSLSKTLRFKAIPVGKTQENIDNKRLLVEDEKRAED
YKGVKKLLDRYYLSFINDVLHSIKLKNLNNYISLFRKKTRTEKENKELENLEINLRKEIAKAFKGNE
GYKSLFKKDIIETILPEFLDDKDEIALVNSFNGFTTAFTGFFDNRENMFSEEAKSTSIAFRCINENL
TRYISNMDIFEKVDAIFDKHEVQEIKEKILNSDYDVEDFFEGEFFNFVLTQEGIDVYNAIIGGFVTE
SGEKIKGLNEYINLYNQKTKQKLPKFKPLYKQVLSDRESLSFYGEGYTSDEEVLEVFRNTLNKN
SEIFSSIKKLEKLFKNFDEYSSAGIFVKNGPAISTISKDIFGEWNVIRDKWNAEYDDIHLKKKAVVT
EKYEDDRRKSFKKIGSFSLEQLQEYADADLSVVEKLKEIIIQKVDEIYKVYGSSEKLFDADFVLEK

FIG. 23 cont'd.

SLKKNDAVVAIMKDLLDSVKSFENYIKAFFGEGKETNRDESFYGDFVLAYDILLKVDHIYDAIRNY
VTQKPYSKDKFKLYFQNPQFMGGWDKDKETDYRATILRYGSKYYLAIMDKKYAKCLQKIDKDD
VNGNYEKINYKLLPGPNKMLPKVFFSKKWMAYYNPSEDIQKIYKNGTFKKGDMFNLNDCHKLID
FFKDSISRYPKWSNAYDFNFSETEKYKDIAGFYREVEEQGYKVSFESASKKEVDKLVEEGKLY
MFQIYNKDFSDKSHGTPNLHTMYFKLLFDENNHGQIRLSGGAELFMRRASLKKEELVVHPANS
PIANKNPDNPKKTTTLSYDVYKDKRFSEDQYELHIPIAINKCPKNIFKINTEVRVLLKHDDNPYVIG
IDRGERNLLYIVVVDGKGNIVEQYSLNEIINNFNGIRIKTDYHSLLDKKEKERFEARQNWTSIENIK
ELKAGYISQVVHKICELVEKYDAVIALEDLNSGFKNSRVKVEKQVYQKFEKMLIDKLNYMVDKKS
NPCATGGALKGYQITNKFESFKSMSTQNGFIFYIPAWLTSKIDPSTGFVNLLKTKYTSIADSKKFI
SSFDRIMYVPEEDLFEFALDYKNFSRTDADYIKKWKLYSYGNRIRIFRNPKKNNVFDWEEVCLT
SAYKELFNKYGINYQQGDIRALLCEQSDKAFYSSFMALMSLMLQMRNSITGRTDVDFLISPVKN
SDGIFYDSRNYEAQENAILPKNADANGAYNIARKVLWAIGQFKKAEDEKLDKVKIAISNKEWLEY
AQTSVKH (SEQ ID NO: 232)

>amino acids 19-1246 of Lachnospiraceae bacterium ND2006 type V CRISPR-associated protein Cpf1
MSKLEKFTNCYSLSKTLRFKAIPVGKTQENIDNKRLLVEDEKRAEDYKGVKKLLDRYYLSFINDV
LHSIKLKNLNNYISLFRKKTRTEKENKELENLEINLRKEIAKAFKGNEGYKSLFKKDIIETILPEFLD
DKDEIALVNSFNGFTTAFTGFFDNRENMFSEEAKSTSIAFRCINENLTRYISNMDIFEKVDAIFDK
HEVQEIKEKILNSDYDVEDFFEGEFFNFVLTQEGIDVYNAIIGGFVTESGEKIKGLNEYINLYNQK
TKQKLPKFKPLYKQVLSDRESLSFYGEGYTSDEEVLEVFRNTLNKNSEIFSSIKKLEKLFKNFDE
YSSAGIFVKNGPAISTISKDIFGEWNVIRDKWNAEYDDIHLKKKAVVTEKYEDDRRKSFKKIGSF
SLEQLQEYADADLSVVEKLKEIIIQKVDEIYKVYGSSEKLFDADFVLEKSLKKNDAVVAIMKDLLD
SVKSFENYIKAFFGEGKETNRDESFYGDFVLAYDILLKVDHIYDAIRNYVTQKPYSKDKFKLYFQ
NPQFMGGWDKDKETDYRATILRYGSKYYLAIMDKKYAKCLQKIDKDDVNGNYEKINYKLLPGP
NKMLPKVFFSKKWMAYYNPSEDIQKIYKNGTFKKGDMFNLNDCHKLIDFFKDSISRYPKWSNA
YDFNFSETEKYKDIAGFYREVEEQGYKVSFESASKKEVDKLVEEGKLYMFQIYNKDFSDKSHG
TPNLHTMYFKLLFDENNHGQIRLSGGAELFMRRASLKKEELVVHPANSPIANKNPDNPKKTTTL
SYDVYKDKRFSEDQYELHIPIAINKCPKNIFKINTEVRVLLKHDDNPYVIGIDRGERNLLYIVVVDG
KGNIVEQYSLNEIINNFNGIRIKTDYHSLLDKKEKERFEARQNWTSIENIKELKAGYISQVVHKICE
LVEKYDAVIALEDLNSGFKNSRVKVEKQVYQKFEKMLIDKLNYMVDKKSNPCATGGALKGYQIT
NKFESFKSMSTQNGFIFYIPAWLTSKIDPSTGFVNLLKTKYTSIADSKKFISSFDRIMYVPEEDLF
EFALDYKNFSRTDADYIKKWKLYSYGNRIRIFRNPKKNNVFDWEEVCLTSAYKELFNKYGINYQ
QGDIRALLCEQSDKAFYSSFMALMSLMLQMRNSITGRTDVDFLISPVKNSDGIFYDSRNYEAQE
NAILPKNADANGAYNIARKVLWAIGQFKKAEDEKLDKVKIAISNKEWLEYAQTSVKH (SEQ ID NO: 233)

>Francisella tularensis subsp. Novicida U112 Cpf1 (FnCpf1) protein
MSIYQEFVNKYSLSKTLRFELIPQGKTLENIKARGLILDDEKRAKDYKKAKQIIDKYHQF
FIEEILSSVCISEDLLQNYSDVYFKLKKSDDDNLQKDFKSAKDTIKKQISEYIKDSEKFK
NLFNQNLIDAKKGQESDLILWLKQSKDNGIELFKANSDITDIDEALEIIKSFKGWTTYFK
GFHENRKNVYSSNDIPTSIIYRIVDDNLPKFLENKAKYESLKDKAPEAINYEQIKKDLAE
ELTFDIDYKTSEVNQRVFSLDEVFEIANFNNYLNQSGITKFNTIIGGKFVNGENTKRKGI
NEYINLYSQQINDKTLKKYKMSVLFKQILSDTESKSFVIDKLEDDSDVVTTMQSFYEQIA
AFKTVEEKSIKETLSLLFDDLKAQKLDLSKIYFKNDKSLTDLSQQVFDDYSVIGTAVLEY
ITQQIAPKNLDNPSKKEQELIAKKTEKAKYLSLETIKLALEEFNKHRDIDKQCRFEEILA
NFAAIPMIFDEIAQNKDNLAQISIKYQNQGKKDLLQASAEDDVKAIKDLLDQTNNLLHKL
KIFHISQSEDKANILDKDEHFYLVFEECYFELANIVPLYNKIRNYITQKPYSDEKFKLNF

FIG. 23 cont'd.

ENSTLANGWDKNKEPDNTAILFIKDDKYYLGVMNKKNNKIFDDKAIKENKGEGYKKIVYK
LLPGANKMLPKVFFSAKSIKFYNPSEDILRIRNHSTHTKNGSPQKGYEKFEFNIEDCRKF
IDFYKQSISKHPEWKDFGFRFSDTQRYNSIDEFYREVENQGYKLTFENISESYIDSVVNQ
GKLYLFQIYNKDFSAYSKGRPNLHTLYWKALFDERNLQDVVYKLNGEAELFYRKQSIPKK
ITHPAKEAIANKNKDNPKKESVFEYDLIKDKRFTEDKFFFHCPITINFKSSGANKFNDEI
NLLLKEKANDVHILSIDRGERHLAYYTLVDGKGNIIKQDTFNIIGNDRMKTNYHDKLAAI
EKDRDSARKDWKKINNIKEMKEGYLSQVVHEIAKLVIEYNAIVVFEDLNFGFKRGRFKVE
KQVYQKLEKMLIEKLNYLVFKDNEFDKTGGVLRAYQLTAPFETFKKMGKQTGIIYYVPAG
FTSKICPVTGFVNQLYPKYESVSKSQEFFSKFDKICYNLDKGYFEFSFDYKNFGDKAAKG
KWTIASFGSRLINFRNSDKNHNWDTREVYPTKELEKLLKDYSIEYGHGECIKAAICGESD
KKFFAKLTSVLNTILQMRNSKTGTELDYLISPVADVNGNFFDSRQAPKNMPQDADANGAY
HIGLKGLMLLGRIKNNQEGKKLNLVIKNEEYFEFVQNRNN (SEQ ID NO: 234)

> Peregrinibacteria bacterium GW2011_GWA_33_10 (PeCpf1) protein
MSNFFKNFTNLYELSKTLRFELKPVGDTLTNMKDHLEYDEKLQTFLKDQNIDDAYQALKP
QFDEIHEEFITDSLESKKAKEIDFSEYLDLFQEKKELNDSEKKLRNKIGETFNKAGEKWK
KEKYPQYEWKKGSKIANGADILSCQDMLQFIKYKNPEDEKIKNYIDDTLKGFFTYFGGFN
QNRANYYETKKEASTAVATRIVHENLPKFCDNVIQFKHIIKRKKDGTVEKTERKTEYLNA
YQYLKNNNKITQIKDAETEKMIESTPIAEKIFDVYYFSSCLSQKQIEEYNRIIGHYNLLI
NLYNQAKRSEGKHLSANEKKYKDLPKFKTLYKQIGCGKKKDLFYTIKCDTEEEANKSRNE
GKESHSVEEIINKAQEAINKYFKSNNDCENINTVPDFINYILTKENYEGVYWSKAAMNTI
SDKYFANYHDLQDRLKEAKVFQKADKKSEDDIKIPEAIELSGLFGVLDSLADWQTTLFKS
SILSNEDKLKIITDSQTPSEALLKMIFNDIEKNMESFLKETNDIITLKKYKGNKEGTEKI
KQWFDYTLAINRMLKYFLVKENKIKGNSLDTNISEALKTLIYSDDAEWFKWYDALRNYLT
QKPQDEAKENKLKLNFDNPSLAGGWDVNKECSNFCVILKDKNEKKYLAIMKKGENTLFQK
EWTEGRGKNLTKKSNPLFEINNCEILSKMEYDFWADVSKMIPKCSTQLKAVVNHFKQSDN
EFIFPIGYKVTSGEKFREECKISKQDFELNNKVFNKNELSVTAMRYDLSSTQEKQYIKAF
QKEYWELLFKQEKRDTKLTNNEIFNEWINFCNKKYSELLSWERKYKDALTNWINFCKYFL
SKYPKTTLFNYSFKESENYNSLDEFYRDVDICSYKLNINTTINKSILDRLVEEGKLYLFE
IKNQDSNDGKSIGHKNNLHTIYWNAIFENFDNRPKLNGEAEIFYRKAISKDKLGIVKGKK
TKNGTEIIKNYRFSKEKFILHVPITLNFCSNNEYVNDIVNTKFYNFSNLHFLGIDRGEKH
LAYYSLVNKNGEIVDQGTLNLPFTDKDGNQRSIKKEKYFYNKQEDKWEAKEVDCWNYNDL
LDAMASNRDMARKNWQRIGTIKEAKNGYVSLVIRKIADLAVNNERPAFIVLEDLNTGFKR
SRQKIDKSVYQKFELALAKKLNFLVDKNAKRDEIGSPTKALQLTPPVNNYGDIENKKQAG
IMLYTRANYTSQTDPATGWRKTIYLKAGPEETTYKKDGKIKNKSVKDQIIETFTDIGFDG
KDYYFEYDKGEFVDEKTGEIKPKKWRLYSGENGKSLDRFRGEREKDKYEWKIDKIDIVKI
LDDLFVNFDKNISLLKQLKEGVELTRNNEHGTGESLRFAINLIQQIRNTGNNERDNDFIL
SPVRDENGKHFDSREYWDKETKGEKISMPSSGDANGAFNIARKGIIMNAHILANSDSKDL
SLFVSDEEWDLHLNNKTEWKKQLNIFSSRKAMAKRKK (SEQ ID NO: 235)

>Parcubacteria bacterium GWC2011_GWC2_44_17 Cpf1 (PbCpf1) protein
MENIFDQFIGKYSLSKTLRFELKPVGKTEDFLKINKVFEKDQTIDDSYNQAKFYFDSLHQ
KFIDAALASDKTSELSFQNFADVLEKQNKIILDKKREMGALRKRDKNAVGIDRLQKEIND
AEDIIQKEKEKIYKDVRTLFDNEAESWKTYYQEREVDGKKITFSKADLKQKGADFLTAAG
ILKVLKYEFPEEKEKEFQAKNQPSLFVEEKENPGQKRYIFDSFDKFAGYLTKFQQTKKNL
YAADGTSTAVATRIADNFIIFHQNTKVFRDKYKNNHTDLGFDEENIFEIERYKNCLLQRE
IEHIKNENSYNKIIGRINKKIKEYRDQKAKDTKLTKSDFPFFKNLDKQILGEVEKEKQLI
EKTREKTEEDVLIERFKEFIENNEERFTAAKKLMNAFCNGEFESEYEGIYLKNKAINTIS
RRWFVSDRDFELKLPQQKSKNKSEKNEPKVKKFISIAEIKNAVEELDGDIFKAVFYDKKI

FIG. 23 cont'd.

IAQGGSKLEQFLVIWKYEFEYLFRDIERENGEKLLGYDSCLKIAKQLGIFPQEKEAREKA
TAVIKNYADAGLGIFQMMKYFSLDDKDRKNTPGQLSTNFYAEYDGYYKDFEFIKYYNEFR
NFITKKPFDEDKIKLNFENGALLKGWDENKEYDFMGVILKKEGRLYLGIMHKNHRKLFQS
MGNAKGDNANRYQKMIYKQIADASKDVPRLLLTSKKAMEKFKPSQEILRIKKEKTFKRES
KNFSLRDLHALIEYYRNCIPQYSNWSFYDFQFQDTGKYQNIKEFTDDVQKYGYKISFRDI
DDEYINQALNEGKMYLFEVVNKDIYNTKNGSKNLHTLYFEHILSAENLNDPVFKLSGMAE
IFQRQPSVNEREKITTQKNQCILDKGDRAYKYRRYTEKKIMFHMSLVLNTGKGEIKQVQF
NKIINQRISSSDNEMRVNVIGIDRGEKNLLYYSVVKQNGEIIEQASLNEINGVNYRDKLI
EREKERLKNRQSWKPVVKIKDLKKGYISHVIHKICQLIEKYSAIVVLEDLNMRFKQIRGG
IERSVYQQFEKALIDKLGYLVFKDNRDLRAPGGVLNGYQLSAPFVSFEKMRKQTGILFYT
QAEYTSKTDPITGFRKNVYISNSASLDKIKEAVKKFDAIGWDGKEQSYFFKYNPYNLADE
KYKNSTVSKEWAIFASAPRIRRQKGEDGYWKYDRVKVNEEFEKLLKVWNFVNPKATDIKQ
EIIKKEKAGDLQGEKELDGRLRNFWHSFIYLFNLVLELRNSFSLQIKIKAGEVIAVDEGV
DFIASPVKPFFTTPNPYIPSNLCWLAVENADANGAYNIARKGVMILKKIREHAKKDPEFK
KLPNLFISNAEWDEAARDWGKYAGTTALNLDH (SEQ ID NO: 236)

>Lachnospiraceae bacterium MA2020 (Lb2Cpf1) protein
MYYESLTKQYPVSKTIRNELIPIGKTLDNIRQNNILESDVKRKQNYEHVKGILDEYHKQL
INEALDNCTLPSLKIAAEIYLKNQKEVSDREDFNKTQDLLRKEVVEKLKAHENFTKIGKK
DILDLLEKLPSISEDDYNALESFRNFYTYFTSYNKVRENLYSDKEKSSTVAYRLINENFP
KFLDNVKSYRFVKTAGILADGLGEEEQDSLFIVETFNKTLTQDGIDTYNSQVGKINSSIN
LYNQKNQKANGFRKIPKMKMLYKQILSDREESFIDEFQSDEVLIDNVESYGSVLIESLKS
SKVSAFFDALRESKGKNVYVKNDLAKTAMSNIVFENWRTFDDLLNQEYDLANENKKKDDK
YFEKRQKELKKNKSYSLEHLCNLSEDSCNLIENYIHQISDDIENIIINNETFLRIVINEH
DRSRKLAKNRKAVKAIKDFLDSIKVLERELKLINSSGQELEKDLIVYSAHEELLVELKQV
DSLYNMTRNYLTKKPFSTEKVKLNFNRSTLLNGWDRNKETDNLGVLLLKDGKYYLGIMNT
SANKAFVNPPVAKTEKVFKKVDYKLLPVPNQMLPKVFFAKSNIDFYNPSSEIYSNYKKGT
HKKGNMFSLEDCHNLIDFFKESISKHEDWSKFGFKFSDTASYNDISEFYREVEKQGYKLT
YTDIDETYINDLIERNELYLFQIYNKDFSMYSKGKLNLHTLYFMMLFDQRNIDDVVYKLN
GEAEVFYRPASISEDELIIHKAGEEIKNKNPNRARTKETSTFSYDIVKDKRYSKDKFTLH
IPITMNFGVDEVKRFNDAVNSAIRIDENVNVIGIDRGERNLLYVVVIDSKGNILEQISLN
SIINKEYDIETDYHALLDEREGGRDKARKDWNTVENIRDLKAGYLSQVVNVVAKLVLKYN
AIICLEDLNFGFKRGRQKVEKQVYQKFEKMLIDKLNYLVIDKSREQTSPKELGGALNALQ
LTSKFKSFKELGKQSGVIYYVPAYLTSKIDPTTGFANLFYMKCENVEKSKRFFDGFDFIR
FNALENVFEFGFDYRSFTQRACGINSKWTVCTNGERIIKYRNPDKNNMFDEKVVVVTDEM
KNLFEQYKIPYEDGRNVKDMIISNEEAEFYRRLYRLLQQTLQMRNSTSDGTRDYIISPVK
NKREAYFNSELSDGSVPKDADANGAYNIARKGLWVLEQIRQKSEGEKINLAMTNAEWLEY
AQTHLL (SEQ ID NO: 237)

>Candidatus Methanoplasma termitum Cpf1 (CMtCpf1) protein
MNNYDEFTKLYPIQKTIRFELKPQGRTMEHLETFNFFEEDRDRAEKYKILKEAIDEYHKK
FIDEHLTNMSLDWNSLKQISEKYYKSREEKDKKVFLSEQKRMRQEIVSEFKKDDRFKDLF
SKKLFSELLKEEIYKKGNHQEIDALKSFDKFSGYFIGLHENRKNMYSDGDEITAISNRIV
NENFPKFLDNLQKYQEARKKYPEWIIKAESALVAHNIKMDEVFSLEYFNKVLNQEGIQRY
NLALGGYVTKSGEKMMGLNDALNLAHQSEKSSKGRIHMTPLFKQILSEKESFSYIPDVFT
EDSQLLPSIGGFFAQIENDKDGNIFDRALELISSYAEYDTERIYIRQADINRVSNVIFGE
WGTLGGLMREYKADSINDINLERTCKKVDKWLDSKEFALSDVLEAIKRTGNNDAFNEYIS
KMRTAREKIDAARKEMKFISEKISGDEESIHIIKTLLDSVQQFLHFFNLFKARQDIPLDG
AFYAEFDEVHSKLFAIVPLYNKVRNYLTKNNLNTKKIKLNFKNPTLANGWDQNKVYDYAS

FIG. 23 cont'd.

LIFLRDGNYYLGIINPKRKKNIKFEQGSGNGPFYRKMVYKQIPGPNKNLPRVFLTSTKGK
KEYKPSKEIIEGYEADKHIRGDKFDLDFCHKLIDFFKESIEKHKDWSKFNFYFSPTESYG
DISEFYLDVEKQGYRMHFENISAETIDEYVEKGDLFLFQIYNKDFVKAATGKKDMHTIYW
NAAFSPENLQDVVVKLNGEAELFYRDKSDIKEIVHREGEILVNRTYNGRTPVPDKIHKKL
TDYHNGRTKDLGEAKEYLDKVRYFKAHYDITKDRRYLNDKIYFHVPLTLNFKANGKKNLN
KMVIEKFLSDEKAHIIGIDRGERNLLYYSIIDRSGKIIDQQSLNVIDGFDYREKLNQREI
EMKDARQSWNAIGKIKDLKEGYLSKAVHEITKMAIQYNAIVVMEELNYGFKRGRFKVEKQ
IYQKFENMLIDKMNYLVFKDAPDESPGGVLNAYQLTNPLESFAKLGKQTGILFYVPAAYT
SKIDPTTGFVNLFNTSSKTNAQERKEFLQKFESISYSAKDGGIFAFAFDYRKFGTSKTDH
KNVWTAYTNGERMRYIKEKKRNELFDPSKEIKEALTSSGIKYDGGQNILPDILRSNNNGL
IYTMYSSFIAAIQMRVYDGKEDYIISPIKNSKGEFFRTDPKRRELPIDADANGAYNIALR
GELTMRAIAEKFDPDSEKMAKLELKHKDWFEFMQTRGD (SEQ ID NO: 238)

>Eubacterium eligens Cpf1 (EeCpf1) protein
MNGNRSIVYREFVGVIPVAKTLRNELRPVGHTQEHIIQNGLIQEDELRQEKSTELKNIMD
DYYREYIDKSLSGVTDLDFTLLFELMNLVQSSPSKDNKKALEKEQSKMREQICTHLQSDS
NYKNIFNAKLLKEILPDFIKNYNQYDVKDKAGKLETLALFNGFSTYFTDFFEKRKNVFTK
EAVSTSIAYRIVHENSLIFLANMTSYKKISEKALDEIEVIEKNNQDKMGDWELNQIFNPD
FYNMVLIQSGIDFYNEICGVVNAHMNLYCQQTKNNYNLFKMRKLHKQILAYTSTSFEVPK
MFEDDMSVYNAVNAFIDETEKGNIIGKLKDIVNKYDELDEKRIYISKDFYETLSCFMSGN
WNLITGCVENFYDENIHAKGKSKEEKVKKAVKEDKYKSINDVNDLVEKYIDEKERNEFKN
SNAKQYIREISNIITDTETAHLEYDDHISLIESEEKADEMKKRLDMYMNMYHWAKAFIVD
EVLDRDEMFYSDIDDIYNILENIVPLYNRVRNYVTQKPYNSKKIKLNFQSPTLANGWSQS
KEFDNNAIILIRDNKYYLAIFNAKNKPDKKIIQGNSDKKNDNDYKKMVYNLLPGANKMLP
KVFLSKKGIETFKPSDYIISGYNAHKHIKTSENFDISFCRDLIDYFKNSIEKHAEWRKYE
FKFSATDSYSDISEFYREVEMQGYRIDWTYISEADINKLDEEGKIYLFQIYNKDFAENST
GKENLHTMYFKNIFSEENLKDIIIKLNGQAELFYRRASVKNPVKHKKDSVLVNKTYKNQL
DNGDVVRIPIPDDIYNEIYKMYNGYIKESDLSEAAKEYLDKVEVRTAQKDIVKDYRYTVD
KYFIHTPITINYKVTARNNVNDMVVKYIAQNDDIHVIGIDRGERNLIYISVIDSHGNIVK
QKSYNILNNYDYKKKLVEKEKTREYARKNWKSIGNIKELKEGYISGVVHEIAMLIVEYNA
IIAMEDLNYGFKRGRFKVERQVYQKFESMLINKLNYFASKEKSVDEPGGLLKGYQLTYVP
DNIKNLGKQCGVIFYVPAAFTSKIDPSTGFISAFNFKSISTNASRKQFFMQFDEIRYCAE
KDMFSFGFDYNNFDTYNITMGKTQWTVYTNGERLQSEFNNARRTGKTKSINLTETIKLLL
EDNEINYADGHDIRIDMEKMDEDKKSEFFAQLLSLYKLTVQMRNSYTEAEEQENGISYDK
IISPVINDEGEFFDSDNYKESDDKECKMPKDADANGAYCIALKGLYEVLKIKSEWTEDGF
DRNCLKLPHAEWLDFIQNKRYE (SEQ ID NO: 239)

>Moraxella bovoculi 237 Cpf1 (MbCpf1) protein
MLFQDFTHLYPLSKTVRFELKPIDRTLEHIHAKNFLSQDETMADMHQKVKVILDDYHRDF
IADMMGEVKLTKLAEFYDVYLKFRKNPKDDELQKQLKDLQAVLRKEIVKPIGNGGKYKAG
YDRLFGAKLFKDGKELGDLAKFVIAQEGESSPKLAHLAHFEKFSTYFTGFHDNRKNMYSD
EDKHTAIAYRLIHENLPRFIDNLQILTTIKQKHSALYDQIINELTASGLDVSLASHLDGY
HKLLTQEGITAYNTLLGGISGEAGSPKIQGINELINSHHNQHCHKSERIAKLRPLHKQIL
SDGMSVSFLPSKFADDSEMCQAVNEFYRHYADVFAKVQSLFDGFDDHQKDGIYVEHKNLN
ELSKQAFGDFALLGRVLDGYYVDVVNPEFNERFAKAKTDNAKAKLTKEKDKFIKGVHSLA
SLEQAIEHYTARHDDESVQAGKLGQYFKHGLAGVDNPIQKIHNNHSTIKGFLERERPAGE
RALPKIKSGKNPEMTQLRQLKELLDNALNVAHFAKLLTTKTTLDNQDGNFYGEFGVLYDE
LAKIPTLYNKVRDYLSQKPFSTEKYKLNFGNPTLLNGWDLNKEKDNFGVILQKDGCYYLA
LLDKAHKKVFDNAPNTGKSIYQKMIYKYLEVRKQFPKVFFSKEAIAINYHPSKELVEIKD

FIG. 23 cont'd.

KGRQRSDDERLKLYRFILECLKIHPKYDKKFEGAIGDIQLFKKDKKGREVPISEKDLFDK
INGIFSSKPKLEMEDFFIGEFKRYNPSQDLVDQYNIYKKIDSNDNRKKENFYNNHPKFKK
DLVRYYYESMCKHEEWEESFEFSKKLQDIGCYVDVNELFTEIETRRLNYKISFCNINADY
IDELVEQGQLYLFQIYNKDFSPKAHGKPNLHTLYFKALFSEDNLADPIYKLNGEAQIFYR
KASLDMNETTIHRAGEVLENKNPDNPKKRQFVYDIIKDKRYTQDKFMLHVPITMNFGVQG
MTIKEFNKKVNQSIQQYDEVNVIGIDRGERHLLYLTVINSKGEILEQCSLNDITTASANG
TQMTTPYHKILDKREIERLNARVGWGEIETIKELKSGYLSHVVHQISQLMLKYNAIVVLE
DLNFGFKRGRFKVEKQIYQNFENALIKKLNHLVLKDKADDEIGSYKNALQLTNNFTDLKS
IGKQTGFLFYVPAWNTSKIDPETGFVDLLKPRYENIAQSQAFFGKFDKICYNADKDYFEF
HIDYAKFTDKAKNSRQIWTICSHGDKRYVYDKTANQNKGAAKGINVNDELKSLFARHHIN
EKQPNLVMDICQNNDKEFHKSLMYLLKTLLALRYSNASSDEDFILSPVANDEGVFFNSAL
ADDTQPQNADANGAYHIALKGLWLLNELKNSDDLNKVKLAIDNQTWLNFAQNR (SEQ ID NO: 240)

>Prevotella disiens Cpf1 (PdCpf1) protein
MENYQEFTNLFQLNKTLRFELKPIGKTCELLEEGKIFASGSFLEKDKVRADNVSYVKKEI
DKKHKIFIEETLSSFSISNDLLKQYFDCYNELKAFKKDCKSDEEEVKKTALRNKCTSIQR
AMREAISQAFLKSPQKKLLAIKNLIENVFKADENVQHFSEFTSYFSGFETNRENFYSDEE
KSTSIAYRLVHDNLPIFIKNIYIFEKLKEQFDAKTLSEIFENYKLYVAGSSLDEVFSLEY
FNNTLTQKGIDNYNAVIGKIVKEDKQEIQGLNEHINLYNQKHKDRRLPFFISLKKQILSD
REALSWLPDMFKNDSEVIKALKGFYIEDGFENNVLTPLATLLSSLDKYNLNGIFIRNNEA
LSSLSQNVYRNFSIDEAIDANAELQTFNNYELIANALRAKIKKETKQGRKSFEKYEEYID
KKVKAIDSLSIQEINELVENYVSEFNSNSGNMPRKVEDYFSLMRKGDFGSNDLIENIKTK
LSAAEKLLGTKYQETAKDIFKKDENSKLIKELLDATKQFQHFIKPLLGTGEEADRDLVFY
GDFLPLYEKFEELTLLYNKVRNRLTQKPYSKDKIRLCFNKPKLMTGWVDSKTEKSDNGTQ
YGGYLFRKKNEIGEYDYFLGISSKAQLFRKNEAVIGDYERLDYYQPKANTIYGSAYEGEN
SYKEDKKRLNKVIIAYIEQIKQTNIKKSIIESISKYPNISDDDKVTPSSLLEKIKKVSID
SYNGILSFKSFQSVNKEVIDNLLKTISPLKNKAEFLDLINKDYQIFTEVQAVIDEICKQK
TFIYFPISNVELEKEMGDKDKPLCLFQISNKDLSFAKTFSANLRKKRGAENLHTMLFKAL
MEGNQDNLDLGSGAIFYRAKSLDGNKPTHPANEAIKCRNVANKDKVSLFTYDIYKNRRYM
ENKFLFHLSIVQNYKAANDSAQLNSSATEYIRKADDLHIIGIDRGERNLLYYSVIDMKGN
IVEQDSLNIIRNNDLETDYHDLLDKREKERKANRQNWEAVEGIKDLKKGYLSQAVHQIAQ
LMLKYNAIIALEDLGQMFVTRGQKIEKAVYQQFEKSLVDKLSYLVDKKRPYNELGGILKA
YQLASSITKNNSDKQNGFLFYVPAWNTSKIDPVTGFTDLLRPKAMTIKEAQDFFGAFDNI
SYNDKGYFEFETNYDKFKIRMKSAQTRWTICTFGNRIKRKKDKNYWNYEEVELTEEFKKL
FKDSNIDYENCNLKEEIQNKDNRKFFDDLIKLLQLTLQMRNSDDKGNDYIISPVANAEGQ
FFDSRNGDKKLPLDADANGAYNIARKGLWNIRQIKQTKNDKKLNLSISSTEWLDFVREKP
YLK (SEQ ID NO: 241)

GENOMIC SAFE HARBORS FOR GENETIC THERAPIES IN HUMAN STEM CELLS AND ENGINEERED NANOPARTICLES TO PROVIDE TARGETED GENETIC THERAPIES

CROSS-REFERENCE TO RELATED APPLICATIONS

This application a Continuation of U.S. application Ser. No. 16/619,211 filed on Dec. 4, 2019, which is a U.S. National Phase Application based on International Patent Application No. PCT/US2018/036154 filed on Jun. 5, 2018, which claims priority to U.S. Provisional Patent Application No. 62/515,474 filed on Jun. 5, 2017, U.S. Provisional Patent Application No. 62/564,129 filed on Sep. 27, 2017, and U.S. Provisional Patent Application No. 62/664,045 filed on Apr. 27, 2018, each of which is incorporated by reference in its entirety as if fully set forth herein.

REFERENCE TO SEQUENCE LISTING

The Sequence Listing associated with this application is provided in XML format in lieu of a paper copy, and is hereby incorporated by reference into the specification. The name of the XML file containing the Sequence Listing is 2T80137.xml. The XML file is 307 KB, was created on Dec. 13, 2022, and is being submitted electronically via Patent Center.

FIELD OF THE DISCLOSURE

The current disclosure provides genomic safe harbors (GSH) for genetic therapies in human stem cells and engineered nanoparticles to provide targeted genetic therapies. The disclosed GSH and/or associated nanoparticles can be used to safely and efficiently treat a variety of genetic, infectious, and malignant diseases.

BACKGROUND OF THE DISCLOSURE

Patient-specific gene therapy has great potential to treat genetic, infectious, and malignant diseases. For example, retrovirus-mediated gene addition into hematopoietic stem cells (HSC) and hematopoietic stem cells and progenitor cells (HSPC) has demonstrated curative outcomes for several genetic diseases over the last 10 years including inherited immunodeficiencies (e.g., X-linked and adenosine deaminase deficient severe combined immunodeficiency (SCID)), hemoglobinopathies, Wiskott-Aldrich syndrome and metachromatic leukodystrophy. Additionally, this treatment approach has also improved outcomes for poor prognosis diagnoses such as glioblastoma. The use of gene-corrected autologous, or "self", HSPC eliminates the risk of graft-host immune responses, negating the need for immunosuppressive drugs. However, effective implementation of HSPC gene therapy faces several major challenges. The current state-of-the-art includes the removal of cells from the patient via bone marrow aspirate or mobilized peripheral blood, sorting this bulk population for autologous HSPC by immunoselection of cells expressing the surface marker CD34, then culturing these cells in the presence of cytokines and the specified therapeutic retrovirus vector before harvesting. Re-administering cells to the patient may require cytoreductive conditioning to permit engraftment of the gene corrected cells. Currently, only centers with Good Manufacturing Practices (GMP) compliant facilities and the infrastructure to support them are capable of administering gene modified cell products. While a simplified manufacturing platform to automate this process in a small, mobile footprint has been developed, severely limited quantities of available therapeutic vectors have continued to create a significant bottleneck to widespread use of the technology.

In addition to the challenge of manufacturing sufficient therapeutic vector quantities, there remains a known risk of genotoxicity and other limitations associated with the use of viral vectors for gene transfer. For example, risks of genotoxicity are evidenced by the development of malignancy due to insertional mutagenesis in patients treated with HSPC gene therapy. This adverse side effect stems from the semi-random nature of retroviral-mediated transgene delivery into the host cell genome. Dysregulation of nearby genes by the inserted transgene sequence has been the molecular basis for clonal expansion and malignant transformation observed in some gene therapy patients, but reciprocal interactions between the inserted transgene and the surrounding genomic context can also cause transgene attenuation or silencing, diminishing therapeutic effects. Other limitations associated with the use of particular viral vectors include induction of immune responses, a decreased efficacy over time in dividing cells (e.g., adeno-associated vectors), an inability to adequately target selected cell types in vivo (e.g., retroviral vectors), and, as indicated, an inability to control insertion site and number of insertions (e.g., lentiviral vectors).

The last 5 years have seen an explosion in gene editing as a safer alternative to retrovirus-mediated gene transfer, made possible by the development of engineered guide RNA and nucleases which target specific DNA sequences and predictably generate DNA double strand breaks (DSB) at the targeted sequence. To date, these programmable complexes have been most effective at providing promising therapies when removal or silencing of a problematic gene (i.e., generating a loss-of-function mutation) is needed. This is because DSBs are most commonly repaired by error-prone non-homologous end joining (NHEJ) which results in oligonucleotide insertions and deletions (indels) at the DSB site.

For gene addition or correction of a specific mutation, less common homology-directed repair (HDR) of the DSB is required. In this situation, a more complex payload including the engineered guide RNA and nuclease as well as a homology-directed repair template must be co-delivered. Proof-of-concept for this approach has been demonstrated in HSPC but also required either tandem electroporation of some gene editing components followed by transduction with non-integrating viral vectors, particularly recombinant adeno-associated viral (rAAV) vectors to deliver DNA templates, or simultaneous electroporation of defined concentrations of engineered nuclease components with chemically modified, single-stranded oligonucleotide template at specified cell concentrations. Moreover, each engineered guide RNA, nuclease and homology-directed repair template had to be uniquely engineered for each specified genetic target, requiring separate evaluation of delivery, activity and specificity in cell lines and HSPC.

Thus, while there have been many exciting breakthroughs in the ability to perform genetic therapies at specific sites within the genome, the continued lack of a safe and potent delivery vehicle has hindered the clinical translation of gene editing systems, in particular, with HSPCs.

The concept of a genomic safe harbor (GSH) for genetic modification was first introduced in 2011 by Papapetrou and colleagues (Nature Biotechnology. 2011; 29 (1): 73-8). The major criteria proposed to define a GSH site are (1) the ability to accommodate new genetic material with, (2) predictable function, and (3) without potentially harmful alterations in host cell genomic activity. The benefit of identifying such a locus would greatly simplify development efforts for targeted gene addition approaches. Several loci have been evaluated in the human genome, but to date no bona fide validated GSH sites that meet the above criteria have been identified. Papapetrou et al., Mol. Ther. 2016; 24 (4): 678-84.

SUMMARY OF THE DISCLOSURE

The current disclosure provides significant advances in the ability to perform genetic therapies for a variety of genetic, infectious, and malignant diseases by providing the identification of genomic safe harbors (GSH) within human hematopoietic stem cells (HSC) and hematopoietic stem cells and progenitor cells (HSPC). In particular embodiments, the GSH additionally qualify as the more rigorously defined universal HSC safe harbor loci, as described in additional detail herein.

The current disclosure also provides nanoparticles specifically engineered to deliver all components required for genetic editing, for example, at the GSH sites. The nanoparticles can be used for therapies where a loss-of-function mutation is needed, but importantly, can also provide all components needed for gene addition or correction of a specific mutation. The described approaches are safe (i.e., no off-target toxicity), reliable (targeted GSH cell chromatin is accessible and amenable to therapeutic cassette addition), scalable, easy to manufacture, synthetic, plug- and-play (i.e., the same basic platform can be used to deliver different therapeutic nucleic acids), and compatible with easy in vivo administration (through, for example, a syringe).

Particular embodiments include a nanoparticle with components to provide a targeted loss-of-function mutation. These embodiments include a targeting element (e.g., guide RNA) and a cutting element (e.g. a nuclease) associated with the surface of the nanoparticle. In particular embodiments, the targeting element is conjugated to the surface of the nanoparticle through a thiol linker. In particular embodiments, the targeting element and/or the cutting element are conjugated to the surface of the nanoparticle through a thiol linker. In particular embodiments, the targeting element is conjugated to the surface of the nanoparticle through a thiol linker and the cutting element is linked to the targeting element to form a ribonucleoprotein (RNP) complex. The targeting element targets the cutting element to a specific site for cutting and NHEJ repair.

Particular embodiments include a nanoparticle with components to provide a targeted gain-of-function mutation (e.g., gene addition or correction). In particular embodiments, these embodiments include a metal nanoparticle (e.g., a gold nanoparticle) associated with a targeting element, a cutting element, a homology-directed repair template, and a therapeutic DNA sequence. The targeting element targets the cutting element to a specific site for cutting, the homology-directed repair template provides for HDR repair, wherein following HDR repair the therapeutic DNA sequence has been inserted within the target site. Together, homology-directed repair templates and therapeutic DNA sequences can be referred to herein as donor templates. In particular embodiments, the targeting element is conjugated to the surface of the nanoparticle through a thiol linker. In particular embodiments, the targeting element and/or the cutting element are conjugated to the surface of the nanoparticle through a thiol linker. In particular embodiments, the targeting element is conjugated to the surface of the nanoparticle through a thiol linker and the cutting element is linked to the targeting element to form a ribonucleoprotein (RNP) complex. In these embodiments, the RNP complex is closer to the surface of the nanoparticle than donor template material. This configuration is beneficial when, for example, the targeting element and/or the cutting element are of bacterial origin. This is because many individuals who may receive nanoparticles described herein may have pre-existing immunity against bacterially-derived components such as bacterially-derived gene-editing components. Including bacterially-derived gene-editing components on an inner layer of the fully formulated nanoparticle allows non-bacterially-derived components (e.g., donor templates) to shield bacterially-derived components (e.g. targeting elements and/or cutting elements) from the patient's immune system. This protects the bacterially-derived components from attack and also avoids or reduces unwanted inflammatory responses against the nanoparticles following administration. In addition, this may allow for repeated administration of the nanoparticles in vivo without inactivation by the host immune response.

Particular embodiments utilize CRISPR gene editing. In particular embodiments, CRISPR gene editing can occur with CRISPR guide RNA (crRNA) and/or a CRISPR nuclease (e.g., Cpf1 (also referred to as Cas12a) or Cas9).

Particular embodiments adopt features that increase the efficiency and/or accuracy of HDR. For example, Cpf1 has a short single crRNA and cuts target DNA in staggered form with 5' 2-4 nucleotide (nt) overhangs called sticky ends. Sticky ends are favorable for HDR, Kim et al. (2016) Nat Biotechnol. 34 (8): 863-8. Moreover, donor templates should be released from the nanoparticles before the genome cut by the RNP occurs to promote HDR. Accordingly, in particular embodiments disclosed herein donor templates are found farther from the surface of the nanoparticle than targeting elements and cutting elements. The current disclosure also unexpectedly found that delivery of gene-editing components on a gold nanoparticle increases the efficiency and/or accuracy of HDR. Accordingly, particular embodiments deliver gene-editing components utilizing gold nanoparticles.

In particular embodiments, targeting molecules can be used to target the nanoparticle to a specific cell so that activity of the gene editing system can be spatially or temporally controlled. For example, the activity and destination of the gene editing system may be controlled by a targeting molecule that selectively delivers the nanoparticle to targeted cells. In particular embodiments, the targeting molecule can include an antibody binding domain that binds CD34. In particular embodiments, pairs of targeting molecule can be used, for example, an antibody binding domain that binds CD34 and an antibody binding domain that binds CD90.

BRIEF DESCRIPTION OF THE SEVERAL VIEWS OF THE DRAWINGS

Many of the drawings submitted herein are better understood in color. Applicant considers the color versions of the drawings as part of the original submission and reserves the right to present color images of the drawings in later proceedings.

FIG. 3. Schematic showing the design and sequence of crRNA (SEQ ID NO: 253) and homology-directed repair template (also referred to herein as a homology template (HT or HDT)) (SEQ ID NOs: 256, 257) for a second GSH location (SEQ ID NOs: 251, 252, 254, 255) within human HSC and HSPC.

FIG. 4. Two GSH sites (SEQ ID NOs: 258, 259) within the human CCR5 gene within chromosome 3p21 along with crRNA (SEQ ID NO: 260) and HT (SEQ ID NOs: 261, 262) for a non-target and target strand. The purpose of choosing CCR5 was to validate the nanoformulation. A well-known naturally-occurring mutation in the CCR5 gene renders a person's blood cells resistant to HIV infection. For purposes of the present disclosure, this site provided a means to compare Cas9 and Cpf1 nucleases directly because there is a DNA sequence near the site of this naturally-occurring mutation that contains an identical cut site for both Cpf1 and Cas9. The PAM mutation in the homology template for the target strand is italicized, bolded, and underlined.

(FIG. 7A) Depiction of an exemplary AuNP configured with all components for gene addition within a GSH. Depicted components include crRNA, a Cpf1 nuclease, and ssDNA to provide a therapeutic nucleic acid sequence (e.g. a gene or corrected portion thereof). The embodiment depicted in FIG. 7A additionally includes a targeting molecule (e.g., an antibody binding domain or an aptamer). (FIG. 7B) Schematic representation of a synthesis process for creating and loading AuNP with exemplary gene editing components. (FIG. 7C) Schematic of a formulated "layered" AuNP which can be used to deliver large oligonucleotides, such as donor templates including homology-directed repair templates, therapeutic DNA sequences, and other potential elements. Donor templates are located farther from the AuNP surface than the depicted ribonucleoprotein complex (RNP) (FIG. 7D) Successful generation of 50 nm AuNP carrying all required gene editing components for insertion of a therapeutic DNA sequence. Transmission electron microscope images of AuNPs and AuNP/CRISPR nanoformulations. The depicted embodiment includes an AuNP associated with crRNA, Cpf1, ssDNA, thiol linkers, polyethylene glycol (PEG) spacers, and PEI2K. More particularly, thiol linkers are attached directly to the surface of the AuNP and crRNA. Use of such a linker allows conjugation of more crRNA to the surface of the AuNP, in part because the spaces reduces repulsion between the negative charge of RNA-based molecules and the negative charge of the AuNP surface. Cpf1 is linked to the crRNA to form an RNP. To improve the efficiency of HDR, ssDNA should be released from the AuNP before the genome cut occurs. Accordingly, ssDNA is found farther from the surface of the AuNP than the RNP.

(FIG. 9A) Localized surface plasmon resonance (LSPR) peaks of synthesized AuNPs. (FIG. 9B) LSPR peaks of the AuNP and AuNP/CRISPR nanoformulations. (FIG. 9C) Gel electrophoresis showing optimal AuNP/ssDNA w/w loading ratio. (FIG. 9D) Loading concentration of AuNP/CRISPR nanoformulations.

FIGS. 10A-10C. Optimal loading concentrations. (FIG. 10A) AuNP/crRNA 50 nm (Ratio 6); AuNP/crRNA 15 nm (Ratio 1); and AuNP/crRNA/Cpf1/PEI/DNA 15 nm (Ratio 0.5); (FIG. 10B) Optimal AuNP 50 nm/DNA w/w ratio; (FIG. 10C) Smaller AuNPs triple the available surface area with the same starting reagent amounts. By decreasing the size, surface area and conjugation ratio of the NPs increase.

(FIG. 11A) HSPC take up fully-loaded AuNPs in vitro. Time lapse imaging on spinning disc confocal microscope. Human mobilized $CD^{34}$+ cells→Culture O/N→Add AuNPs (4 hours)→Analyze. (FIG. 11B) Confocal microscope imaging showing the uptake of CRISPR editing components into $CD^{34}$+ cells.

FIGS. 12A-12D. Graphs showing the gene cutting efficiency in K562 cells and $CD^{34}$+ cells. (FIGS. 12A, 12B) Tracking Indels by Decomposition (TIDE) assay results showing percent cutting efficiency in K562 cells and $CD^{34}$+ cells. (FIG. 12C) Percent viability after delivery with AuNPs and electroporation method. (FIG. 12D) Administration dose of CRISPR components.

(FIG. 15A) 10 μg/mL AuNP is an optimal concentration for HDR in $CD^{34}$+ cells where maximum gene editing is achieved without loss in viability. The same protocol was used as described in relation to FIG. 13, except that $CD^{34}$+ cells were initially obtained from a different human donor. (FIGS. 15B, 15C) Cell viability analysis by Live-Dead assay; (FIG. 15D) representative cell viability results in bar graph format.

(FIG. 18A) There is no significant impact on HSPC fitness in vitro by any nuclease or delivery method as determined by a first colony-forming assay in methylcellulose (H4434). $CD^{34}$+ cells were seeded at 200 cells per 35 mm plate with a total incubation time of 14 days. (FIG. 18B) Improved HSPC secondary plating fitness in vitro with AuNP/Cpf1. Colony plates from (FIG. 18A) were harvested and 10% of the resulting cell suspension was re-plated into a second colony-forming assay in Methylcellulose (H4434). This is a simple test to determine whether long-term colony-initiating cells were impacted by the experimental conditions. The total incubation time was 14 days. The only significant difference observed was in the number of colonies for the AuNP+Cpf1/crRNA treated cells, which displayed more long-term colonies-forming cells. No significant differences were observed in the type of colonies formed in each experimental group.

(FIG. 20A) 10% HDR was observed by TIDE without significant indels at the target locus in human $CD^{34}$+ cells at the time of transplant. (FIG. 20B) Both T7EI and Notl restriction digest were only observed in cells that received fully-loaded AuNP nanoformulations. (FIG. 20C) Interestingly, increased colony-forming capacity for this donor was noted only when cells were treated with AuNPs. No significant differences were observed in the types of colonies formed across each condition.

(FIGS. 21A, 21B) Mice transplanted with AuNP-treated cells displayed higher levels of human CD45+ cell engraftment than mice transplanted with mock cells. (FIGS. 21C, 21D) No significant differences in the frequency of human CD20+ cells were observed across groups. (FIGS. 21E, 21F) No significant differences in the frequency of human CD14+ cells were observed across groups. (FIGS. 21G, 21H) Significant differences in the frequency of human CD3+ cells were observed at 14 weeks and in the mice receiving fully-loaded AuNPs who displayed the lowest overall human engraftment. This result may be an artifact of low engraftment levels.

FIG. 23. Sequences supporting the disclosure.

DETAILED DESCRIPTION

Figure 1:
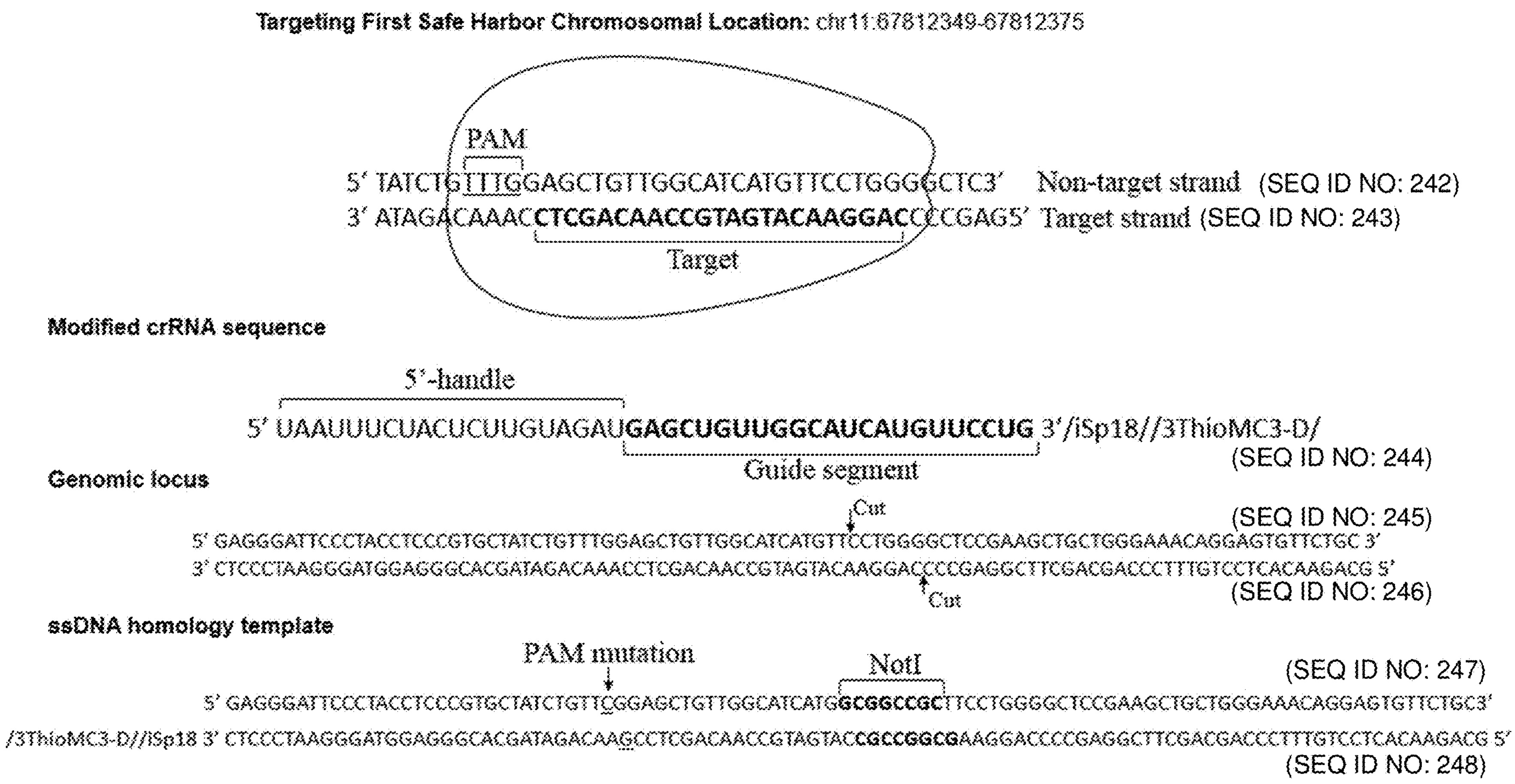
FIG. 1. Schematic showing the design and sequence of clustered regularly interspaced short palindromic repeat (CRISPR) RNA (crRNA) (SEQ ID NO: 244) and homology templates (HT) (SEQ ID NOs: 247, 248) for a genomic safe harbor (GSH) location (SEQ ID NOs: 242, 243, 245, 246) to allow targeted genome editing within human hematopoietic stem cells (HSC) and hematopoietic stem cells and progenitor cells (HSPC).

Patient-specific gene therapy has great potential to treat genetic, infectious, and malignant diseases. For example, retrovirus-mediated gene addition into hematopoietic stem cells (HSC) and hematopoietic stem cells and progenitor cells (HSPC) has demonstrated curative outcomes for several genetic diseases over the last 10 years including inherited immunodeficiencies (e.g., X-linked and adenosine deaminase deficient severe combined immunodeficiency (SCID)), hemoglobinopathies, Wiskott-Aldrich syndrome and metachromatic leukodystrophy. Additionally, this treatment approach has also improved outcomes for poor prognosis diagnoses such as glioblastoma. The use of gene-corrected autologous, or "self", HSPC eliminates the risk of graft-host immune responses, negating the need for immunosuppressive drugs. However, effective implementation of HSPC gene therapy faces several major challenges. The current state-of-the-art includes the removal of cells from the patient via bone marrow aspirate or mobilized peripheral blood, sorting this bulk population for autologous HSPC by immunoselection of cells expressing the surface marker CD34, then culturing these cells in the presence of cytokines and the specified therapeutic retrovirus vector before harvesting. Re-administering cells to the patient may require cytoreductive conditioning to permit engraftment of the gene corrected cells. Currently, only centers with Good Manufacturing Practices (GMP) compliant facilities and the infrastructure to support them are capable of administering gene modified cell products. While a simplified manufacturing platform to automate this process in a small, mobile footprint has been developed, severely limited quantities of available therapeutic vectors have continued to create a significant bottleneck to widespread use of the technology.

In addition to the challenge of manufacturing sufficient therapeutic vector quantities, there remains a known risk of genotoxicity associated with the use of retroviral vectors for gene transfer evidenced by the development of malignancy due to insertional mutagenesis in patients treated with HSPC gene therapy. This adverse side effect stems from the semi-random nature of retroviral-mediated transgene delivery into the host cell genome. Dysregulation of nearby genes by the inserted transgene sequence has been the molecular basis for clonal expansion and malignant transformation observed in some gene therapy patients, but reciprocal interactions between the inserted transgene and the surrounding genomic context can also cause transgene attenuation or silencing, diminishing therapeutic effects.

The last 5 years have seen an explosion in gene editing as a safer alternative to retrovirus-mediated gene transfer, made possible by the development of engineered guide RNA associated with nucleases which target specific DNA sequences and predictably generate DNA double strand breaks (DSB) at the targeted sequence. To date, these programmable complexes have been most effective at providing promising therapies when removal or silencing of a problematic gene (i.e., generating a loss-of-function mutation) is needed. This is because DSBs are most commonly repaired by error-prone non-homologous end joining (NHEJ) which results in oligonucleotide insertions and deletions (indels) at the DSB site.

For gene addition or correction of a specific mutation, less common homology-directed repair (HDR) of the DSB is required. In this situation, a more complex payload including the engineered guide RNA and nuclease, and a homology-directed repair template with homology to the target DSB locus must be co-delivered. Proof-of-concept for this approach has been demonstrated in HSPC but also required either tandem electroporation of genome editing components followed by transduction with non-integrating viral vectors, particularly recombinant adeno-associated viral (rAAV) vectors to deliver DNA templates, or simultaneous electroporation of defined concentrations of engineered nuclease components with chemically modified, single-stranded oligonucleotide template at specified cell concentrations. Moreover, each guide RNA, nuclease and homology-directed repair template had to be uniquely engineered for each specified genetic target, requiring separate evaluation of delivery, activity and specificity in cell lines and HSPC.

Thus, while there have been many exciting breakthroughs in the ability to perform genetic therapies at specific sites within the genome, the continued lack of a safe and potent delivery vehicle has hindered the clinical translation of gene editing systems, in particular, with HSPCs.

The concept of a genomic safe harbor (GSH) for genetic modification was first introduced in 2011 by Papapetrou and colleagues (Nature Biotechnology. 2011; 29 (1): 73-8). The major criteria proposed to define a GSH site are (1) the ability to accommodate new genetic material with, (2) predictable function, and (3) without potentially harmful alterations in host cell genomic activity. The benefit of identifying such a locus would greatly simplify development efforts for targeted gene addition approaches. Several loci have been evaluated in the human genome, but to date no bona fide validated GSH sites that meet the above criteria have been identified. Papapetrou et al., Mol. Ther. 2016; 24 (4): 678-84.

The current disclosure provides significant advances in the ability to perform genetic therapies for a variety of genetic, infectious, and malignant diseases by providing the identification of genomic safe harbors (GSH) within human hematopoietic stem cells (HSC) and hematopoietic stem cells and progenitor cells (HSPC). Some of the identified GSH additionally qualify as the more rigorously defined universal HSC safe harbor loci, as described in additional detail herein.

The current disclosure also provides nanoparticles specifically engineered to deliver all components required for genetic editing, for example, at the GSH sites. The nanoparticles can be used for therapies where a loss-of-function mutation is needed, but importantly, can also provide all components needed for gene addition or correction of a specific mutation. The described approaches are safe (i.e., no off-target toxicity), reliable (targeted GSH cell chromatin is accessible and amenable to therapeutic additions), scalable, easy to manufacture, synthetic, plug- and-play (i.e., the same basic platform can be used to deliver different therapeutic nucleic acids), and compatible with easy in vivo administration (through, for example, a syringe).

Particular embodiments include a nanoparticle with components to provide a targeted loss-of-function mutation. These embodiments include a targeting element (e.g., guide RNA) and a cutting element (e.g. a nuclease) associated with the surface of the nanoparticle. In particular embodiments, the targeting element is conjugated to the surface of the nanoparticle through a thiol linker. In particular embodiments, the targeting element and/or the cutting element are conjugated to the surface of the nanoparticle through a thiol linker. In particular embodiments, the targeting element is conjugated to the surface of the nanoparticle through a thiol linker and the cutting element is linked to the targeting element to form a ribonucleoprotein (RNP) complex. The targeting element targets the cutting element to a specific site for cutting and NHEJ repair.

Particular embodiments include a nanoparticle with components to provide a targeted gain-of-function mutation (e.g., gene addition or correction). These embodiments include a targeting element, a cutting element, a homology-directed repair template, and a therapeutic DNA sequence associated with the surface of the nanoparticle. The targeting element targets the cutting element to a specific site for cutting, the homology-directed repair template provides for HDR repair, wherein following HDR repair the therapeutic DNA sequence has been inserted within the target site. Together, homology-directed repair templates and therapeutic DNA sequences can be referred to herein as donor templates. In particular embodiments, the targeting element is conjugated to the surface of the nanoparticle through a thiol linker. In particular embodiments, the targeting element and/or the cutting element are conjugated to the surface of the nanoparticle through a thiol linker. In particular embodiments, the targeting element is conjugated to the surface of the nanoparticle through a thiol linker and the cutting element is linked to the targeting element to form a ribonucleoprotein (RNP) complex. In these embodiments, the RNP complex is closer to the surface of the nanoparticle than donor template material. This configuration is beneficial when, for example, the targeting element and/or the cutting element are of bacterial origin. This is because many individuals who may receive nanoparticles described herein may have pre-existing immunity against bacterially-derived components, such as bacterially-derived gene-editing components. Including bacterially-derived gene-editing components on an inner layer of the fully formulated nanoparticle allows non-bacterially-derived components (e.g., donor templates) to shield bacterially-derived components (e.g. targeting elements and/or cutting elements) from the patient's immune system. This protects the bacterially-derived components from attack and also avoids or reduces unwanted inflammatory responses against the nanoparticles following administration. In addition, this may allow for repeated administration of the nanoparticles in vivo without inactivation by the host immune response.

Particular embodiments utilize CRISPR gene editing. In particular embodiments, CRISPR gene editing can occur with CRISPR guide RNA (crRNA) and/or a CRISPR nuclease (e.g., Cpf1 or Cas9).

Particular embodiments adopt features that increase the efficiency and/or accuracy of HDR. For example, Cpf1 has a short single crRNA and cuts target DNA in staggered form with 5' 2-4 nucleotide (nt) overhangs called sticky ends. Sticky ends are favorable for HDR, Kim et al. (2016) Nat Biotechnol. 34 (8): 863-8. Moreover, donor templates should be released from the nanoparticles before the genome cut by the RNP occurs to promote HDR. Accordingly, in particular embodiments disclosed herein donor templates are found farther from the surface of the nanoparticle than targeting elements and cutting elements. The current disclosure also unexpectedly found that delivery of gene-editing components on a gold nanoparticle increases the efficiency and/or accuracy of HDR. Accordingly, particular embodiments deliver gene-editing components utilizing gold nanoparticles.

In particular embodiments, targeting molecules can be used to target the nanoparticle to a specific cell so that activity of the gene editing system can be spatially or temporally controlled. For example, the activity and destination of the gene editing system may be controlled by a targeting molecule that binds a cell surface marker, such as CD34 or CD90.

In embodiments utilizing gene-editing components of bacterial origin, the current disclosure also takes into account that many individuals who may receive nanoparticles described herein may have pre-existing immunity against such components. To address this potential pre-existing immunity, gene-editing components of bacterial origin may be directly conjugated to the surface of nanoparticles followed by addition of donor templates. In this configuration, donor templates can shield the gene-editing components from immune attack and avoid or reduce unwanted inflammatory responses against the nanoparticles following administration.

The following aspects of the disclosure are now described with additional detail and options to support the teachings of the disclosure as follows: (I) Genomic Safe Harbors (GSH) and Universal HSC Safe Harbor Loci in Human HSC and HSPC; (II) Gene Editing Systems and Components to Target and Modify GSH Sites; (III) Nanoparticles; (IV) Conjugation of Active Components to Nanoparticles; (V) Gene Editing Efficiency; (VI) Nanoparticle Compositions and Cell Formulations; (VII) Exemplary Methods of Use; and (VIII) Reference Levels Derived from Control Populations; (IX) Kits; and (X) Exemplary Embodiments.

(I) Genomic Safe Harbors (GSH) and Universal HSC Safe Harbor Loci in Human HSC and HSPC. As indicated, one drawback with existing gene therapies is that the insertion site of retroviral vectors cannot be adequately controlled. Gene editing systems allow control over the target sites of genetic therapies, however, before the current disclosure, no bona fide validated GSH sites had been identified in the human genome (Papapetrou et al., Mol. Ther. 2016; 24 (4): 678-84), as the concept had been proposed by Papapetrou and colleagues in Nature Biotechnology. 2011; 29 (1): 73-8) (i.e., (1) the ability to accommodate new genetic material with, (2) predictable function, and (3) without potentially harmful alterations in host cell genomic activity).

One of the challenges of the incorporation of genetic material in cells is determining where within the chromosomes the genetic material can be safely incorporated. The present disclosure solves this problem by providing chromatin-accessible regions in the $CD^{34}$+ cell and CD34 subtype (CD45RA- and $CD90^{+}$) in human and non-human primate cells (see, e.g., WO 2017/218948 and Radtke et al., Sci. Transl. Med. 2017; 9 (414) which have high editing efficiency and low probability of disrupting cellular potential. In particular embodiments, the sites qualify as universal HSC safe harbor loci. In particular embodiments, to meet the criteria of a universal HSC safe harbor loci, chromatin sites must be >150 kb away from a known oncogene, >30 kb away from a known transcription start site; and have no overlap with coding mRNA. In particular embodiments, to meet the criteria of a universal HSC safe harbor loci, chromatin sites must be >200 kb away from a known oncogene, >40 kb away from a known transcription start site; and have no overlap with coding mRNA. In particular embodiments, to meet the criteria of a universal HSC safe harbor loci, chromatin sites must be >300 kb away from a known oncogene, >50 kb away from a known transcription start site; and have no overlap with coding mRNA. In particular embodiments, a universal HSC safe harbor loci meets the preceding criteria (>150 kb, >200 kb or >300 kb away from a known transcription start site; and have no overlap with coding mRNA >40 kb, or >50 kb away from a known transcription start site with no overlap with coding mRNA) and additionally is 100% homologous between the non-human primate and the human genome to permit rapid clinical translation of these gene edited populations. In particular embodiments, a universal HSC safe harbor loci meets the preceding criteria and demonstrates a 1:1 ratio of forward: reverse orientations of LV integration further demonstrating the loci does not impact surrounding genetic material.

The process to identify GSH within the human genome began by evaluating the biological outcome of long-term engraftment of lentivirus (LV) gene modified, autologous $CD^{34}$+ cells in the pigtailed macaque (M. Nemestrina), an established non-human primate model used for HSC and HSPC gene therapy preclinical evaluations. A high-throughput analysis of sites of LV integration was used to identify candidate GSH loci. LVs can transduce non-dividing cells, and integrate preferentially into active transcription units in the host cell genome. The locus of integration is determined at the time of gene transfer and is inherited by each daughter cell. 150,000 LV integration sites identified in blood cells collected from twelve animals over a period of 2-7 years after transplant were parsed into 1,077 25 kb genomic windows displaying significantly enriched frequencies of integration relative to the rest of the genome (Table 1).

TABLE 1

Identification of candidate GSH loci from LV integration sites identified in vivo in nonhuman primate recipients of autologous HSPC therapy

| Parsing Step Performed (Top to Bottom) | Number of Events |
|---|---|
| Total IS identified in 12 monkeys | 148,283 |
| Total number of 25 kb genomic windows containing IS | >95,000 |
| 25 kb genomic windows significantly enriched for IS | 1,077 |
| 25 kb genomic windows with 1:1 ratio of forward:reverse IS orientation | 664 |
| 25 kb genomic windows containing IS identified in 3 or more biological replicates | 662 |
| 25 kb windows with ≥90% homology to human genome | 171 |
| 25 kb windows ≥ 300 kb away from known oncogenes | 122 |
| 25 kb windows ≥ 50 kb away from TSS | 24 |
| 25 kb windows associated with constitutive transcriptional activity in whole blood | 2 |

IS: integration sites
TSS: transcription start site

A benign accessible locus would be expected to display a 1:1 ratio of forward: reverse orientations of LV integration. The list was thus further parsed into 664 genomic windows with equivalent forward and reverse orientation of integration events. Of these, 662 windows contained integration events which were represented by 3 or more biological replicates (≥3 of 12 monkeys analyzed).

The windows were filtered based on homology to the human genome (hg38) and a total of 171 windows were identified with >90% homology. To increase safety, these windows were cross-referenced against the COSMIC cancer gene database. Windows were only retained if they were >300 kb away from a known oncogene. This filter resulted in 122 windows. Any windows within 50 kb of a transcription start site were removed, which resulted in 24 windows, all of which were preferentially located in intronic sequences. Two genomic regions were highly enriched in these 24 windows: chromosome 11q13.2 and chromosome 16p12.1.

Both of these gene-rich loci are constitutively expressed in blood cells, indicating that (1) expression of transgenes is not expected to transactivate nearby genes which should be silenced in blood cells, and (2) inserted transgene sequences will not be attenuated or silenced during hematopoietic differentiation [University of California at Santa Cruz (UCSC) Genome Browser and ENCODE]. These two loci were further analyzed by the following criteria: target sub-domains were identified as unique sequences with (1) 100% homology between the primate (RheMac3) and human (hg38) genomes, and (2) no overlap with coding mRNA. The latter criteria excluded chromosome 16p12.1 as a GSH locus because it overlaps with multiple mRNAs.

The following sites identified by the analysis are 100% homologous between the human genome and the rhesus genome.

TABLE 2

Sites Identified by Analysis that are 100% Homologous between the Human Genome and the Rhesus Genome

| Location on the Human Genome | Location on the Rhesus Genome |
|---|---|
| chr11: 67812226-67812252 | chr20: 5298821-5298847 |
| chr11: 67812280-67812306 | chr20: 5298873-5298899 |
| chr11: 67812349-67812375 | chr20: 5298938-5298964 |
| chr11: 67812179-67812205 | chr20: 5298774-5298800 |
| chr11: 67812443-67812469 | chr20: 5299024-5299050 |
| chr11: 67931439-67931465 | chr20: 5455480-5455506 |
| chr11: 67931473-67931499 | chr20: 5455446-5455472 |
| chr11: 67931516-67931542 | chr20: 5455403-5455429 |
| chr11: 67931362-67931388 | chr20: 5455557-5455583 |

These areas of chromosome 11q13.2 represent universal HSC safe harbor loci sites. The following sites also demonstrated permissiveness to genetic modification without adverse biological consequences, even under selective pressure in vivo and represent GSH sites: chr11: 67523429-67533593; chr11: 67681215-67741765; chr11: 67805337-67845629; chr11: 67895738-67941098; chr5: 66425982-66457233; chr8: 28980753-29006178; chr16: 28151114-28175716; chr1: 39189118-39214131; chr17: 2149700-2174592; chr14: 35658075-35685512; chr18: 9198556-9223041;chr5: 140463887-140488886; chr11: 68563075-68588007; chr2: 43459415-43484174; chr11: 68517649-68542970; chr1: 8600474-8624530; chr12: 50609483-50635221; chr16: 28175717-28199134; chr17: 63329602-63353111; chr1: 107643312-107672400; chr17: 65870579-65895504; chr2: 224533608-224559225; chr14: 22272733-22296704; and chr15: 50094713-50119187. In particular embodiments, chr11: 67681215-67741765, chr11: 67805337-67845629, and/or chr11: 67895738-67941098 are targeted for genetic modification.

Universal HSC safe harbor window loci on chr11 that are particularly relevant for gene editing (as described in more detail in relation to gene editing below) include: 67935219-67935243; 67911598-67911622; 67939901-67939925; 67927758-67927782; 67917930-67917954; 67918042-67918066; 67931473-67931497; 67936715-67936739; 67921126-7921150; 67914940-67914964; 67928284-67928308; 67936068-67936092; 67922372-67922396; 67811255-67811279; 67840351-67840375; 67821576-67821600; 67827279-67827303; 67822563-7822587; 67823914-67823938; 67818875-67818899; 67811907-67811931; 67811630-67811654; 7836644-67836668; 67806757-67806781; 67823923-67823947; 67841379-67841403; 67808086-7808110; 67823903-67823927; 67686904-67686928; 67692610-67692634; 67692462-67692486; 67692618-67692642; 67705405-67705429; 67686651-67686675; 67686788-67686812; 67684033-7684057; 67681565-67681589; 67704652-67704676; 67689328-67689352; 67688546-67688570; 67693464-67693488; 67682343-67682367; 67689948-67689972; 67684785-67684809; 67684738-67684762; 67684260-67684284; 67684173-67684197; 67687315-67687339; 67682671-67682695; 67691534-67691558; 67690743-67690767; 67693746-67693770; 67690174-67690198; 67692535-67692559; 67687605-67687629; 67694747-67694771; 67681441-67681465; 67691508-67691532; 67692057-67692081; 67692573-67692597; 67690331-67690355; 67697247-67697271; 67695745-67695769; 67695241-67695265; 67691931-67691955; 67691017-67691041; 67694689-67694713; 67721934-67721958; 67696164-67696188; 67736715-67736739; 67681498-67681522; 67690926-67690950; 67694271-67694295; 67682715-67682739; 67694107-67694131; 67692129-67692153; 67721153-67721177; 67726733-67726757; 67694551-67694575; 67684767-67684791; 67686717-67686741; 67692858-67692882; 67694890-67694914; 7706343-67706367; 67681596-67681620; 67684153-67684177; 67690025-67690049; 67691225-67691249; 67692361-67692385; 67692291-67692315; 67684752-67684776; 67690917-67690941; 67695354-67695378; 67685964-67685988; 67690852-67690876; 67698221-67698245; 67713445-67713469; 67693965-67693989; 67689830-67689854; 67690151-67690175; 67718079-67718103; 67692663-67692687; 67684143-67684167; 67702560-67702584; 67689807-67689831; 67734305-67734329; 67691410-67691434; 67691162-67691186; 67702695-67702719; 67689612-67689636; 67697284-67697308; 67691567-67691591; 67685635-67685659; 67689900-67689924; 67696035-67696059; 67687462-67687486; 67689863-67689887; 67690831-67690855; 67696956-67696980; 67703966-67703990; 67692382-67692406; 67693741-67693765; 67682707-67682731; 67689891-67689915; 67695833-67695857; 67689800-67689824; 67693566-67693590; 67681587-67681611; 67702113-67702137; 67701288-67701312; 67689761-67689785; 67723825-67723849; 67686892-67686916; 67698097-67698121; 67687614-67687638; 67703251-67703275; 67690109-67690133; 67719750-67719774; 67691762-67691786; 67691654-67691678; 67695445-67695469; 67694579-67694603; 67693002-67693026; 67731932-67731956; 67689608-67689632; 67691726-67691750; 67704995-67705019; 67694095-67694119; 67688285-67688309; 67692918-67692942; 67735442-67735466; 67694119-67694143; 67694791-67694815; 67695843-67695867; 67695032-67695056; 67703734-67703758; 67690809-67690833; 67697085-67697109; 67690629-67690653; 67701642-67701666; 67693639-67693663; 67703876-67703900; 67690054-67690078; 67695062-67695086; 67689878-67689902; 67696347-67696371; 67694806-67694830; 67690245-67690269; 67695377-67695401; 67694295-67694319; 67705602-67705626; 67693729-67693753; 67694696-67694720; 67694318-67694342; 67697768-67697792; 67694989-67695013; 67687551-67687575; 67694309-67694333; 67693926-67693950; 67693602-67693626; 67693896-67693920; 67718020-67718044; 67700346-67700370; 67696171-67696195; 67729142-67729166; 67684112-67684136; 67693375-67693399; 67691807-67691831; 67700198-67700222; 67697504-67697528; 67701370-67701394; 67703871-67703895; 67683323-67683347; and 67/690,737-67690761. These sites represent SEQ ID NOs. 1-194 as provided in Table 3 below.

While GSH loci described herein are ideally suited for genetic manipulation in HSC including a subset for $CD^{34}$+ cells, $CD^{34}$+CD45RA-$CD90^{+}$ HSC), other appropriate blood cells types include hematopoietic progenitor cells (HPC), hematopoietic stem and progenitor cell (HSPCs), T cells, natural killer (NK) cells, B cells, macrophages, monocytes, mesenchymal stem cells (MSC), white blood cell (WBC), mononuclear cell (MNC), endothelial cells (EC), stromal cells, and bone marrow fibroblasts. These cell types can collectively be referred to as "blood cells".

(II) Gene Editing Systems and Components to Target and Modify GSH Sites. Identification of the above-described GSH and more rigorously defined universal HSC safe harbor loci allows targeting with gene editing systems, greatly increasing the safety of genetic therapies. Within the teachings of the current disclosure, any gene editing system capable of precise sequence targeting and modification can be used. These systems typically include a targeting element for precise targeting and a cutting element for cutting the targeted genetic site. Guide RNA is one example of a targeting element while various nucleases provide examples of cutting elements. Targeting elements and cutting elements can be separate molecules or linked, for example, by a nanoparticle. Alternatively, a targeting element and a cutting element can be linked together into one dual purpose molecule. When insertion of a therapeutic nucleic acid sequence is intended, the systems also include a homology-directed repair template (which can include homology arms) associated with the therapeutic nucleic acid sequence. As detailed further below, however, different gene editing systems can adopt different components and configurations while maintaining the ability to precisely target, cut, and modify selected genomic sites.

Particular embodiments utilize zinc finger nucleases (ZFNs) as gene editing agents. ZFNs are a class of site-specific nucleases engineered to bind and cleave DNA at specific positions. ZFNs are used to introduce double strand breaks (DSBs) at a specific site in a DNA sequence which enables the ZFNs to target unique sequences within a genome in a variety of different cells. Moreover, subsequent to double-stranded breakage, homology-directed repair (HDR) or non-homologous end joining (NHEJ) takes place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, Fokl endonuclease. The Fokl domain functions as a dimer requiring two constructs with unique DNA binding domains for sites on the target sequence. The Fokl cleavage domain cleaves within a five or six base pair spacer sequence separating the two inverted half-sites.

For additional information regarding ZFNs, see Kim, et al. Proceedings of the National Academy of Sciences of the United States of America 93, 1156-1160 (1996); Wolfe, et al. Annual review of biophysics and biomolecular structure 29, 183-212 (2000); Bibikova, et al. Science 300, 764 (2003); Bibikova, et al. Genetics 161, 1169-1175 (2002); Miller, et al. The EMBO journal 4, 1609-1614 (1985); and Miller, et al. Nature biotechnology 25, 778-785 (2007)].

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing DSBs in the DNA, which induce repair mechanisms in cells. Generally, two TALENs must bind and flank each side of the target DNA site for the DNA cleavage domain to dimerize and induce a DSB. The DSB is repaired in the cell by NHEJ or HDR if an exogenous double-stranded donor DNA fragment is present.

As indicated, TALENs have been engineered to bind a target sequence of, for example, an endogenous genome, and cut DNA at the location of the target sequence. The TALEs of TALENs are DNA binding proteins secreted by Xanthomonas bacteria. The DNA binding domain of TALEs include a highly conserved 33 or 34 amino acid repeat, with divergent residues at the 12th and 13th positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant Fokl endonucleases. For additional information regarding TALENs, see Boch, et al. Science 326, 1509-1512 (2009); Moscou, & Bogdanove, Science 326, 1501 (2009); Christian, et al. Genetics 186, 757-761 (2010); and Miller, et al. Nature biotechnology 29, 143-148 (2011).

Particular embodiments utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

In particular embodiments, GSH can be targeted using CRISPR gene editing systems. The CRISPR nuclease system is a prokaryotic immune system that confers resistance to foreign genetic elements such as plasmids and phages and provides a form of acquired immunity. CRISPRs are DNA loci containing short repetitions of base sequences. In the context of a prokaryotic immune system, each repetition is followed by short segments of spacer DNA belonging to foreign genetic elements that the prokaryote was exposed to. This CRISPR array of repeats interspersed with spacers can be transcribed into RNA. The RNA can be processed to a mature form and associate with a cas (CRISPR-associated) nuclease. A CRISPR-Cas system including an RNA having a sequence that can hybridize to the foreign genetic elements and Cas nuclease can then recognize and cut these exogenous genetic elements in the genome.

A CRISPR-Cas system does not require the generation of customized proteins to target specific sequences, but rather a single Cas enzyme can be programmed by a short guide RNA molecule (crRNA) to recognize a specific DNA target. The CRISPR-Cas systems of bacterial and archaeal adaptive immunity show extreme diversity of protein composition and genomic loci architecture. The CRISPR-Cas system loci have more than 50 gene families and there are no strictly universal genes, indicating fast evolution and extreme diversity of loci architecture. So far, adopting a multi-pronged approach, there is comprehensive cas gene identification of 395 profiles for 93 Cas proteins. Classification includes signature gene profiles plus signatures of locus architecture. A new classification of CRISPR-Cas systems is proposed in which these systems are broadly divided into two classes, Class 1 with multi-subunit effector complexes and Class 2 with single-subunit effector modules exemplified by the Cas9 protein. Efficient gene editing in human $CD^{34}$+ cells using electroporation of CRISPR/Cas9 mRNA and single-stranded oligodeoxyribonucleotide (ssODN) as a donor template for HDR has been demonstrated. De Ravin et al. Sci Transl Med. 2017; 9 (372): eaah3480. Novel effector proteins associated with Class 2 CRISPR-Cas systems may be developed as powerful genome engineering tools and the prediction of putative novel effector proteins and their engineering and optimization is important. In addition to the Class 1 and Class 2 CRISPR-Cas systems, more recently a putative Class 2, Type V CRISPR-Cas class exemplified by Cpf1 has been identified Zetsche et al. (2015) Cell 163 (3): 759-771.

Additional information regarding CRISPR-Cas systems and components thereof are described in, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

The Cpf1 nuclease particularly can provide added flexibility in target site selection by means of a short, three base pair recognition sequence (TTN), known as the protospacer-adjacent motif or PAM. Cpf1's cut site is at least 18 bp away from the PAM sequence, thus the enzyme can repeatedly cut a specified locus after indel (insertion and deletion) formation, increasing the efficiency of HDR. Moreover, staggered DSBs with sticky ends permit orientation-specific donor template insertion, which is advantageous in non-dividing cells.

Three windows of identified GSH sites on chromosome 11q13.2 were searched for Cpf1 target sites that contained the most preferred PAM sequence (TTTA) and an adjacent 21 bp of DNA which was completely unique to the human genome. A total of 194 target cut sites were identified by these criteria and are listed in Table 3. Each of these identified sequences provides a beneficial site to specifically target for gene therapy. The disclosed nucleic acid sequences are shown using standard letter abbreviations for nucleotide bases, as defined in 37 C.F.R. 1.822. Only one strand of each nucleic acid sequence is shown, but the complementary strand is understood as included by any reference to the displayed strand in the following Table 3 and/or as provided herein:

TABLE 3

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* Exact Match | One bp Off | Two bp Off |
|---|---|---|---|---|
| 67935219-67935243 | TTTAAAAAAAGTCTTCATAA TAAAA (SEQ ID NO: 1) | 1 | 0 | 0 |
| 67911598-67911622 | TTTACTTCTGTGCACCCAT AGACTC (SEQ ID NO: 2) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* Exact Match | One bp Off | Two bp Off |
|---|---|---|---|---|
| 67939901-67939925 | TTTAACTCTGCCATGGGTG CCAGGA (SEQ ID NO: 3) | 1 | 0 | 0 |
| 67927758-67927782 | TTTAGCCACTGTGAGAAAC AGTTTA (SEQ ID NO: 4) | 1 | 0 | 0 |
| 67917930-67917954 | TTTATAAGGCTAAGTAGTA TTCTAT (SEQ ID NO: 5) | 1 | 0 | 0 |
| 67918042-67918066 | TTTATCCACTAATTGTTGAT GGGCA (SEQ ID NO: 6) | 1 | 0 | 0 |
| 67931473-67931497 | TTTATTTTCTTTTTGGTAAG AAGGA (SEQ ID NO: 7) | 1 | 0 | 0 |
| 67936715-67936739 | TTTAAAATAATCGTCATTCT TTTTG (SEQ ID NO: 8) | 1 | 0 | 0 |
| 67921126-67921150 | TTTATATTAATCCTTGTATG TCTGA (SEQ ID NO: 9) | 1 | 0 | 0 |
| 67914940-67914964 | TTTAAATGGATAAGTTAGG CTGGGC (SEQ ID NO: 10) | 1 | 0 | 0 |
| 67928284-67928308 | TTTACACAAACTGTACTTGT AGGTA (SEQ ID NO: 11) | 1 | 0 | 0 |
| 67936068-67936092 | TTTAGTGAGGAAAAACTAC ATTTAT (SEQ ID NO: 12) | 1 | 0 | 0 |
| 67922372-67922396 | TTTAAAAAGGGAAAATTAG GGAGAA (SEQ ID NO: 13) | 1 | 0 | 0 |
| 67811255-67811279 | TTTACTAAATGACCTCTTC GCCAAA (SEQ ID NO: 14) | 1 | 0 | 0 |
| 67840351-67840375 | TTTAGTGATATGAAAAGAA CCATGC (SEQ ID NO: 15) | 1 | 0 | 0 |
| 67821576-67821600 | TTTAAATTTTCCAGTGTCTC AGTGT (SEQ ID NO: 16) | 1 | 0 | 0 |
| 67827279-67827303 | TTTAAGCCTGAAAACCTAA AAAATG (SEQ ID NO: 17) | 1 | 0 | 0 |
| 67822563-67822587 | TTTAAAAATTAGCTGCGTT GGTGGT (SEQ ID NO: 18) | 1 | 0 | 0 |
| 67823914-67823938 | TTTAGCTGCTTTAAAATGT GAACTC (SEQ ID NO: 19) | 1 | 0 | 0 |
| 67818875-67818899 | TTTAATCTCAAGTCACTTCT CTAGG (SEQ ID NO: 20) | 1 | 0 | 0 |
| 67811907-67811931 | TTTAAACGCTCGTTAGATC ACTGGA (SEQ ID NO: 21) | 1 | 0 | 0 |
| 67811630-67811654 | TTTAAGGCAGGAATCAGGG TGCCAT (SEQ ID NO: 22) | 1 | 0 | 0 |
| 67836644-67836668 | TTTAAAAAAATCCCAGGTG ACCCTA (SEQ ID NO: 23) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* Exact Match | One bp Off | Two bp Off |
|---|---|---|---|---|
| 67806757-67806781 | TTTAATCTTGCAGGGACAGGAAGGA (SEQ ID NO: 24) | 1 | 0 | 0 |
| 67823923-67823947 | TTTAAAATGTGAACTCCAAATCAGG (SEQ ID NO: 25) | 1 | 0 | 0 |
| 67841379-67841403 | TTTATTATTTCGTTGTTTTTCCTCT (SEQ ID NO: 26) | 1 | 0 | 0 |
| 67808086-67808110 | TTTATCTTGGTGTTTGAACTCGGAT (SEQ ID NO: 27) | 1 | 0 | 0 |
| 67823903-67823927 | TTTACTGCCCATTTAGCTGCTTTAA (SEQ ID NO: 28) | 1 | 0 | 0 |
| 67686904-67686928 | TTTAACTTGATTACCTTATAGTCAA (SEQ ID NO: 29) | 1 | 0 | 0 |
| 67692610-67692634 | TTTATATATTTAACTTCTGTATTTT (SEQ ID NO: 30) | 1 | 0 | 0 |
| 67692462-67692486 | TTTATCTGCTATAGCTAACAAATTT (SEQ ID NO: 31) | 1 | 0 | 0 |
| 67692618-67692642 | TTTAACTTCTGTATTTTCTAAAACT (SEQ ID NO: 32) | 1 | 0 | 0 |
| 67705405-67705429 | TTTATAACACACCAGCATCAGTTAC (SEQ ID NO: 33) | 1 | 0 | 0 |
| 67686651-67686675 | TTTATTATCTTTCCTGTTTTCTAAT (SEQ ID NO: 34) | 1 | 0 | 0 |
| 67686788-67686812 | TTTAATATTAACATTTGCTAATTTC (SEQ ID NO: 35) | 1 | 0 | 0 |
| 67684033-67684057 | TTTAAAAGGCCAGATGTCAATTCAG (SEQ ID NO: 36) | 1 | 0 | 0 |
| 67681565-67681589 | TTTATGCAGATAGATATATATTTTT (SEQ ID NO: 37) | 1 | 0 | 0 |
| 67704652-67704676 | TTTAATCACTGGATCATGGACCTAA (SEQ ID NO: 38) | 1 | 0 | 0 |
| 67689328-67689352 | TTTAGTGTTTCTTAGAAACTTAACA (SEQ ID NO: 39) | 1 | 0 | 0 |
| 67688546-67688570 | TTTACAGCAGTGCCATTCACAATGG (SEQ ID NO: 40) | 1 | 0 | 0 |
| 67693464-67693488 | TTTATAGGCCCAGGTCTAGATCTGG (SEQ ID NO: 41) | 1 | 0 | 0 |
| 67682343-67682367 | TTTAGCCCTATCTTATCCATATGGA (SEQ ID NO: 42) | 1 | 0 | 0 |
| 67689948-67689972 | TTTATGTCTAGTACTTAGGGCAGTA (SEQ ID NO: 43) | 1 | 0 | 0 |
| 67684785-67684809 | TTTACAATTAATTGTAGTTCTTTGA (SEQ ID NO: 44) | 1 | 0 | 0 |
| 67684738-67684762 | TTTATTTTCTTAGATTTACTCTGTA (SEQ ID NO: 45) | 1 | 0 | 0 |
| 67684260-67684284 | TTTAAAAACTGGGTTTACAAATAAA (SEQ ID NO: 46) | 1 | 0 | 0 |
| 67684173-67684197 | TTTAAACATTTTGACTGTAGCCATT (SEQ ID NO: 47) | 1 | 0 | 0 |
| 67687315-67687339 | TTTATGACTGTTTCATGTGTGCTCA (SEQ ID NO: 48) | 1 | 0 | 0 |
| 67682671-67682695 | TTTATAACCTCACCTTTGGCTTTTA (SEQ ID NO: 49) | 1 | 0 | 0 |
| 67691534-67691558 | TTTAGAAGTCCATATAAGGGGATGC (SEQ ID NO: 50) | 1 | 0 | 0 |
| 67690743-67690767 | TTTACTGTTAATTAGTCCTTGCTTA (SEQ ID NO: 51) | 1 | 0 | 0 |
| 67693746-67693770 | TTTATCTATGAACCTCATAGGTCCT (SEQ ID NO: 52) | 1 | 0 | 0 |
| 67690174-67690198 | TTTACTATAGTTAATTGGAACACTT (SEQ ID NO: 53) | 1 | 0 | 0 |
| 67692535-67692559 | TTTAACGTTAAATCTCTTTCTAACA (SEQ ID NO: 54) | 1 | 0 | 0 |
| 67687605-67687629 | TTTATCTCCTTTAAATTCCCATGTT (SEQ ID NO: 55) | 1 | 0 | 0 |
| 67694747-67694771 | TTTAGTCCAAATAAAGCAACAATAC (SEQ ID NO: 56) | 1 | 0 | 0 |
| 67681441-67681465 | TTTATCCATTCCCAACCACAAAGAA (SEQ ID NO: 57) | 1 | 0 | 0 |
| 67691508-67691532 | TTTAATTTCTCCACTTGATTAACTT (SEQ ID NO: 58) | 1 | 0 | 0 |
| 67692057-67692081 | TTTAGCCAAAGGACATGCCTAAAAT (SEQ ID NO: 59) | 1 | 0 | 0 |
| 67692573-67692597 | TTTAGGAATTAATAAAAATTGTATA (SEQ ID NO: 60) | 1 | 0 | 0 |
| 67690331-67690355 | TTTAATGCATCCATAAACAGAACTG (SEQ ID NO: 61) | 1 | 0 | 0 |
| 67697247-67697271 | TTTAGGGTGGTTCTCCTGGGATTTT (SEQ ID NO: 62) | 1 | 0 | 0 |
| 67695745-67695769 | TTTATCCCTTACGCATGAGGTCCCT (SEQ ID NO: 63) | 1 | 0 | 0 |
| 67695241-67695265 | TTTACACAAGCAACACCAGCTGCAG (SEQ ID NO: 64) | 1 | 0 | 0 |
| 67691931-67691955 | TTTAAATACTTGACAAAAAAGATTG (SEQ ID NO: 65) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* Exact Match | One bp Off | Two bp Off |
|---|---|---|---|---|
| 67691017-67691041 | TTTAAAAGGGGTCTCTACTAAATCT (SEQ ID NO: 66) | 1 | 0 | 0 |
| 67694689-67694713 | TTTAATCTTTATCTGACCTAAATTT (SEQ ID NO: 67) | 1 | 0 | 0 |
| 67721934-67721958 | TTTATAAAGAAATTCCGCAAGAACT (SEQ ID NO: 68) | 1 | 0 | 0 |
| 67696164-67696188 | TTTATGATTTAAAGGGGAAGCTTTG (SEQ ID NO: 69) | 1 | 0 | 0 |
| 67736715-67736739 | TTTAATGCTTTCAACATCGATTGCT (SEQ ID NO: 70) | 1 | 0 | 0 |
| 67681498-67681522 | TTTACGGAGAGGATACAAAGATCCT (SEQ ID NO: 71) | 1 | 0 | 0 |
| 67690926-67690950 | TTTAAGATCTTCCTATAATTATAGC (SEQ ID NO: 72) | 1 | 0 | 0 |
| 67694271-67694295 | TTTAATTTTTGTTGGAGTCTTTTCT (SEQ ID NO: 73) | 1 | 0 | 0 |
| 67682715-67682739 | TTTATTTTTTAAAACCAGAACATTT (SEQ ID NO: 74) | 1 | 0 | 0 |
| 67694107-67694131 | TTTAGTTCTCTTTTTATACTCCAAA (SEQ ID NO: 75) | 1 | 0 | 0 |
| 67692129-67692153 | TTTACTAAGAATAGTGTAGGGGTTA (SEQ ID NO: 76) | 1 | 0 | 0 |
| 67721153-67721177 | TTTACTATTTCCCATCTTATGTATA (SEQ ID NO: 77) | 1 | 0 | 0 |
| 67726733-67726757 | TTTAGCAGGTGTCTTGATCCCCCTT (SEQ ID NO: 78) | 1 | 0 | 0 |
| 67694551-67694575 | TTTATTTTCTAGTCCCCCTTTGATC (SEQ ID NO: 79) | 1 | 0 | 0 |
| 67684767-67684791 | TTTAAAATCATCTTATTGTTTACAA (SEQ ID NO: 80) | 1 | 0 | 0 |
| 67686717-67686741 | TTTAGAGAGATATATTTTCCTCTAG (SEQ ID NO: 81) | 1 | 0 | 0 |
| 67692858-67692882 | TTTAAAAGTGGTCACAAGTGGGGGA (SEQ ID NO: 82) | 1 | 0 | 0 |
| 67694890-67694914 | TTTACTAGAAACCTTTCCCATATTG (SEQ ID NO: 83) | 1 | 0 | 0 |
| 67706343-67706367 | TTTATTGCTCTGTAACAGATTACCA (SEQ ID NO: 84) | 1 | 0 | 0 |
| 67681596-67681620 | TTTACCAGCCATCTTAGAACAAATT (SEQ ID NO: 85) | 1 | 0 | 0 |
| 67684153-67684177 | TTTACAGAATTCGCTTTCCCTTTAA (SEQ ID NO: 86) | 1 | 0 | 0 |
| 67690025-67690049 | TTTATTAAGCTAAACCTAGGTACAA (SEQ ID NO: 87) | 1 | 0 | 0 |
| 67691225-67691249 | TTTAGGATCACCTTAACTTGGTGAG (SEQ ID NO: 88) | 1 | 0 | 0 |
| 67692361-67692385 | TTTACTATTTCCCCTGGAGTCTTTA (SEQ ID NO: 89) | 1 | 0 | 0 |
| 67692291-67692315 | TTTAATAAGTCTTTTGATTACAGGC (SEQ ID NO: 90) | 1 | 0 | 0 |
| 67684752-67684776 | TTTACTCTGTAGCTTTTTAAAATCA (SEQ ID NO: 91) | 1 | 0 | 0 |
| 67690917-67690941 | TTTACTTCTTTTAAGATCTTCCTAT (SEQ ID NO: 92) | 1 | 0 | 0 |
| 67695354-67695378 | TTTACTTTGCTCTGTGAACAGAGTT (SEQ ID NO: 93) | 1 | 0 | 0 |
| 67685964-67685988 | TTTAATTCCTGTTTCATTTTCCCAT (SEQ ID NO: 94) | 1 | 0 | 0 |
| 67690852-67690876 | TTTAGGGCGTGACTGTGAATAACTC (SEQ ID NO: 95) | 1 | 0 | 0 |
| 67698221-67698245 | TTTATTCAATTTCTCCTAAGTCTGC (SEQ ID NO: 96) | 1 | 0 | 0 |
| 67713445-67713469 | TTTAAAAATATTTAGCAACTGGGAC (SEQ ID NO: 97) | 1 | 0 | 0 |
| 67693965-67693989 | TTTACGTTCCCAGATCGTATTTCTT (SEQ ID NO: 98) | 1 | 0 | 0 |
| 67689830-67689854 | TTTAGTTCATGGCAAGCAAGTCATT (SEQ ID NO: 99) | 1 | 0 | 0 |
| 67690151-67690175 | TTTAGGCCACCAATTGGGGGCATTT (SEQ ID NO: 100) | 1 | 0 | 0 |
| 67718079-67718103 | TTTACCAACCATCACTGCCATCGTC (SEQ ID NO: 101) | 1 | 0 | 0 |
| 67692663-67692687 | TTTAACCCCAGAAACTGTTAATTCC (SEQ ID NO: 102) | 1 | 0 | 0 |
| 67684143-67684167 | TTTATAGTTATTTACAGAATTCGCT (SEQ ID NO: 103) | 1 | 0 | 0 |
| 67702560-67702584 | TTTATTTGTGCAACAATGGGGAATT (SEQ ID NO: 104) | 1 | 0 | 0 |
| 67689807-67689831 | TTTAATAAAGCAATAGGAAGACGTT (SEQ ID NO: 105) | 1 | 0 | 0 |
| 67734305-67734329 | TTTAAGTCACAGGGGTGTAGACCCT (SEQ ID NO: 106) | 1 | 0 | 0 |
| 67691410-67691434 | TTTAGTGACCACCCTACTCTATTGT (SEQ ID NO: 107) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* Exact Match | One bp Off | Two bp Off |
|---|---|---|---|---|
| 67691162-67691186 | TTTAATAGAATAGCCTCATATTTTA (SEQ ID NO: 108) | 1 | 0 | 0 |
| 67702695-67702719 | TTTAACCACTCCCACTCCCAATTAC (SEQ ID NO: 109) | 1 | 0 | 0 |
| 67689612-67689636 | TTTAGATGGAACTAGCATTCCACAA (SEQ ID NO: 110) | 1 | 0 | 0 |
| 67697284-67697308 | TTTAAAAGTAGCAGCTTAAGCCAGA (SEQ ID NO: 111) | 1 | 0 | 0 |
| 67691567-67691591 | TTTAGTTAATTTCTTATATAAGAGC (SEQ ID NO: 112) | 1 | 0 | 0 |
| 67685635-67685659 | TTTAAGGTAGATCTGTGCAGGGGGA (SEQ ID NO: 113) | 1 | 0 | 0 |
| 67689900-67689924 | TTTACTCCTCCCGAAGAGGATGGAT (SEQ ID NO: 114) | 1 | 0 | 0 |
| 67696035-67696059 | TTTAACATAGATATTGAAGTCAGAG (SEQ ID NO: 115) | 1 | 0 | 0 |
| 67687462-67687486 | TTTATCATATTACTATTTTGCCAGT (SEQ ID NO: 116) | 1 | 0 | 0 |
| 67689863-67689887 | TTTAGTTACATGATTTTTAAGAGTT (SEQ ID NO: 117) | 1 | 0 | 0 |
| 67690831-67690855 | TTTACCTGGTTCTGTAAATATTTTA (SEQ ID NO: 118) | 1 | 0 | 0 |
| 67696956-67696980 | TTTATTATGTGAGTGATAAATTTGA (SEQ ID NO: 119) | 1 | 0 | 0 |
| 67703966-67703990 | TTTACACCCCCCACCCCCGAGGCCT (SEQ ID NO: 120) | 1 | 0 | 0 |
| 67692382-67692406 | TTTAACTGAACATGTGTTGGAGGAA (SEQ ID NO: 121) | 1 | 0 | 0 |
| 67693741-67693765 | TTTAATTTATCTATGAACCTCATAG (SEQ ID NO: 122) | 1 | 0 | 0 |
| 67682707-67682731 | TTTATTTTTTTATTTTTTAAAACCA (SEQ ID NO: 123) | 1 | 0 | 0 |
| 67689891-67689915 | TTTATCCTTTTTACTCCTCCCGAAG (SEQ ID NO: 124) | 1 | 0 | 0 |
| 67695833-67695857 | TTTAAACTTTTTTAAATAGGTAAAG (SEQ ID NO: 125) | 1 | 0 | 0 |
| 67689800-67689824 | TTTAATTTTTAATAAAGCAATAGGA (SEQ ID NO: 126) | 1 | 0 | 0 |
| 67693566-67693590 | TTTACATATAGTTTTTGAGCClIII (SEQ ID NO: 127) | 1 | 0 | 0 |
| 67681587-67681611 | TTTAAAAGTTTTACCAGCCATCTTA (SEQ ID NO: 128) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* Exact Match | One bp Off | Two bp Off |
|---|---|---|---|---|
| 67702113-67702137 | TTTATTTGGGCTATTTGCCAAACAG (SEQ ID NO: 129) | 1 | 0 | 0 |
| 67701288-67701312 | TTTAACTATGGTTCCTTTAAATCAG (SEQ ID NO: 130) | 1 | 0 | 0 |
| 67689761-67689785 | TTTATAAGGGGACAATCCAACATCT (SEQ ID NO: 131) | 1 | 0 | 0 |
| 67723825-67723849 | TTTATTCGGACCCGTGCTACAACTT (SEQ ID NO: 132) | 1 | 0 | 0 |
| 67686892-67686916 | TTTATTATCCATTTTAACTTGATTA (SEQ ID NO: 133) | 1 | 0 | 0 |
| 67698097-67698121 | TTTATCAGTTGTCCAATTTGTGGTG (SEQ ID NO: 134) | 1 | 0 | 0 |
| 67687614-67687638 | TTTAAATTCCCATGTTGCAACCCTA (SEQ ID NO: 135) | 1 | 0 | 0 |
| 67703251-67703275 | TTTAATAATTTTTCTACTTATACTT (SEQ ID NO: 136) | 1 | 0 | 0 |
| 67690109-67690133 | TTTACCCAGTGGGTAAAATGATCTA (SEQ ID NO: 137) | 1 | 0 | 0 |
| 67719750-67719774 | TTTAGGTGTATGATACTTTTAGTGC (SEQ ID NO: 138) | 1 | 0 | 0 |
| 67691762-67691786 | TTTAGGTTCTACATATTGAAGCTTT (SEQ ID NO: 139) | 1 | 0 | 0 |
| 67691654-67691678 | TTTAAGTTCTTGTTTGGTTCGGGGC (SEQ ID NO: 140) | 1 | 0 | 0 |
| 67695445-67695469 | TTTATTCATCACAACAGGTAAGTCC (SEQ ID NO: 141) | 1 | 0 | 0 |
| 67694579-67694603 | TTTAAAGGATAAAGAATAATATAGG (SEQ ID NO: 142) | 1 | 0 | 0 |
| 67693002-67693026 | TTTATTTTCACATCCACAGCTCCTA (SEQ ID NO: 143) | 1 | 0 | 0 |
| 67731932-67731956 | TTTAGTCCCCGCATCGTGTGGGGGG (SEQ ID NO: 144) | 1 | 0 | 0 |
| 67689608-67689632 | TTTATTTAGATGGAACTAGCATTCC (SEQ ID NO: 145) | 1 | 0 | 0 |
| 67691726-67691750 | TTTATCTGCACTTATTAAATGGCCT (SEQ ID NO: 146) | 1 | 0 | 0 |
| 67704995-67705019 | TTTATCCTTGGACATAATTAAAGAA (SEQ ID NO: 147) | 1 | 0 | 0 |
| 67694095-67694119 | TTTAACAGTGGCTTTAGTTCTCTTT (SEQ ID NO: 148) | 1 | 0 | 0 |
| 67688285-67688309 | TTTAGTACAGCAGCCTGAACTGACT (SEQ ID NO: 149) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* Exact Match | One bp Off | Two bp Off |
|---|---|---|---|---|
| 67692918-67692942 | TTTAAAACGACCTGGTCTCCCGCAT (SEQ ID NO: 150) | 1 | 0 | 0 |
| 67735442-67735466 | TTTACTCTGTGACAATATATTCTAT (SEQ ID NO: 151) | 1 | 0 | 0 |
| 67694119-67694143 | TTTATACTCCAAACTTCAGACCCAG (SEQ ID NO: 152) | 1 | 0 | 0 |
| 67694791-67694815 | TTTAAATTTAGTTTTTTTATTATCT (SEQ ID NO: 153) | 1 | 0 | 0 |
| 67695843-67695867 | TTTAAATAGGTAAAGGCAGGGAGGA (SEQ ID NO: 154) | 1 | 0 | 0 |
| 67695032-67695056 | TTTAACTCCTCTTTTTCTTTCTGGA (SEQ ID NO: 155) | 1 | 0 | 0 |
| 67703734-67703758 | TTTAATTTGGGAATATTGGGTTAAT (SEQ ID NO: 156) | 1 | 0 | 0 |
| 67690809-67690833 | TTTAGAGTCAGTATAGATGGTTTTT (SEQ ID NO: 157) | 1 | 0 | 0 |
| 67697085-67697109 | TTTATGCTGGGAACCGGAGGGCTGG (SEQ ID NO: 158) | 1 | 0 | 0 |
| 67690629-67690653 | TTTAAAAGAAAAGTTAGGTTGGTGT (SEQ ID NO: 159) | 1 | 0 | 0 |
| 67701642-67701666 | TTTATGTTGTACATGCCACAAAAAA (SEQ ID NO: 160) | 1 | 0 | 0 |
| 67693639-67693663 | TTTAGTAATGTCTGGCCAACTGTGA (SEQ ID NO: 161) | 1 | 0 | 0 |
| 67703876-67703900 | TTTATTTCTTGTTGGGAGGATGAGG (SEQ ID NO: 162) | 1 | 0 | 0 |
| 67690054-67690078 | TTTAATTAAGGCTTTGACTGCATTA (SEQ ID NO: 163) | 1 | 0 | 0 |
| 67695062-67695086 | TTTACACTCTTCACTCGCTTTGTCC (SEQ ID NO: 164) | 1 | 0 | 0 |
| 67689878-67689902 | TTTAAGAGTTTGATTTATCCTTTTT (SEQ ID NO: 165) | 1 | 0 | 0 |
| 67696347-67696371 | TTTAGCTATTTGTTATGGCAGCAAC (SEQ ID NO: 166) | 1 | 0 | 0 |
| 67694806-67694830 | TTTATTATCTTTCCAATACTTTAAC (SEQ ID NO: 167) | 1 | 0 | 0 |
| 67690245-67690269 | TTTAAGGCTTGTTTATTTGTGTTTT (SEQ ID NO: 168) | 1 | 0 | 0 |
| 67695377-67695401 | TTTATCTGGTCCCCGAGGCAGTGCA (SEQ ID NO: 169) | 1 | 0 | 0 |
| 67694295-67694319 | TTTAAAGAAGGATATTTAGAATTTT (SEQ ID NO: 170) | 1 | 0 | 0 |
| 67705602-67705626 | TTTAAAGGTAGGCCTCAAAAAGAAC (SEQ ID NO: 171) | 1 | 0 | 0 |
| 67693729-67693753 | TTTATTTGTTCTTTTAATTTATCTA (SEQ ID NO: 172) | 1 | 0 | 0 |
| 67694696-67694720 | TTTATCTGACCTAAATTTTGACCAA (SEQ ID NO: 173) | 1 | 0 | 0 |
| 67694318-67694342 | TTTAGGCTCCTGGGATTCACAAGAA (SEQ ID NO: 174) | 1 | 0 | 0 |
| 67697768-67697792 | TTTACTGGCAAACTGGGAGGAGAGA (SEQ ID NO: 175) | 1 | 0 | 0 |
| 67694989-67695013 | TTTAACCTTAACGTGCTTGAGGTTT (SEQ ID NO: 176) | 1 | 0 | 0 |
| 67687551-67687575 | TTTATTTCTATATTTTGAGGACATG (SEQ ID NO: 177) | 1 | 0 | 0 |
| 67694309-67694333 | TTTAGAATTTTTAGGCTCCTGGGAT (SEQ ID NO: 178) | 1 | 0 | 0 |
| 67693926-67693950 | TTTATGATTTGCTGCCAGAACATTT (SEQ ID NO: 179) | 1 | 0 | 0 |
| 67693602-67693626 | TTTATTGATTTTTTAAATTTTCTAA (SEQ ID NO: 180) | 1 | 0 | 0 |
| 67693896-67693920 | TTTATCCCACTGCGGGTCCTGAGCA (SEQ ID NO: 181) | 1 | 0 | 0 |
| 67718020-67718044 | TTTATAATTTCCATGCTTTTTCAGT (SEQ ID NO: 182) | 1 | 0 | 0 |
| 67700346-67700370 | TTTATCTGTAATTCTGCAGACCCTC (SEQ ID NO: 183) | 1 | 0 | 0 |
| 67696171-67696195 | TTTAAAGGGGAAGCTTTGAAGAGGA (SEQ ID NO: 184) | 1 | 0 | 0 |
| 67729142-67729166 | TTTACCTGCCGGTAGTCCTTGGTCC (SEQ ID NO: 185) | 1 | 0 | 0 |
| 67684112-67684136 | TTTACCAATGTGTTCTAAGTTTTCA (SEQ ID NO: 186) | 1 | 0 | 0 |
| 67693375-67693399 | TTTAAAAAAATAAATACTGACCTTG (SEQ ID NO: 187) | 1 | 0 | 0 |
| 67691807-67691831 | TTTATCTTGTAGGTGGTTAAGAACT (SEQ ID NO: 188) | 1 | 0 | 0 |
| 67700198-67700222 | TTTATTTCTTTTCACGAATTGCTGG (SEQ ID NO: 189) | 1 | 0 | 0 |
| 67697504-67697528 | TTTATGTGGTGTTCAGAGCCCCAGG (SEQ ID NO: 190) | 1 | 0 | 0 |
| 67701370-67701394 | TTTATCGGTGTTATTGATGATCATT (SEQ ID NO: 191) | 1 | 0 | 0 |

TABLE 3-continued

Universal HSC Safe Harbor Loci with Cpf1 Target Sites that Contain the Most Preferred PAM Sequence with 21 Adjacent Base Pairs that are Unique to the Human Genome

| Universal HSC Safe Harbor‡ Window on chr11: | Cpf1 Target Sequence (TTTA = PAM†) | Number of Sequences Identified in the Human Genome (hg38)* Exact Match | One bp Off | Two bp Off |
|---|---|---|---|---|
| 67703871-67703895 | TTTATTTTATTTCTTGTTGG GAGGA (SEQ ID NO: 192) | 1 | 0 | 0 |
| 67683323-67683347 | TTTAAATTGGCTATAAATCT TTGAC (SEQ ID NO: 193) | 1 | 0 | 0 |
| 67690737-67690761 | TTTACCTTTACTGTTAATTA GTCCT (SEQ ID NO: 194) | 1 | 0 | 0 |

‡GSH: loci identified by retrospective analysis of lentivirus integration sites in transplanted autologous gene modified blood stem and progenitor cells.
†PAM: protospacer adjacent motif sequence. TTTV is the denoted PAM recognition site for Cpf1; however, the strongest preference is for TTTA.
^ All sequences are depicted 5' to 3'.

crRNA for target SEQ ID NO: 132 includes UAAUUUCUACUCUUGUAGAUUUCGGACCCGUGCUACAACUU (SEQ ID NO: 195).

crRNA for target SEQ ID NO: 108 includes UAAUUUCUACUCUUGUAGAUAUAGAAUAGCCUCAUAUUUUA (SEQ ID NO: 196)

Cpf1 crRNA target sites and PAM sites within chr11: 67681215-67741765 include TTTGTGTCCCCGTTTTGGTTGGTAAAC (SEQ ID NO: 197), TTTAAAAATCAATACCGATAATAATGA (SEQ ID NO: 198), and TTTCTTAATATGAATATTAATATCGGT (SEQ ID NO: 199) (PAM sites italicized).

Cpf1 crRNA target sites and PAM sites within chr11: 67805337-67845629 include TTTCCGTATCTGGAAGGGGCATCTTGG (SEQ ID NO: 200) at 67812179-67812205, TTTCCTTAGGACCGGAAGGATTACAGC (SEQ ID NO: 201) at 67812226-67812252, TTTGCCTAAAAGGCACTATGTCAAATG (SEQ ID NO: 202) at 67812280-67812306, TTTGGAGCTGTTGGCATCATGTTCCTG (SEQ ID NO: 203) at 67812349-67812375, and TTTGATTCTTTTCTATCTCAGGACAGA (SEQ ID NO: 204) (PAM sites italicized).

Cpf1 crRNA target sites and PAM sites within chr11: 67895738-67941098 include: TTTATAGACATCCCACACTGTAGTTCT (SEQ ID NO: 205) at 67931362-67931388, TTTATTAATTTGAGAACCAACATAAGG (SEQ ID NO: 206) at 67931439-67931465, TTTATTTTCTTTTTGGTAAGAAGGAAC (SEQ ID NO: 207) at 67931473-67931499, and TTTCACACACACACACACACACACACA (SEQ ID NO: 208) at 67931516-67931542 (PAM sites italicized).

In particular embodiments, a Cpf1 crRNA target sequence includes TTTGGAGCTGTTGGCATCATGTTCCTG (SEQ ID NO: 203), and a crRNA for the target includes UAAUUUCUACUCUUGUAGAUGAGCUGUUGGCAUCAUGUUCCUG (SEQ ID NO: 209).

In particular embodiments, a Cpf1 crRNA target sequence includes TTTATCCAAACCTCCTAAATGATAC (SEQ ID NO: 210) located at chr11: 67839126-67839150, and a crRNA for the target includes: UAAUUUCUACUCUUGUAGAUUCCAAACCUCCUAAAUGAUAC (SEQ ID NO: 211).

In particular embodiments, a Cpf1 crRNA target sequence includes TTTACACCCGATCCACTGGGGAGCA (SEQ ID NO: 212) located at chr3: 46373915-46373939, and a crRNA for the target includes UAAUUUCUACUCUUGUAGAUCACCCGAUCCACUGGGGAGCA (SEQ ID NO: 260).

crRNAs were also designed based on the following 27 nt CRISPR/Cpf1 cut site sequence: TTTTTGATTCTTTTCTATCTCAGGACA (SEQ ID NO: 213) located within chr11: 67812443-67812469.

Homology-directed repair templates for HDR were also designed for nuclease-guide pairs with symmetric or asymmetric homology arms as described by Richardson et al., Nat Biotechnol. 2016; 34 (3): 339-44. Each donor template included homology arms (homology-directed repair template) flanking a 20 bp random DNA barcode element for clone tracking, upstream of a human phosphoglycerate kinase (PGK) promoter (e.g., SEQ ID NO: 214) driving expression of an enhanced green fluorescent protein (GFP) reporter gene (for experimental purposes, but akin to a therapeutic DNA sequence in clinical use). Humanized Cpf1 protein was synthesized by a commercial manufacturer (Aldevron), and guide RNA with two modifications, an atom oligoehtylene glycol spacer and a 3' terminal thiol was also obtained from a commercial source (Integrated DNA Technologies). Single-stranded homology template DNA (ssODN) was also synthesized by a commercial manufacturer (Integrated DNA Technologies). For examples of such sequences, see FIGS. 1, 3, 4, and 16.

As indicated, in particular embodiments, gene editing systems to provide a genetic therapy within a GSH will include guide RNA and a nuclease. In particular embodiments, donor templates can be used, especially when performing a gain-of-function therapy or a precise loss-of-function therapy. In particular embodiments, gene editing systems include a homology-directed repair template and a therapeutic nucleic acid sequence.

All nucleic acid-based components of gene editing systems can be single stranded, double stranded, or may have mix of single stranded and double stranded regions. For example, guide RNA or a donor template may be a single-stranded DNA, a single-stranded RNA, a double-stranded DNA, or a double-stranded RNA. In particular embodiments utilizing nanoparticles described herein, the end of a nucleic acid farthest from the nanoparticle surface may be protected (e.g., from exonucleolytic degradation) by methods known to those of skill in the art. For example, one or more dideoxynucleotide residues can be added to the 3' terminus of a linear molecule and/or self-complementary oligonucleotides are ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include addition of terminal amino group(s) and the use of modified internucleotide linkages such as, for example, phosphorothioates, phosphoramidates, and O-methyl ribose or deoxyribose residues. Chemically modified mRNA can be used to increase intracellular stability, while asymmetric homology arms and phosphorothioate modification can be incorporated into the ssODN to improve HDR efficiency. In particular embodiments utilizing nanoparticles described herein, nucleic acids may be protected from electrostatic (charge-based) repulsions by, for example, addition of a charge shielding spacer. In particular embodiments, a charge shielding spacer can include an 18 atom oligoethylene glycol (OEG) spacer added to one or both ends. In particular embodiments, a charge shielding spacer can include a 10-26 atom oligoethylene glycol (OEG) spacer added to one or both ends.

Donor templates can be of any length, e.g., 10 nucleotides or more, 50 nucleotides or more, 100 nucleotides or more, 250 nucleotides or more, 500 nucleotides or more, 1000 nucleotides or more, 5000 nucleotides or more, etc.

In particular embodiments, a homology-directed repair template is designed to serve as a template in homologous recombination, such as within or near a target sequence nicked or cleaved by an enzyme (e.g., nuclease) of a gene editing system. A homology-directed repair template polynucleotide may be of any suitable length, such as 10, 15, 20, 25, 50, 75, 100, 150, 200, 500, 1000, 2000, 3000, 4000, 5000, or more nucleotides. In particular embodiments, the homology-directed repair template polynucleotide is complementary to a portion of a polynucleotide including the target sequence. When optimally aligned, a homology-directed repair template polynucleotide overlaps with one or more nucleotides of a target sequence (e.g., 1, 5, 10, 15, 20, 25, 30, 35, 40, 45, 50, 60, 70, 80, 90, 100 or more nucleotides).

In particular embodiments, the homology-directed repair template can include sufficient homology to a genomic sequence at the cleavage site, e.g. 70%, 80%, 85%, 90%, 95%, or 100% homology with the nucleotide sequences flanking the cleavage site, e.g., within 50 bases or less of the cleavage site, e.g., within 30 bases, within 15 bases, within 10 bases, within 5 bases, or immediately flanking the cleavage site, to support HDR between it and the genomic sequence to which it bears homology. 25, 50, 100, or 200 nucleotides, or more than 200 nucleotides of sequence homology between a homology-directed repair template and a targeted genomic sequence (or any integral value between 10 and 200 nucleotides, or more) can support HDR. Homology arms or flanking sequences are generally identical to the genomic sequence, for example, to the genomic region in which the double stranded break (DSB) occurs. However, absolute identity is not required.

In particular embodiments, the donor template includes a heterologous therapeutic nucleic acid sequence flanked by two regions of homology, such that homology-directed repair between the target DNA region and the two flanking sequences results in insertion of the heterologous therapeutic nucleic acid sequence at the target region.

In some examples, homology arms or flanking sequences of homology-directed repair templates are asymmetrical.

As indicated, in particular embodiments, donor templates include a therapeutic nucleic acid sequence. Therapeutic nucleic acid sequences can include a corrected gene sequence; a complete gene sequence and/or one or more regulatory elements associated with expression of the gene. A corrected gene sequence can be a portion of a gene requiring correction or can provide a complete replacement copy of a gene. A corrected gene sequence can provide a complete copy of a gene, without necessarily replacing an existing defective gene. One of ordinary skill in the art will recognize that removal of a defective gene when providing a corrected copy may or may not be required. When inserting a gene within a genetic safe harbor, a therapeutic nucleic acid sequence should include a coding region and all regulatory elements required for its expression.

Examples of therapeutic genes and gene products include skeletal protein 4.1, glycophorin, p55, the Duffy allele, globin family genes; WAS; phox; dystrophin; pyruvate kinase; CLN3; ABCD1; arylsulfatase A; SFTPB; SFTPC; NLX2.1; ABCA3; GATA1; ribosomal protein genes; TERT; TERC; DKC1; TINF2; CFTR; LRRK2; PARK2; PARK7; PINK1; SNCA; PSEN1; PSEN2; APP; SOD1; TDP43; FUS; ubiquilin 2; C9ORF72, a231; αvβ3; αvβ5; αvβ63; BOB/GPR15; Bonzo/STRL-33/TYMSTR; CCR2; CCR3; CCR5; CCR8; CD4; CD46; CD55; CXCR4; aminopeptidase-N; HHV-7; ICAM; ICAM-1; PRR2/HveB; HveA; α-dystroglycan; LDLR/a2MR/LRP; PVR; PRR1/HveC, laminin receptor, 101F6, 123F2, 53BP2, abl, ABLI, ADP, aFGF, APC, ApoAl, ApoAIV, ApoE, ATM, BAI-1, BDNF, Beta*(BLU), bFGF, BLC1, BLC6, BRCA1, BRCA2, CBFA1, CBL, C-CAM, CFTR, CNTF, COX-1, CSFIR, CTS-1, cytosine deaminase, DBCCR-1, DCC, Dp, DPC-4, E1A, E2F, EBRB2, erb, ERBA, ERBB, ETS1, ETS2, ETV6, Fab, FancA, FancB, FancC, FancD1, FancD2, FancE, FancF, FancG, Fancl, FancJ, FancL, FancM, FancN, FancO, FancP, FancQ, FancR, FancS, FancT, FancU, FancV, and FancW, FCC, FGF, FGR, FHIT, fms, FOX, FUS 1, FUS1, FYN, G-CSF, GDAIF, Gene 21, Gene 26, GM-CSF, GMF, gsp, HCR, HIC-1, HRAS, hst, IGF, IL-1, IL-2, IL-3, IL-4, IL-5, IL-6, IL-7, IL-8, IL-9, IL-10, IL-11 IL-12, ING1, interferon α, interferon β, interferon γ, IRF-1, JUN, KRAS, LCK, LUCA-1, LUCA-2, LYN, MADH4, MADR2, MCC, mda7, MDM2, MEN-I, MEN-II, MLL, MMAC1, MYB, MYC, MYCL1, MYCN, neu, NF-1, NF-2, NGF, NOEY1, NOEY2, NRAS, NT3, NT5, OVCA1, p16, p21, p27, p53, p57, p73, p300, PGS, PIM1, PL6, PML, PTEN, raf, Rap1A, ras, Rb, RB1, RET, rks-3, ScFv, scFV ras, SEM A3, SRC, TAL1, TCL3, TFPI, thrombospondin, thymidine kinase, TNF, TP53, trk, T-VEC, VEGF, VHL, WT1, WT-1, YES, zac1, iduronidase, IDS, GNS, HGSNAT, SGSH, NAGLU, GUSB, GALNS, GLB1, ARSB, HYAL1, F8, F9, HBB, CYB5R3, γC, JAK3, IL7RA, RAG1, RAG2, DCLRE1C, PRKDC, LIG4, NHEJ1, CD3D, CD3E, CD3Z, CD3G, PTPRC, ZAP70, LCK, AK2, ADA, PNP, WHN, CHD7, ORAI1, STIM1, CORO1A, CIITA, RFXANK, RFX5, RFXAP, RMRP, DKC1, TERT, TINF2, DCLRE1B, and SLC46A1.

In particular embodiments, a therapeutic gene includes a coding sequence for a therapeutic expression product (e.g., protein, RNA) and all associated regulatory elements (e.g., promoters, etc.) to result in expression of the gene product.

In particular embodiments, a therapeutic nucleic acid sequence (e.g., a gene) can be selected for incorporation into a GSH to provide for in vivo selection of the genetically modified cell. For example, in vivo selection using a cell-growth switch allows a minor population of genetically modified cells to be inducibly amplified. A strategy to achieve in vivo selection has been to employ drug selection while coexpressing a transgene that conveys chemoresistance, such as 06-methylguanine-DNA-methyltransferase (MGMT). An alternate approach is to confer an enhanced proliferative potential upon gene-modified HSC through the delivery of the homeobox transcription factor HOXB4. In particular embodiments, a suicide gene can be incorporated into the genetically modified cell so that such population of cells can be eliminated, for example, by administration of a drug that activities the suicide gene. See, for example, Cancer Gene Ther. 2012 August; 19 (8): 523-9; PLOS One. 2013; 8 (3): e59594. and Molecular Therapy-Oncolytics (2016) 3, 16011.

Particular embodiments include contacting a blood cell with a gene editing system capable of inserting a donor template at a target blood cell GSH. In particular embodiments, the gene editing system includes crRNA capable of hybridizing to a target sequence within the GSH, and a nucleic acid encoding a nuclease enzyme such as Cpf1 or Cas9. In particular embodiments, Cas9 or Cpf1 coding sequences can include SEQ ID NOs: 215-227. In particular embodiments, Cas9 or Cpf1 amino acid sequences can include SEQ ID NOs: 228-241.

Figure 2:
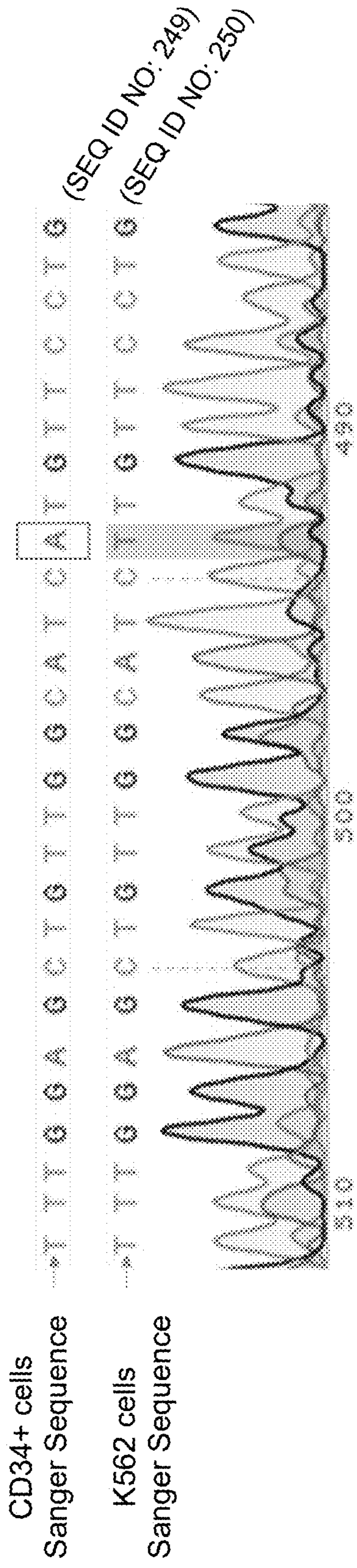
FIG. 2. A trace of a Sanger sequencing result showing a mutation in one target GSH site in K562 cells (SEQ ID NOs: 249 and 250).
Figure 5:
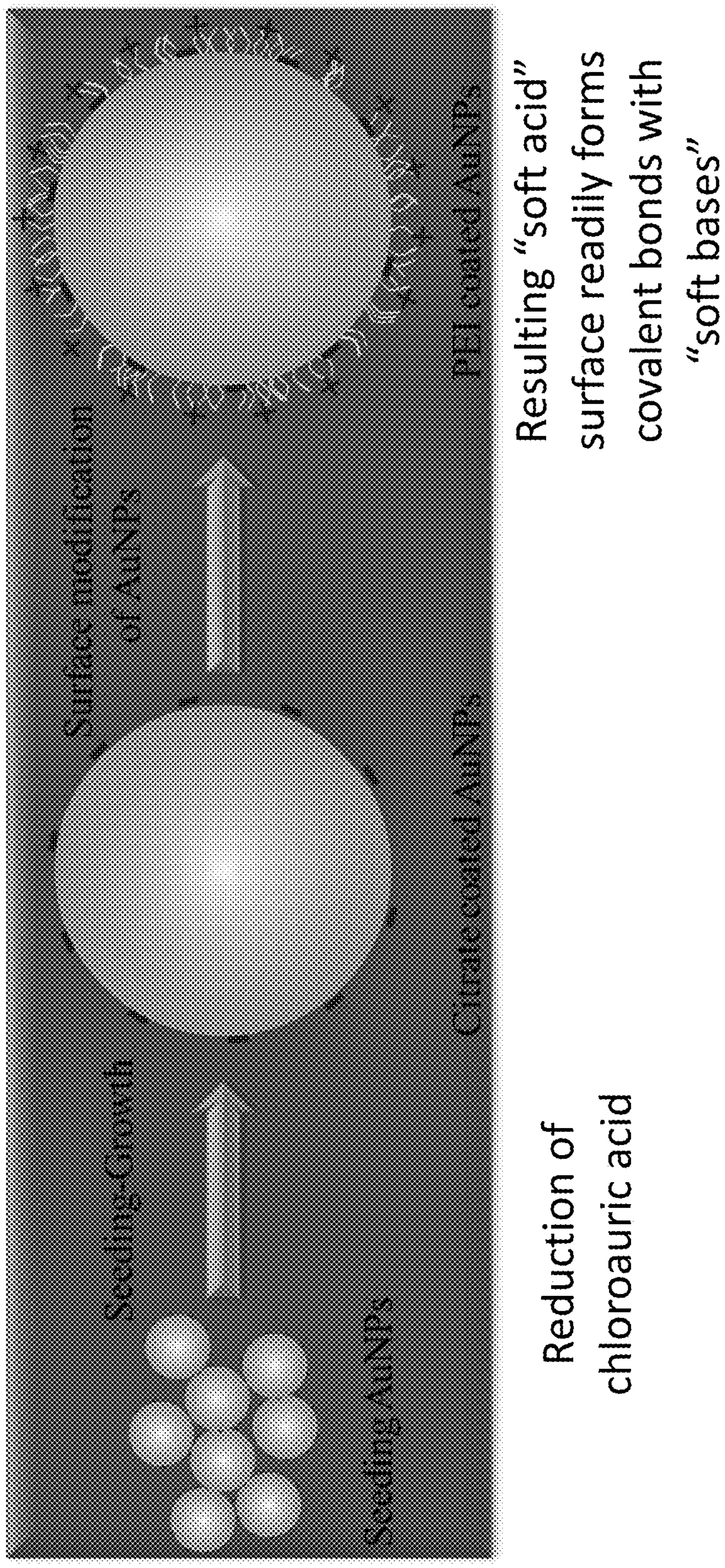
FIG. 5. Schematic of early production scheme for gold nanoparticles (AuNPs), a scalable, synthetic delivery scaffold with established in vivo compatibility.

In a particular exemplary embodiment, a Cpf1/crRNA gene editing system was designed to target the chr11: 67812349-67812375 genomic safe harbor (GSH) location (FIG. 1). Sanger sequencing results in K562 for this location spotted a A>T mutation in 15 bp after the PAM site (TTTG; FIG. 2) which resulted in lower cutting efficiency in this cell line compared to $CD^{34}$+ cells. Also it has been shown that the cutting efficiency for the TTTA PAM site is higher than TTTG or TTTC. Therefore, another GSH location was identified in chromosome 11 (chr11: 67839126-67839150) with a TTTA PAM site which can increase cutting efficiency (FIG. 3). In addition, a SNP screen in this location did not identify any common SNP. Homology-directed repair templates (HT) were also designed. Synthesized HTs were 100 bp ssDNA bearing NotI restriction site for the assessment of HDR (FIGS. 1 and 3).

(III) Nanoparticles. As indicated previously, delivery methods of gene editing systems that do not rely on electroporation or viral vectors are needed. In addition to providing GSH and associated targeting gene editing components, the current disclosure also provides engineered nanoparticles that allow delivery of the gene editing components. The nanoparticles are engineered to include all components for targeted gene editing, for example, within a GSH. When a therapeutic use need only de-activate a problematic gene, the nanoparticles need only be associated with a targeting element and a cutting element (although other components may be included as necessary or helpful for a particular purpose). When a therapeutic use adds or corrects a gene, the nanoparticles are associated with a targeting element, a cutting element, and a donor template.

Particular embodiments utilize colloidal metal nanoparticles. A colloidal metal includes any water-insoluble metal particle or metallic compound dispersed in liquid water. A colloid metal can be a suspension of metal particles in aqueous solution. Any metal that can be made in colloidal form can be used, including gold, silver, copper, nickel, aluminum, zinc, calcium, platinum, palladium, and iron. In particular embodiments, gold nanoparticles are used, e.g., prepared from $HAuCl_4$. In particular embodiments, the nanoparticles are non-gold nanoparticles that are coated with gold to make gold-coated nanoparticles.

Methods for making colloidal metal nanoparticles, including gold colloidal nanoparticles from $HAuCl_4$, are known to those having ordinary skill in the art. For example, the methods described herein as well as those described elsewhere (e.g., US 2001/005581; 2003/0118657; and 2003/0053983) can be used to make nanoparticles.

In particular exemplary embodiments, AuNPs were synthesized in three different size ranges (15, 50, 100 nm) by an optimized Turkevich and seeding-growth methods (Shahbazi, et al., Nanomedicine (Lond), 2017. 12 (16): p. 1961-1973; Shahbazi, et al., Nanotechnology, 2017. 28 (2): p. 025103; Turkevich, et al. Discussions of the Faraday Society, 1951. 11 (0): p. 55-75; Perrault & Chan, Journal of the American Chemical Society, 2009. 131 (47): p. 17042-17043). In the first step, seed AuNPs of 15 nm were synthesized by bringing 100 ml of 0.25 mM gold (III) chloride trihydrate solution to the boiling point and adding 1 mL of 3.33% trisodium citrate dehydrate solution. Synthesis of nanoparticles was carried out in high stirring speeds over 10 min. Prepared nanoparticles were cooled down to 4° C. and used in the following growth step.

In order to prepare AuNPs in 50 nm and 100 nm size ranges, two different 100 ml of 0.25 mM gold (III) chloride trihydrate solutions were prepared and in mild stirring conditions 2440 μL and 304 L of seed AuNPs were added separately to synthesize 50 nm and 100 nm AuNPs, respectively. To these solutions was added 1 mL of 15 mM trisodium citrate dehydrate solution and the mixture was brought to the highest stirring speed. Then, 1 mL of 25 mM hydroquinone solution was added and synthesis was continued over 30 min for 50 nm AuNPs and 5 h for 100 nm AuNPs. Finally, synthesized nanoparticles were purified by centrifuging at 5000×g and dispersing in ultra-pure water.

While AuNPs are particularly described, nanoparticles encompassed in the present disclosure may be provided in different forms, e.g., as solid nanoparticles (e.g., metal such as silver, gold, iron, titanium), non-metal, lipid-based solids, polymers, suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present disclosure.

Semi-solid and soft nanoparticles have been manufactured, and are within the scope of the present disclosure. A nanoparticle of a semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

A nanoparticle can include any suitable material, e.g., a biocompatible material. The biocompatible material can be a polymer. Suitable nanoparticle polymers include polystyrene, silicone rubber, polycarbonate, polyurethanes, polypropylenes, polymethylmethacrylate, polyvinyl chloride, polyesters, polyethers, and polyethylene. Examples of specific polymers include poly(caprolactone) (PCL), ethylene vinyl acetate polymer (EVA), poly(lactic acid) (PLA), poly (L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), poly anhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyethylenimine (PEI), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho) esters, poly(butyric acid), poly(valeric acid), poly(lactide-co-caprolactone), trimethylene carbonate, and polyvinylpyrrolidone.

In particular embodiments, the nanoparticle is a lipid nanoparticle. A lipid nanoparticle can include one or more lipids, and one or more of the polymers listed above.

Lipidoid compounds are also particularly useful in the administration of gene editing system components. In particular embodiments, aminoalcohol lipidoid compounds are combined with gene editing system components to be delivered to a cell or a subject to form microparticles, nanoparticles, liposomes, or micelles. The gene editing system components to be delivered by the particles, liposomes, or micelles may be a polynucleotide, protein, peptide, or small molecule. Aminoalcohol lipidoid compounds may be combined with other aminoalcohol lipidoid compounds, polymers (synthetic or natural), surfactants, cholesterol, carbohydrates, proteins, lipids, etc. to form particles.

Figure 6:
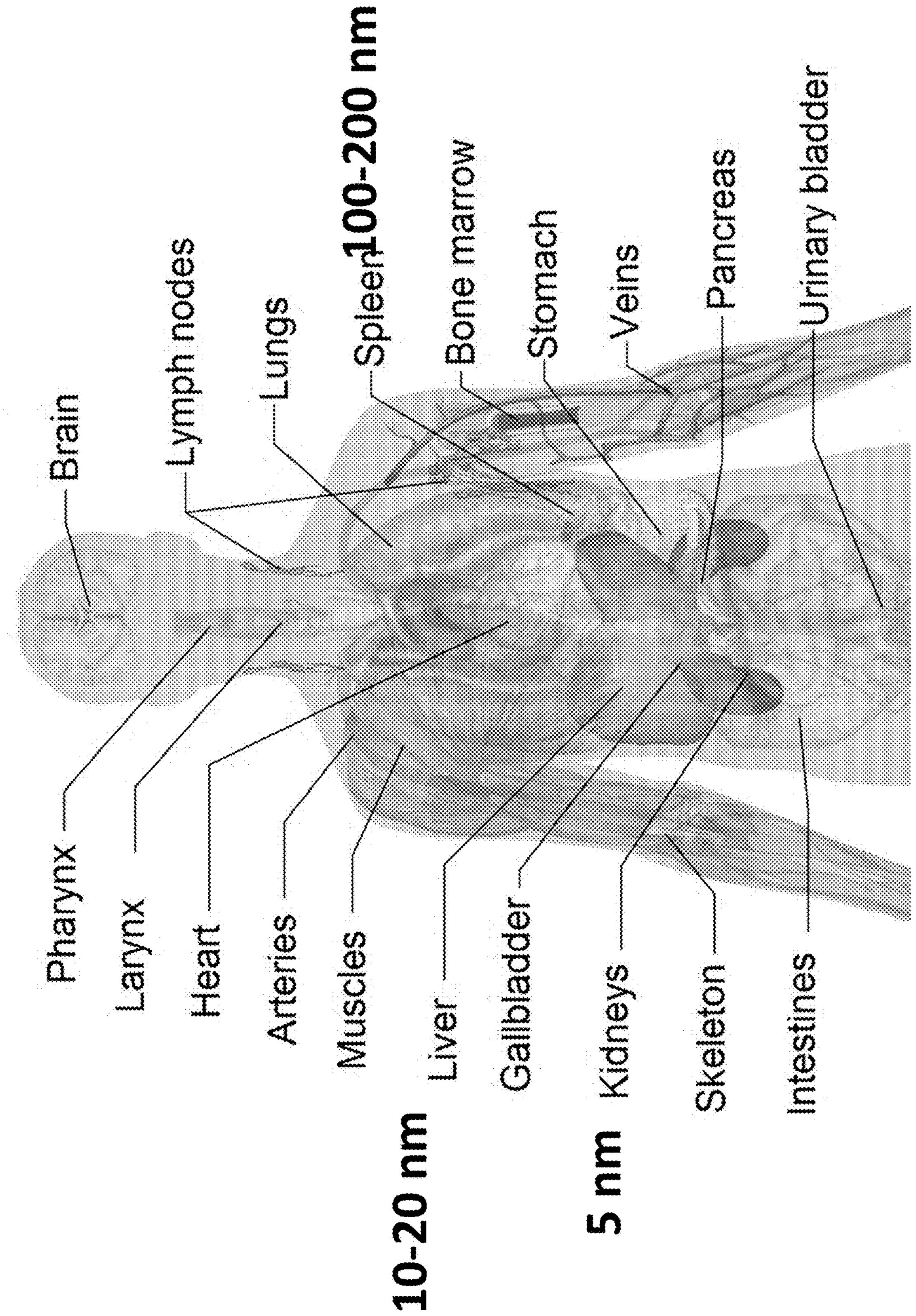
FIG. 6. AuNP size determines destination tissue/elimination pathway in humans.

As depicted in FIG. 6, the size of an AuNP can be selected to affect biodistribution within the human body. Nanoparticles suitable for use in the present disclosure can be any shape and can range in size from 5 nm-1000 nm in size, e.g., from 5 nm-10 nm, 5-50 nm, 5 nm-75 nm, 5 nm-40 nm, 10 nm-30, or 20 nm-30 nm. Nanoparticles can also have a size in the range of from 10 nm-15 nm, 15 nm-20 nm, 20 nm-25 nm, 25 nm-30 nm, 30 nm-35 nm, 35 nm-40 nm, 40 nm-45 nm, or 45 nm-50 nm, 50 nm-55 nm, 55 nm-60 nm, 60 nm-65 nm, 65 nm-70 nm, 70 nm-75 nm, 75 nm-80 nm, 80 nm-85 nm, 85 nm-90 nm, 90 nm-95 nm, 95 nm-100 nm, 100 nm-105 nm, 105 nm-110 nm, 110 nm-115 nm, 115 nm-120 nm, 120 nm-125 nm, 125 nm-130 nm, 130 nm-135 nm, 135 nm-140 nm, 140 nm-145 nm, 145 nm-150 nm, 100 nm-500 nm, 100 nm-150 nm, 150 nm-200 nm, 200 nm-250 nm, 250 nm-300 nm, 300 nm-350 nm, 350 nm-400 nm, 400 nm-450 nm, or 450 nm-500 nm. In particular embodiments, nanoparticles greater than 550 nm are excluded. This is because particles or aggregrated particles of >600 nm are not amenable to cellular uptake.

Particular embodiments can also include nanoparticles associated with targeting molecules. Targeting molecules can be used to target the nanoparticle to a specific cell so that activity of the gene editing system can be spatially or temporally controlled. For example, the activity and destination of the gene editing system can be controlled by a targeting molecule that has binding affinity for a cell surface protein or other localized cellular component.

In particular embodiments, targeting molecules include antibodies or binding domains thereof that result in selective delivery of nanoparticles to selected cell types. In particular embodiments, selective delivery is exclusive to a selected cell population. In particular embodiments, at least 65%, 70%, 75%, 80%, 85%, 90%, 95% or 99% of administered nanoparticles are delivered to a selected cell population.

In particular embodiments, binding domains include cell marker ligands, receptor ligands, antibodies, peptides, peptide aptamers, nucleic acids, nucleic acid aptamers, spiegelmers or combinations thereof. Within the context of selected cell targeting ligands, binding domains include any substance that binds to another substance to form a complex capable of supporting selective delivery.

As indicated, "antibodies" are one example of binding domains and include whole antibodies or binding fragments of an antibody, e.g., Fv, Fab, Fab', $F(ab')_2$, Fc, and single chain Fv fragments (scFvs) or any biologically effective fragments of an immunoglobulin that bind specifically to a motif expressed by a selected cell type. Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies.

Antibodies from human origin or humanized antibodies have lowered or no immunogenicity in humans and have a lower number of non-immunogenic epitopes compared to non-human antibodies. Antibodies and their fragments will generally be selected to have a reduced level of antigenicity in human subjects.

In particular embodiments, HSCs are targeted for selective delivery of nanoparticles. In particular embodiments, HSCs are targeted for selective delivery with binding domains that selectively bind CD34 and CD90. In particular embodiments, HSC can be targeted for selective delivery with one or more binding domains that selectively bind known antigens expressed on the surface of HSCs and HSPCs: CD34, CD46, CD90, CD133, Sca-1 and/or CD117.

Mature T cells can be targeted for selective delivery with binding domains that selectively bind CD3. Activated T-cells can be targeted for selective delivery with binding domains that selectively bind 4-1BB (CD137), CD69, and/or CD25. T helper cells can be targeted for selective delivery with binding domains that selectively bind CD4.Cytotoxic T-cells can be targeted for selective delivery with binding domains that selectively bind CD8. "Central memory" T-cells (or "TCM") can be targeted for selective delivery with binding domains that selectively bind CD62L, CCR7, CD25, CD127, CD45RO, and/or CD95. "Effector memory" T-cell (or "TEM") can be targeted for selective delivery with binding domains that selectively bind granzyme B and/or perforin. Regulatory T cells ("TREG") can be targeted for selective delivery with binding domains that selectively bind CD25, CTLA-4, GITR, GARP and/or LAP. "Naive" T-cells can be targeted for selective delivery with binding domains that selectively bind CD62L, CCR7, CD28, CD127 and/or CD45RA.

Natural killer cells (also known as NK cells, K cells, and killer cells) can be targeted for selective delivery with binding domains that selectively bind CD8, CD16 and/or CD56.

Macrophages (and their precursors, monocytes) can be targeted for selective delivery with binding domains that selectively bind CD11b, F4/80; CD68; CD11c; IL-4Ra; and/or CD163.

Immature dendritic cells (i.e., pre-activation) can be targeted for selective delivery with binding domains that selectively bind: CD1a, CD1b, CD1c, CD1d, CD21, CD35, CD39, CD40, CD86, CD101, CD148, CD209, and/or DEC-205.

B cells can be targeted for selective delivery with binding domains that selectively bind CD5, CD19, CD20, CD21, CD22, CD35, CD40, CD52, and/or CD80.

Lymphocyte function-associated antigen 1 (LFA-1) is expressed by all T-cells, B-cells, and monocytes/macrophages. Accordingly, selected cell targeting ligands can bind LFA-1 to achieve selective delivery of nanoparticles to T-cells, B-cells, and monocytes/macrophages.

In particular embodiments, a targeting molecule can be responsive to, i.e. activated or inactivated by, an effector on or in the cell. In particular embodiments, other components within a sequence can include regulatory nucleotides such as a promoter element, a small interfering or hairpin RNA or a microRNA to control expression of another gene in the same cell, or a DNA barcode for cellular tracking.

Aptamers may be designed to facilitate selective delivery, including delivery across the cellular membrane, to intracellular compartments, or into the nucleus. Such a structure can include, either in addition to the one or more aptamer(s) or without such one or more aptamer(s), moiety(ies) so as to render the guide deliverable, inducible or responsive to (for example activatable or inactivatable by) a selected effector, for example responds to normal or pathological physiological conditions, including without limitation pH, hypoxia, $O_2$ concentration, temperature, protein concentration, enzymatic concentration, lipid structure, light exposure, mechanical disruption (e.g., ultrasound waves), magnetic fields, electric fields, or electromagnetic radiation. Methods of making aptamers and conjugating such aptamers to the surface of a nanoparticle are known in the art, see for example Huang et al. *Anal. Chem.,* 2008, 80 (3), pp 567-572.

In particular embodiments, an RNA aptamer sequence has binding affinity for an aptamer ligand on or in the cell. In particular embodiments, the aptamer ligand is on the cell, for example so that it is at least partially available on the extra-cellular face or side of the cell membrane. For example, the aptamer ligand may be a cell-surface protein. The aptamer ligand may therefore be one part of a fusion protein, one other part of the fusion protein having a membrane anchor or membrane-spanning domain. In particular embodiments, the aptamer ligand is in the cell. For example, the aptamer ligand may be internalized within a cell, i.e. within (beyond) the cell membrane, for example in the cytoplasm, within an organelle (including mitochondria), within an endosome, or in the nucleus. In particular embodiments, an aptamer can include a donor template sequence, which can include an HDR template and a therapeutic nucleic acid sequence.

(IV) Conjugation of Active Components to Nanoparticles. As indicated, a variety of active components can be conjugated to the nanoparticles disclosed herein for targeted gene editing. For example, nucleic acids that are gene editing system components can be conjugated directly or indirectly, and covalently or noncovalently, to the surface of the nanoparticle. For example, a nucleic acid may be covalently bonded at one end of the nucleic acid to the surface of the nanoparticle.

Nucleic acids conjugated to the nanoparticle can have a length of from 10 nucleotides (nt) 1000 nt, e.g., 1 nt-25 nt, 25 nt-50 nt, 50 nt-100 nt, 100 nt-250 nt, 250 nt-500 nt, 500 nt-1000 nt or greater than 1000 nt. In particular embodiments, nucleic acids modified by conjugation to a linker do not exceed 50 nt or 40 nt in length.

When conjugated indirectly through, for example, an intervening linker, any type of molecule can be used as a linker. For example, a linker can be an aliphatic chain including at least two carbon atoms (e.g., 3, 4, 5, 6, 7, 8, 9, 10, 11, 12, 13, 14, or more carbon atoms), and can be substituted with one or more functional groups including a ketone, ether, ester, amide, alcohol, amine, urea, thiourea, sulfoxide, sulfone, sulfonamide, and/or disulfide.

In particular embodiments the linker includes a disulfide at the free end (e.g. the end not conjugated to the guide RNA) that couples the nanoparticle surface. In particular embodiments, the disulfide is a C2-C10 disulfide, that is it can be an aliphatic chain terminating in a disulfide that includes 2, 3, 4, 5, 6, 7, 8, 9, or 10 carbon atoms, although it is envisioned that longer aliphatic chains can be used. In particular embodiments, the disulfide is a 3 carbon disulfide (C3 S-S). Linkers can have either sulfhydryl groups (SH) or disulfide groups (S-S) or a different number of sulfur atoms. In particular embodiments, a thiol modification can be introduced without using a linker. In particular embodiments, a nuclease enzyme is delivered as a protein pre-conjugated with its guide RNA (a ribonucleoprotein (RNP) complex). In this formulation, the guide RNA molecule is bound to the nanoparticle and the nuclease enzyme, by default, can be also bound (see, for example, FIGS. 7B and 7D).

One advance disclosed herein is the ability to modify CRISPR components for linkage to a nanoparticle. This is because most of the modifications in CRISPR components can compromise cutting efficiency. For example, Li et al. (Engineering CRISPR-Cpf1 crRNAs and mRNAs to maximize genome editing efficiency. 2017. 1: p. 0066) indicated that the 5' end of Cpf1 crRNA is not safe for any modification because such modifications result in the abrogation of the crRNA binding to Cpf1 nuclease. Disclosed herein is a modification to the 3' end of crRNA that does not compromise cutting efficiency. In particular embodiments, in the first step of conjugation to a nanoparticle the 3' end of the crRNA is modified with an 18-atom hexa-ethyleneglycol spacer (18 spacer) and 3 carbon disulfide (C3 S-S) to attach the crRNA to the surface of AuNPs.

Based on the foregoing, in particular embodiments, for example when the nanoparticle includes gold, a linker can be any thiol-containing molecule. Reaction of a thiol group with Au results in a covalent sulfide (—S—) bond. AuNPs have high affinity to thiol (—SH) and dithiol (S-S) groups and semi-covalent bonds occur between the surface of AuNP and sulfur groups (Hakkinen, Nat Chem, 2012. 4 (6): p. 443-455). In particular embodiments, thiol groups can be added to nucleic acids to facilitate attachment to the surface of AuNPs. This approach can improve nucleic acid uptake and stability (see, e.g., Mirkin, et al., A Nature, 1996. 382 (6592): p. 607-609).

Figure 7A:
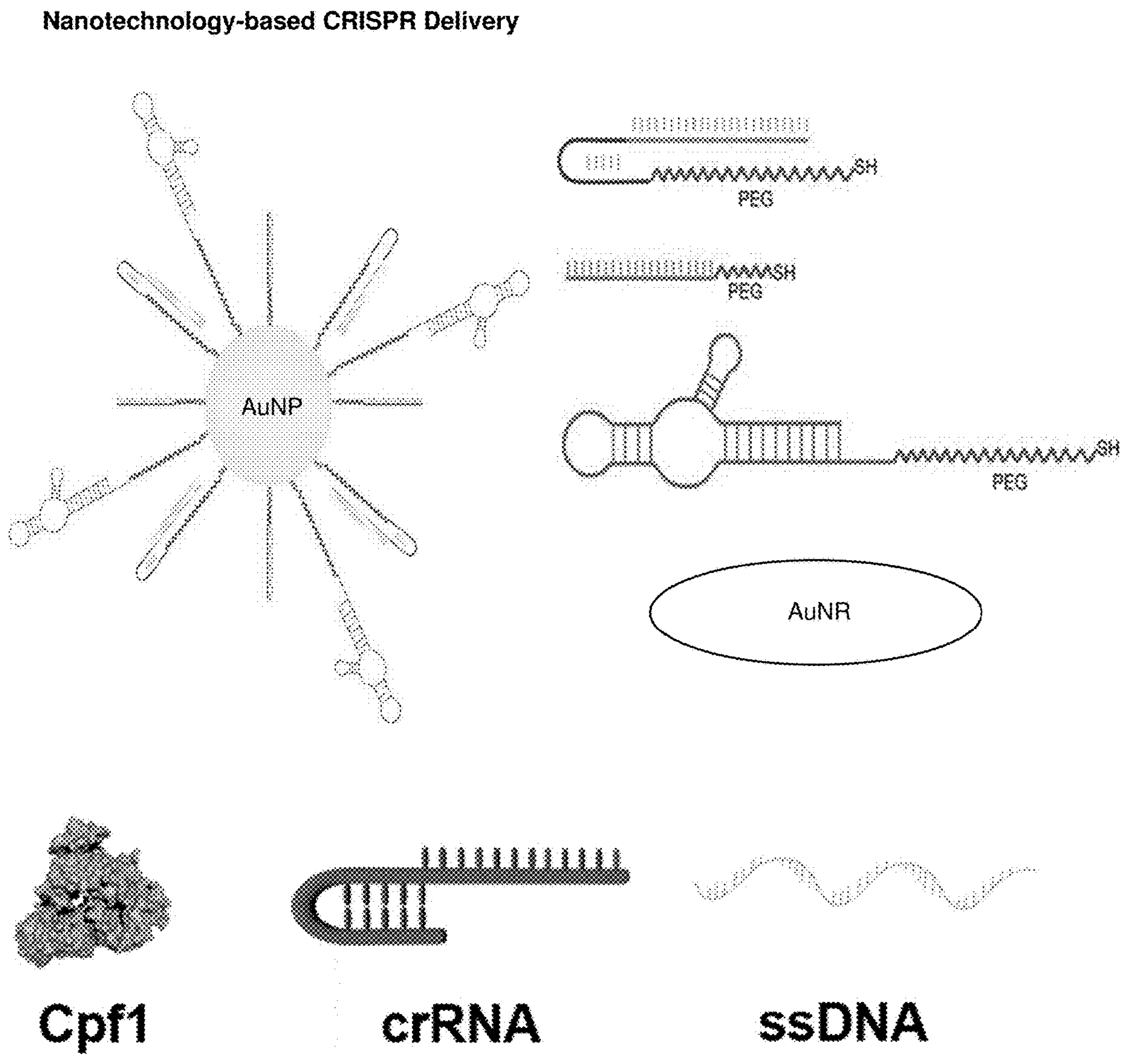
FIGS. 7A-7D. Schematics depicting an exemplary AuNP associated with all gene editing components required for gene addition and/or correction.
Figure 7B:
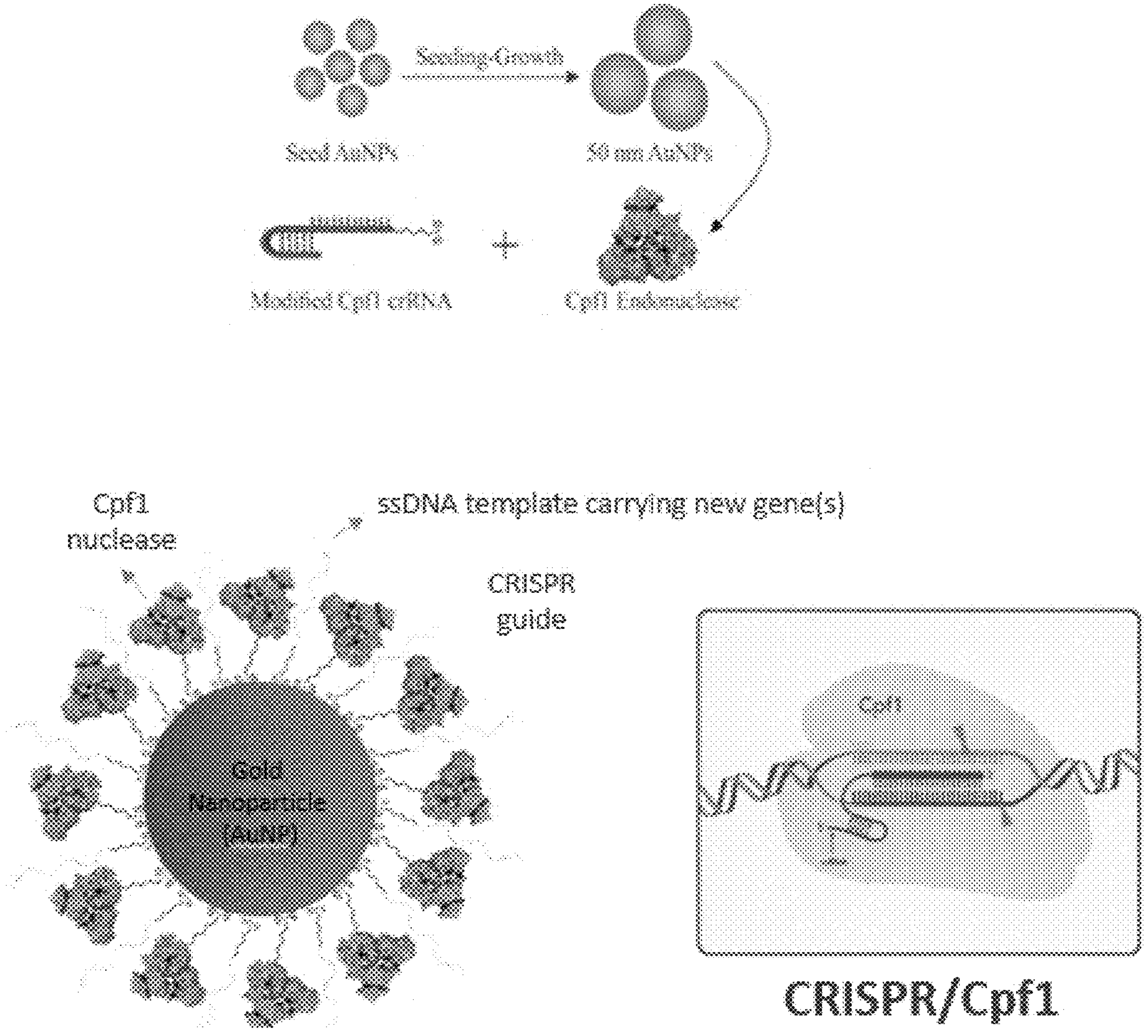
Figure 7C:
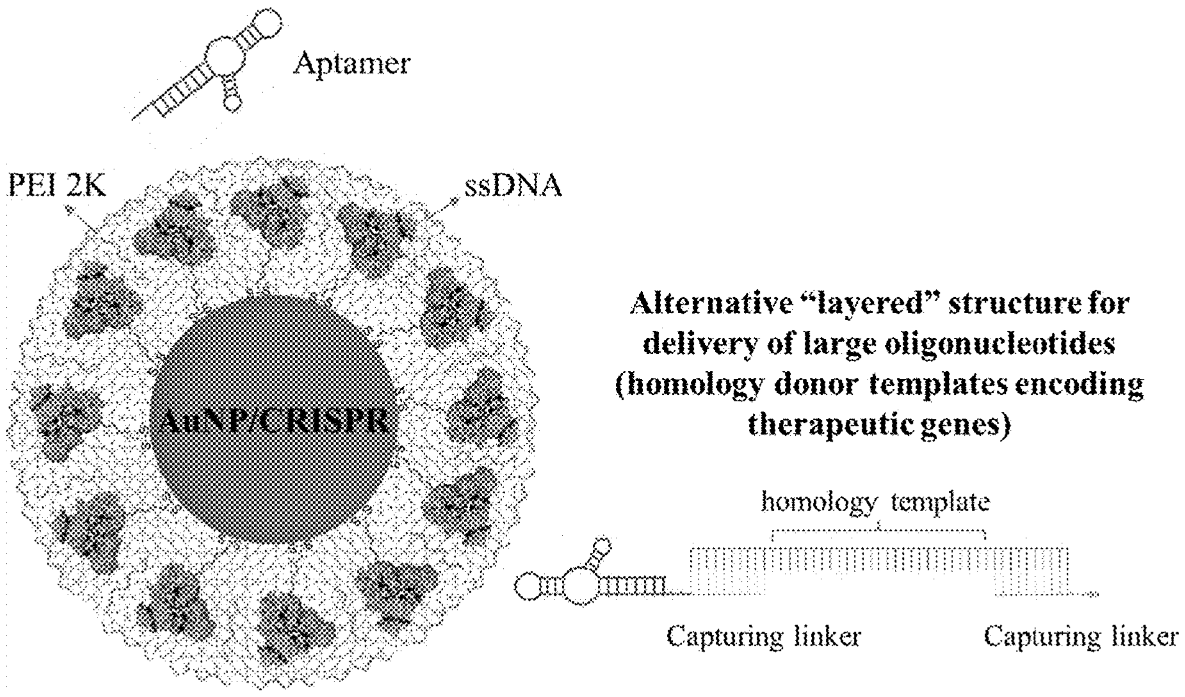
Figure 7D:
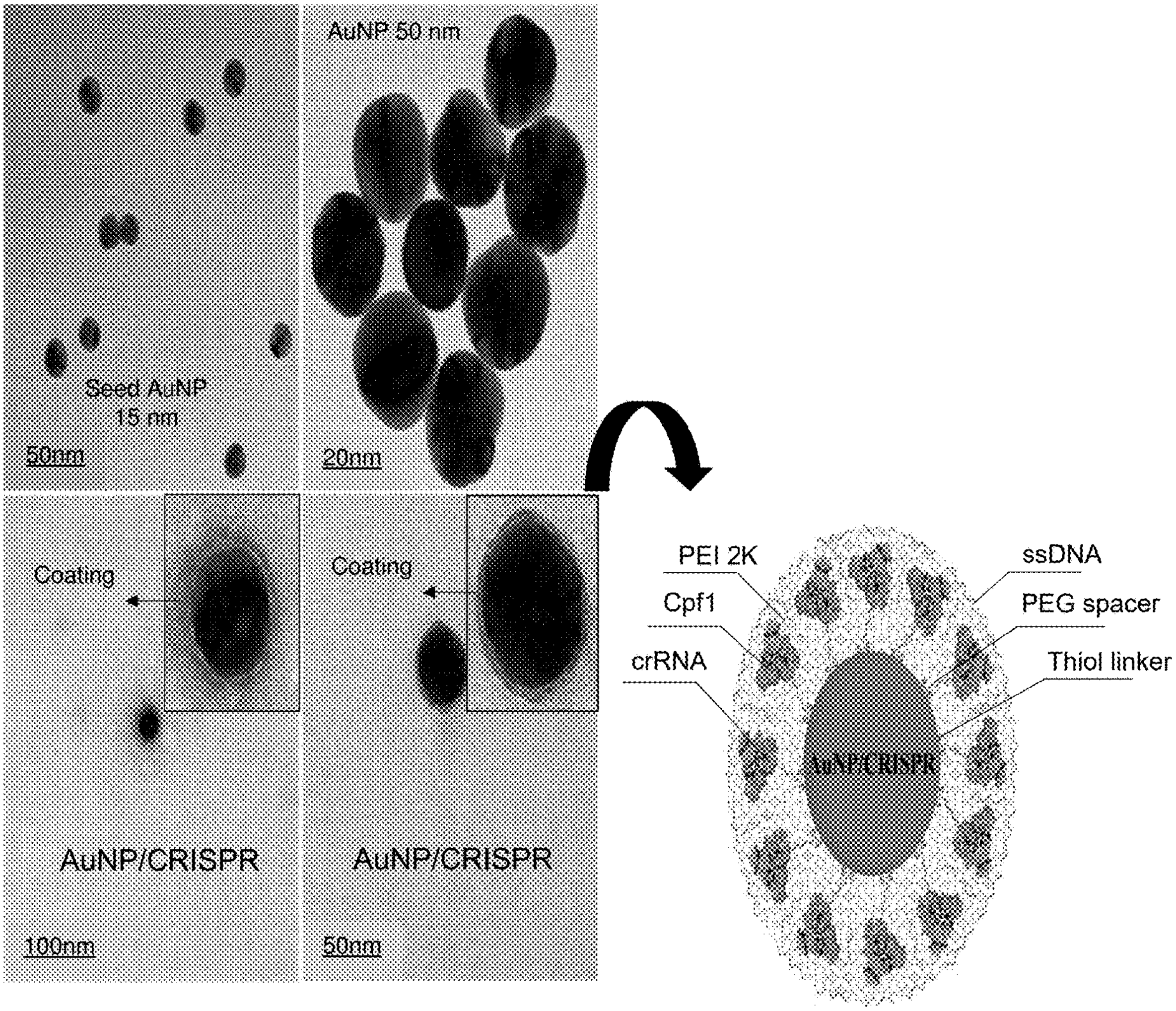
Figure 8:
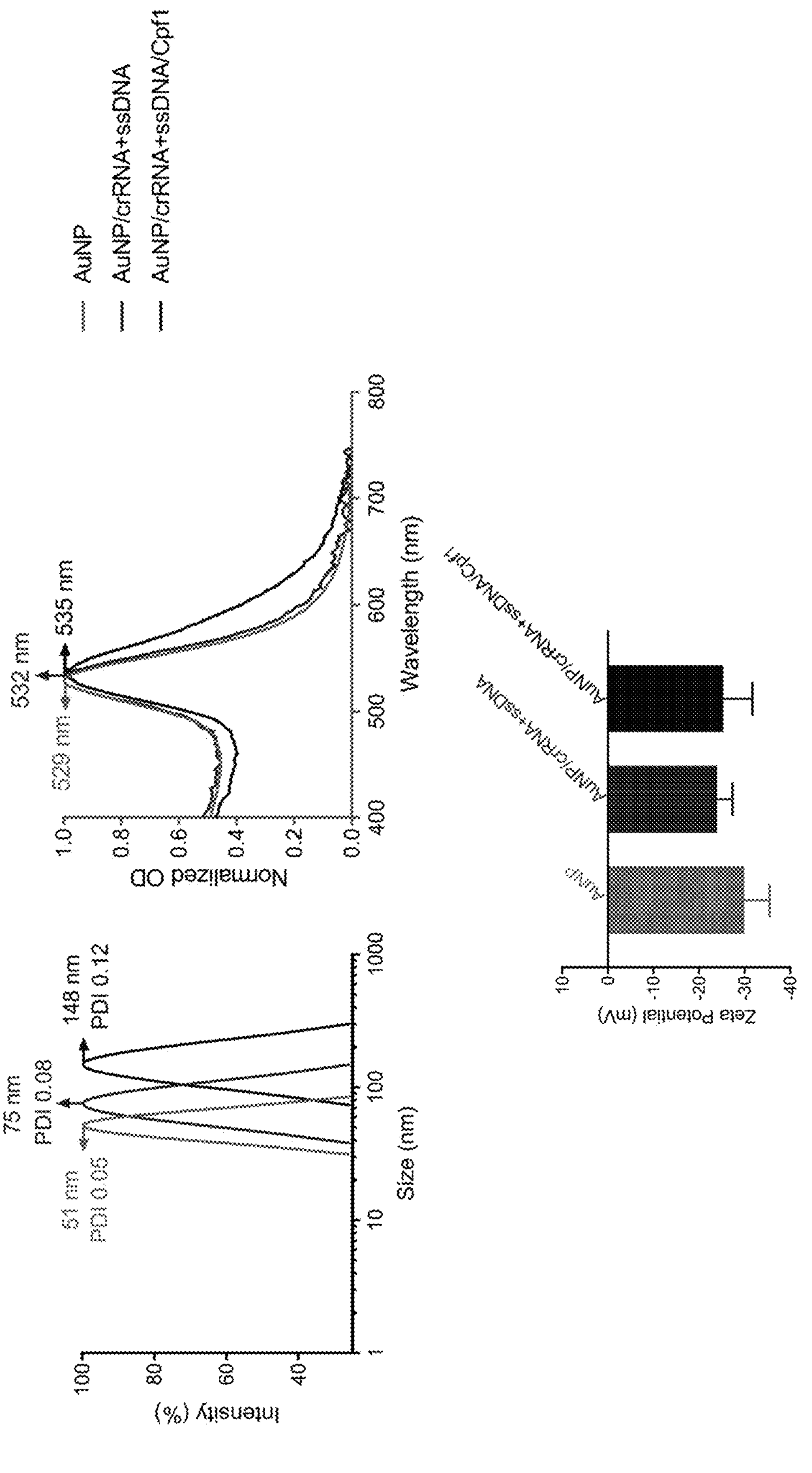
FIG. 8. Fully-loaded AuNPs are monodisperse and display good zeta potential.
Figure 10B:
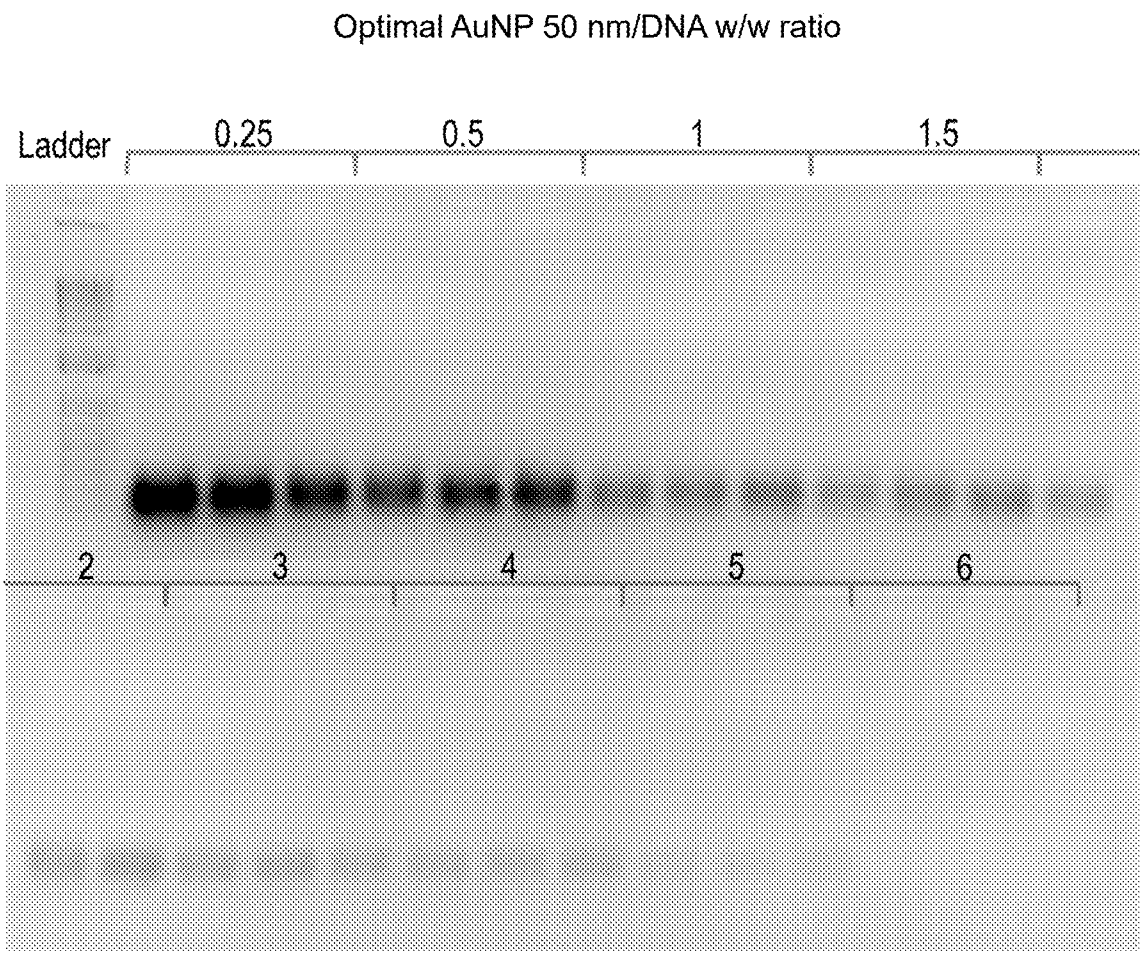
Figure 10C:
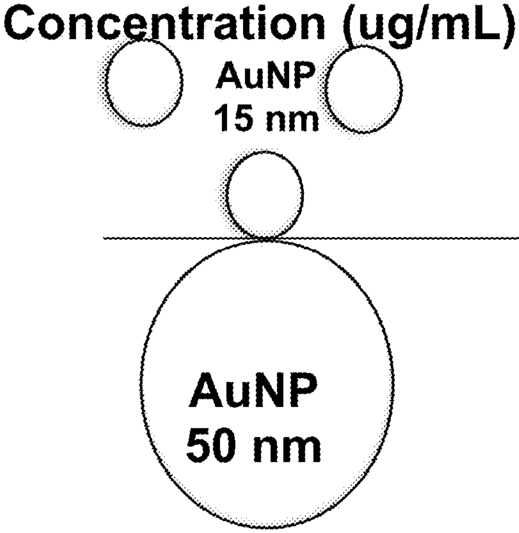
Figure 11A:
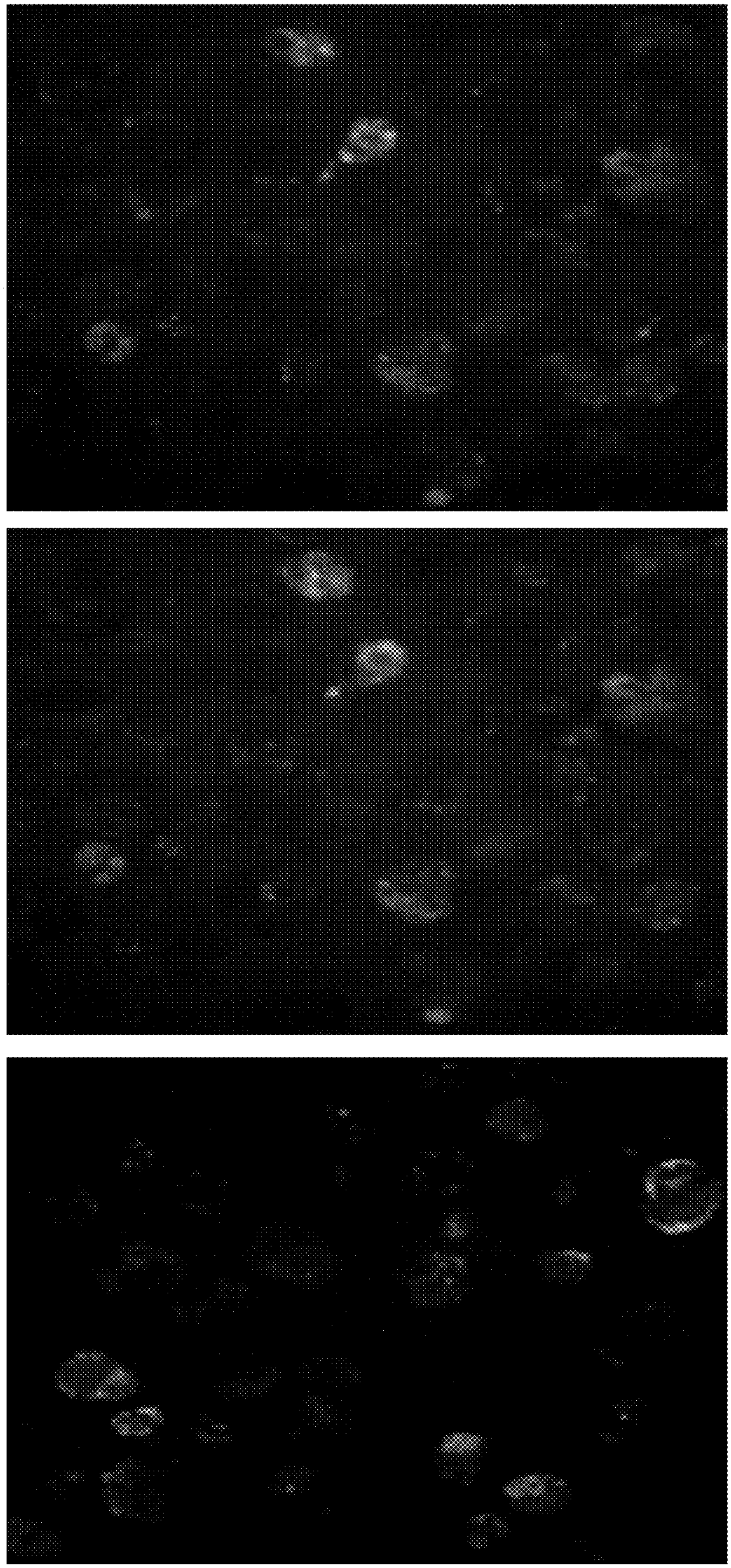
FIGS. 11A, 11B.
Figure 11B:
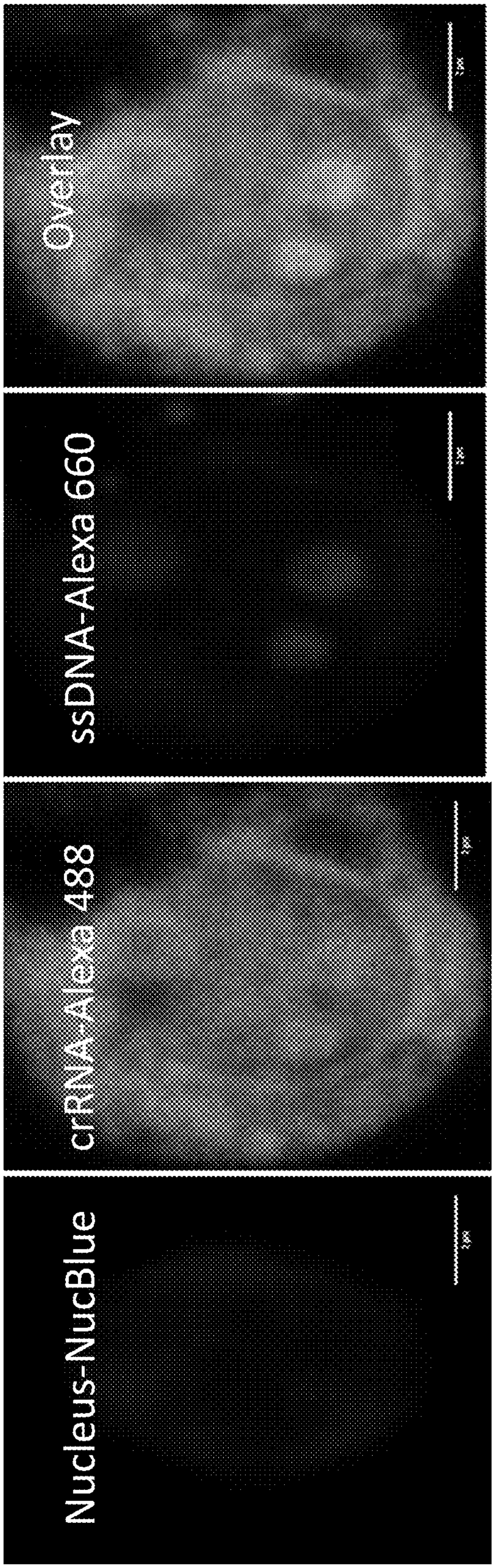

Using an optimized two step method of seeding-growth, highly monodisperse AuNPs were synthesized in 3 different size ranges (15 nm, 50 nm, 100 nm) and conjugated with Cpf1 crRNA and endonuclease (FIGS. 7B, 7D, 10C). Because of the strong electrostatic repulsion between the negatively charged surface and negatively charged crRNA it is difficult to attach the crRNA to the surface of AuNPs without, for example, the thiol modification. In particular embodiments, in the second step, after purification of the crRNA conjugated AuNPs, Cpf1 endonuclease is added and incubated with crRNA conjugated AuNPs to facilitate its binding to the 5' handle of the crRNA (Dong, et al., Nature, 2016. 532 (7600): p. 522-526). The compact structure of the designed nanoformulation containing both crRNA and Cpf1 endonuclease results in a conformation which increases the stability against degrading agents and facilitates the uptake of the AuNP/CRISPR nanoformulation by cells owing to an overall neutral charge (i.e., zeta potential). While special relevance was given to optimizing the disclosed nanoformulation for CRISPR/Cpf1, the same concept may be applied to other CRISPR classes. Also, along with the crRNA and Cpf1 endonuclease, 18 spacer thiol modified single stranded DNA (ssDNA) can be attached to the surface of AuNPs to obtain a novel nanoformulation with the aim of being used in homology directed repair (HDR).

In particular embodiments, a spacer-thiol linker can be added to either of the Cpf1 or Cas9 proteins themselves or engineered variants of the foregoing (e.g., as described below), by addition of a cysteine residue on either the N- or C-terminus. The nuclease protein can then be added as a first layer on the gold nanoparticle surface. This spacer-thiol linker can increase the stability of the protein and increase cutting efficiency. In particular embodiments, an RNA complex is formed between crRNA and nuclease and then attached to the surface of gold nanoparticles through a spacer-thiol linker.

As indicated previously, adding gene-editing components of a bacterial origin as a first loading step can provide beneficial shielding of these components following administration to a subject with pre-existing immunity to the component. The shielding can be due to other gene-editing components (e.g., donor templates) and need not rely on a protective polymer shell. In particular embodiments, a polymer shell is excluded. In particular embodiments, the shielding may permit serial in vivo administration.

In particular embodiments, crRNAs can be added to AuNPs in different AuNP/crRNA w/w ratios (0.25, 0.5, 1, 1.5, 2, 3, 4, 5, 6) and mixed. Citrate buffer with the pH of 3 can be added to the mixture in 10 mM concentration to screen the negative repulsion between negatively charged crRNA and AuNP. After stirring for 5 min, nanoparticles can be centrifuged down and the unbound crRNA can be visualized by agarose gel electrophoresis. After determining the optimal conjugation concentration, 1 μL of 63 μM Cpf1 nuclease can be added to AuNP/crRNA solution and incubated for 20 min.

Importantly, the use of a citrate buffer provides significant advantages in manufacturing. Previous methods have relied on the use of NaCl to screen the negatively-charged nanoparticle surface and reduce repulsion of similarly negatively-charged DNA. However, NaCl can cause irreversible aggregation of gold nanoparticles, so it must be added gradually over time with incremental changes in concentration. Generally, NaCl must be added over a 48 hour time period to avoid aggregation. When citrate buffer is used with a pH of 3, this binding can happen with higher efficiency in less than 3 minutes. Zhang, et al. (2012). Journal of the American Chemical Society 134 (17): 7266-7269 reducing the cost of goods and time in the GMP manufacturing facility.

Size and morphology of prepared AuNP/CRISPR nanoformulations can be characterized by imaging under transmission electron microscope (TEM). AuNPs (4 μL) can be added to copper grids and allowed to dry out overnight. Imaging is carried out at 120 kV.

CRISPR coating can be visualized by negative staining electron microscopy. AuNP/CRISPR nanoformulation can be stained with 0.7% uranyl formate and 2% uranyl acetate, respectively. Stained sample (4 μL) can be added to carbon-coated copper grid and incubated for 1 min and blotted with a piece of filter paper. After three washing cycles with 20 μl stain solution, 4 μl stain solution can be added to the grids and blotted and air dried.

Also, AuNP/CRISPR nanoformulations can be characterized by Nanodrop UV-visible spectrophotometer by analyzing the shifts in localized surface plasmon resonance (LSPR) peak of the AuNPs before and after conjugation with CRISPR components.

In particular embodiments, a nanoparticle is layered, such as during synthesis to include PEI or other positively charged polymer for increasing surface area and conjugating larger ssDNA or other molecules, such as targeting molecules and/or large donor templates (see, for example, FIG. 7C). This nanoformulation can be prepared in a layer by layer form and positively charged polymers (such as; PEI in different molecular weights and forms) can be used to coat the negatively charged surface of either gold nanoparticles or CRISPR coated gold nanoparticles to attach either gene editing components and other components (such as antibody binding domains). Layering essentially increases the surface area of the nanoparticle available for conjugating molecules such as large oligonucleotides with or without other proteins.

In particular embodiments, PEI can be added as a second layer and ssDNA can be added as a third layer. Alternatively, the conjugation steps can be changed by adding ssDNA as a second layer and PEI as a third layer. In particular embodiments, PEI, polymers, and ssDNA are not included as a first layer, as this layer can be reserved for RNP complexes coupled to linkers.

Figure 9A:
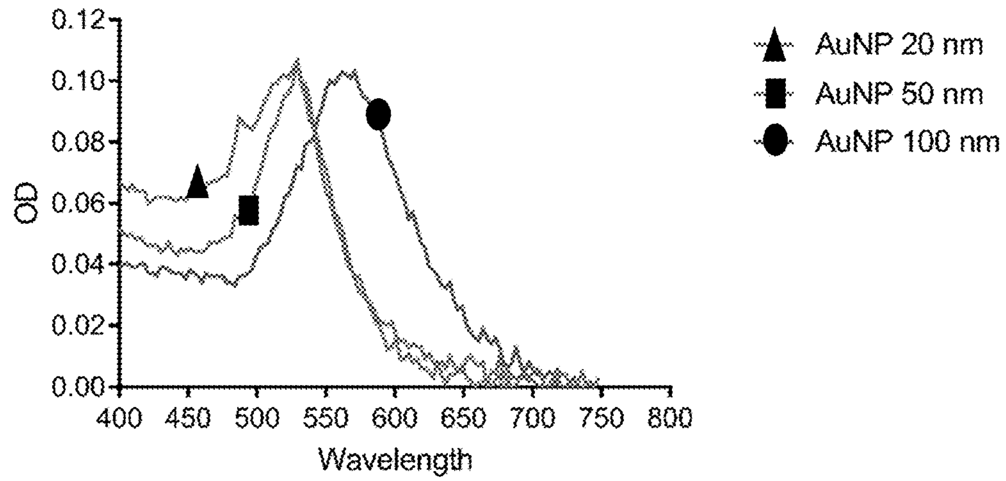
FIGS. 9A-9D. Graphs and digital images showing the characteristic properties of synthesized AuNPs and optimal loading concentrations.
Figure 9B:
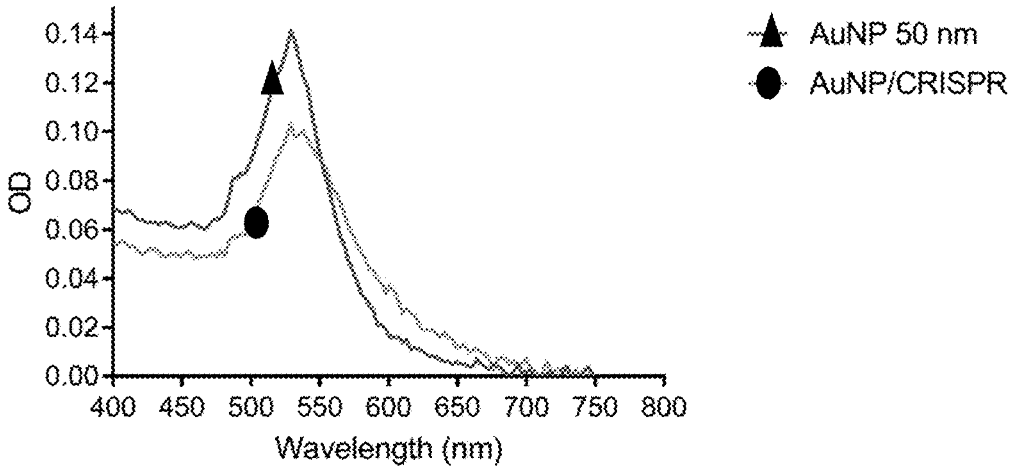

In particular embodiments, a multilayered nanoformulation of the disclosure has an average size of 25-30 nm and is highly monodisperse. Transmission electron microscope images (TEM) and localized surface plasmon resonance shifts (LSPR) of gold nanoparticles (AuNPs) showed a uniform surface coating without any aggregation (FIGS. 9A, 9B). Given the synthetic nature of the entire delivery system, all components can be assembled within a few hours, as opposed to previous approaches which required multiple days due to, for example, use of NaCl as a charge screen.

Figure 9C:
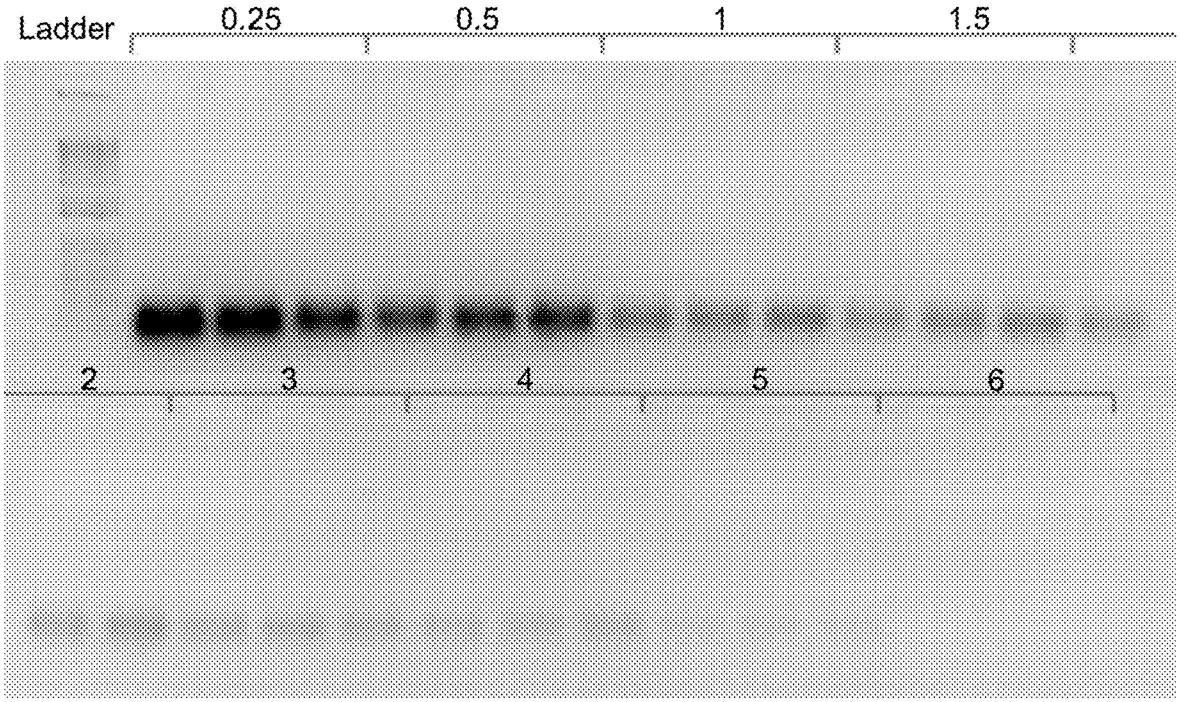
Figure 9D:
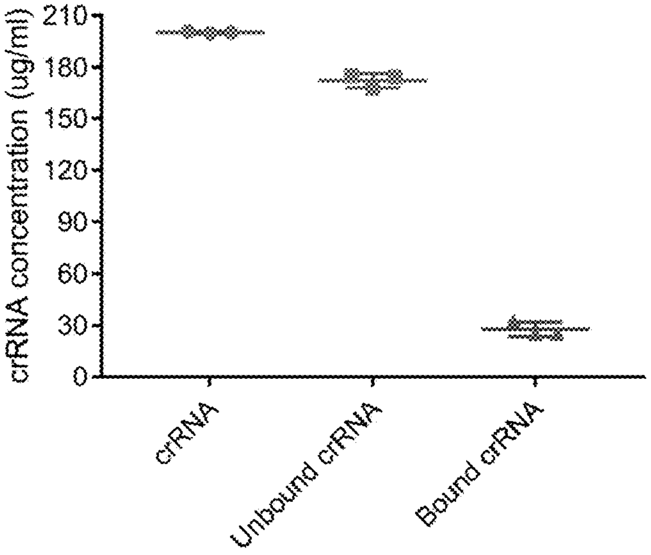

As shown in FIGS. 7D and 9A, synthesized nanoparticles were highly monodisperse and successful 4 nm coating without any aggregation was achieved which increased the size of the nanoparticles to 54 nm after coating for 50 nm AuNPs. Also, decrease in the intensity and red shifting of the localized surface plasmon (LSPR) of AuNPs showed the successful conjugation with CRISPR components without any aggregation (FIG. 9A). Also, oligonucleotide loading studies with the model 18 spacer C3 S-S modified ssDNA in different AuNP/ssDNA w/w ratios showed that the ratio of 6 is optimal to carry out the conjugation (FIG. 9C). Using this optimal loading ratio crRNA was loaded on the surface of AuNPs in 30 g/mL concentration (FIG. 9D). These data help calculate the exact application dosage for gene editing studies.

The described approaches resulted in a highly potent, loaded, CRISPR nanoformulation capable of delivering both synthetic, non-chemically modified CRISPR Cpf1 or CRISPR Cas9 ribonucleoproteins along with a ssDNA homology template for insertion of new DNA, without the need for electroporation (FIG. 7D). In particular embodiments, the hydrodynamic size of a fully loaded AuNP is 150-190 nm, 160-185 nm, 170-180 nm or 176 nm.

(V) Gene Editing Efficiency. The optimal concentrations of crRNA, hAsCpf1 RNA and ssODN for electroporation were determined in K562 cells. The optimal concentration displays the highest viability and GFP expression. K562 cells were cultured in 24 well plates in $1\times10^5$ cells/well concentration. Iscove's Modified Dulbecco's Medium (IMDM) with 10% FBS and 1% PenStrep was used to culture the cells. $CD^{34}$+ cells were cultured in 24 well plates in $5\times10^5$ cells/well concentration. Culture conditions for $CD^{34}$+ cells were the same as K562 cells with required growth factors. AuNP/CRISPR nanoformulations were added in 25 nM concentration to the wells and editing efficiency was evaluated after 48 h incubation. Electroporation of the cells was performed with a Harvard Apparatus ECM 830 Square Wave Electroporation System using BTX Express Solution (USA). in 1 mm cuvettes in 250 V and 5 ms pulse duration. 1 mm BTX cuvettes with a 2 mm gap width were used to electroporate 1-3 million K562 cells at 250V for 5 milliseconds. Cells were resuspended in culture media and analyzed following electroporation.

Figure 14:
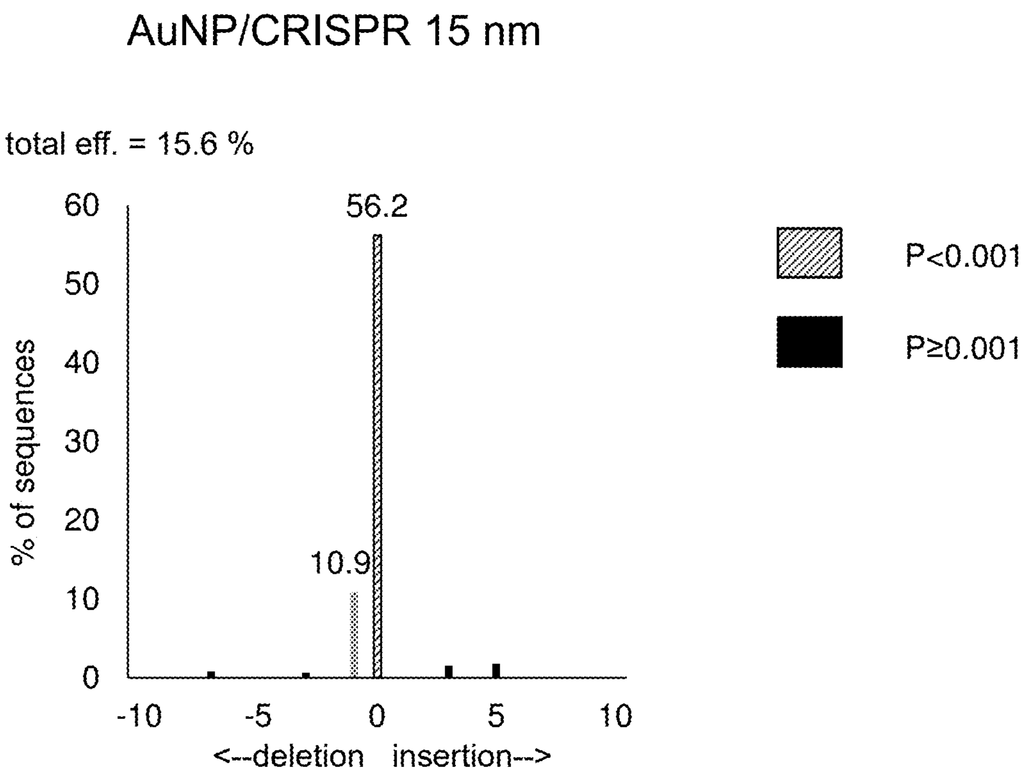
FIG. 14. TIDE assay results showing indels after editing with AuNP/CRISPR nanoformulations in $CD^{34}$+ cells.
Figure 14:
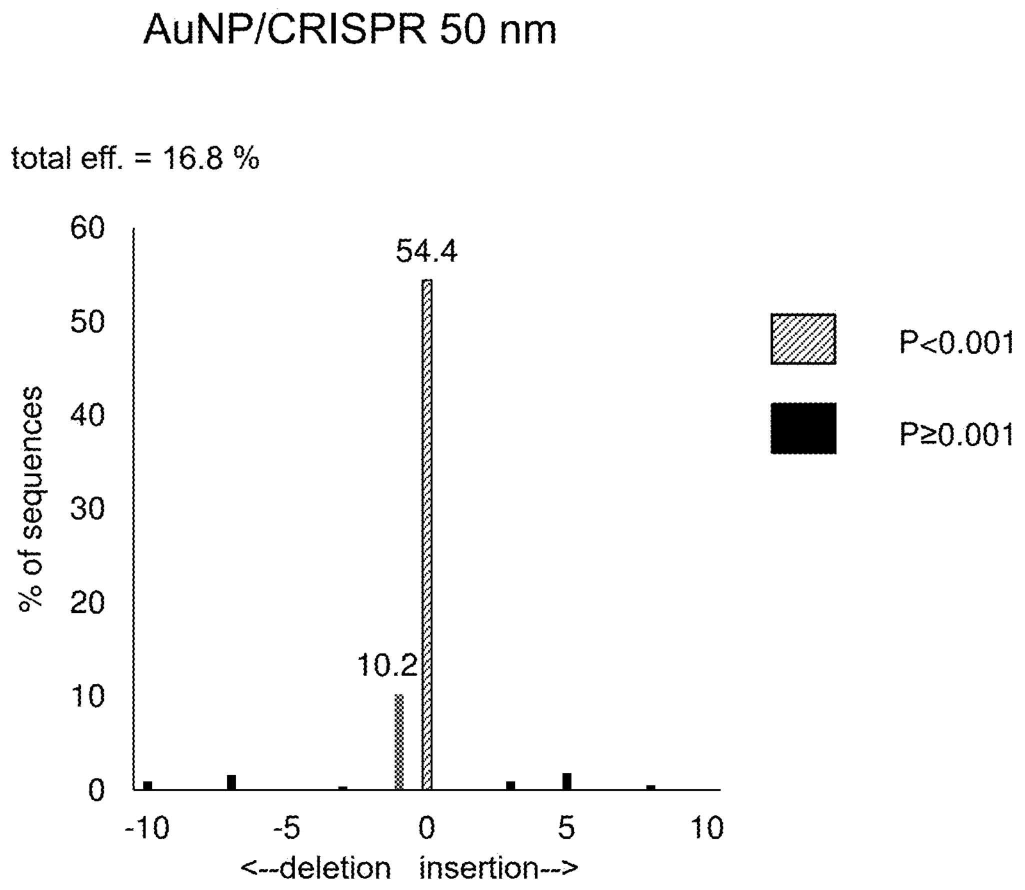
Figure 14:
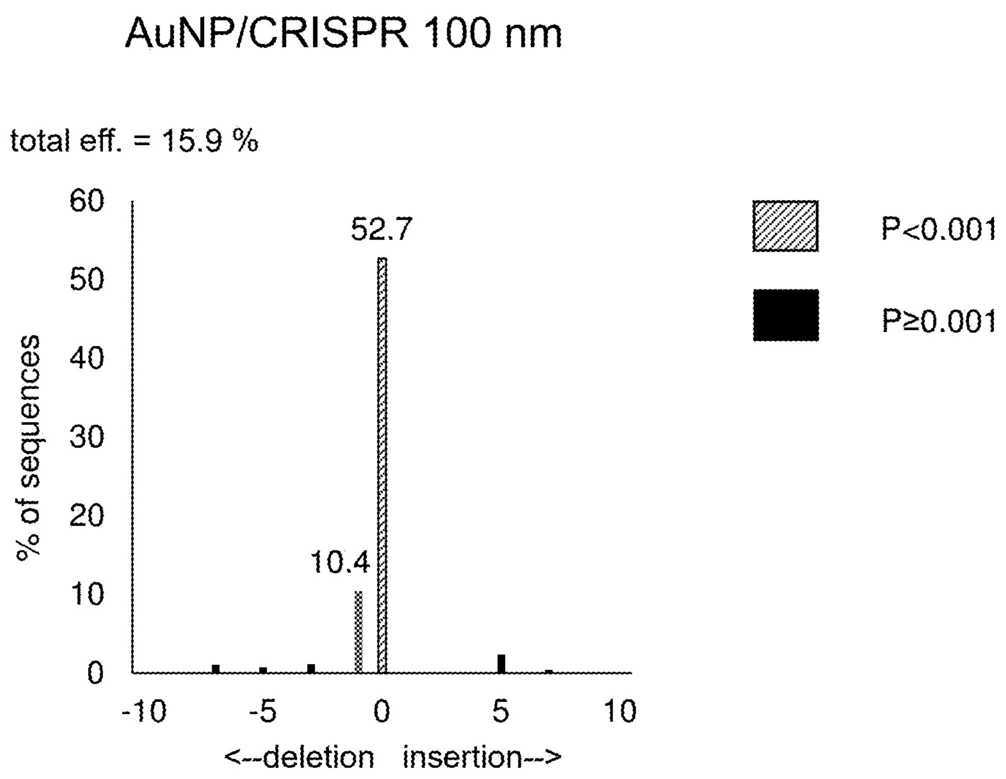
Figure 15A:
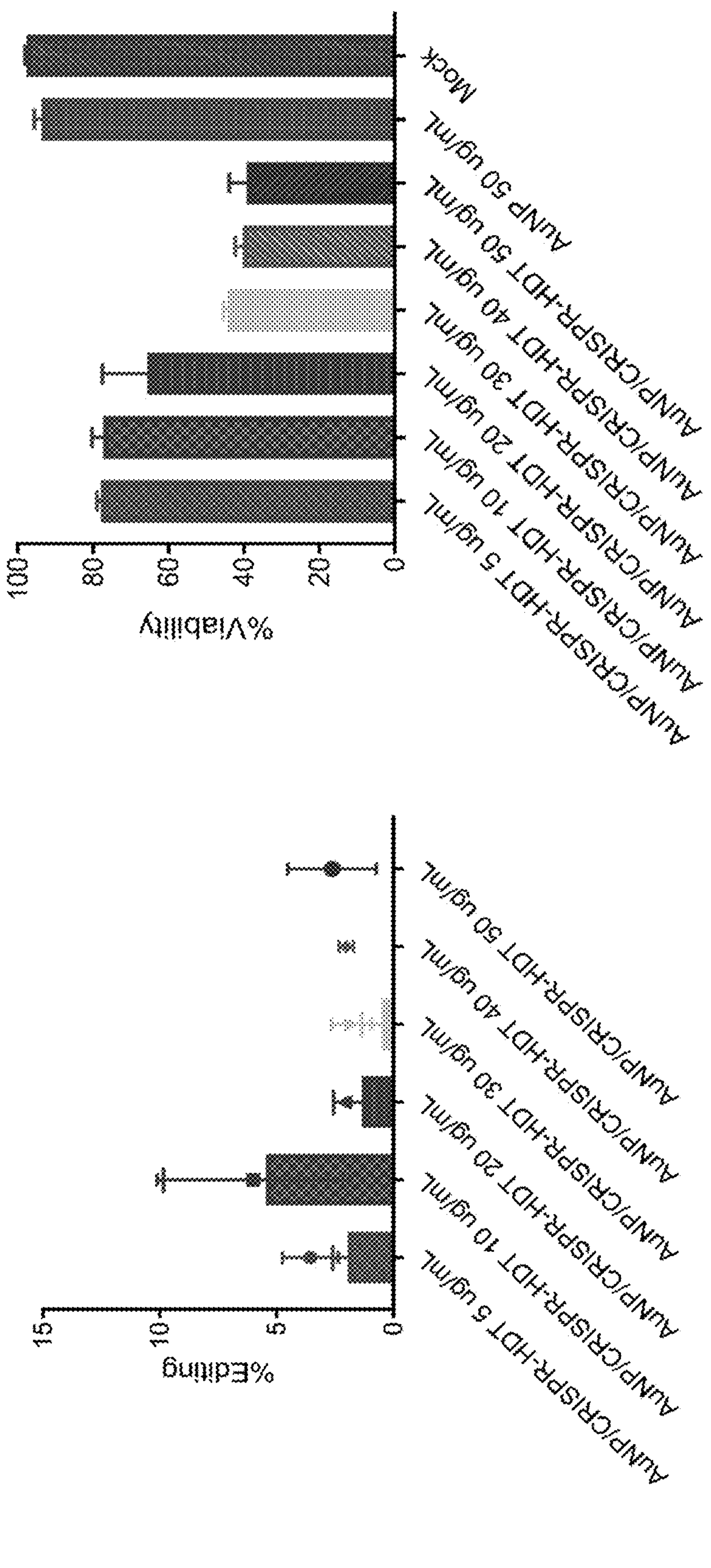
FIGS. 15A-15D.
Figure 15B:
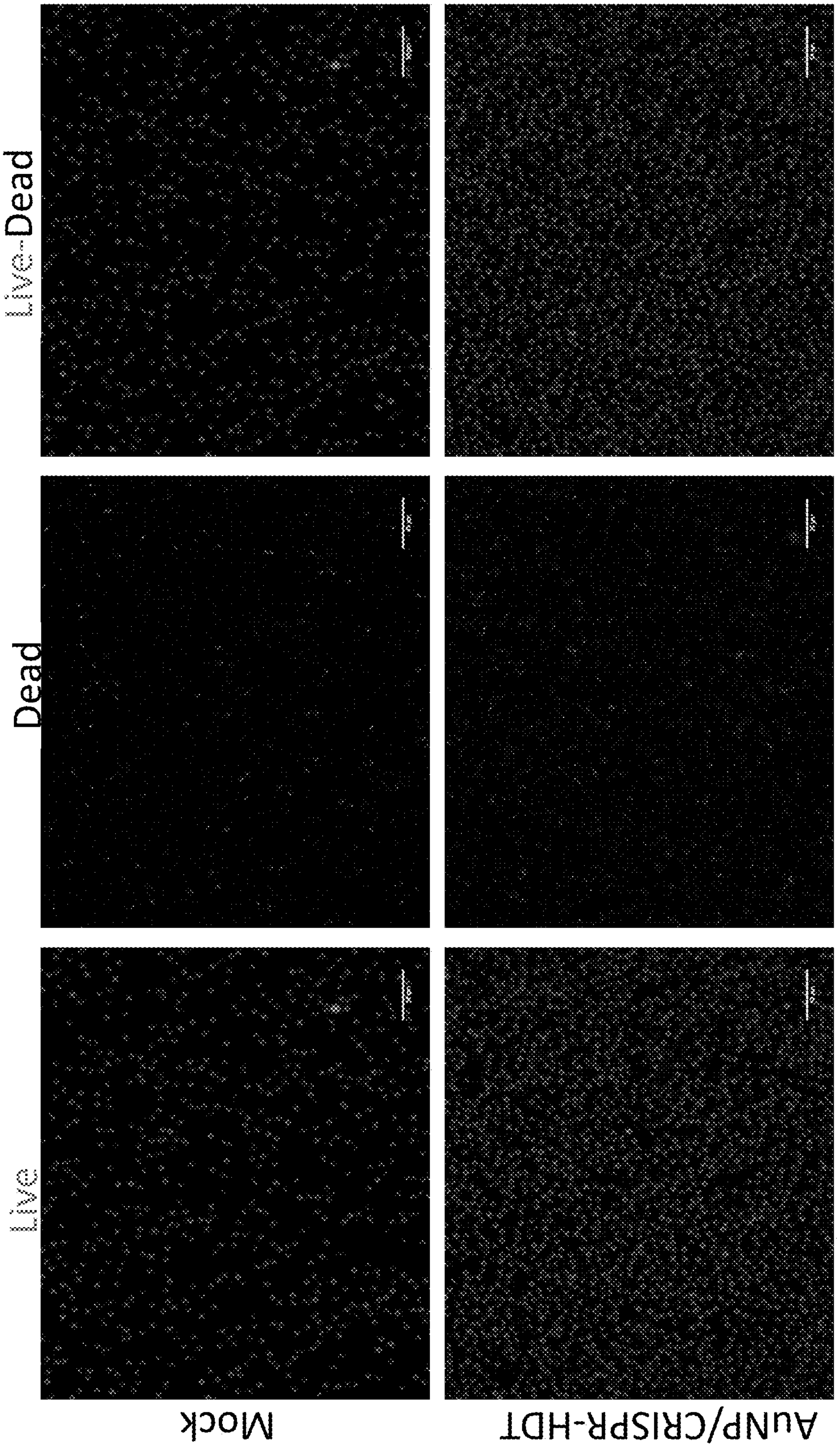
Figure 15C:
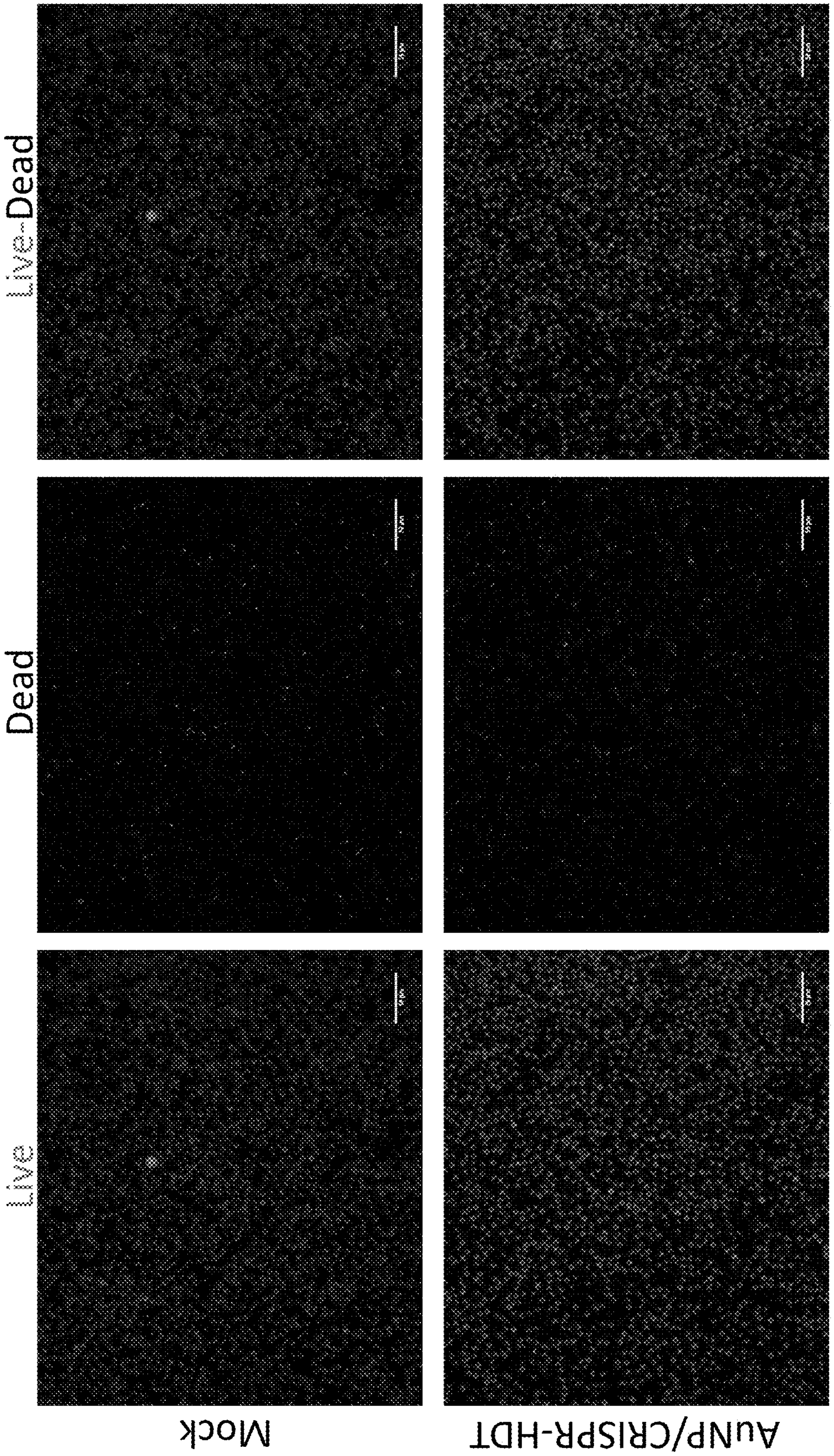
Figure 15D:
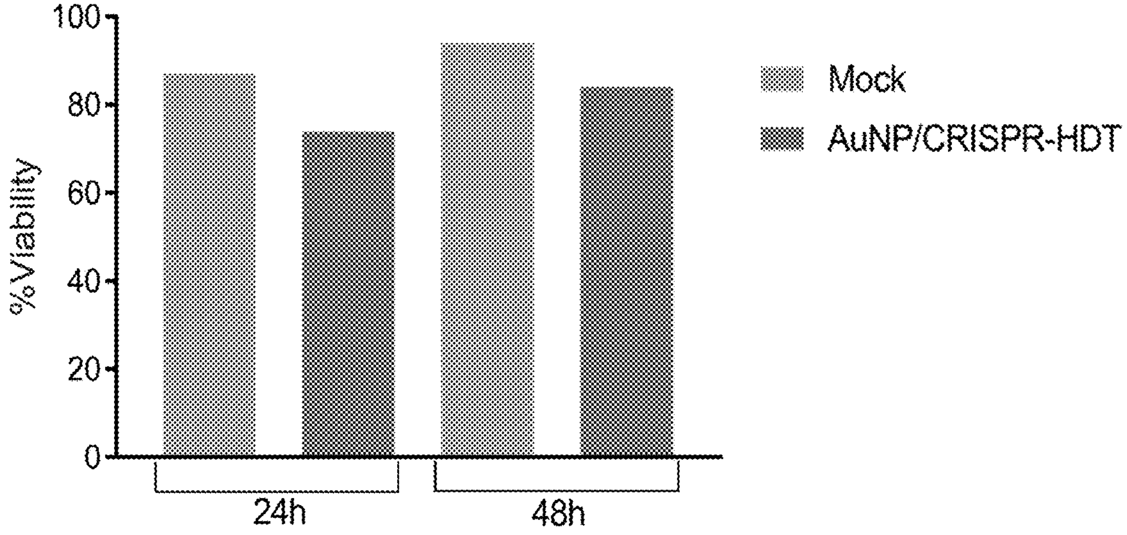

AuNP/CRISPR nanoformulations targeting the chr11: 67812349-67812375 location were able to successfully cut the target site in very low crRNA and Cpf1 endonuclease concentrations (25 nM) in comparison to electroporation method in which a higher amount of crRNA and Cpf1 was used (126 nM) (FIG. 12A) to achieve the same efficiency of cutting. Cutting efficiency for this site was low due to the A>T mutation 15 bp after the PAM site (FIG. 2). In the next test, the same location was targeted in primary $CD^{34}$+ cells and it was shown that AuNP/CRISPR nanoformulations were able to target the site in a very low crRNA and Cpf1 endonuclease concentrations with very good cutting efficiency without raising any toxic effects (FIGS. 12B, 12C, and 14). Unfortunately, electroporation of the primary $CD^{34}$+ cells adversely affected the viability of the cells and no cutting was seen for electroporated cells. Calculated concentration for AuNP/CRISPR nanoformulation was 5 fold lower than required concentration for electroporation method (FIG. 12D). As previously mentioned by Kim et al. (Nat Biotechnol, 2016. 34 (8): p. 863-8), the rate of deletions to insertions was higher with the CRISPR Cpf1 gene editing system (FIG. 14)

Figure 16:
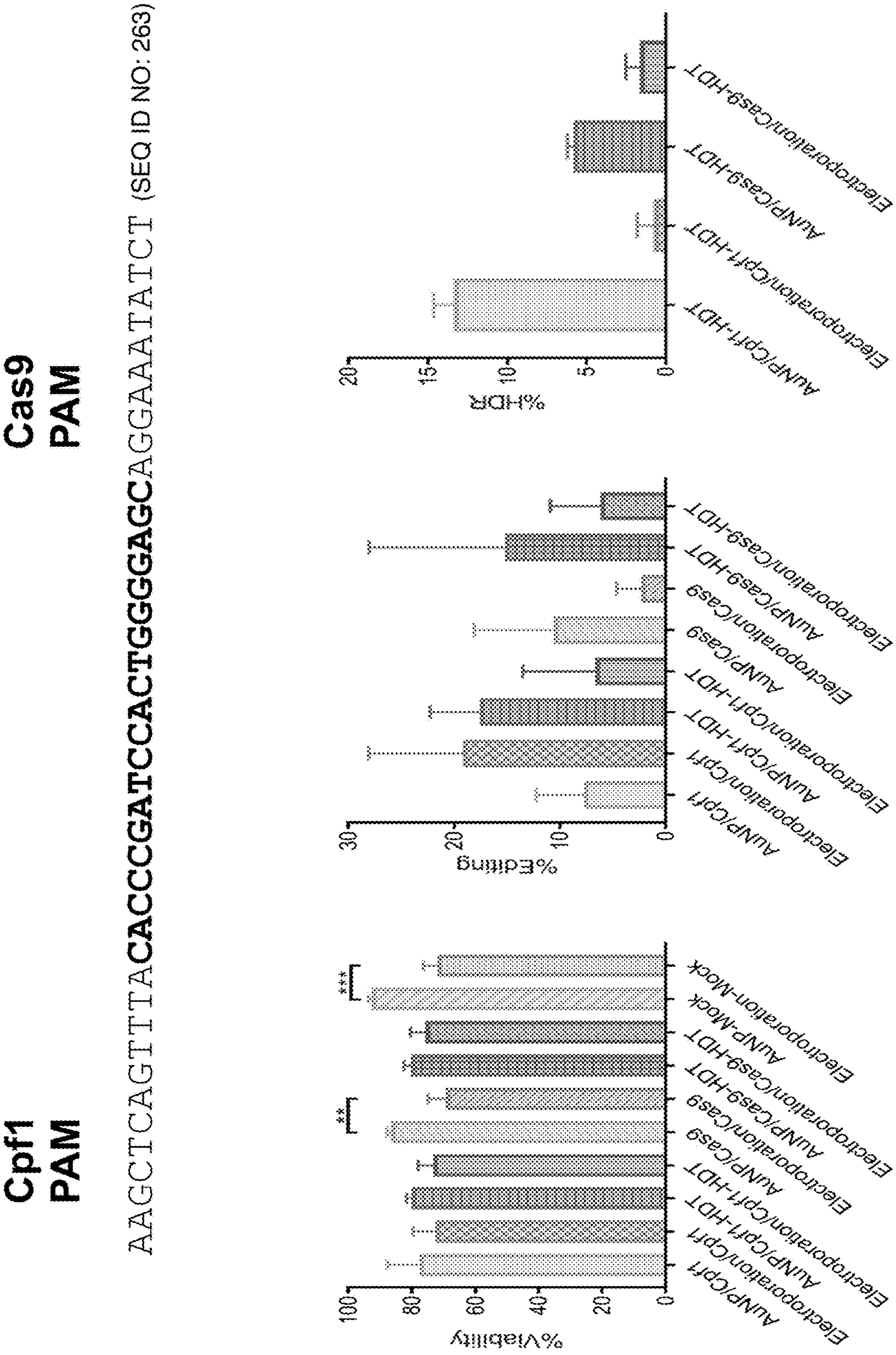
FIG. 16. The goal of the study leading to the data presented in FIG. 16 was to compare Cpf1 and Cas9 delivered by AuNP or electroporation, respectively. The same procedures were used as described in relation to FIG. 13, except that $CD^{34}$+ cells were initially obtained from a different human donor. All formulation conditions were the same such that the only variables are Cpf1 vs. Cas9; AuNP vs. Electroporation; homology-directed repair template (HDT; ssODN) present vs. absent. Electroporation conditions: 1 mm electroporation cuvets; 125 mV; 5 ms. Editing analysis by TIDE. A CCR5 non-target sequence of CCR5 locus is depicted (SEQ ID NO: 263).
Figure 17A:
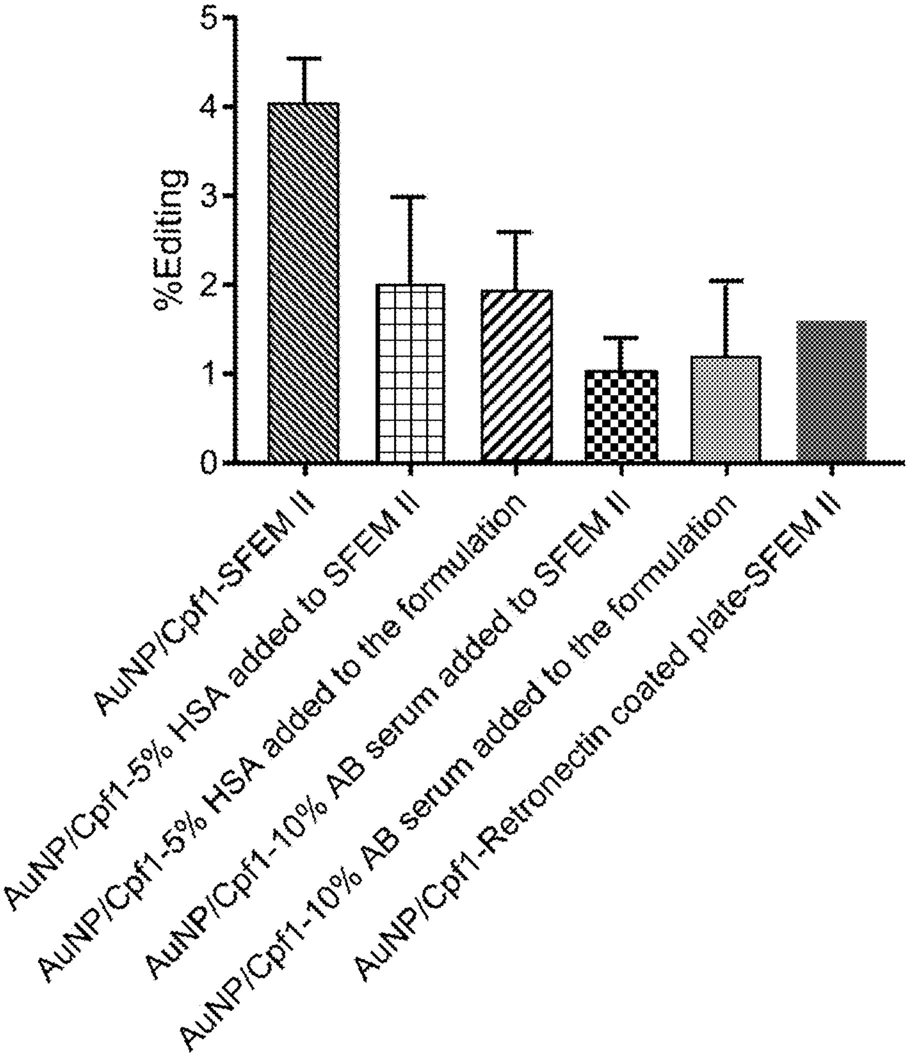
FIGS. 17A-17C. Serum-free, HSPC-supportive media conditions improve (17A) editing, (17B) HDR, and (17C) cell viability.
Figure 17B:
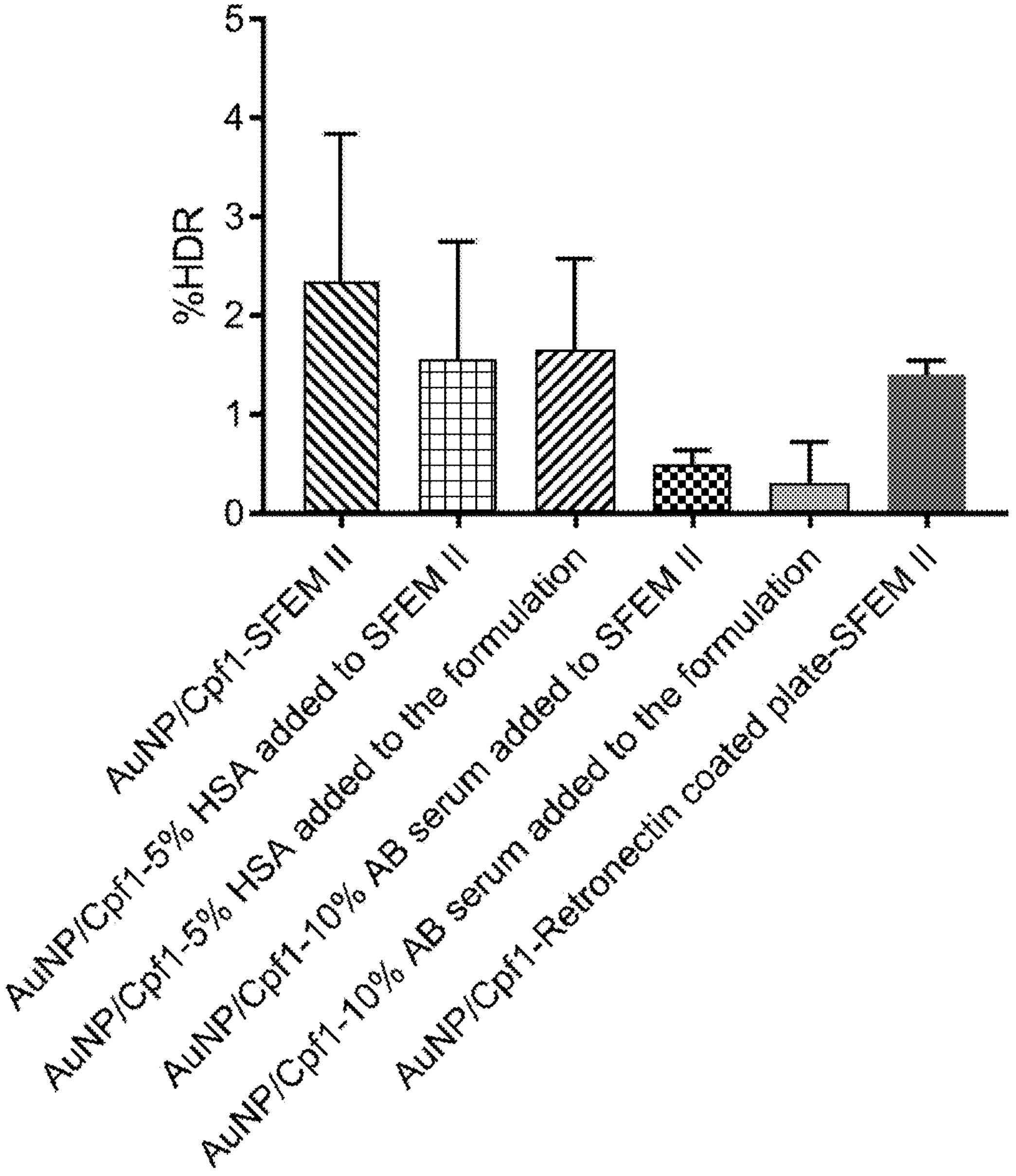
Figure 17C:
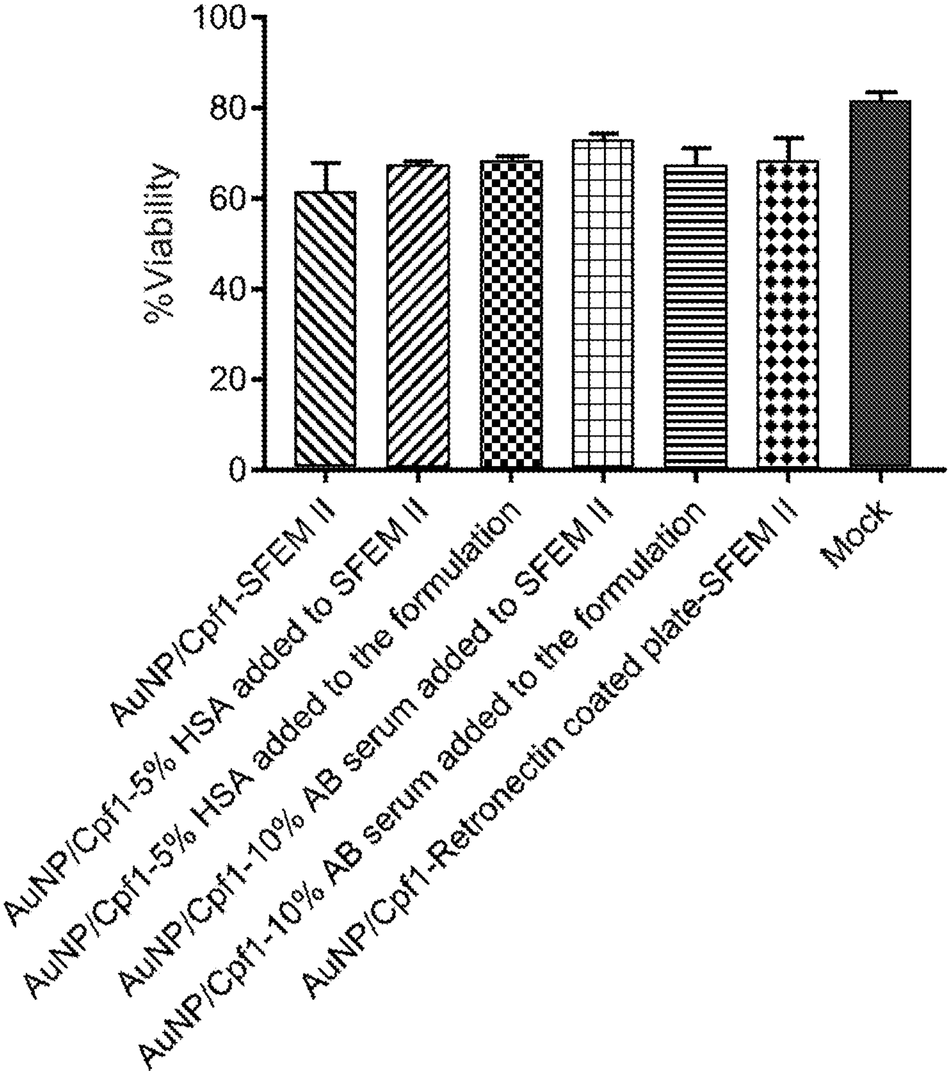
Figure 18A:
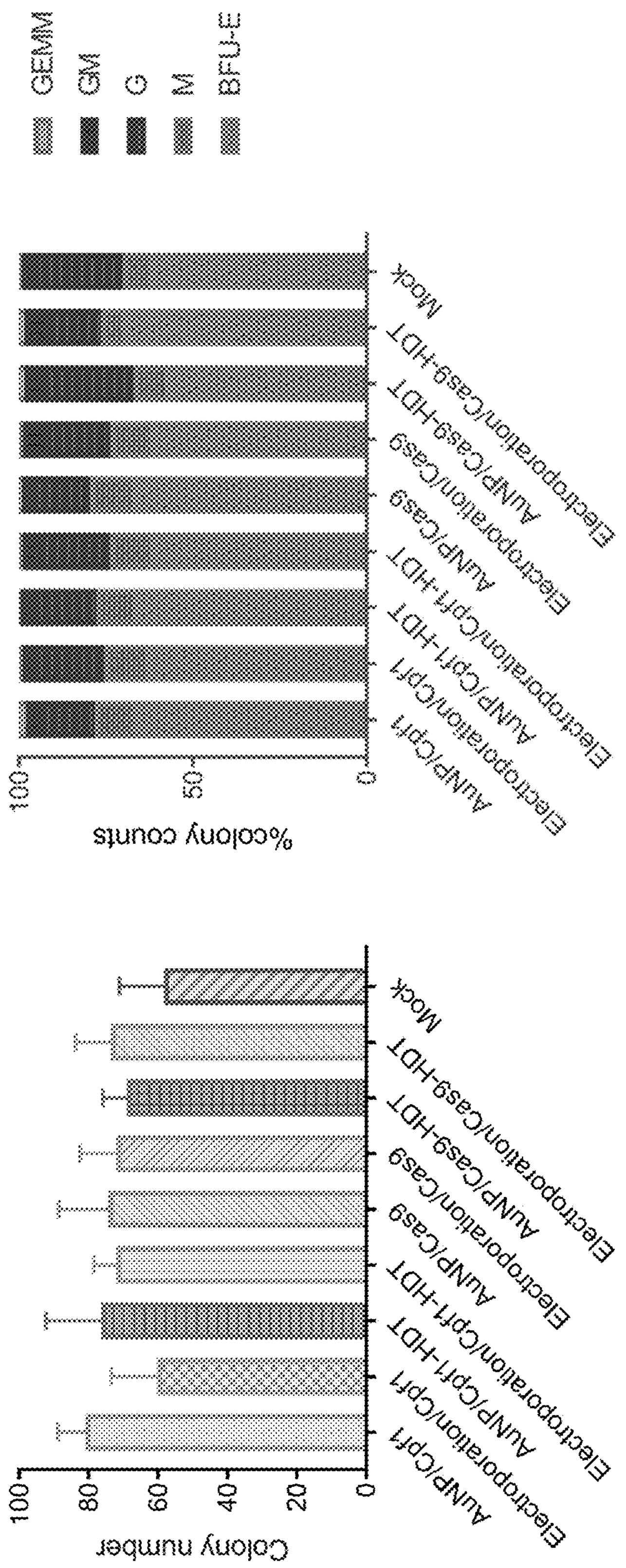
FIGS. 18A, 18B.
Figure 18B:
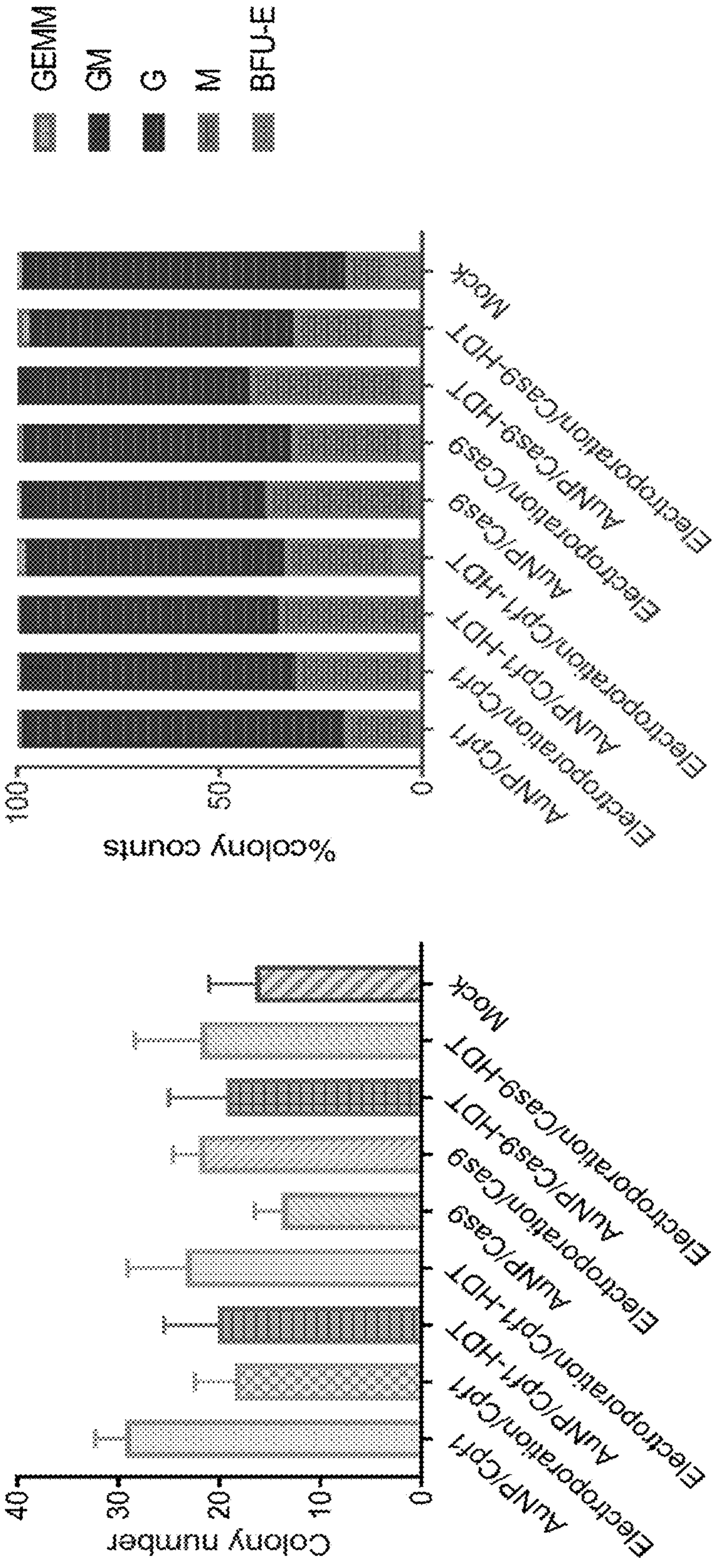
Figure 19:
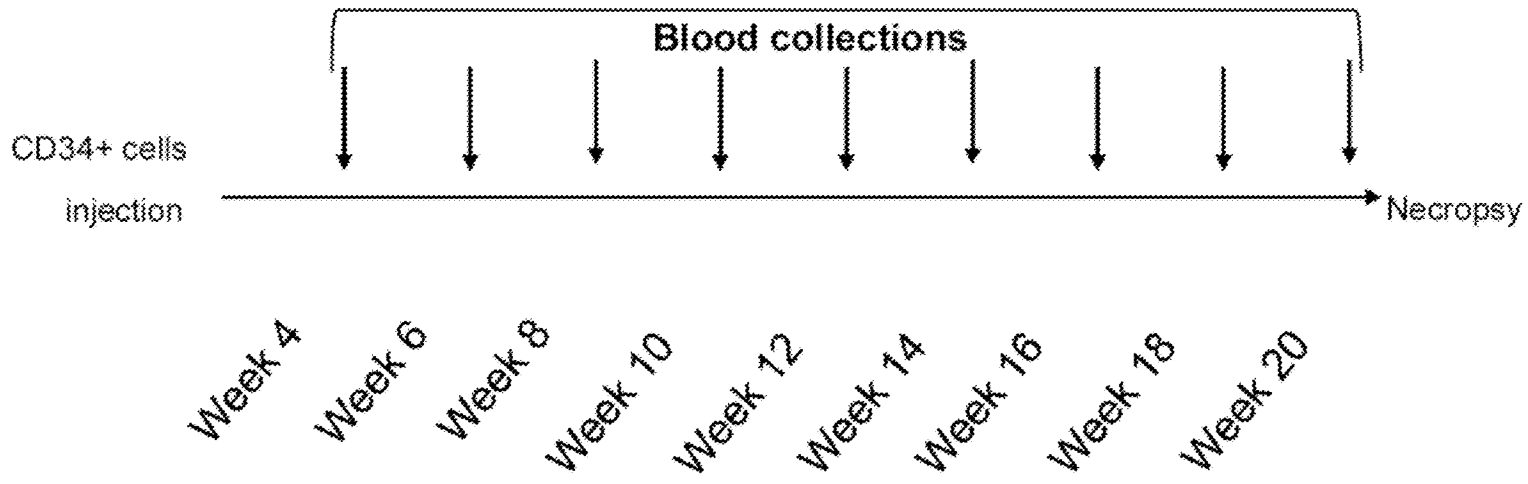
FIG. 19. AuNP-treated $CD^{34}$+ cells engraft in vivo. Experimental notes and methodology. The same procedures were used as described in relation to FIG. 13, except that $CD^{34}$+ cells were initially obtained from a different human donor. After 48 hours, cells were harvested, washed, and injected into sublethally irradiated adult (8-12 week) NSG mice. Cell reserves were used to assess plate colony assays and to isolate gDNA for PCR amplification and analysis.

As shown in FIG. 16, AuNP-mediated gene delivery improves Cas9 performance, however, Cpf1 is better for HDR. AuNP treated cells demonstrated higher viability compared to electroporated cells. For Cas9, AuNP mediated delivery improved total editing and HDR, relative to electroporation. For Cpf1 delivered without a homology-directed repair template (HDT), electroporation resulted in higher total gene editing (indels). This suggests that electroporation itself may impact the repair pathway used or the frequency of Cpf1 cutting at the target site. Addition of HDT to the Cpf1 formulation improved total editing and resulted in the highest HDR rates. Together, these data suggest that the fully-loaded formulation of AuNP+Cpf1/crRNA+HDT results in the highest rates of HDR with minimal indel formation. This is ideal for a number of target loci for gene editing.

Figure 13:
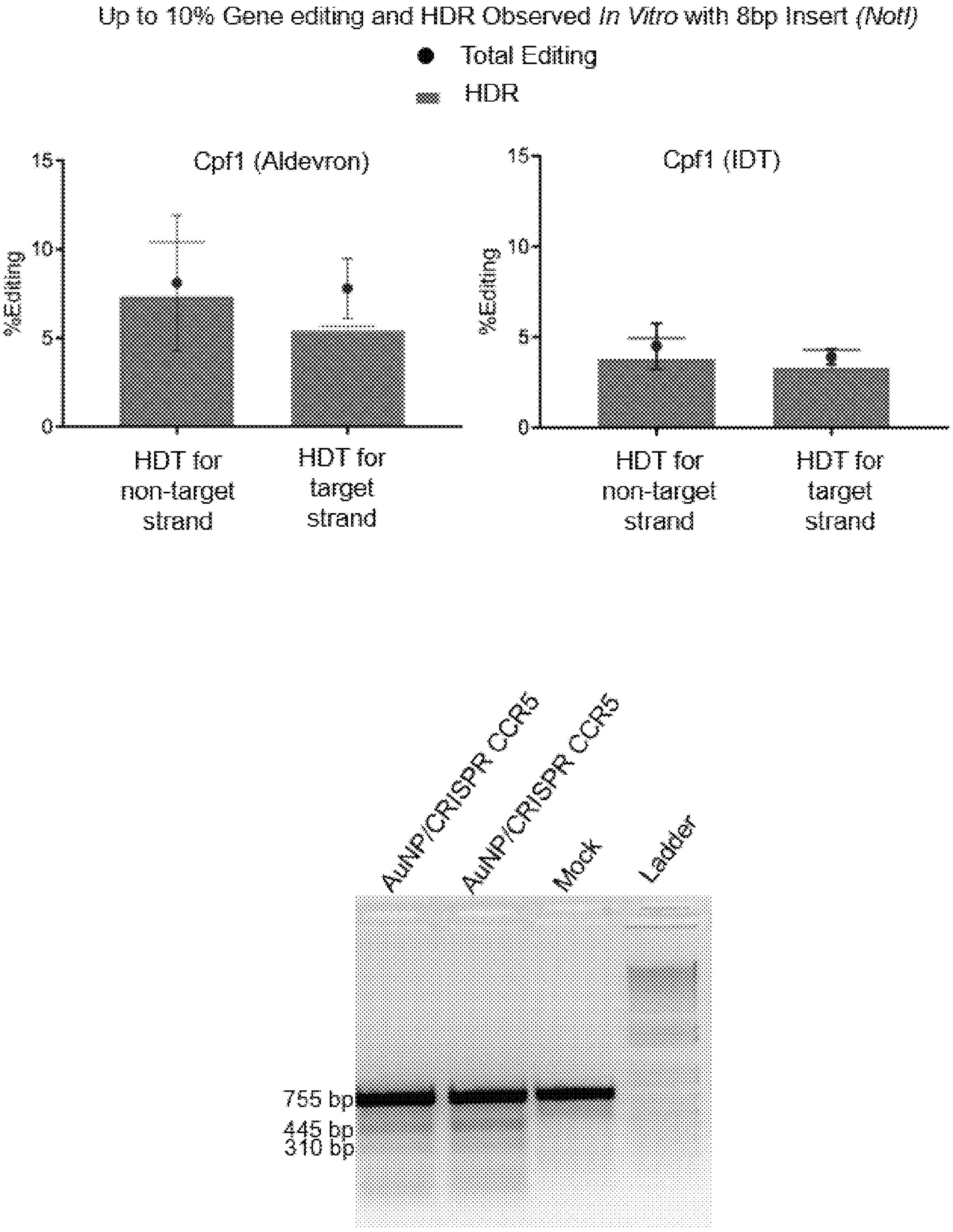
FIG. 13. Up to 10% gene editing and HDR was observed in vitro in primary $CD^{34}$+ cells obtained from a G-CSF mobilized healthy adult donor. $CD^{34}$+ cells were thawed using a rapid-thaw method and cultured overnight in Iscove's Modified Dulbecco's Medium (IMDM) containing 10% FBS and 1% Pen/Strep. The following morning, AuNPs were seeded and assembled as follows: seed; add crRNA with a PEG spacer to prevent electrostatic repulsions; add Cpf1 protein and allow RNPs to form; coat with 2K branched PEI and ssODN. In this example, there were no chemical modifications of crRNA other than terminal thiol additions to promote covalent bonding with the AuNP surface for attachment. SsODN was used as the homology-directed repair template (HDT), here a 8 bp insert using a Notl site flanked by 40nt of homology (symmetric) to CCR5 target locus. Formulated AuNPs were added to cells and incubated for 48 hours with gentle plate mixing. After 48 hours, cells were harvested, washed, and gDNA was isolated for PCR amplification and analysis.
Figure 13:
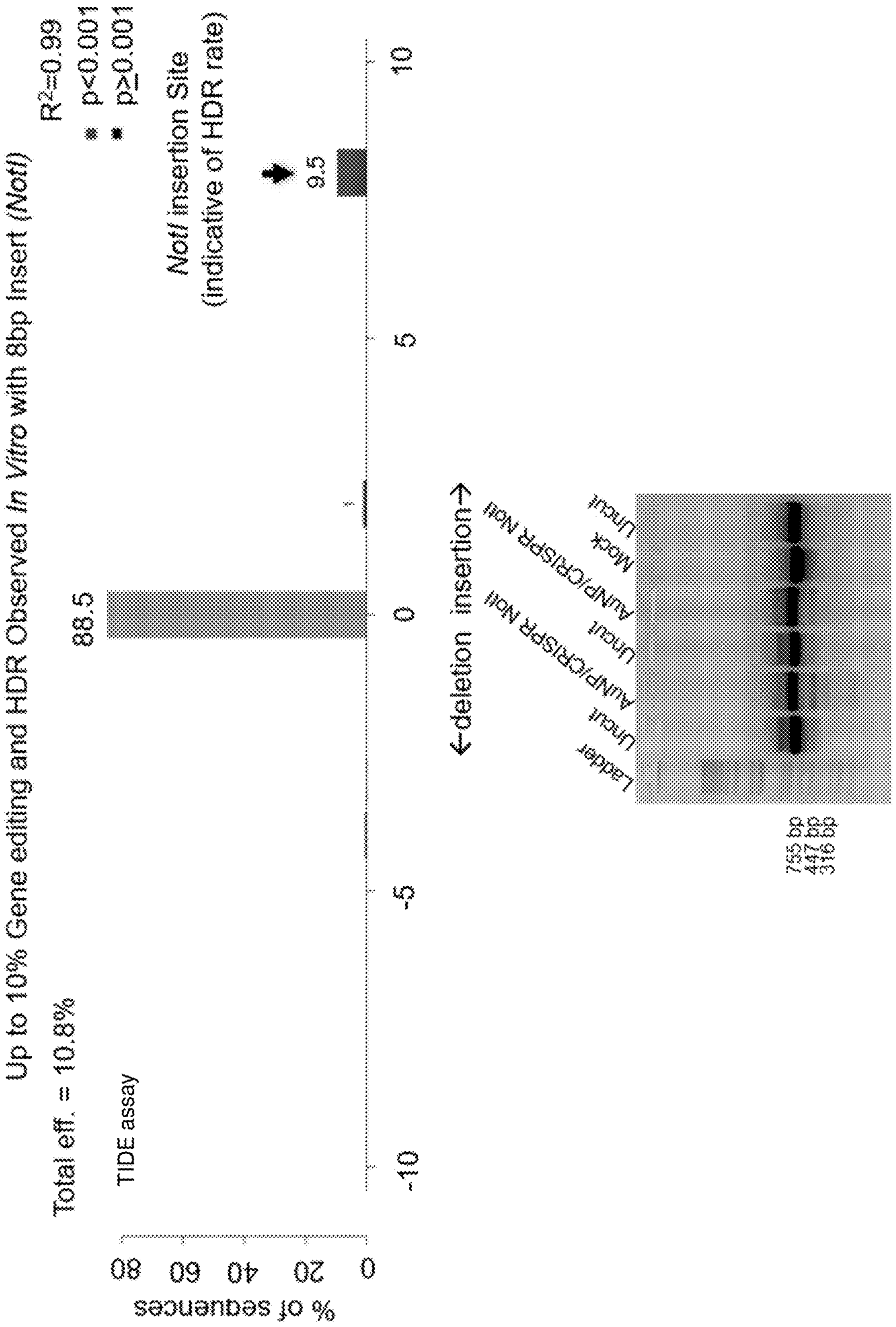
Figure 20A:
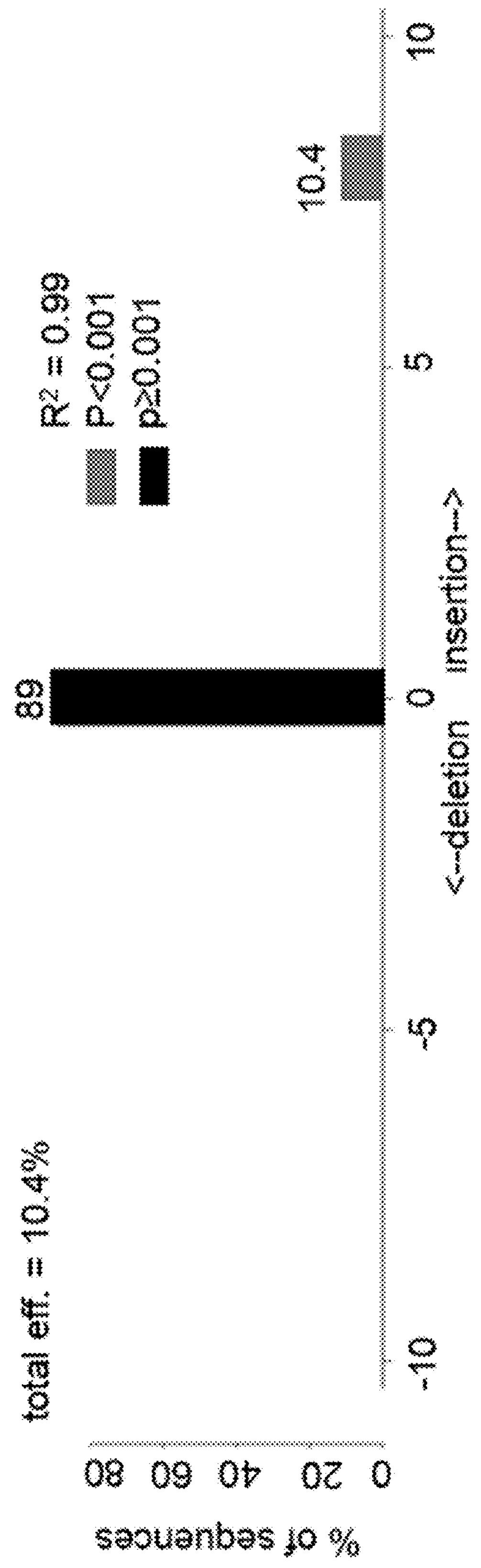
FIGS. 20A-20C. In vitro analysis of cells transplanted into NSG mice.
Figure 20B:
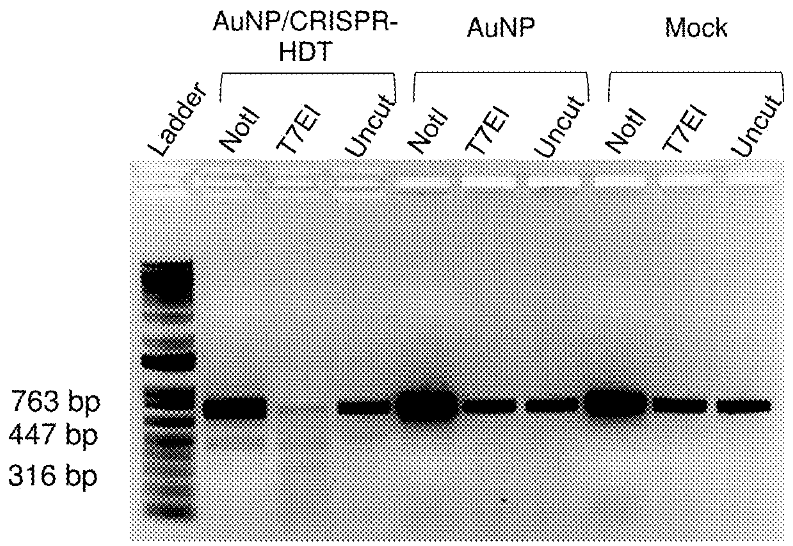
Figure 20C:
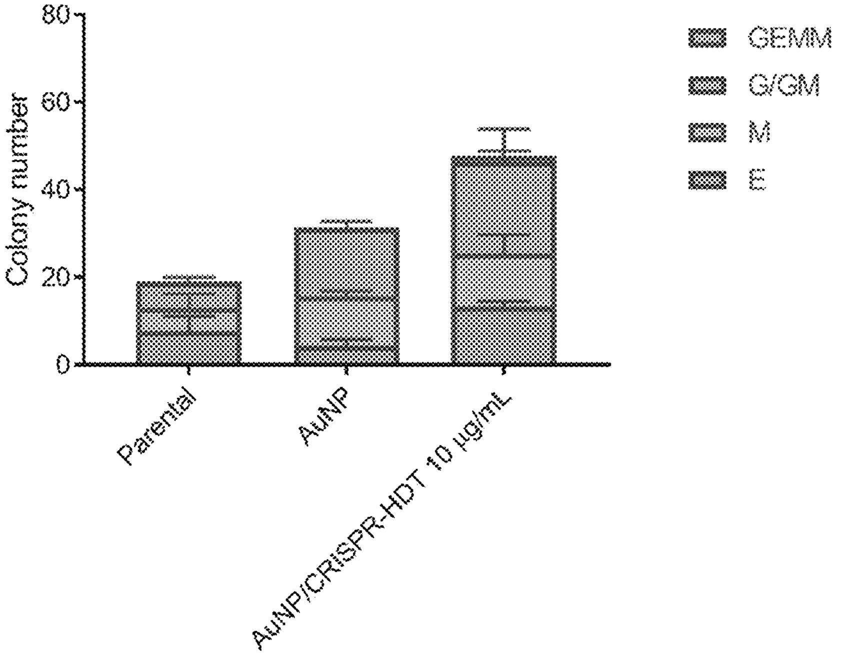
Figure 21A:
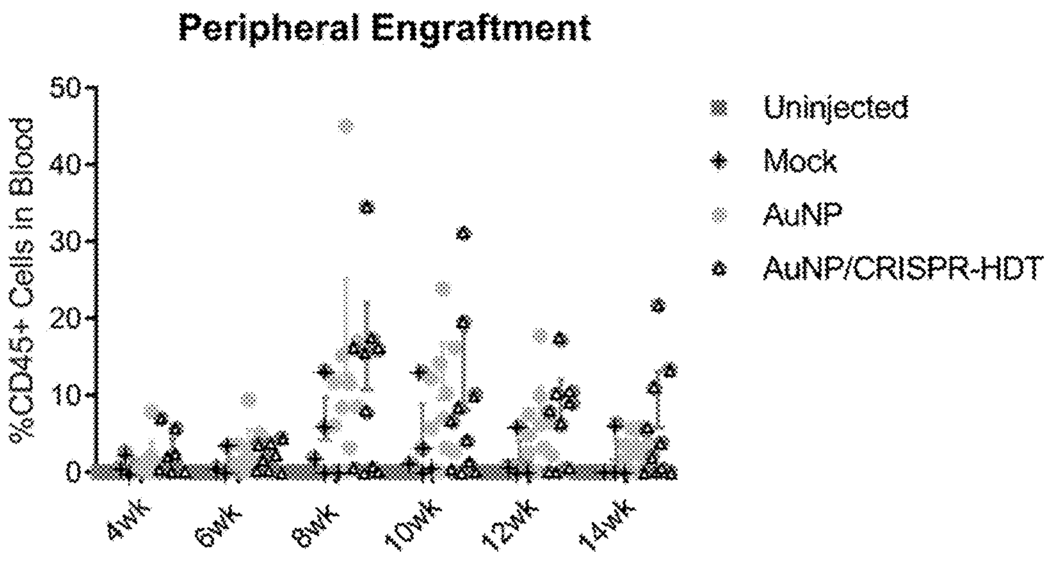
FIGS. 21A-21J. In vivo analysis of cells transplanted into NSG mice. AuNP-treated $hCD^{34}$+ cells engraft better than mock-treated cells.
Figure 21B:
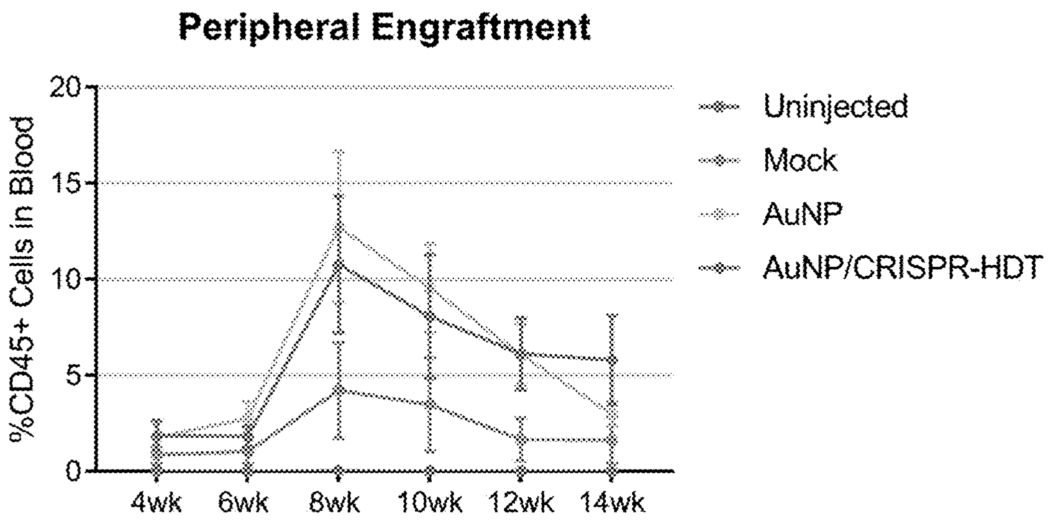
Figure 21C:
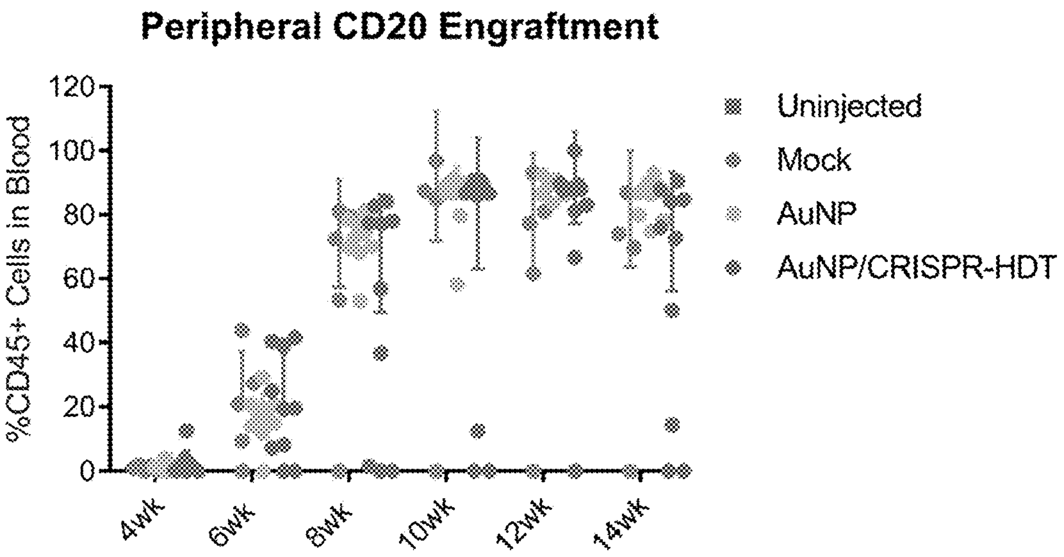
Figure 21D:
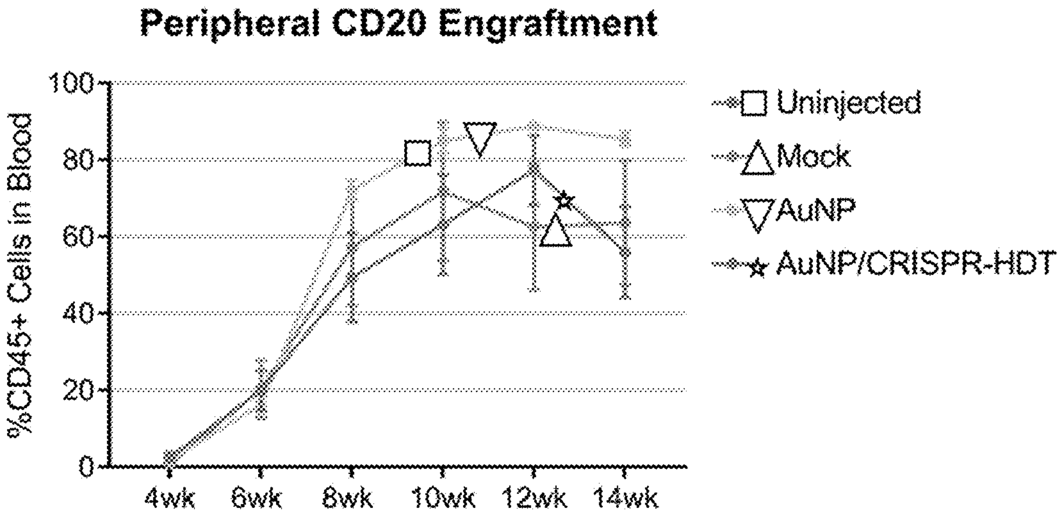
Figure 21E:
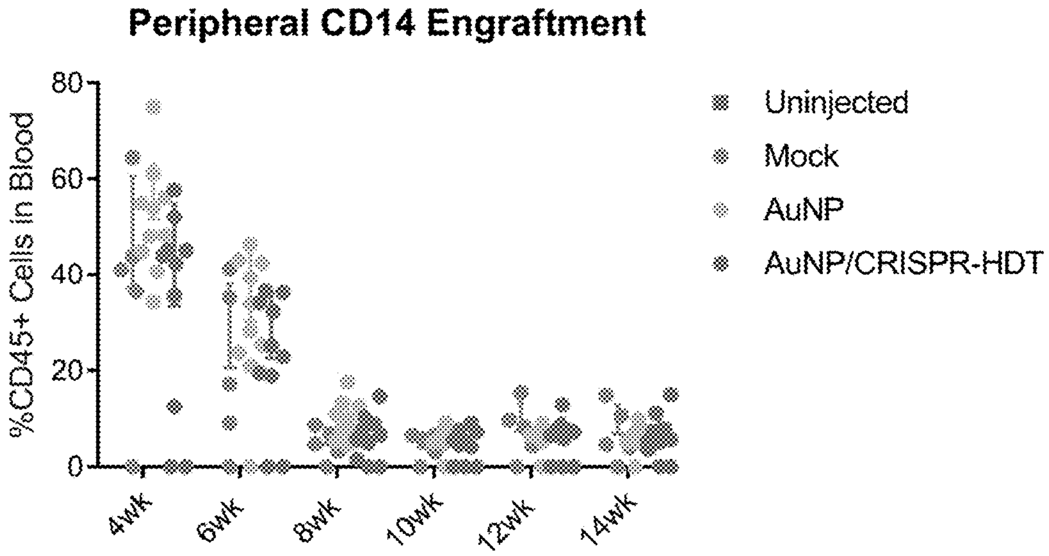
Figure 21F:
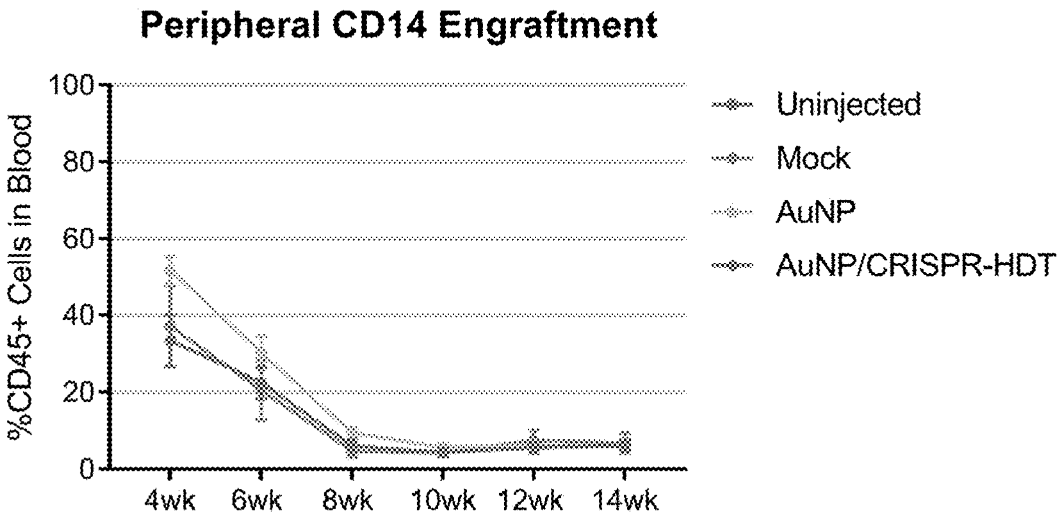
Figure 21G:
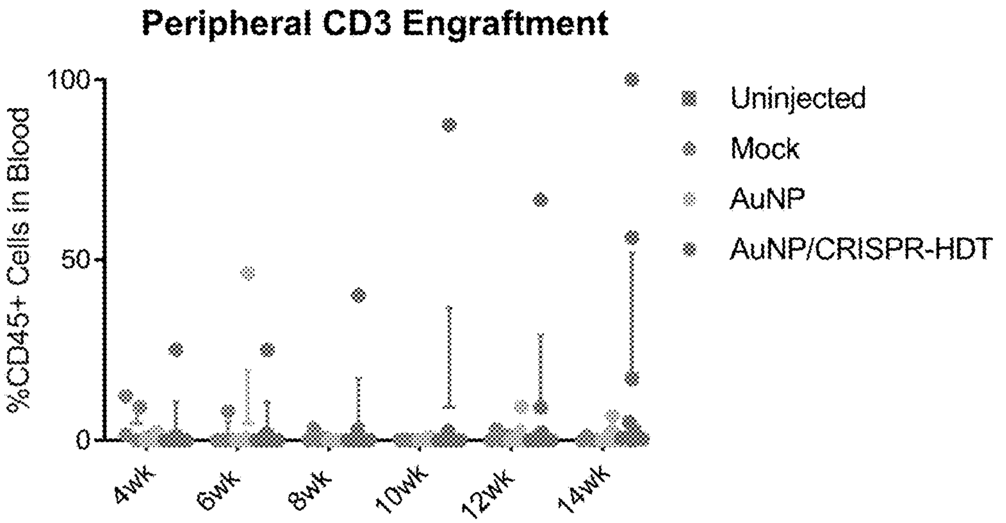
Figure 21H:
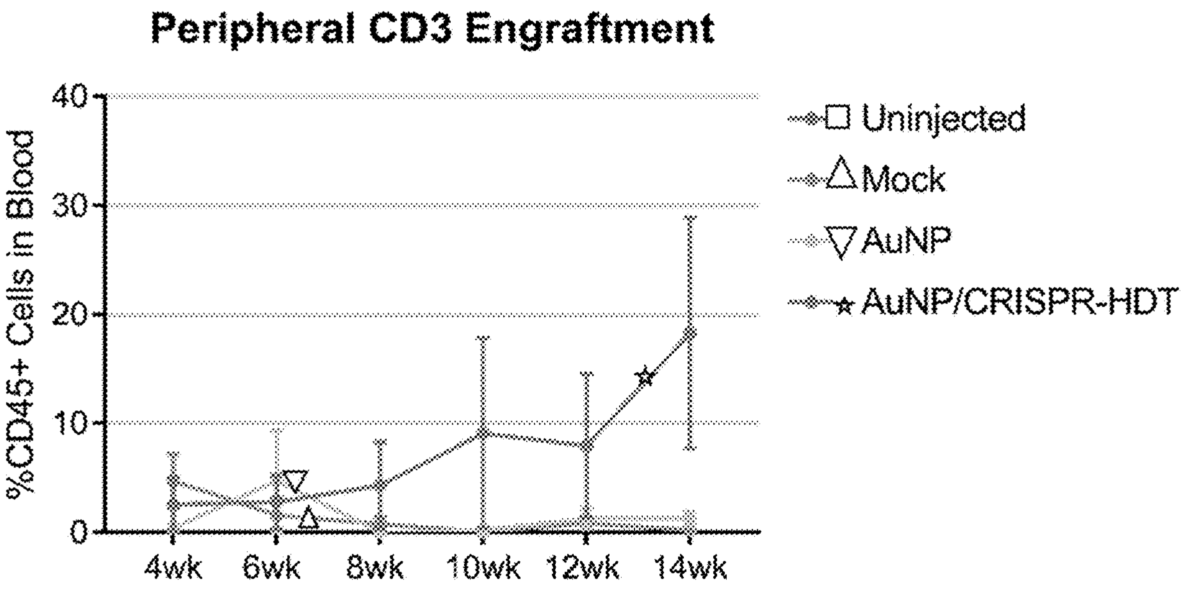
Figure 21I:
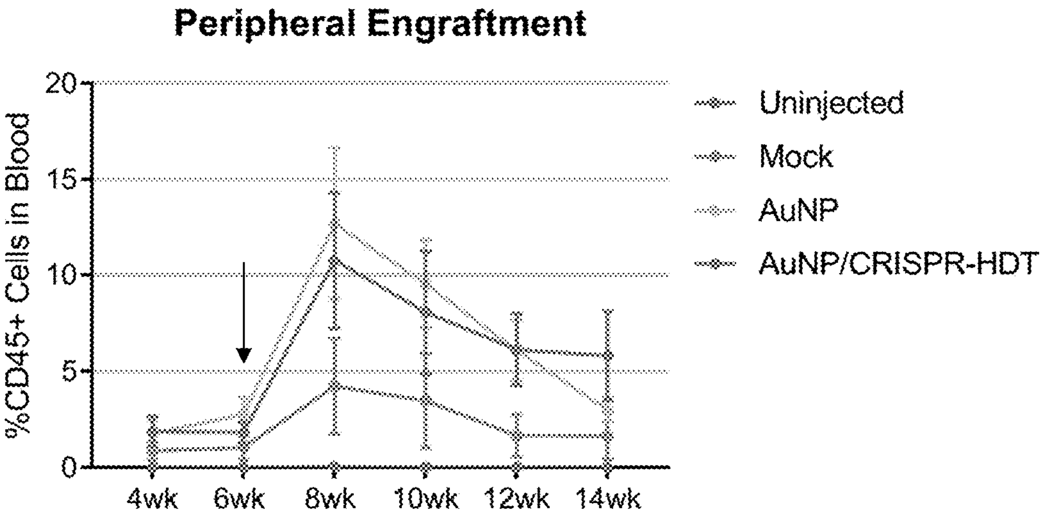
Figure 21J:
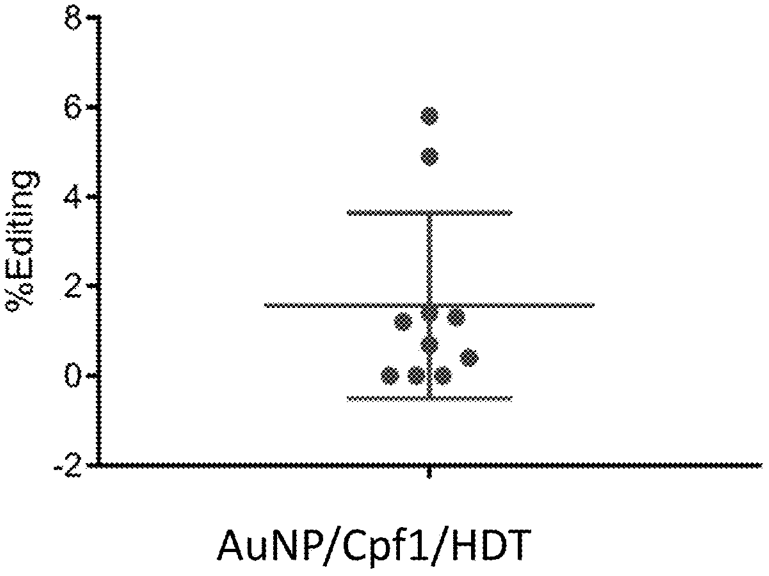
Figure 22:
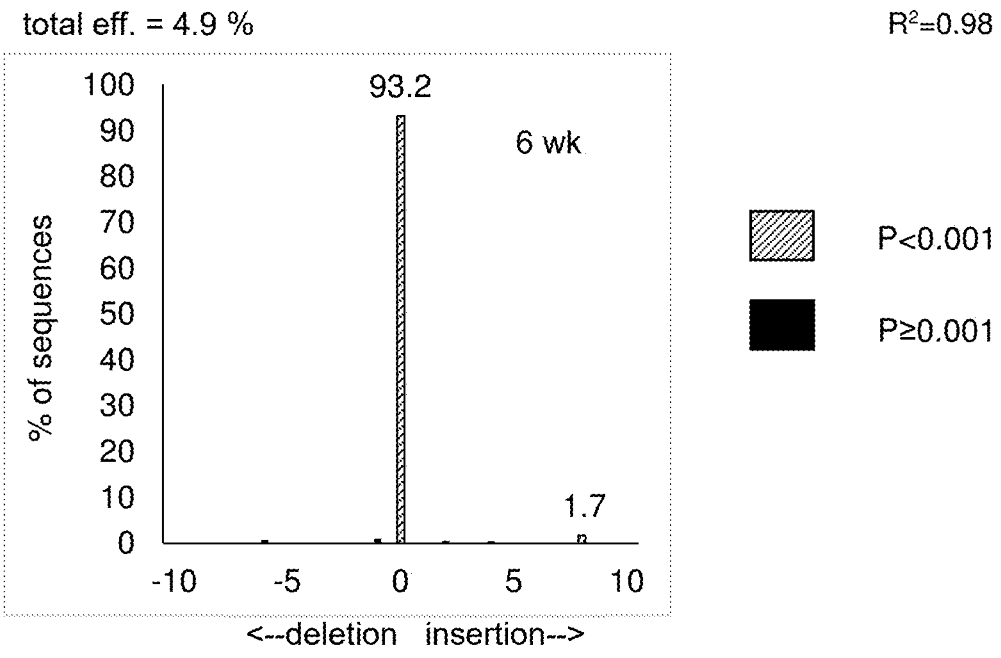
FIG. 22. Early post-transplant analysis suggests gene edited cell engraftment. Peripheral blood was collected for gDNA analysis at 6 weeks after transplant (arrow in FIG. 21I). Across all mice treated with fully-loaded AuNPs, 7/10 displayed detectable editing ranging from 0.5-6% by TIDE. In one mouse (5% total editing), 1.7% HDR was observed by TIDE analysis.

Confocal microscopy demonstrated that disclosed nanoformulations avoided lysosomal entrapment and successfully localized to the nucleus of $CD^{34}$+primary hematopoietic cells from healthy donors. Knock-in frequencies of up to 10% were demonstrated using a Not/restriction enzyme template with homology arm lengths of +40 nucleotides to a CCR5 locus without cytotoxicity. Designing template to the non-target DNA strand yielded a higher homology directed repair (HDR) efficiency (FIG. 13), with clear 447 bp and 316 bp cut bands following digestion with Notl and T7EI enzymes (FIG. 20B). Direct comparison of Cpf1 and Cas9 nuclease activity at the same CCR5 target site demonstrated a Cpf1 bias for HDR and template knock-in over Cas9, which preferentially generated indels. Xenotransplantation of CRISPR Cpf1 nanoformulation-treated human $CD^{34}$+ cells into immune deficient mice demonstrated an early increased trend in engraftment compared to non-treated cells, suggesting an unknown benefit of nanoformulation-treated HSPCs. The frequency of CCR5 genetically modified cell engraftment was the same as observed in culture, with 10% of human cells displaying Notl template addition in vivo.

(VI) Nanoparticle Compositions and Cell Formulations. Nanoparticles disclosed herein can be formulated into compositions for administration to subjects.

In particular embodiments, blood cells can be obtained from a subject or donor and genetically modified (e.g., within a GSH) before administration to the subject to treat a condition. Common sources of appropriate blood cells include mobilized peripheral blood samples, bone marrow samples, and/or umbilical cord blood.

Exemplary carriers for nanoparticle compositions and/or cell formulations include saline, buffered saline, physiological saline, water, Hanks' solution, Ringer's solution, Nonnosol-R (Abbott Labs), Plasma-Lyte A® (Baxter Laboratories, Inc., Morton Grove, IL), glycerol, ethanol, and combinations thereof. In particular embodiments, nanoparticle compositions and/or cell formulations are administered to subjects as soon as reasonably possible following their initial formulation.

In particular embodiments, carriers can be supplemented with human serum albumin (HSA) or other human serum components or fetal bovine serum or other species serum components. In particular embodiments, a carrier for infusion includes buffered saline with 5% HSA or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent component adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, nanoparticle compositions and/or cell formulations can include a local anesthetic such as lidocaine to ease pain at a site of injection.

Therapeutically effective amounts of nanoparticles within a composition can include at least 0.1% w/v or w/w particles; at least 1% w/v or w/w particles; at least 10% w/v or w/w particles; at least 20% w/v or w/w particles; at least 30% w/v or w/w particles; at least 40% w/v or w/w particles; at least 50% w/v or w/w particles; at least 60% w/v or w/w particles; at least 70% w/v or w/w particles; at least 80% w/v or w/w particles; at least 90% w/v or w/w particles; at least 95% w/v or w/w particles; or at least 99% w/v or w/w particles.

Therapeutically effective amounts of cells within cell-based formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

The nanoparticle compositions and/or cell formulations disclosed herein can be prepared for administration by, for example, injection, infusion, perfusion, or lavage.

In particular embodiments, it can be necessary or beneficial to freeze dry a nanoparticle composition and/or to cryopreserve a cell-based formulation. Such techniques are well known to those of ordinary skill in the art.

(VII) Exemplary Methods of Use. Hematopoietic stem cells (HSC) are stem cells that can give rise to all blood cell types such as the white blood cells of the immune system (e.g., virus-fighting T cells and antibody-producing B cells) and red blood cells. The therapeutic administration of HSC can be used to treat a variety of adverse conditions including immune deficiency diseases, blood disorders, malignant cancers, infections, and radiation exposure (e.g., cancer treatment, accidental, or attack-based). As examples, more than 80 primary immune deficiency diseases are recognized by the World Health Organization. These diseases are characterized by an intrinsic defect in the immune system in which, in some cases, the body is unable to produce any or enough antibodies against infection. In other cases, cellular defenses to fight infection fail to work properly. Typically, primary immune deficiencies are inherited disorders.

Examples of diseases that can be treated using the nanoparticle compositions or cell formulations of the disclosure include a monogenetic blood disorder, hemophilia, Grave's Disease, rheumatoid arthritis, pernicious anemia, Multiple Sclerosis (MS), inflammatory bowel disease, systemic lupus erythematosus (SLE), Wiskott-Aldrich syndrome (WAS), chronic granulomatous disease (CGD), Battens disease, adrenoleukodystrophy (ALD) or metachromatic leukodystrophy (MLD), muscular dystrophy, pulmonary aveolar proteinosis (PAP), pyruvate kinase deficiency, Shwachmann-Diamond-Blackfan anemia, dyskeratosis congenita, cystic fibrosis, Parkinson's disease, Alzheimer's disease, amyotrophic lateral sclerosis (Lou Gehrig's disease), acute lymphoblastic leukemia (ALL), acute myelogenous leukemia (AML), agnogenic myeloid metaplasia, amegakaryocytosis/congenital thrombocytopenia, ataxia telangiectasia, β-thalassemia major, CLL, chronic myelogenous leukemia (CML), chronic myelomonocytic leukemia, common variable immune deficiency (CVID), complement disorders, congenital (X-linked) agammaglobulinemia, familial erythrophagocytic lymphohistiocytosis, Hodgkin's lymphoma, Hurler's syndrome, hyper IgM, IgG subclass deficiency, juvenile myelomonocytic leukemia, mucopolysaccharidoses, multiple myeloma, myelodysplasia, non-Hodgkin's lymphoma, paroxysmal nocturnal hemoglobinuria (PNH), primary immunodeficiency diseases with antibody deficiency, pure red cell aplasia, refractory anemia, selective IgA deficiency, severe aplastic anemia, SCD, and/or specific antibody deficiency.

Particular embodiments include treatment of bacterial and/or parasitic infections. One exemplary parasite includes malaria-causing Plasmodium.

The compositions and formulations disclosed herein can be used for treating subjects (humans, veterinary animals (dogs, cats, reptiles, birds, etc.), livestock (horses, cattle, goats, pigs, chickens, etc.), and research animals (monkeys, rats, mice, fish, etc.). In particular embodiments, subjects are human patients. Nanoparticles described herein can be customized for any target while GSH sites are specific to humans and non-human primates.

Treating subjects includes delivering therapeutically effective amounts. Therapeutically effective amounts include those that provide effective amounts, prophylactic treatments, and/or therapeutic treatments.

An "effective amount" is the amount of a formulation necessary to result in a desired physiological change in a subject. Effective amounts are often administered for research purposes.

Assay for HSPC functionality. The most robust assay for HSPC functionality is the ability to reconstitute hematopoiesis in a conditioned recipient. In particular embodiments, human HSPC are xenotransplanted following electroporation of an optimal CRISPR/Cpf1 pair and ssODN combination into sub-lethally irradiated neonatal NOD/SCIDgamma$^{null}$ (NSG) mice. The hematology, engraftment and persistence of GFP+ cells is then monitored by flow cytometry across blood cell lineages and time for 20 weeks after transplant. Genomic DNA (gDNA) is also isolated from blood, BM and spleen of transplanted animals at the time of necropsy for DNA barcode sequencing to determine the number of clones contributing to GFP+ cell hematopoiesis observed in vivo. Animals receiving HSPC modified with CRISPR/Cpf1 and ssODN are monitored for GFP+ cells by flow cytometry across blood cell lineages and time. Genomic DNA (gDNA) is isolated from blood, BM and spleen of transplanted animals at the time of necropsy for DNA barcode sequencing to determine the number of clones contributing to GFP+ cell hematopoiesis observed in vivo, in addition to more thorough evaluation of indel formation and persistence.

A "prophylactic treatment" includes a treatment administered to a subject who does not display signs or symptoms of a condition to be treated or displays only early signs or symptoms of the condition to be treated such that treatment is administered for the purpose of diminishing, preventing, or decreasing the risk of developing the condition. Thus, a prophylactic treatment functions as a preventative treatment against a condition.

A "therapeutic treatment" includes a treatment administered to a subject who displays symptoms or signs of a condition and is administered to the subject for the purpose of reducing the severity or progression of the condition.

The actual dose and amount of a therapeutic composition or formulation administered to a particular subject can be determined by a physician, veterinarian, or researcher taking into account parameters such as physical and physiological factors including target; body weight; type of condition; severity of condition; upcoming relevant events, when known; previous or concurrent therapeutic interventions; idiopathy of the subject; and route of administration, for example. In addition, in vitro and in vivo assays can optionally be employed to help identify optimal dosage ranges.

Therapeutically effective amounts can be administered through any appropriate administration route such as by, injection, infusion, perfusion, or lavage.

In particular embodiments, methods of the present disclosure can restore BM function in a subject in need thereof. In particular embodiments, restoring BM function can include improving BM repopulation with gene corrected cells as compared to a subject in need thereof not administered a therapy described herein. Improving BM repopulation with gene corrected cells can include increasing the percentage of cells that are gene corrected. In particular embodiments, the cells are selected from white blood cells and BM derived cells. In particular embodiments, the percentage of cells that are gene corrected can be measured using an assay selected from quantitative real time PCR and flow cytometry.

In particular embodiments, methods of the present disclosure can normalize primary and secondary antibody responses to immunization in a subject in need thereof.

Normalizing primary and secondary antibody responses to immunization can include restoring B-cell and/or T-cell cytokine signaling programs functioning in class switching and memory response to an antigen.

Normalizing primary and secondary antibody responses to immunization can be measured by a bacteriophage immunization assay. In particular embodiments, restoration of B-cell and/or T-cell cytokine signaling programs can be assayed after immunization with the T-cell dependent neoantigen bacteriophage φX174. In particular embodiments, normalizing primary and secondary antibody responses to immunization can include increasing the level of IgA, IgM, and/or IgG in a subject in need thereof to a level comparable to a reference level derived from a control population. In particular embodiments, normalizing primary and secondary antibody responses to immunization can include increasing the level of IgA, IgM, and/or IgG in a subject in need thereof to a level greater than that of a subject in need thereof not administered a gene therapy described herein. The level of IgA, IgM, and/or IgG can be measured by, for example, an immunoglobulin test. In particular embodiments, the immunoglobulin test includes antibodies binding IgG, IgA, IgM, kappa light chain, lambda light chain, and/or heavy chain. In particular embodiments, the immunoglobulin test includes serum protein electrophoresis, immunoelectrophoresis, radial immunodiffusion, nephelometry and turbidimetry. Commercially available immunoglobulin test kits include MININEPH™ (Binding site, Birmingham, UK), and immunoglobulin test systems from Dako (Denmark) and Dade Behring (Marburg, Germany). In particular embodiments, a sample that can be used to measure immunoglobulin levels includes a blood sample, a plasma sample, a cerebrospinal fluid sample, and a urine sample.

In particular embodiments, methods of the present disclosure can improve the kinetics and/or clonal diversity of lymphocyte reconstitution in a subject in need thereof. In particular embodiments, improving the kinetics of lymphocyte reconstitution can include increasing the number of circulating T lymphocytes to within a range of a reference level derived from a control population. In particular embodiments, improving the kinetics of lymphocyte reconstitution can include increasing the absolute CD3+lymphocyte count to within a range of a reference level derived from a control population. A range of a reference level can be a range of values observed in or exhibited by normal (i.e., non-immuno-compromised) subjects for a given parameter. In particular embodiments, improving the kinetics of lymphocyte reconstitution can include reducing the time required to reach normal lymphocyte counts as compared to a subject in need thereof not administered a therapy described herein. In particular embodiments, improving the kinetics of lymphocyte reconstitution can include increasing the frequency of gene corrected lymphocytes as compared to a subject in need thereof not administered a therapy described herein. In particular embodiments, improving the kinetics of lymphocyte reconstitution can include increasing diversity of clonal repertoire of gene corrected lymphocytes in the subject as compared to a subject in need thereof not administered a gene therapy described herein.

In particular embodiments, methods of the present disclosure can restore T-cell mediated immune responses in a subject in need thereof. Restoration of T-cell mediated immune responses can include restoring thymic output and/or restoring normal T lymphocyte development.

In particular embodiments, restoring thymic output can include restoring the frequency of CD3+ T cells expressing CD45RA in PB to a level comparable to that of a reference level derived from a control population. In particular embodiments, restoring thymic output can include restoring the number of T cell receptor excision circles (TRECs) per 106 maturing T cells to a level comparable to that of a reference level derived from a control population. The number of TRECs per 106 maturing T cells can be determined as described in Kennedy D R et al. (2011) Vet Immunol Immunopathol 142:36-48.

In particular embodiments, restoring normal T lymphocyte development includes restoring the ratio of CD4+ cells: CD8+ cells to 2. In particular embodiments, restoring normal T lymphocyte development includes detecting the presence of αβTCR in circulating T-lymphocytes. The presence of αβTCR in circulating T-lymphocytes can be detected, for example, by flow cytometry using antibodies that bind an a and/or B chain of a TCR. In particular embodiments, restoring normal T lymphocyte development includes detecting the presence of a diverse TCR repertoire comparable to that of a reference level derived from a control population. TCR diversity can be assessed by TCRVβ spectratyping, which analyzes genetic rearrangement of the variable region of the TCRβ gene. Robust, normal spectratype profiles can be characterized by a Gaussian distribution of fragments sized across 17 families of TCRVβ segments. In particular embodiments, restoring normal T lymphocyte development includes restoring T-cell specific signaling pathways. Restoration of T-cell specific signaling pathways can be assessed by lymphocyte proliferation following exposure to the T cell mitogen phytohemagglutinin (PHA). In particular embodiments, restoring normal T lymphocyte development includes restoring white blood cell count, neutrophil cell count, monocyte cell count, lymphocyte cell count, and/or platelet cell count to a level comparable to a reference level derived from a control population.

In particular embodiments, a therapeutically effective treatment induces or increases production of hemoglobin; induces or increases production of beta-globin, or alpha-globin; and/or increases the availability of oxygen to cells in the body.

In particular embodiments, a therapeutically effective treatment increases blood cell counts, improves blood cell function, and/or increases oxygenation of cells.

In particular embodiments, a therapeutically effective treatment increases the production of coagulation/clotting factor VIII or coagulation/clotting factor IX, causes the production of normal versions of coagulation factor VIII or coagulation factor IX, reduces the production of antibodies to coagulation/clotting factor VIII or coagulation/clotting factor IX, and/or causes the proper formation of blood clots.

In particular embodiments, a therapeutically effective treatment causes the degradation of mucopolysaccharides in lysosomes, reduces, eliminates, prevents, or delays the swelling in various organs, including the head (exp. Macrosephaly), the liver, spleen, tongue, or vocal cords; reduces fluid in the brain; reduces heart valve abnormalities; prevents or dilates narrowing airways, reduces or prevent upper respiratory conditions like infections and sleep apnea; and/or reduces, eliminates, prevents, or delays the destruction of neurons and/or the symptoms associated with the destruction of neurons.

In particular embodiments, therapeutically effective amounts may provide function to immune and other blood cells, reduce or eliminate an immune-mediated condition; and/or reduce or eliminate a symptom of the immune-mediated condition.

In particular embodiments, particular methods of use include in the treatment of conditions where corrected cells have a selective advantage over non-corrected cells. For example, in FA and SCID, corrected cells have an advantage and only transducing the therapeutic gene into a "few" HSPCs is sufficient for therapeutic efficacy.

Additional methods of treatment can be found in International Patent Application PCT/US2016/014378, filed Jan. 21, 2016 and U.S. Provisional Application Nos. 62/351,761, filed Jun. 17, 2016 and 62/428,994, filed Dec. 1, 2016, each of which is specifically incorporated herein in their entirety.

(VIII) Reference Levels Derived from Control Populations. Obtained values for parameters associated with a therapy described herein can be compared to a reference level derived from a control population, and this comparison can indicate whether a therapy described herein is effective for a subject in need thereof. Reference levels can be obtained from one or more relevant datasets from a control population. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual data points; e.g., mean, median, median of the mean, etc. Alternatively, a reference level or dataset to create a reference level can be obtained from a service provider such as a laboratory, or from a database or a server on which the dataset has been stored.

A reference level from a dataset can be derived from previous measures derived from a control population. A "control population" is any grouping of subjects or samples of like specified characteristics. The grouping could be according to, for example, clinical parameters, clinical assessments, therapeutic regimens, disease status, severity of condition, etc. In particular embodiments, the grouping is based on age range (e.g., 0-2 years) and non-immunocompromised status. In particular embodiments, a normal control population includes individuals that are age-matched to a test subject and non-immune compromised. In particular embodiments, age-matched includes, e.g., 0-6 months old; 0-1 year old; 0-2 years old; 0-3 years old; 10-15 years old, as is clinically relevant under the circumstances. In particular embodiments, a control population can include those that have an immune deficiency and have not been administered a therapeutically effective amount In particular embodiments, the relevant reference level for values of a particular parameter associated with a therapy described herein is obtained based on the value of a particular corresponding parameter associated with a therapy in a control population to determine whether a therapy disclosed herein has been therapeutically effective for a subject in need thereof.

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the p-value. The p-value represents the probability of obtaining a given result equivalent to a particular data point, where the data point is the result of random chance alone. A result is often considered significant (not random chance) at a p-value less than or equal to 0.05. In particular embodiments, a sample value is "comparable to" a reference level derived from a normal control population if the sample value and the reference level are not statistically significantly different.

(IX) Kits. The disclosure also provides kits containing any one or more of the elements disclosed in the methods and compositions herein. In particular embodiments, a kit can include guide RNA and a nuclease capable of cutting a target sequence in a blood cell GSH and an HDR template. Elements may be provided individually or in combinations, and may be provided in any suitable container, such as a vial, a bottle, a bag or a tube. In some embodiments, the kit includes instructions in one or more languages, for example in more than one language.

In particular embodiments, a kit includes one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g., in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from 7 to 10. In some embodiments, the kit includes a homologous recombination template polynucleotide.

Exemplary Embodiments: a gene editing sequence to target a genomic safe harbor disclosed herein (see, e.g., FIG. 1, 3, 4); a nanoparticle conjugated to gene editing sequences disclosed herein (see, e.g., FIG. 1, 3, 4); a CRISPR gene editing sequence modified at the 3' end.

1. A method of genetically modifying a cell at a target sequence within chromosome 11 including SEQ ID NOs. 1-194, 197-208, 210, 213, 242, 245, 251, or 254 including: contacting the cell with a targeting element, a cutting element, and a homology-directed repair template wherein the contacting results in (i) cutting within the target sequence; and (ii) homology-directed repair (HDR).
2. The method of embodiment 1, wherein the targeting element, the cutting element and the homology-directed repair template are part of a CRISPR gene editing system, a meganuclease gene editing system, a zinc finger nuclease (ZFN) gene editing system, or a transcription activator-like effector-based nuclease (TALEN) gene editing system.
3. The method of embodiment 1 or 2, wherein the targeting element is crRNA that hybridizes to one of SEQ ID NOs. 1-194, 197-208, 210, 213, 242, 245, 251, or 254.
4. The method of any of embodiments 1-3, wherein the cutting element is Cpf1 or Cas 9.
5. The method of embodiment 4, wherein the Cpf1 or Cas9 includes a sequence selected from SEQ ID NOs: 215-241.
6. The method of embodiment 4, wherein the Cpf1 is a variant of a Cpf1 selected from SEQ ID NOs: 216-227, or 229-241.
7. The method of any of embodiments 1-6, wherein the homology-directed repair template includes homology arms to the target sequence, and wherein the homology-directed repair template is part of a donor template further including a therapeutic gene that results in expression of a therapeutic gene product.

8. The method of embodiment 7, wherein the therapeutic gene or therapeutic gene product is selected from skeletal protein 4.1, glycophorin, p55, the Duffy allele, globin family genes; WAS; phox; dystrophin; pyruvate kinase; CLN3; ABCD1; arylsulfatase A; SFTPB; SFTPC; NLX2.1; ABCA3; GATA1; ribosomal protein genes; TERT; TERC; DKC1; TINF2; CFTR; LRRK2; PARK2; PARK7; PINK1; SNCA; PSEN1; PSEN2; APP; SOD1; TDP43; FUS; ubiquilin 2; C9ORF72, a2β1; αvβ3; αvβ5; αvβ63; BOB/GPR15; Bonzo/STRL-33/TYMSTR; CCR2; CCR3; CCR5; CCR8; CD4; CD46; CD55; CXCR4; aminopeptidase-N; HHV-7; ICAM; ICAM-1; PRR2/HveB; HveA; α-dystroglycan; LDLR/α2MR/LRP; PVR; PRR1/HveC, laminin receptor, 101F6, 123F2, 53BP2, abl, ABLI, ADP, aFGF, APC, ApoAl, ApoAIV, ApoE, ATM, BAI-1, BDNF, Beta*(BLU), bFGF, BLC1, BLC6, BRCA1, BRCA2, CBFA1, CBL, C-CAM, CFTR, CNTF, COX-1, CSFIR, CTS-1, cytosine deaminase, DBCCR-1, DCC, Dp, DPC-4, E1A, E2F, EBRB2, erb, ERBA, ERBB, ETS1, ETS2, ETV6, Fab, FancA, FancB, FancC, FancD1, FancD2, FancE, FancF, FancG, Fancl, FancJ, FancL, FancM, FancN, FancO, FancP, FancQ, FancR, FancS, FancT, FancU, FancV, and FancW, FCC, FGF, FGR, FHIT, fms, FOX, FUS 1, FUS1, FYN, G-CSF, GDAIF, Gene 21, Gene 26, GM-CSF, GMF, gsp, HCR, HIC-1, HRAS, hst, IGF, IL-1, IL-2, IL-3, IL-4, IL-5, IL-6, IL-7, IL-8, IL-9, IL-10, IL-11 IL-12, ING1, interferon α, interferon β, interferon γ, IRF-1, JUN, KRAS, LCK, LUCA-1, LUCA-2, LYN, MADH4, MADR2, MCC, mda7, MDM2, MEN-I, MEN-II, MLL, MMAC1, MYB, MYC, MYCL1, MYCN, neu, NF-1, NF-2, NGF, NOEY1, NOEY2, NRAS, NT3, NT5, OVCA1, p16, p21, p27, p53, p57, p73, p300, PGS, PIM1, PL6, PML, PTEN, raf, Rap1A, ras, Rb, RB1, RET, rks-3, ScFv, scFV ras, SEM A3, SRC, TAL1, TCL3, TFPI, thrombospondin, thymidine kinase, TNF, TP53, trk, T-VEC, VEGF, VHL, WT1, WT-1, YES, zac1, iduronidase, IDS, GNS, HGSNAT, SGSH, NAGLU, GUSB, GALNS, GLB1, ARSB, HYAL1, F8, F9, HBB, CYB5R3, yC, JAK3, IL7RA, RAG1, RAG2, DCLRE1C, PRKDC, LIG4, NHEJ1, CD3D, CD3E, CD3Z, CD3G, PTPRC, ZAP70, LCK, AK2, ADA, PNP, WHN, CHD7, ORAI1, STIM1, CORO1A, CIITA, RFXANK, RFX5, RFXAP, RMRP, DKC1, TERT, TINF2, DCLRE1B, and SLC46A1.

9. The method of embodiment 7 or 8, wherein the homology arms are 40 nucleotides (nt)-1000 nt.

10. The method of any of embodiments 1-9, wherein the targeting element and the cutting element are separate molecules or are part of a single dual-purpose molecule.

11. The method of any of embodiments 1-10, wherein the targeting element and the cutting element are coupled to a nanoparticle.

12. The method of embodiment 11, wherein the nanoparticle includes a gold nanoparticle.

13. The method of any of embodiments 1-12 wherein the targeting element and/or the cutting element are conjugated to a spacer.

14. The method of embodiment 13 wherein the spacer includes a thiol modification.

15. The method of embodiment 14 wherein the thiol modification is covalently linked to the surface of the nanoparticle.

16. The method of any of embodiments 13-15 wherein the targeting element includes a 3' end and a 5' end, and wherein the 3' end is conjugated to the spacer.

17. The method of any of embodiments 11-16 wherein the nanoparticle is associated with at least two layers wherein the first layer includes the targeting element and the second layer includes a donor template including a therapeutic gene and homology-directed repair templates; and wherein at least a portion of the second layer is farther from the surface of the nanoparticle than the first layer.

18. The method of any of embodiments 11-17, wherein the nanoparticle is coupled to a targeting molecule.

19. The method of embodiment 18, wherein the targeting molecule includes a CD34 binding domain or a CD90 binding domain.

20. The method of any of embodiments 1-19, wherein the cell includes a hematopoietic stem cell (HSC), a hematopoietic progenitor cell (HPC), a hematopoietic stem and progenitor cell (HSPC), a T cell, a natural killer (NK) cell, a B cell, a macrophage, a monocyte, a mesenchymal stem cell (MSC), a white blood cell (WBC), a mononuclear cell (MNC), a endothelial cell (EC), a stromal cell, and/or a bone marrow fibroblast.

21. The method of embodiment 20, wherein the blood cell includes a $CD^{34}$+CD45RA-$CD90^{+}$ HSC.

22. The method of embodiment 20 or 21, wherein the blood cell is a human blood cell.

23. The method of any of embodiments 1-22, wherein the cutting results in a staggered DNA double strand break with a 2-4-nt 5' overhangs.

24. The method of any of embodiments 1-23 utilizing at least one of the following target sequence crRNA pairs: (i) target: SEQ ID NO: 132/crRNA: SEQ ID NO: 195; (ii) target: SEQ ID NO: 108/crRNA: SEQ ID NO: 196; (iii) target: SEQ ID NO: 203/crRNA: SEQ ID NO: 209; (iv) target: SEQ ID NO: 210/crRNA: SEQ ID NO: 211; (v) target: SEQ ID NO: 242/crRNA: SEQ ID NO: 244; and (vi) target: SEQ ID NO: 251/crRNA: SEQ ID NO: 253.

25. A nanoparticle associated with at least two active layers wherein the first layer includes a DNA targeting element and a cutting element and wherein the second layer includes a donor template including a therapeutic gene and homology-directed repair templates; and wherein at least portions of the second layer are farther from the surface of the nanoparticle than the first layer.

26. The nanoparticle of embodiment 24 wherein the targeting element hybridizes to one of SEQ ID NOs. 1-194, 197-208, 210, 212, 213, 242, 245, 251, 254, 258, or 263.

27. The nanoparticle of embodiment 25 or 26, wherein the DNA targeting element is crRNA with a 3' end and a 5' end, wherein the 3' end is conjugated to a spacer.

28. The nanoparticle of any of embodiments 25-27 wherein the DNA targeting element is crRNA with a 3' end and a 5' end, wherein the 5' end is conjugated to the cutting element.

29. The nanoparticle of embodiment 27 or 28 wherein the spacer includes a thiol modification that is covalently linked to the surface of the nanoparticle.

30. The nanoparticle of any of embodiments 25-29 wherein the cutting element is Cpf1 or Cas 9.

31. The nanoparticle of any of embodiments 27-30, wherein the crRNA includes SEQ ID NOs: 195, 196, 209, 211, 244, 253, 260, or 264.
32. The nanoparticle of embodiments 30 or 31, wherein the Cpf1 or Cas9 includes a sequence selected from SEQ ID NOs: 215-241.
33. The nanoparticle of any of embodiments 30-32, wherein the Cpf1 includes a variant of a Cpf1 selected from SEQ ID NOs: 216-227, or 229-241.
34. The nanoparticle of any of embodiments 25-33, wherein the nanoparticle is a gold nanoparticle.
35. The nanoparticle of any of embodiments 25-34, wherein the nanoparticle is coupled to a targeting molecule.
36. The nanoparticle of embodiment 35, wherein the targeting molecule includes a CD34 binding domain or a CD90 binding domain.
37. A therapeutic formulation including a nanoparticle of any of embodiments 24-35.
38. A cell genetically-modified by a method of any of embodiments 1-24 or a nanoparticle of any of embodiments 25-36.
39. The cell of embodiment 38, wherein the cell is a hematopoietic stem cell (HSC), a hematopoietic progenitor cell (HPC), a hematopoietic stem and progenitor cell (HSPC), a T cell, a natural killer (NK) cell, a B cell, a macrophage, a monocyte, a mesenchymal stem cell (MSC), a white blood cell (WBC), a mononuclear cell (MNC), a endothelial cell (EC), a stromal cell, and/or a bone marrow fibroblast.
40. The cell of embodiment 38 or 39, wherein the cell is a $CD^{34}$+CD45RA-$CD90^{+}$ HSC.
41. The cell of any of embodiments 38-40, wherein the cell is a human blood cell.
42. A therapeutic formulation including a cell of any of embodiments 38-41.
43. A method of providing a therapeutic nucleic acid sequence to a patient in need thereof including administering a therapeutic formulation of embodiment 37 and/or 42, to the patient thereby providing a therapeutic nucleic acid sequence to the patient.

Variants of protein and/or nucleic acid sequences disclosed herein can also be used. Variants include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein and nucleic acid sequences described or disclosed herein wherein the variant exhibits substantially similar or improved biological function.

"% sequence identity" refers to a relationship between two or more sequences, as determined by comparing the sequences. In the art, "identity" also means the degree of sequence relatedness between protein and nucleic acid sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. "Default values" will mean any set of values or parameters, which originally load with the software when first initialized.

In particular embodiments, variant proteins include conservative amino acid substitutions. In particular embodiments, a conservative amino acid substitution may not substantially change the structural characteristics of the reference sequence (e.g., a replacement amino acid should not tend to break a helix that occurs in the reference sequence, or disrupt other types of secondary structure that characterizes the reference sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden & J. Tooze, eds., Garland Publishing, New York, N.Y. (1991)); and Thornton et al., Nature, 354:105 (1991).

In particular embodiments, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W. H. Freeman and Company.

As indicated previously, in particular embodiments, variants include engineered Cpf1s. For example, US 2018/

0030425 describes engineered Cpf1 nucleases from Lachnospiraceae bacterium ND2006 and Acidaminococcus sp. BV3L6 with altered and improved target specificity. Particular variants include Lachnospiraceae bacterium ND2006 of SEQ ID NO: 232, e.g., at least including amino acids 19-1246 of SEQ ID NO: 232, with mutations (i.e., replacement of the native amino acid with a different amino acid, e.g., alanine, glycine, or serine), at one or more of the following positions: S203, N274, N278, K290, K367, K532, K609, K915, Q962, K963, K966, K1002, and/or S1003 of SEQ ID NO: 232 (or at positions analogous thereto, e.g., S185, N256, N260, K272, K349, K514, K591, K897, Q944, K945, K948, K984, and/or S985 of SEQ ID NO: 233). SEQ ID NO: 233 is identical to SEQ ID NO: 232 but lacks the first 18 amino acids. Particular Cpf1 variants can also include Acidaminococcus sp. BV3L6 Cpf1 (AsCpf1) of SEQ ID NO: 230, e.g., at least comprising amino acids 1-1307 of SEQ ID NO: 230, with mutations (i.e., replacement of the native amino acid with a different amino acid, e.g., alanine, glycine, or serine (except where the native amino acid is serine)), at one or more of the following positions: N178, S186, N278, N282, R301, T315, S376, N515, K523, K524, K603, K965, Q1013, Q1014, and/or K1054 of SEQ ID NO: 230. In particular embodiments, engineered Cpf1 variants include eCfp1.

Other Cpf1 variants include Cpf1 homologs and orthologs of the Cpf1 polypeptides disclosed in Zetsche et al. (2015) Cell 163:759-771 as well as the Cpf1 polypeptides disclosed in U.S. 2016/0208243. Examples of Cpf1 sequences include SEQ ID NOs: 216-227 and 229-241 disclosed herein.

Other engineered Cpf1 variants are known to those of ordinary skill in the art and included within the scope of the current disclosure (see, e.g., WO/2017/184768).

Exemplary Manufacturing Embodiment.

| Parameter | Disclosed Embodiment |
|---|---|
| Size of AuNP Core | 15 nm |
| AuNP Synthesis Method | Turkevich (1951) |
| Starting solution | 0.25 mM chloroauric acid ($HAuCl_4$) |
| 1st synthesis step | Bring above solution to boiling point and reduce by adding 3.33% sodium citrate (Na3C6H5O7) while stirring vigorously (700 rpm) under a reflux system |
| 2nd synthesis step | Reduce by adding 3.33% sodium citrate ($Na_3C_6H_5O_7$) while stirring vigorously (700 rpm) under a reflux system |
| Cleanup step | Wash AuNPs 3× |
| Initial Resuspension | Rnase free molecular grade water ($H_2O$) |
| First Loading Step | 10 micrograms/mL AuNP added to crRNA (Cpf1/Cas12a) or crRNA + tracrRNA (Cas9) solution at a weight/weight ratio of 0.5 |
| Second Loading Step | 10 mM Citrate buffer (pH 3.0) added and mixed for 5 min. Nanoconjugates are centrifuged at 20000 × g for 20 minutes at room temperature and re-dispersed in 0.9% sodium choloride. |
| Third Loading Step | Add nuclease protein (Cpf1/Cas12a or Cas9) to nanoconjugate solution at a weight/weight ratio of 0.6 |
| Fourth Loading Step | Add 0.005% branched polyethylenimine (2000 MW) and mix by pipetting. |
| Fifth Loading Step | Add single stranded DNA template (ssODN) to nanoconjugates in a weight to weight ratio of 1.0 |
| Final Resuspension | RNase free water |
| Guide RNA Loaded | Guide RNA (crRNA) with the following modifications: For Cpf1 (Cas12a): 1. 3' 18-atom oligo ethylene glycol (OEG) spacer (iSp18) 2. 3' terminal thiol For Cas9: (unmodified tracrRNA) 1. 5' 18-atom oligo ethylene glycol (OEG) spacer (iSp18) 2. 5' terminal thiol |
| Nuclease Loaded | Cpf1 (Cas12a), Cas9, or Mega-TAL |
| ssODN Loaded | Unmodified homology-directed template with symmetric or asymmetric homolgy arms of any length, up to a total of 3 kilobases in total |
| Final actual size of fully loaded AuNP | 25-30 nm |
| Final hydrodynamic size of fully loaded AuNP | 176 nm |

Example 1. Synthesizing Gold Nanoparticle Cores. Gold nanoparticles (AuNPs) of 15 nm size range were synthesized by Turkevich's method with slight modification. Turkevich, et al., (1951). Discussions of the Faraday Society 11 (0): 55-75.). 0.25 mM Chloroauric acid solution was brought to the boiling point and reduced by adding 3.33% sodium citrate solution and stirred vigorously under reflux system for 10 min. Synthesized nanoparticles were washed three times and re-dispersed in highly pure water.

Cpf1 and Cas9 Guide RNA Structures. Single Cpf1 guide RNA was ordered from commercial source, Integrated DNA Technologies; IDT), with two custom modifications on the 3' end. The first modification included an 18-atom oligo ethylene glycol (OEG) spacer (iSp18), and the second modification included a thiol modification. The OEG spacer (e.g. polyethylene glycol (PEG) or hexaethylene glycol (HEG), etc.), was at a ratio of 1 per oligonucleotide and served to prevent electrostatic repulsion between oligonucleotides. While an 18-atom spacer was used, other lengths are also appropriate. The thiol modification was also added at a ratio of 1 per oligonucleotide and served as the basis for covalent interactions to bind the oligonucleotide to the surface of the gold nanoparticle.

5'-/AltR1/rUrA rArUrU rUrCrU rArCrU rCrUrU rGrUrA rGrArU rCrArC rCrCrG rArUrC rCrArC rUrGrG rGrGrA rGrCrA/iSp18//3ThioMC3-D/-3' (SEQ ID NO: 260)

For cas9, a two-part guide system including tracrRNA and crRNA was used. crRNA for Cas9 was ordered from IDT with the same 18 spacer-thiol modifications as above, but on the 5' end.

5'-/5ThioMC6-D//iSp18/rCrA rCrCrC rGrArU rCrCrA rCrUrG rGrGrG rArGrC rGrUrU rUrUrA rGrArG rCrUrA rUrGrC rU/AltR2/-3' (SEQ ID NO: 264)

The accompanying tracrRNA was unmodified.

Preparing the AuNP/CRISPR Nanoformulation. crRNAs with 18 spacer-thiol modifications were used. AuNPs in 10 μg/mL concentration was added to crRNA solution in AuNP/crRNA w/w ratio of 0.5. Following that, citrate buffer with the pH of 3 was added in 10 mM concentration and mixed for 5 min. Prepared AuNP/crRNA nanoconjugates were centrifuged down and re-dispersed in PBS. Then, Cpf1 nuclease was added in AuNP/Cpf1 w/w ratio of 0.6. Polyethylenimine (PEI) of 2000 MW was added in 0.005% concentration and mixed thoroughly. In the final step, ssDNA template was added in the AuNP/ssDNA w/w ratio of 1.

Prophetic Example 1. The translational relevance of the pigtail macaque (M. nemestrina) model in terms of cross-reactivity of human reagents and scale has been previously established. This model has served as an important step in clinical translation of HSPC gene therapy. For example, this model has been used to critically evaluate the hematologic potential and safety of LV gene modified and CCR5 edited HSPC, and to track the fate and persistence of these cells in vivo over years. Optimal crRNA pairs identified as above are paired with an optimal nanoparticle delivery strategy identified as above to gene modify autologous HSPC from three nonhuman primates for autologous transplantation after myeloablative, total body irradiation. Safety and feasibility is assessed by measuring product fitness in vitro and in vivo.

In more detail, autologous transplant is performed for $CD^{34}$+$CD90^{+}$CD45RA-HSPC after nanoparticle-mediated CRISPR/Cpf1 GSH editing and reporter transgene insertion. Three juvenile pigtail macaques are primed with recombinant human granulocyte colony stimulating factor (GCS-F; 100 mcg/kg/day×4 days) and stem cell factor (SCF; 50 mcg/kg/day×4 days) as subcutaneous injections. Bone marrow is harvested into heparin on the 4th day of priming. The leukocytes are isolated by ammonium chloride lysis and are labeled with IgM monoclonal antibody 12-8 ($CD^{34}$+) at 4° C. for 30 minutes, washed, and incubated with rat monoclonal anti-mouse IgM microbeads for 30 minutes at 4° C., washed, and then immunoselected. All additional selection procedures will be conducted as described above. The optimal nanoparticle formulation and treatment protocol identified as above is used to accomplish GSH gene editing and targeted GFP transgene insertion. During ex vivo HSPC manipulation monkeys receive myeloablative total body irradiation (1020cGy) as four fractionated doses over 2 days from a linear accelerator. Gene modified HSPC are formulated in PlasmaLyte and autologous serum for intravenous re-infusion 24 hours after the last irradiation dose is delivered. Animals receive supportive care as needed (transfusions, intravenous fluids, etc.).

Gene modified HSPC products will be tested for viability, in vitro colony-forming capacity (CFC), sterility, mycoplasma, endotoxin, cell phenotype, indel formation and transgene expression. All test protocols to be applied are approved for use in phase I clinical trials of autologous cell therapy. Safety is determined by the ability to generate autologous nanoparticle-treated cells which are considered suitable for infusion (i.e., sterile, mycoplasma-free, low endotoxin, >70% viable). Feasibility is determined by the viable cell yield throughout the process and the success of GSH editing and reporter transgene insertion at scale. The target cell dose at infusion is ≥125,000 $CD^{34}$+$CD90^{+}$ CD45RA: cells per kilogram of body weight based on our preliminary data.

Safety in vivo is measured by hematologic recovery kinetics and supportive care needs after transplant, as well as clonality of engrafted gene edited cells. Peripheral blood is collected daily from each transplanted animal and analyzed by an automated hematology analyzer until hematologic recovery is observed. Recovery is defined as an absolute neutrophil count >500/mcL and platelets >50,000/mcL for 3 consecutive measurements with an increasing trend observed in both parameters. After hematologic recovery, peripheral blood is collected at least twice per month. Flow cytometry is performed regularly to monitor engraftment levels of nanoparticle-treated cells which express reporter transgene (GFP), as well as lineage markers to determine the extent of multi-lineage reconstitution. Genomic DNA (gDNA) is extracted from these samples and subjected to analysis by Surveyor and DNA barcode and GSH locus sequencing as described above. For DNA barcode sequencing, a single round of PCR amplification is performed and resulting reactions are submitted for sequencing using the Illumina MiSeq platform. Sequence reads are subjected to bioinformatics processing to identify unique barcode events and relative clonal contributions as a measure of clone abundance. Clones are mapped as a function of time and contribution. For GSH locus sequencing the primers corresponding to the optimal crRNA pair identified above are used to sequence the GSH locus. The frequency of engrafted cells containing indels versus reporter transgene cassettes is determined.

This study establishes the scaled protocol for nanoparticle-mediated GSH editing and targeted reporter gene insertion. This protocol serves as the basis for evaluating clinically therapeutic transgene delivery across many disease targets. The results of this study provide the basis for evaluation of strategies for improving gene edited HSPC engraftment and differentiation in this clinically relevant and translational large animal model.

Prophetic Example 2. Validate optimal GSH locus for gene editing in $CD^{34}$+CD45RA-$CD90^{+}$ cells. Healthy donor bone marrow (BM) aspirates are obtained from a commercial provider or under an IRB Protocol. Mobilized peripheral blood products (mAPH) are obtained from healthy donors post granulocyte-colony stimulating factor (G-CSF) administration and leukapheresis collection. For BM, red blood cells are depleted by hetastarch sedimentation, and $CD^{34}$+ cells are immune-selected. For mAPH a standard immunoselection of $CD^{34}$+ cells is performed. Resulting CD34-enriched products from both HSPC sources are stained with antibodies specific to CD90 and CD45RA and the target HSPC population ($CD90^{+}$CD45RA-) is collected by fluorescence-activated cell sorting as previously described [Radtke et al., Sci. Transl. Med. 2017; 9 (414).].

$CD^{34}$+CD45RA-$CD90^{+}$ cells are targeted with multiple CRISPR/Cpf1 nucleases designed for a candidate GSH identified. Specificity and function is evaluated in vitro and in vivo to identify the optimal GSH locus. Chemically modified mRNA is used to increase intracellular stability, while homology arms and phosphorothioate modification is incorporated into the ssODN to improve HDR efficiency.

Cells are suspended in StemSpan media containing recombinant human growth factors stem cell factor (SCF), thrombopoietin (TPO) and fms-like tyrosine kinase 3 ligand (flt3-L) and incubated at 30° C. for 24 hours. Media is changed the following day and cultures will be prepared for subsequent analysis and infusion. Viability is monitored by flow cytometry and/or trypan blue staining.

At least three methods can be applied to determine the efficiency and specificity of gene addition. First, flow cytometry can be used to assess GFP and/or therapeutic gene expression. This shows the frequency of cells with cassette incorporation and GFP/therapeutic gene expression/function. Second, the Surveyor assay (Ran et al. Cell. 2013; 154 (6): 1380-1389) is used to determine the frequency of indels versus transgene insertion at the target locus. Briefly, cells are pelleted and DNA extracted and purified. Resulting DNA is quantified and subjected to PCR using primers designed to the locus targeted by the specific CRISPR/Cpf1 nuclease pair. Appropriate mismatch-containing controls are PCR amplified. Following PCR, products are denatured and re-annealed to form heteroduplexes, which are subsequently treated with Surveyor enzyme and analyzed by gel electrophoresis. Imaging and densitometry are then used to calculate an editing efficiency for each locus. Finally, BLISS is applied to identify off-target DSBs (Yan et al. Nat Commun 2017; 8:15058). Cells are first transferred to glass slides by cytospinning, followed by permeabilization and fixation. In situ DSBs are polished and ligated to synthetic oligonucleotides containing a unique sample barcode and multiplex identifier, followed by an RA5 Illumina sequencing adaptor and T7 promoter. DNA is then purified and subjected to sonication followed by in vitro transcription and prepared as a library for Illumina-based sequencing. This permits identification of genomic locations of off-target DSBs and quantitation of DSB frequency as the number of reads corresponding to a specific genomic location for a given number of cells immobilized onto the original slide. Following these analyses, the optimal CRISPR/Cpf1 pair and ssODN combination is identified for further analysis in vivo, for example as described below. The optimal combination demonstrates the highest efficiency of barcoded transgene insertion at the desired locus with minimal toxicity in vitro and the lowest frequency of off-target DSB formation across donors and HSPC sources (BM and mAPH).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in gene editing at a targeted GSH site.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of +20% of the stated value; +19% of the stated value; +18% of the stated value; +17% of the stated value; +16% of the stated value; +15% of the stated value; +14% of the stated value; +13% of the stated value; +12% of the stated value; +11% of the stated value; +10% of the stated value; +9% of the stated value; +8% of the stated value; +7% of the stated value; +6% of the stated value; +5% of the stated value; +4% of the stated value; +3% of the stated value; +2% of the stated value; or +1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Particular embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A therapeutic formulation comprising a nanoparticle (NP) and a pharmaceutically acceptable carrier, the NP comprising:

- a metallic core associated with a first NP layer and a second NP layer, wherein the first NP layer comprises: a crRNA with a 3' end and a 5' end,
  - wherein the 3' end is conjugated to a spacer with a thiol modification, and the 5' end is conjugated to a nuclease to form a crRNA-nuclease ribonucleoprotein (RNP) complex,
  - wherein the thiol modification is covalently linked to the surface of the metallic NP core and
  - wherein the crRNA-nuclease RNP complex binds a target PAM-site within human (h) chromosome (chr) 11 at positions 67681215-67741765; 67691162-67691186; 67723825-67723849; 67805337-67845629; 67812349-67812375; 67812443-67812469; 67839126-67839150; or 67895738-67941098 or hchr3 at positions 46373915-46373939,
  - and wherein the second NP layer comprises a donor template comprising a therapeutic gene and homology-directed repair templates, and wherein the second NP layer is farther from the surface of the metallic core than the first NP layer.

2. The therapeutic formulation of claim 1, wherein the metallic core is gold.

3. The therapeutic formulation of claim 1, where the nanoparticle further comprises a polymer coating.

4. The therapeutic formulation of claim 1, wherein the crRNA-nuclease RNP complex binds to one of SEQ ID Nos: 1-194, 197-208, 213, 242, 245, 251, 254, 258, or 263.

5. The therapeutic formulation of claim 1, wherein the nuclease is Cpf1 or Cas 9.

6. The therapeutic formulation of claim 1, wherein the crRNA comprises SEQ ID NO:

195, 196, 209, 211, 244, 253, 260, or 264.

7. The therapeutic formulation of claim 1, wherein the nuclease comprises a sequence selected from SEQ ID NOs: 215-241 or a variant of a Cpf1 selected from SEQ ID NOs: 216-227, or 229-241.

8. The therapeutic formulation of claim 1, wherein the nanoparticle is coupled to a targeting molecule.

9. The therapeutic formulation of claim 8, wherein the targeting molecule comprises a CD34 binding domain or a CD90 binding domain.

10. The therapeutic formulation of claim 1, wherein the nanoparticles have an average diameter of 25-30 nm.

11. The therapeutic formulation of claim 1, wherein the nanoparticles have a hydrodynamic size of 150-190 nm, 160-185 nm, 170-180 nm, or 176 nm.

12. A method of providing a therapeutic gene to a patient in need thereof comprising administering the therapeutic formulation of claim 1 to the patient thereby providing the therapeutic gene to the patient.

13. The method of claim 12, wherein the therapeutic formulation is administered by injection, infusion, perfusion, or lavage.

14. A method of providing a therapeutic gene to a patient in need thereof comprising administering a therapeutic formulation to the patient,

- wherein the therapeutic formulation comprises a cell genetically modified by a nanoparticle (NP) comprising a metallic NP core associated with a first NP layer and a second NP layer, wherein the first NP layer comprises a crRNA with a 3' end and a 5' end, wherein the 3' end is conjugated to a spacer with a thiol modification, and the 5' end is conjugated to a nuclease to form a crRNA-nuclease ribonucleoprotein (RNP) complex, wherein the thiol modification is covalently linked to a surface of the metallic NP core and wherein the crRNA-nuclease RNP complex binds a target PAM-site within human (h) chromosome (chr) 11 at positions 67681215-67741765; 67691162-67691186; 67723825-67723849; 67805337-67845629; 67812349-67812375; 67812443-67812469; 67839126-67839150; or 67895738-67941098 or hchr3 at positions 46373915-46373939;

and wherein the second NP layer comprises a donor template comprising a therapeutic gene and homology-directed repair templates; and wherein the second NP layer is farther from the surface of the metallic NP core than the first NP layer, thereby providing the therapeutic gene to the patient.

15. The method of claim 14, wherein the therapeutic formulation further comprises serum components.

16. The method of claim 14, wherein the patient in need thereof has been diagnosed with a monogenetic blood disorder, hemophilia, Grave's Disease, rheumatoid arthritis, pernicious anemia, Multiple Sclerosis (MS), inflammatory bowel disease, systemic lupus erythematosus (SLE), Wiskott-Aldrich syndrome (WAS), chronic granulomatous disease (CGD), Battens disease, adrenoleukodystrophy (ALD) or metachromatic leukodystrophy (MLD), muscular dystrophy, pulmonary aveolar proteinosis (PAP), pyruvate kinase deficiency, Shwachmann-Diamond-Blackfan anemia, dyskeratosis congenita, cystic fibrosis, Parkinson's disease, Alzheimer's disease, amyotrophic lateral sclerosis (Lou Gehrig's disease), acute lymphoblastic leukemia (ALL), acute myelogenous leukemia (AML), agnogenic myeloid metaplasia, amegakaryocytosis/congenital thrombocytopenia, ataxia telangiectasia, β-thalassemia major, CLL, chronic myelogenous leukemia (CML), chronic myelomonocytic leukemia, common variable immune deficiency (CVID), complement disorders, congenital (Xlinked) agammaglobulinemia, familial erythrophagocytic lymphohistiocytosis, Hodgkin's lymphoma, Hurler's syndrome, hyper IgM, IgG subclass deficiency, juvenile myelomonocytic leukemia, mucopolysaccharidoses, multiple myeloma, myelodysplasia, non-Hodgkin's lymphoma, paroxysmal nocturnal hemoglobinuria (PNH), primary immunodeficiency diseases with antibody deficiency, pure red cell aplasia, refractory anemia, selective IgA deficiency, severe aplastic anemia, SCD, specific antibody deficiency, a bacterial infection, or a parasitic infection.

17. The method of claim 14, wherein the therapeutic formulation is administered by injection, infusion, perfusion, or lavage.

18. The method of claim 14, wherein the cell is a hematopoietic stem cell (HSC), a hematopoietic progenitor cell (HPC), a hematopoietic stem and progenitor cell (HSPC), a T cell, a natural killer (NK) cell, a B cell, a macrophage, a monocyte, a mesenchymal stem cell (MSC), a white blood cell (WBC), a mononuclear cell (MNC), an endothelial cell (EC), a stromal cell, and/or a bone marrow fibroblast.

19. The method of claim 14, wherein the cell is a $CD^{34}$+CD45RA-$CD90^{+}$ HSC.

20. The method of claim 14, wherein the cell is a human blood cell.

* * * * *

SEQUENCE LISTING

```
Sequence total quantity: 264
SEQ ID NO: 1          moltype = DNA  length = 25
FEATURE               Location/Qualifiers
source                1..25
                      mol_type = genomic DNA
                      organism = Homo sapiens
SEQUENCE: 1
tttaaaaaaa gtcttcataa taaaa                                        25

SEQ ID NO: 2          moltype = DNA  length = 25
FEATURE               Location/Qualifiers
source                1..25
                      mol_type = genomic DNA
                      organism = Homo sapiens
SEQUENCE: 2
tttacttctg tgcacccata gactc                                        25

SEQ ID NO: 3          moltype = DNA  length = 25
FEATURE               Location/Qualifiers
source                1..25
                      mol_type = genomic DNA
                      organism = Homo sapiens
SEQUENCE: 3
tttaactctg ccatgggtgc cagga                                        25

SEQ ID NO: 4          moltype = DNA  length = 25
FEATURE               Location/Qualifiers
source                1..25
                      mol_type = genomic DNA
                      organism = Homo sapiens
SEQUENCE: 4
tttagccact gtgagaaaca gttta                                        25

SEQ ID NO: 5          moltype = DNA  length = 25
FEATURE               Location/Qualifiers
source                1..25
                      mol_type = genomic DNA
                      organism = Homo sapiens
SEQUENCE: 5
tttataaggc taagtagtat tctat                                        25

SEQ ID NO: 6          moltype = DNA  length = 25
FEATURE               Location/Qualifiers
source                1..25
                      mol_type = genomic DNA
                      organism = Homo sapiens
SEQUENCE: 6
tttatccact aattgttgat gggca                                        25

SEQ ID NO: 7          moltype = DNA  length = 25
FEATURE               Location/Qualifiers
source                1..25
                      mol_type = genomic DNA
                      organism = Homo sapiens
SEQUENCE: 7
tttattttct ttttggtaag aagga                                        25

SEQ ID NO: 8          moltype = DNA  length = 25
FEATURE               Location/Qualifiers
source                1..25
                      mol_type = genomic DNA
                      organism = Homo sapiens
SEQUENCE: 8
tttaaaataa tcgtcattct ttttg                                        25
```

```
SEQ ID NO: 9            moltype = DNA  length = 25
FEATURE                 Location/Qualifiers
source                  1..25
                        mol_type = genomic DNA
                        organism = Homo sapiens
SEQUENCE: 9
tttatattaa tccttgtatg tctga                                         25

SEQ ID NO: 10           moltype = DNA  length = 25
FEATURE                 Location/Qualifiers
source                  1..25
                        mol_type = genomic DNA
                        organism = Homo sapiens
SEQUENCE: 10
tttaaatgga taagttaggc tgggc                                         25

SEQ ID NO: 11           moltype = DNA  length = 25
FEATURE                 Location/Qualifiers
source                  1..25
                        mol_type = genomic DNA
                        organism = Homo sapiens
SEQUENCE: 11
tttacacaaa ctgtacttgt aggta                                         25

SEQ ID NO: 12           moltype = DNA  length = 25
FEATURE                 Location/Qualifiers
source                  1..25
                        mol_type = genomic DNA
                        organism = Homo sapiens
SEQUENCE: 12
tttagtgagg aaaaactaca tttat                                         25

SEQ ID NO: 13           moltype = DNA  length = 25
FEATURE                 Location/Qualifiers
source                  1..25
                        mol_type = genomic DNA
                        organism = Homo sapiens
SEQUENCE: 13
tttaaaaagg gaaaattagg gagaa                                         25

SEQ ID NO: 14           moltype = DNA  length = 25
FEATURE                 Location/Qualifiers
source                  1..25
                        mol_type = genomic DNA
                        organism = Homo sapiens
SEQUENCE: 14
tttactaaat gacctcttcg ccaaa                                         25

SEQ ID NO: 15           moltype = DNA  length = 25
FEATURE                 Location/Qualifiers
source                  1..25
                        mol_type = genomic DNA
                        organism = Homo sapiens
SEQUENCE: 15
tttagtgata tgaaaagaac catgc                                         25

SEQ ID NO: 16           moltype = DNA  length = 25
FEATURE                 Location/Qualifiers
source                  1..25
                        mol_type = genomic DNA
                        organism = Homo sapiens
SEQUENCE: 16
tttaaatttt ccagtgtctc agtgt                                         25

SEQ ID NO: 17           moltype = DNA  length = 25
FEATURE                 Location/Qualifiers
source                  1..25
                        mol_type = genomic DNA
                        organism = Homo sapiens
SEQUENCE: 17
tttaagcctg aaaacctaaa aaatg                                         25

SEQ ID NO: 18           moltype = DNA  length = 25
FEATURE                 Location/Qualifiers
source                  1..25
                        mol_type = genomic DNA
                        organism = Homo sapiens
SEQUENCE: 18
tttaaaaatt agctgcgttg gtggt                                         25
```

```
SEQ ID NO: 19          moltype = DNA  length = 25
FEATURE                Location/Qualifiers
source                 1..25
                       mol_type = genomic DNA
                       organism = Homo sapiens
SEQUENCE: 19
tttagctgct ttaaaatgtg aactc                                          25

SEQ ID NO: 20          moltype = DNA  length = 25
FEATURE                Location/Qualifiers
source                 1..25
                       mol_type = genomic DNA
                       organism = Homo sapiens
SEQUENCE: 20
tttaatctca agtcacttct ctagg                                          25

SEQ ID NO: 21          moltype = DNA  length = 25
FEATURE                Location/Qualifiers
source                 1..25
                       mol_type = genomic DNA
                       organism = Homo sapiens
SEQUENCE: 21
tttaaacgct cgttagatca ctgga                                          25

SEQ ID NO: 22          moltype = DNA  length = 25
FEATURE                Location/Qualifiers
source                 1..25
                       mol_type = genomic DNA
                       organism = Homo sapiens
SEQUENCE: 22
tttaaggcag gaatcagggt gccat                                          25

SEQ ID NO: 23          moltype = DNA  length = 25
FEATURE                Location/Qualifiers
source                 1..25
                       mol_type = genomic DNA
                       organism = Homo sapiens
SEQUENCE: 23
tttaaaaaaa tcccaggtga cccta                                          25

SEQ ID NO: 24          moltype = DNA  length = 25
FEATURE                Location/Qualifiers
source                 1..25
                       mol_type = genomic DNA
                       organism = Homo sapiens
SEQUENCE: 24
tttaatcttg cagggacagg aagga                                          25

SEQ ID NO: 25          moltype = DNA  length = 25
FEATURE                Location/Qualifiers
source                 1..25
                       mol_type = genomic DNA
                       organism = Homo sapiens
SEQUENCE: 25
tttaaaatgt gaactccaaa tcagg                                          25

SEQ ID NO: 26          moltype = DNA  length = 25
FEATURE                Location/Qualifiers
source                 1..25
                       mol_type = genomic DNA
                       organism = Homo sapiens
SEQUENCE: 26
tttattattt cgttgttttt cctct                                          25

SEQ ID NO: 27          moltype = DNA  length = 25
FEATURE                Location/Qualifiers
source                 1..25
                       mol_type = genomic DNA
                       organism = Homo sapiens
SEQUENCE: 27
tttatcttgg tgtttgaact cggat                                          25

SEQ ID NO: 28          moltype = DNA  length = 25
FEATURE                Location/Qualifiers
source                 1..25
                       mol_type = genomic DNA
                       organism = Homo sapiens
SEQUENCE: 28
```

```
tttactgccc atttagctgc tttaa                                        25

SEQ ID NO: 29          moltype = DNA  length = 25
FEATURE                Location/Qualifiers
source                 1..25
                       mol_type = genomic DNA
                       organism = Homo sapiens
SEQUENCE: 29
tttaacttga ttaccttata gtcaa                                        25

SEQ ID NO: 30          moltype = DNA  length = 25
FEATURE                Location/Qualifiers
source                 1..25
                       mol_type = genomic DNA
                       organism = Homo sapiens
SEQUENCE: 30
tttatatatt taacttctgt atttt                                        25

SEQ ID NO: 31          moltype = DNA  length = 25
FEATURE                Location/Qualifiers
source                 1..25
                       mol_type = genomic DNA
                       organism = Homo sapiens
SEQUENCE: 31
tttatctgct atagctaaca aattt                                        25

SEQ ID NO: 32          moltype = DNA  length = 25
FEATURE                Location/Qualifiers
source                 1..25
                       mol_type = genomic DNA
                       organism = Homo sapiens
SEQUENCE: 32
tttaacttct gtattttcta aaact                                        25

SEQ ID NO: 33          moltype = DNA  length = 25
FEATURE                Location/Qualifiers
source                 1..25
                       mol_type = genomic DNA
                       organism = Homo sapiens
SEQUENCE: 33
tttataacac accagcatca gttac                                        25

SEQ ID NO: 34          moltype = DNA  length = 25
FEATURE                Location/Qualifiers
source                 1..25
                       mol_type = genomic DNA
                       organism = Homo sapiens
SEQUENCE: 34
tttattatct ttcctgtttt ctaat                                        25

SEQ ID NO: 35          moltype = DNA  length = 25
FEATURE                Location/Qualifiers
source                 1..25
                       mol_type = genomic DNA
                       organism = Homo sapiens
SEQUENCE: 35
tttaatatta acatttgcta atttc                                        25

SEQ ID NO: 36          moltype = DNA  length = 25
FEATURE                Location/Qualifiers
source                 1..25
                       mol_type = genomic DNA
                       organism = Homo sapiens
SEQUENCE: 36
tttaaaaggc cagatgtcaa ttcag                                        25

SEQ ID NO: 37          moltype = DNA  length = 25
FEATURE                Location/Qualifiers
source                 1..25
                       mol_type = genomic DNA
                       organism = Homo sapiens
SEQUENCE: 37
tttatgcaga tagatatata ttttt                                        25

SEQ ID NO: 38          moltype = DNA  length = 25
FEATURE                Location/Qualifiers
source                 1..25
                       mol_type = genomic DNA
                       organism = Homo sapiens
```

```
SEQUENCE: 38
tttaatcact ggatcatgga cctaa                                     25

SEQ ID NO: 39          moltype = DNA  length = 25
FEATURE                Location/Qualifiers
source                 1..25
                       mol_type = genomic DNA
                       organism = Homo sapiens
SEQUENCE: 39
tttagtgttt cttagaaact taaca                                     25

SEQ ID NO: 40          moltype = DNA  length = 25
FEATURE                Location/Qualifiers
source                 1..25
                       mol_type = genomic DNA
                       organism = Homo sapiens
SEQUENCE: 40
tttacagcag tgccattcac aatgg                                     25

SEQ ID NO: 41          moltype = DNA  length = 25
FEATURE                Location/Qualifiers
source                 1..25
                       mol_type = genomic DNA
                       organism = Homo sapiens
SEQUENCE: 41
tttataggcc caggtctaga tctgg                                     25

SEQ ID NO: 42          moltype = DNA  length = 25
FEATURE                Location/Qualifiers
source                 1..25
                       mol_type = genomic DNA
                       organism = Homo sapiens
SEQUENCE: 42
tttagcccta tcttatccat atgga                                     25

SEQ ID NO: 43          moltype = DNA  length = 25
FEATURE                Location/Qualifiers
source                 1..25
                       mol_type = genomic DNA
                       organism = Homo sapiens
SEQUENCE: 43
tttatgtcta gtacttaggg cagta                                     25

SEQ ID NO: 44          moltype = DNA  length = 25
FEATURE                Location/Qualifiers
source                 1..25
                       mol_type = genomic DNA
                       organism = Homo sapiens
SEQUENCE: 44
tttacaatta attgtagttc tttga                                     25

SEQ ID NO: 45          moltype = DNA  length = 25
FEATURE                Location/Qualifiers
source                 1..25
                       mol_type = genomic DNA
                       organism = Homo sapiens
SEQUENCE: 45
tttattttct tagatttact ctgta                                     25

SEQ ID NO: 46          moltype = DNA  length = 25
FEATURE                Location/Qualifiers
source                 1..25
                       mol_type = genomic DNA
                       organism = Homo sapiens
SEQUENCE: 46
tttaaaaact gggtttacaa ataaa                                     25

SEQ ID NO: 47          moltype = DNA  length = 25
FEATURE                Location/Qualifiers
source                 1..25
                       mol_type = genomic DNA
                       organism = Homo sapiens
SEQUENCE: 47
tttaaacatt ttgactgtag ccatt                                     25

SEQ ID NO: 48          moltype = DNA  length = 25
FEATURE                Location/Qualifiers
source                 1..25
                       mol_type = genomic DNA
```

```
                        organism = Homo sapiens
SEQUENCE: 48
tttatgactg tttcatgtgt gctca                                         25

SEQ ID NO: 49           moltype = DNA  length = 25
FEATURE                 Location/Qualifiers
source                  1..25
                        mol_type = genomic DNA
                        organism = Homo sapiens
SEQUENCE: 49
tttataacct cacctttggc tttta                                         25

SEQ ID NO: 50           moltype = DNA  length = 25
FEATURE                 Location/Qualifiers
source                  1..25
                        mol_type = genomic DNA
                        organism = Homo sapiens
SEQUENCE: 50
tttagaagtc catataaggg gatgc                                         25

SEQ ID NO: 51           moltype = DNA  length = 25
FEATURE                 Location/Qualifiers
source                  1..25
                        mol_type = genomic DNA
                        organism = Homo sapiens
SEQUENCE: 51
tttactgtta attagtcctt gctta                                         25

SEQ ID NO: 52           moltype = DNA  length = 25
FEATURE                 Location/Qualifiers
source                  1..25
                        mol_type = genomic DNA
                        organism = Homo sapiens
SEQUENCE: 52
tttatctatg aacctcatag gtcct                                         25

SEQ ID NO: 53           moltype = DNA  length = 25
FEATURE                 Location/Qualifiers
source                  1..25
                        mol_type = genomic DNA
                        organism = Homo sapiens
SEQUENCE: 53
tttactatag ttaattggaa cactt                                         25

SEQ ID NO: 54           moltype = DNA  length = 25
FEATURE                 Location/Qualifiers
source                  1..25
                        mol_type = genomic DNA
                        organism = Homo sapiens
SEQUENCE: 54
tttaacgtta aatctctttc taaca                                         25

SEQ ID NO: 55           moltype = DNA  length = 25
FEATURE                 Location/Qualifiers
source                  1..25
                        mol_type = genomic DNA
                        organism = Homo sapiens
SEQUENCE: 55
tttatctcct ttaaattccc atgtt                                         25

SEQ ID NO: 56           moltype = DNA  length = 25
FEATURE                 Location/Qualifiers
source                  1..25
                        mol_type = genomic DNA
                        organism = Homo sapiens
SEQUENCE: 56
tttagtccaa ataaagcaac aatac                                         25

SEQ ID NO: 57           moltype = DNA  length = 25
FEATURE                 Location/Qualifiers
source                  1..25
                        mol_type = genomic DNA
                        organism = Homo sapiens
SEQUENCE: 57
tttatccatt cccaaccaca aagaa                                         25

SEQ ID NO: 58           moltype = DNA  length = 25
FEATURE                 Location/Qualifiers
source                  1..25
```

```
                        mol_type = genomic DNA
                        organism = Homo sapiens
SEQUENCE: 58
tttaatttct ccacttgatt aactt                                              25

SEQ ID NO: 59           moltype = DNA  length = 25
FEATURE                 Location/Qualifiers
source                  1..25
                        mol_type = genomic DNA
                        organism = Homo sapiens
SEQUENCE: 59
tttagccaaa ggacatgcct aaaat                                              25

SEQ ID NO: 60           moltype = DNA  length = 25
FEATURE                 Location/Qualifiers
source                  1..25
                        mol_type = genomic DNA
                        organism = Homo sapiens
SEQUENCE: 60
tttaggaatt aataaaaatt gtata                                              25

SEQ ID NO: 61           moltype = DNA  length = 25
FEATURE                 Location/Qualifiers
source                  1..25
                        mol_type = genomic DNA
                        organism = Homo sapiens
SEQUENCE: 61
tttaatgcat ccataaacag aactg                                              25

SEQ ID NO: 62           moltype = DNA  length = 25
FEATURE                 Location/Qualifiers
source                  1..25
                        mol_type = genomic DNA
                        organism = Homo sapiens
SEQUENCE: 62
tttagggtgg ttctcctggg atttt                                              25

SEQ ID NO: 63           moltype = DNA  length = 25
FEATURE                 Location/Qualifiers
source                  1..25
                        mol_type = genomic DNA
                        organism = Homo sapiens
SEQUENCE: 63
tttatccctt acgcatgagg tccct                                              25

SEQ ID NO: 64           moltype = DNA  length = 25
FEATURE                 Location/Qualifiers
source                  1..25
                        mol_type = genomic DNA
                        organism = Homo sapiens
SEQUENCE: 64
tttacacaag caacaccagc tgcag                                              25

SEQ ID NO: 65           moltype = DNA  length = 25
FEATURE                 Location/Qualifiers
source                  1..25
                        mol_type = genomic DNA
                        organism = Homo sapiens
SEQUENCE: 65
tttaaatact tgacaaaaaa gattg                                              25

SEQ ID NO: 66           moltype = DNA  length = 25
FEATURE                 Location/Qualifiers
source                  1..25
                        mol_type = genomic DNA
                        organism = Homo sapiens
SEQUENCE: 66
tttaaaaggg gtctctacta aatct                                              25

SEQ ID NO: 67           moltype = DNA  length = 25
FEATURE                 Location/Qualifiers
source                  1..25
                        mol_type = genomic DNA
                        organism = Homo sapiens
SEQUENCE: 67
tttaatcttt atctgaccta aattt                                              25

SEQ ID NO: 68           moltype = DNA  length = 25
FEATURE                 Location/Qualifiers
```

```
source                  1..25
                        mol_type = genomic DNA
                        organism = Homo sapiens
SEQUENCE: 68
tttataaaga aattccgcaa gaact                                         25

SEQ ID NO: 69           moltype = DNA  length = 25
FEATURE                 Location/Qualifiers
source                  1..25
                        mol_type = genomic DNA
                        organism = Homo sapiens
SEQUENCE: 69
tttatgattt aaaggggaag ctttg                                         25

SEQ ID NO: 70           moltype = DNA  length = 25
FEATURE                 Location/Qualifiers
source                  1..25
                        mol_type = genomic DNA
                        organism = Homo sapiens
SEQUENCE: 70
tttaatgctt tcaacatcga ttgct                                         25

SEQ ID NO: 71           moltype = DNA  length = 25
FEATURE                 Location/Qualifiers
source                  1..25
                        mol_type = genomic DNA
                        organism = Homo sapiens
SEQUENCE: 71
tttacggaga ggatacaaag atcct                                         25

SEQ ID NO: 72           moltype = DNA  length = 25
FEATURE                 Location/Qualifiers
source                  1..25
                        mol_type = genomic DNA
                        organism = Homo sapiens
SEQUENCE: 72
tttaagatct tcctataatt atagc                                         25

SEQ ID NO: 73           moltype = DNA  length = 25
FEATURE                 Location/Qualifiers
source                  1..25
                        mol_type = genomic DNA
                        organism = Homo sapiens
SEQUENCE: 73
tttaattttt gttggagtct tttct                                         25

SEQ ID NO: 74           moltype = DNA  length = 25
FEATURE                 Location/Qualifiers
source                  1..25
                        mol_type = genomic DNA
                        organism = Homo sapiens
SEQUENCE: 74
tttatttttt aaaaccagaa cattt                                         25

SEQ ID NO: 75           moltype = DNA  length = 25
FEATURE                 Location/Qualifiers
source                  1..25
                        mol_type = genomic DNA
                        organism = Homo sapiens
SEQUENCE: 75
tttagttctc tttttatact ccaaa                                         25

SEQ ID NO: 76           moltype = DNA  length = 25
FEATURE                 Location/Qualifiers
source                  1..25
                        mol_type = genomic DNA
                        organism = Homo sapiens
SEQUENCE: 76
tttactaaga atagtgtagg ggtta                                         25

SEQ ID NO: 77           moltype = DNA  length = 25
FEATURE                 Location/Qualifiers
source                  1..25
                        mol_type = genomic DNA
                        organism = Homo sapiens
SEQUENCE: 77
tttactattt cccatcttat gtata                                         25

SEQ ID NO: 78           moltype = DNA  length = 25
```

```
FEATURE                Location/Qualifiers
source                 1..25
                       mol_type = genomic DNA
                       organism = Homo sapiens
SEQUENCE: 78
tttagcaggt gtcttgatcc ccctt                                            25

SEQ ID NO: 79          moltype = DNA  length = 25
FEATURE                Location/Qualifiers
source                 1..25
                       mol_type = genomic DNA
                       organism = Homo sapiens
SEQUENCE: 79
tttattttct agtccccctt tgatc                                            25

SEQ ID NO: 80          moltype = DNA  length = 25
FEATURE                Location/Qualifiers
source                 1..25
                       mol_type = genomic DNA
                       organism = Homo sapiens
SEQUENCE: 80
tttaaaatca tcttattgtt tacaa                                            25

SEQ ID NO: 81          moltype = DNA  length = 25
FEATURE                Location/Qualifiers
source                 1..25
                       mol_type = genomic DNA
                       organism = Homo sapiens
SEQUENCE: 81
tttagagaga tatattttcc tctag                                            25

SEQ ID NO: 82          moltype = DNA  length = 25
FEATURE                Location/Qualifiers
source                 1..25
                       mol_type = genomic DNA
                       organism = Homo sapiens
SEQUENCE: 82
tttaaaagtg gtcacaagtg gggga                                            25

SEQ ID NO: 83          moltype = DNA  length = 25
FEATURE                Location/Qualifiers
source                 1..25
                       mol_type = genomic DNA
                       organism = Homo sapiens
SEQUENCE: 83
tttactagaa acctttccca tattg                                            25

SEQ ID NO: 84          moltype = DNA  length = 25
FEATURE                Location/Qualifiers
source                 1..25
                       mol_type = genomic DNA
                       organism = Homo sapiens
SEQUENCE: 84
tttattgctc tgtaacagat tacca                                            25

SEQ ID NO: 85          moltype = DNA  length = 25
FEATURE                Location/Qualifiers
source                 1..25
                       mol_type = genomic DNA
                       organism = Homo sapiens
SEQUENCE: 85
tttaccagcc atcttagaac aaatt                                            25

SEQ ID NO: 86          moltype = DNA  length = 25
FEATURE                Location/Qualifiers
source                 1..25
                       mol_type = genomic DNA
                       organism = Homo sapiens
SEQUENCE: 86
tttacagaat tcgctttccc tttaa                                            25

SEQ ID NO: 87          moltype = DNA  length = 25
FEATURE                Location/Qualifiers
source                 1..25
                       mol_type = genomic DNA
                       organism = Homo sapiens
SEQUENCE: 87
tttattaagc taaacctagg tacaa                                            25
```

```
SEQ ID NO: 88          moltype = DNA  length = 25
FEATURE                Location/Qualifiers
source                 1..25
                       mol_type = genomic DNA
                       organism = Homo sapiens
SEQUENCE: 88
tttaggatca ccttaacttg gtgag                                         25

SEQ ID NO: 89          moltype = DNA  length = 25
FEATURE                Location/Qualifiers
source                 1..25
                       mol_type = genomic DNA
                       organism = Homo sapiens
SEQUENCE: 89
tttactattt cccctggagt cttta                                         25

SEQ ID NO: 90          moltype = DNA  length = 25
FEATURE                Location/Qualifiers
source                 1..25
                       mol_type = genomic DNA
                       organism = Homo sapiens
SEQUENCE: 90
tttaataagt cttttgatta caggc                                         25

SEQ ID NO: 91          moltype = DNA  length = 25
FEATURE                Location/Qualifiers
source                 1..25
                       mol_type = genomic DNA
                       organism = Homo sapiens
SEQUENCE: 91
tttactctgt agctttttaa aatca                                         25

SEQ ID NO: 92          moltype = DNA  length = 25
FEATURE                Location/Qualifiers
source                 1..25
                       mol_type = genomic DNA
                       organism = Homo sapiens
SEQUENCE: 92
tttacttctt ttaagatctt cctat                                         25

SEQ ID NO: 93          moltype = DNA  length = 25
FEATURE                Location/Qualifiers
source                 1..25
                       mol_type = genomic DNA
                       organism = Homo sapiens
SEQUENCE: 93
tttactttgc tctgtgaaca gagtt                                         25

SEQ ID NO: 94          moltype = DNA  length = 25
FEATURE                Location/Qualifiers
source                 1..25
                       mol_type = genomic DNA
                       organism = Homo sapiens
SEQUENCE: 94
tttaattcct gtttcatttt cccat                                         25

SEQ ID NO: 95          moltype = DNA  length = 25
FEATURE                Location/Qualifiers
source                 1..25
                       mol_type = genomic DNA
                       organism = Homo sapiens
SEQUENCE: 95
tttagggcgt gactgtgaat aactc                                         25

SEQ ID NO: 96          moltype = DNA  length = 25
FEATURE                Location/Qualifiers
source                 1..25
                       mol_type = genomic DNA
                       organism = Homo sapiens
SEQUENCE: 96
tttattcaat ttctcctaag tctgc                                         25

SEQ ID NO: 97          moltype = DNA  length = 25
FEATURE                Location/Qualifiers
source                 1..25
                       mol_type = genomic DNA
                       organism = Homo sapiens
SEQUENCE: 97
tttaaaaata tttagcaact gggac                                         25
```

```
SEQ ID NO: 98          moltype = DNA  length = 25
FEATURE                Location/Qualifiers
source                 1..25
                       mol_type = genomic DNA
                       organism = Homo sapiens
SEQUENCE: 98
tttacgttcc cagatcgtat ttctt                                          25

SEQ ID NO: 99          moltype = DNA  length = 25
FEATURE                Location/Qualifiers
source                 1..25
                       mol_type = genomic DNA
                       organism = Homo sapiens
SEQUENCE: 99
tttagttcat ggcaagcaag tcatt                                          25

SEQ ID NO: 100         moltype = DNA  length = 25
FEATURE                Location/Qualifiers
source                 1..25
                       mol_type = genomic DNA
                       organism = Homo sapiens
SEQUENCE: 100
tttaggccac caattggggg cattt                                          25

SEQ ID NO: 101         moltype = DNA  length = 25
FEATURE                Location/Qualifiers
source                 1..25
                       mol_type = genomic DNA
                       organism = Homo sapiens
SEQUENCE: 101
tttaccaacc atcactgcca tcgtc                                          25

SEQ ID NO: 102         moltype = DNA  length = 25
FEATURE                Location/Qualifiers
source                 1..25
                       mol_type = genomic DNA
                       organism = Homo sapiens
SEQUENCE: 102
tttaacccca gaaactgtta attcc                                          25

SEQ ID NO: 103         moltype = DNA  length = 25
FEATURE                Location/Qualifiers
source                 1..25
                       mol_type = genomic DNA
                       organism = Homo sapiens
SEQUENCE: 103
tttatagtta tttacagaat tcgct                                          25

SEQ ID NO: 104         moltype = DNA  length = 25
FEATURE                Location/Qualifiers
source                 1..25
                       mol_type = genomic DNA
                       organism = Homo sapiens
SEQUENCE: 104
tttatttgtg caacaatggg gaatt                                          25

SEQ ID NO: 105         moltype = DNA  length = 25
FEATURE                Location/Qualifiers
source                 1..25
                       mol_type = genomic DNA
                       organism = Homo sapiens
SEQUENCE: 105
tttaataaag caataggaag acgtt                                          25

SEQ ID NO: 106         moltype = DNA  length = 25
FEATURE                Location/Qualifiers
source                 1..25
                       mol_type = genomic DNA
                       organism = Homo sapiens
SEQUENCE: 106
tttaagtcac aggggtgtag accct                                          25

SEQ ID NO: 107         moltype = DNA  length = 25
FEATURE                Location/Qualifiers
source                 1..25
                       mol_type = genomic DNA
                       organism = Homo sapiens
SEQUENCE: 107
```

```
tttagtgacc accctactct attgt                                        25

SEQ ID NO: 108          moltype = DNA  length = 25
FEATURE                 Location/Qualifiers
source                  1..25
                        mol_type = genomic DNA
                        organism = Homo sapiens
SEQUENCE: 108
tttaatagaa tagcctcata tttta                                        25

SEQ ID NO: 109          moltype = DNA  length = 25
FEATURE                 Location/Qualifiers
source                  1..25
                        mol_type = genomic DNA
                        organism = Homo sapiens
SEQUENCE: 109
tttaaccact cccactccca attac                                        25

SEQ ID NO: 110          moltype = DNA  length = 25
FEATURE                 Location/Qualifiers
source                  1..25
                        mol_type = genomic DNA
                        organism = Homo sapiens
SEQUENCE: 110
tttagatgga actagcattc cacaa                                        25

SEQ ID NO: 111          moltype = DNA  length = 25
FEATURE                 Location/Qualifiers
source                  1..25
                        mol_type = genomic DNA
                        organism = Homo sapiens
SEQUENCE: 111
tttaaaagta gcagcttaag ccaga                                        25

SEQ ID NO: 112          moltype = DNA  length = 25
FEATURE                 Location/Qualifiers
source                  1..25
                        mol_type = genomic DNA
                        organism = Homo sapiens
SEQUENCE: 112
tttagttaat ttcttatata agagc                                        25

SEQ ID NO: 113          moltype = DNA  length = 25
FEATURE                 Location/Qualifiers
source                  1..25
                        mol_type = genomic DNA
                        organism = Homo sapiens
SEQUENCE: 113
tttaaggtag atctgtgcag gggga                                        25

SEQ ID NO: 114          moltype = DNA  length = 25
FEATURE                 Location/Qualifiers
source                  1..25
                        mol_type = genomic DNA
                        organism = Homo sapiens
SEQUENCE: 114
tttactcctc ccgaagagga tggat                                        25

SEQ ID NO: 115          moltype = DNA  length = 25
FEATURE                 Location/Qualifiers
source                  1..25
                        mol_type = genomic DNA
                        organism = Homo sapiens
SEQUENCE: 115
tttaacatag atattgaagt cagag                                        25

SEQ ID NO: 116          moltype = DNA  length = 25
FEATURE                 Location/Qualifiers
source                  1..25
                        mol_type = genomic DNA
                        organism = Homo sapiens
SEQUENCE: 116
tttatcatat tactattttg ccagt                                        25

SEQ ID NO: 117          moltype = DNA  length = 25
FEATURE                 Location/Qualifiers
source                  1..25
                        mol_type = genomic DNA
                        organism = Homo sapiens
```

```
SEQUENCE: 117
tttagttaca tgatttttaa gagtt                                          25

SEQ ID NO: 118          moltype = DNA  length = 25
FEATURE                 Location/Qualifiers
source                  1..25
                        mol_type = genomic DNA
                        organism = Homo sapiens
SEQUENCE: 118
tttacctggt tctgtaaata tttta                                          25

SEQ ID NO: 119          moltype = DNA  length = 25
FEATURE                 Location/Qualifiers
source                  1..25
                        mol_type = genomic DNA
                        organism = Homo sapiens
SEQUENCE: 119
tttattatgt gagtgataaa tttga                                          25

SEQ ID NO: 120          moltype = DNA  length = 25
FEATURE                 Location/Qualifiers
source                  1..25
                        mol_type = genomic DNA
                        organism = Homo sapiens
SEQUENCE: 120
tttacacccc ccacccccga ggcct                                          25

SEQ ID NO: 121          moltype = DNA  length = 25
FEATURE                 Location/Qualifiers
source                  1..25
                        mol_type = genomic DNA
                        organism = Homo sapiens
SEQUENCE: 121
tttaactgaa catgtgttgg aggaa                                          25

SEQ ID NO: 122          moltype = DNA  length = 25
FEATURE                 Location/Qualifiers
source                  1..25
                        mol_type = genomic DNA
                        organism = Homo sapiens
SEQUENCE: 122
tttaatttat ctatgaacct catag                                          25

SEQ ID NO: 123          moltype = DNA  length = 25
FEATURE                 Location/Qualifiers
source                  1..25
                        mol_type = genomic DNA
                        organism = Homo sapiens
SEQUENCE: 123
tttatttttt tattttttaa aacca                                          25

SEQ ID NO: 124          moltype = DNA  length = 25
FEATURE                 Location/Qualifiers
source                  1..25
                        mol_type = genomic DNA
                        organism = Homo sapiens
SEQUENCE: 124
tttatccttt ttactcctcc cgaag                                          25

SEQ ID NO: 125          moltype = DNA  length = 25
FEATURE                 Location/Qualifiers
source                  1..25
                        mol_type = genomic DNA
                        organism = Homo sapiens
SEQUENCE: 125
tttaaacttt tttaaatagg taaag                                          25

SEQ ID NO: 126          moltype = DNA  length = 25
FEATURE                 Location/Qualifiers
source                  1..25
                        mol_type = genomic DNA
                        organism = Homo sapiens
SEQUENCE: 126
tttaattttt aataaagcaa tagga                                          25

SEQ ID NO: 127          moltype = DNA  length = 25
FEATURE                 Location/Qualifiers
source                  1..25
                        mol_type = genomic DNA
```

```
                         organism = Homo sapiens
SEQUENCE: 127
tttacatata gtttttgagc ctttt                                            25

SEQ ID NO: 128           moltype = DNA  length = 25
FEATURE                  Location/Qualifiers
source                   1..25
                         mol_type = genomic DNA
                         organism = Homo sapiens
SEQUENCE: 128
tttaaaagtt ttaccagcca tctta                                            25

SEQ ID NO: 129           moltype = DNA  length = 25
FEATURE                  Location/Qualifiers
source                   1..25
                         mol_type = genomic DNA
                         organism = Homo sapiens
SEQUENCE: 129
tttatttggg ctatttgcca aacag                                            25

SEQ ID NO: 130           moltype = DNA  length = 25
FEATURE                  Location/Qualifiers
source                   1..25
                         mol_type = genomic DNA
                         organism = Homo sapiens
SEQUENCE: 130
tttaactatg gttcctttaa atcag                                            25

SEQ ID NO: 131           moltype = DNA  length = 25
FEATURE                  Location/Qualifiers
source                   1..25
                         mol_type = genomic DNA
                         organism = Homo sapiens
SEQUENCE: 131
tttataaggg gacaatccaa catct                                            25

SEQ ID NO: 132           moltype = DNA  length = 25
FEATURE                  Location/Qualifiers
source                   1..25
                         mol_type = genomic DNA
                         organism = Homo sapiens
SEQUENCE: 132
tttattcgga cccgtgctac aactt                                            25

SEQ ID NO: 133           moltype = DNA  length = 25
FEATURE                  Location/Qualifiers
source                   1..25
                         mol_type = genomic DNA
                         organism = Homo sapiens
SEQUENCE: 133
tttattatcc attttaactt gatta                                            25

SEQ ID NO: 134           moltype = DNA  length = 25
FEATURE                  Location/Qualifiers
source                   1..25
                         mol_type = genomic DNA
                         organism = Homo sapiens
SEQUENCE: 134
tttatcagtt gtccaatttg tggtg                                            25

SEQ ID NO: 135           moltype = DNA  length = 25
FEATURE                  Location/Qualifiers
source                   1..25
                         mol_type = genomic DNA
                         organism = Homo sapiens
SEQUENCE: 135
tttaaattcc catgttgcaa cccta                                            25

SEQ ID NO: 136           moltype = DNA  length = 25
FEATURE                  Location/Qualifiers
source                   1..25
                         mol_type = genomic DNA
                         organism = Homo sapiens
SEQUENCE: 136
tttaataatt tttctactta tactt                                            25

SEQ ID NO: 137           moltype = DNA  length = 25
FEATURE                  Location/Qualifiers
source                   1..25
```

```
                        mol_type = genomic DNA
                        organism = Homo sapiens
SEQUENCE: 137
tttacccagt gggtaaaatg atcta                                              25

SEQ ID NO: 138          moltype = DNA  length = 25
FEATURE                 Location/Qualifiers
source                  1..25
                        mol_type = genomic DNA
                        organism = Homo sapiens
SEQUENCE: 138
tttaggtgta tgatactttt agtgc                                              25

SEQ ID NO: 139          moltype = DNA  length = 25
FEATURE                 Location/Qualifiers
source                  1..25
                        mol_type = genomic DNA
                        organism = Homo sapiens
SEQUENCE: 139
tttaggttct acatattgaa gcttt                                              25

SEQ ID NO: 140          moltype = DNA  length = 25
FEATURE                 Location/Qualifiers
source                  1..25
                        mol_type = genomic DNA
                        organism = Homo sapiens
SEQUENCE: 140
tttaagttct tgtttggttc ggggc                                              25

SEQ ID NO: 141          moltype = DNA  length = 25
FEATURE                 Location/Qualifiers
source                  1..25
                        mol_type = genomic DNA
                        organism = Homo sapiens
SEQUENCE: 141
tttattcatc acaacaggta agtcc                                              25

SEQ ID NO: 142          moltype = DNA  length = 25
FEATURE                 Location/Qualifiers
source                  1..25
                        mol_type = genomic DNA
                        organism = Homo sapiens
SEQUENCE: 142
tttaaaggat aaagaataat atagg                                              25

SEQ ID NO: 143          moltype = DNA  length = 25
FEATURE                 Location/Qualifiers
source                  1..25
                        mol_type = genomic DNA
                        organism = Homo sapiens
SEQUENCE: 143
tttattttca catccacagc tccta                                              25

SEQ ID NO: 144          moltype = DNA  length = 25
FEATURE                 Location/Qualifiers
source                  1..25
                        mol_type = genomic DNA
                        organism = Homo sapiens
SEQUENCE: 144
tttagtcccc gcatcgtgtg ggggg                                              25

SEQ ID NO: 145          moltype = DNA  length = 25
FEATURE                 Location/Qualifiers
source                  1..25
                        mol_type = genomic DNA
                        organism = Homo sapiens
SEQUENCE: 145
tttatttaga tggaactagc attcc                                              25

SEQ ID NO: 146          moltype = DNA  length = 25
FEATURE                 Location/Qualifiers
source                  1..25
                        mol_type = genomic DNA
                        organism = Homo sapiens
SEQUENCE: 146
tttatctgca cttattaaat ggcct                                              25

SEQ ID NO: 147          moltype = DNA  length = 25
FEATURE                 Location/Qualifiers
```

```
source                  1..25
                        mol_type = genomic DNA
                        organism = Homo sapiens
SEQUENCE: 147
tttatccttg gacataatta aagaa                                        25

SEQ ID NO: 148          moltype = DNA  length = 25
FEATURE                 Location/Qualifiers
source                  1..25
                        mol_type = genomic DNA
                        organism = Homo sapiens
SEQUENCE: 148
tttaacagtg gctttagttc tcttt                                        25

SEQ ID NO: 149          moltype = DNA  length = 25
FEATURE                 Location/Qualifiers
source                  1..25
                        mol_type = genomic DNA
                        organism = Homo sapiens
SEQUENCE: 149
tttagtacag cagcctgaac tgact                                        25

SEQ ID NO: 150          moltype = DNA  length = 25
FEATURE                 Location/Qualifiers
source                  1..25
                        mol_type = genomic DNA
                        organism = Homo sapiens
SEQUENCE: 150
tttaaaacga cctggtctcc cgcat                                        25

SEQ ID NO: 151          moltype = DNA  length = 25
FEATURE                 Location/Qualifiers
source                  1..25
                        mol_type = genomic DNA
                        organism = Homo sapiens
SEQUENCE: 151
tttactctgt gacaatatat tctat                                        25

SEQ ID NO: 152          moltype = DNA  length = 25
FEATURE                 Location/Qualifiers
source                  1..25
                        mol_type = genomic DNA
                        organism = Homo sapiens
SEQUENCE: 152
tttatactcc aaacttcaga cccag                                        25

SEQ ID NO: 153          moltype = DNA  length = 25
FEATURE                 Location/Qualifiers
source                  1..25
                        mol_type = genomic DNA
                        organism = Homo sapiens
SEQUENCE: 153
tttaaattta gtttttttat tatct                                        25

SEQ ID NO: 154          moltype = DNA  length = 25
FEATURE                 Location/Qualifiers
source                  1..25
                        mol_type = genomic DNA
                        organism = Homo sapiens
SEQUENCE: 154
tttaaatagg taaaggcagg gagga                                        25

SEQ ID NO: 155          moltype = DNA  length = 25
FEATURE                 Location/Qualifiers
source                  1..25
                        mol_type = genomic DNA
                        organism = Homo sapiens
SEQUENCE: 155
tttaactcct ctttttcttt ctgga                                        25

SEQ ID NO: 156          moltype = DNA  length = 25
FEATURE                 Location/Qualifiers
source                  1..25
                        mol_type = genomic DNA
                        organism = Homo sapiens
SEQUENCE: 156
tttaatttgg gaatattggg ttaat                                        25

SEQ ID NO: 157          moltype = DNA  length = 25
```

```
FEATURE                 Location/Qualifiers
source                  1..25
                        mol_type = genomic DNA
                        organism = Homo sapiens
SEQUENCE: 157
tttagagtca gtatagatgg ttttt                                          25

SEQ ID NO: 158          moltype = DNA  length = 25
FEATURE                 Location/Qualifiers
source                  1..25
                        mol_type = genomic DNA
                        organism = Homo sapiens
SEQUENCE: 158
tttatgctgg gaaccggagg gctgg                                          25

SEQ ID NO: 159          moltype = DNA  length = 25
FEATURE                 Location/Qualifiers
source                  1..25
                        mol_type = genomic DNA
                        organism = Homo sapiens
SEQUENCE: 159
tttaaaagaa aagttaggtt ggtgt                                          25

SEQ ID NO: 160          moltype = DNA  length = 25
FEATURE                 Location/Qualifiers
source                  1..25
                        mol_type = genomic DNA
                        organism = Homo sapiens
SEQUENCE: 160
tttatgttgt acatgccaca aaaaa                                          25

SEQ ID NO: 161          moltype = DNA  length = 25
FEATURE                 Location/Qualifiers
source                  1..25
                        mol_type = genomic DNA
                        organism = Homo sapiens
SEQUENCE: 161
tttagtaatg tctggccaac tgtga                                          25

SEQ ID NO: 162          moltype = DNA  length = 25
FEATURE                 Location/Qualifiers
source                  1..25
                        mol_type = genomic DNA
                        organism = Homo sapiens
SEQUENCE: 162
tttatttctt gttgggagga tgagg                                          25

SEQ ID NO: 163          moltype = DNA  length = 25
FEATURE                 Location/Qualifiers
source                  1..25
                        mol_type = genomic DNA
                        organism = Homo sapiens
SEQUENCE: 163
tttaattaag gctttgactg catta                                          25

SEQ ID NO: 164          moltype = DNA  length = 25
FEATURE                 Location/Qualifiers
source                  1..25
                        mol_type = genomic DNA
                        organism = Homo sapiens
SEQUENCE: 164
tttacactct tcactcgctt tgtcc                                          25

SEQ ID NO: 165          moltype = DNA  length = 25
FEATURE                 Location/Qualifiers
source                  1..25
                        mol_type = genomic DNA
                        organism = Homo sapiens
SEQUENCE: 165
tttaagagtt tgatttatcc ttttt                                          25

SEQ ID NO: 166          moltype = DNA  length = 25
FEATURE                 Location/Qualifiers
source                  1..25
                        mol_type = genomic DNA
                        organism = Homo sapiens
SEQUENCE: 166
tttagctatt tgttatggca gcaac                                          25
```

```
SEQ ID NO: 167          moltype = DNA  length = 25
FEATURE                 Location/Qualifiers
source                  1..25
                        mol_type = genomic DNA
                        organism = Homo sapiens
SEQUENCE: 167
tttattatct ttccaatact ttaac                                         25

SEQ ID NO: 168          moltype = DNA  length = 25
FEATURE                 Location/Qualifiers
source                  1..25
                        mol_type = genomic DNA
                        organism = Homo sapiens
SEQUENCE: 168
tttaaggctt gtttatttgt gtttt                                         25

SEQ ID NO: 169          moltype = DNA  length = 25
FEATURE                 Location/Qualifiers
source                  1..25
                        mol_type = genomic DNA
                        organism = Homo sapiens
SEQUENCE: 169
tttatctggt ccccgaggca gtgca                                         25

SEQ ID NO: 170          moltype = DNA  length = 25
FEATURE                 Location/Qualifiers
source                  1..25
                        mol_type = genomic DNA
                        organism = Homo sapiens
SEQUENCE: 170
tttaaagaag gatatttaga atttt                                         25

SEQ ID NO: 171          moltype = DNA  length = 25
FEATURE                 Location/Qualifiers
source                  1..25
                        mol_type = genomic DNA
                        organism = Homo sapiens
SEQUENCE: 171
tttaaaggta ggcctcaaaa agaac                                         25

SEQ ID NO: 172          moltype = DNA  length = 25
FEATURE                 Location/Qualifiers
source                  1..25
                        mol_type = genomic DNA
                        organism = Homo sapiens
SEQUENCE: 172
tttatttgtt cttttaattt atcta                                         25

SEQ ID NO: 173          moltype = DNA  length = 25
FEATURE                 Location/Qualifiers
source                  1..25
                        mol_type = genomic DNA
                        organism = Homo sapiens
SEQUENCE: 173
tttatctgac ctaaattttg accaa                                         25

SEQ ID NO: 174          moltype = DNA  length = 25
FEATURE                 Location/Qualifiers
source                  1..25
                        mol_type = genomic DNA
                        organism = Homo sapiens
SEQUENCE: 174
tttaggctcc tgggattcac aagaa                                         25

SEQ ID NO: 175          moltype = DNA  length = 25
FEATURE                 Location/Qualifiers
source                  1..25
                        mol_type = genomic DNA
                        organism = Homo sapiens
SEQUENCE: 175
tttactggca aactgggagg agaga                                         25

SEQ ID NO: 176          moltype = DNA  length = 25
FEATURE                 Location/Qualifiers
source                  1..25
                        mol_type = genomic DNA
                        organism = Homo sapiens
SEQUENCE: 176
tttaacctta acgtgcttga ggttt                                         25
```

```
SEQ ID NO: 177         moltype = DNA  length = 25
FEATURE                Location/Qualifiers
source                 1..25
                       mol_type = genomic DNA
                       organism = Homo sapiens
SEQUENCE: 177
tttatttcta tattttgagg acatg                                          25

SEQ ID NO: 178         moltype = DNA  length = 25
FEATURE                Location/Qualifiers
source                 1..25
                       mol_type = genomic DNA
                       organism = Homo sapiens
SEQUENCE: 178
tttagaattt ttaggctcct gggat                                          25

SEQ ID NO: 179         moltype = DNA  length = 25
FEATURE                Location/Qualifiers
source                 1..25
                       mol_type = genomic DNA
                       organism = Homo sapiens
SEQUENCE: 179
tttatgattt gctgccagaa cattt                                          25

SEQ ID NO: 180         moltype = DNA  length = 25
FEATURE                Location/Qualifiers
source                 1..25
                       mol_type = genomic DNA
                       organism = Homo sapiens
SEQUENCE: 180
tttattgatt ttttaaattt tctaa                                          25

SEQ ID NO: 181         moltype = DNA  length = 25
FEATURE                Location/Qualifiers
source                 1..25
                       mol_type = genomic DNA
                       organism = Homo sapiens
SEQUENCE: 181
tttatcccac tgcgggtcct gagca                                          25

SEQ ID NO: 182         moltype = DNA  length = 25
FEATURE                Location/Qualifiers
source                 1..25
                       mol_type = genomic DNA
                       organism = Homo sapiens
SEQUENCE: 182
tttataattt ccatgctttt tcagt                                          25

SEQ ID NO: 183         moltype = DNA  length = 25
FEATURE                Location/Qualifiers
source                 1..25
                       mol_type = genomic DNA
                       organism = Homo sapiens
SEQUENCE: 183
tttatctgta attctgcaga ccctc                                          25

SEQ ID NO: 184         moltype = DNA  length = 25
FEATURE                Location/Qualifiers
source                 1..25
                       mol_type = genomic DNA
                       organism = Homo sapiens
SEQUENCE: 184
tttaaagggg aagctttgaa gagga                                          25

SEQ ID NO: 185         moltype = DNA  length = 25
FEATURE                Location/Qualifiers
source                 1..25
                       mol_type = genomic DNA
                       organism = Homo sapiens
SEQUENCE: 185
tttacctgcc ggtagtcctt ggtcc                                          25

SEQ ID NO: 186         moltype = DNA  length = 25
FEATURE                Location/Qualifiers
source                 1..25
                       mol_type = genomic DNA
                       organism = Homo sapiens
SEQUENCE: 186
```

```
tttaccaatg tgttctaagt tttca                                          25

SEQ ID NO: 187         moltype = DNA  length = 25
FEATURE                Location/Qualifiers
source                 1..25
                       mol_type = genomic DNA
                       organism = Homo sapiens
SEQUENCE: 187
tttaaaaaaa taaatactga ccttg                                          25

SEQ ID NO: 188         moltype = DNA  length = 25
FEATURE                Location/Qualifiers
source                 1..25
                       mol_type = genomic DNA
                       organism = Homo sapiens
SEQUENCE: 188
tttatcttgt aggtggttaa gaact                                          25

SEQ ID NO: 189         moltype = DNA  length = 25
FEATURE                Location/Qualifiers
source                 1..25
                       mol_type = genomic DNA
                       organism = Homo sapiens
SEQUENCE: 189
tttatttctt ttcacgaatt gctgg                                          25

SEQ ID NO: 190         moltype = DNA  length = 25
FEATURE                Location/Qualifiers
source                 1..25
                       mol_type = genomic DNA
                       organism = Homo sapiens
SEQUENCE: 190
tttatgtggt gttcagagcc ccagg                                          25

SEQ ID NO: 191         moltype = DNA  length = 25
FEATURE                Location/Qualifiers
source                 1..25
                       mol_type = genomic DNA
                       organism = Homo sapiens
SEQUENCE: 191
tttatcggtg ttattgatga tcatt                                          25

SEQ ID NO: 192         moltype = DNA  length = 25
FEATURE                Location/Qualifiers
source                 1..25
                       mol_type = genomic DNA
                       organism = Homo sapiens
SEQUENCE: 192
tttattttat ttcttgttgg gagga                                          25

SEQ ID NO: 193         moltype = DNA  length = 25
FEATURE                Location/Qualifiers
source                 1..25
                       mol_type = genomic DNA
                       organism = Homo sapiens
SEQUENCE: 193
tttaaattgg ctataaatct ttgac                                          25

SEQ ID NO: 194         moltype = DNA  length = 25
FEATURE                Location/Qualifiers
source                 1..25
                       mol_type = genomic DNA
                       organism = Homo sapiens
SEQUENCE: 194
tttaccttta ctgttaatta gtcct                                          25

SEQ ID NO: 195         moltype = RNA  length = 41
FEATURE                Location/Qualifiers
misc_feature           1..41
                       note = crRNA for SEQ ID NO: 132
source                 1..41
                       mol_type = other RNA
                       organism = synthetic construct
SEQUENCE: 195
taatttctac tcttgtagat ttcggacccg tgctacaact t                        41

SEQ ID NO: 196         moltype = RNA  length = 41
FEATURE                Location/Qualifiers
misc_feature           1..41
```

```
                         note = crRNA for Cpf1 target site of SEQ ID NO: 108
source                   1..41
                         mol_type = other RNA
                         organism = synthetic construct
SEQUENCE: 196
taatttctac tcttgtagat atagaatagc ctcatatttt a                        41

SEQ ID NO: 197           moltype = DNA  length = 27
FEATURE                  Location/Qualifiers
source                   1..27
                         mol_type = genomic DNA
                         organism = Homo sapiens
SEQUENCE: 197
tttgtgtccc cgttttggtt ggtaaac                                        27

SEQ ID NO: 198           moltype = DNA  length = 27
FEATURE                  Location/Qualifiers
source                   1..27
                         mol_type = genomic DNA
                         organism = Homo sapiens
SEQUENCE: 198
tttaaaaatc aataccgata ataatga                                        27

SEQ ID NO: 199           moltype = DNA  length = 27
FEATURE                  Location/Qualifiers
source                   1..27
                         mol_type = genomic DNA
                         organism = Homo sapiens
SEQUENCE: 199
tttcttaata tgaatattaa tatcggt                                        27

SEQ ID NO: 200           moltype = DNA  length = 27
FEATURE                  Location/Qualifiers
source                   1..27
                         mol_type = genomic DNA
                         organism = Homo sapiens
SEQUENCE: 200
tttccgtatc tggaaggggc atcttgg                                        27

SEQ ID NO: 201           moltype = DNA  length = 27
FEATURE                  Location/Qualifiers
source                   1..27
                         mol_type = genomic DNA
                         organism = Homo sapiens
SEQUENCE: 201
tttccttagg accggaagga ttacagc                                        27

SEQ ID NO: 202           moltype = DNA  length = 27
FEATURE                  Location/Qualifiers
source                   1..27
                         mol_type = genomic DNA
                         organism = Homo sapiens
SEQUENCE: 202
tttgcctaaa aggcactatg tcaaatg                                        27

SEQ ID NO: 203           moltype = DNA  length = 27
FEATURE                  Location/Qualifiers
source                   1..27
                         mol_type = genomic DNA
                         organism = Homo sapiens
SEQUENCE: 203
tttggagctg ttggcatcat gttcctg                                        27

SEQ ID NO: 204           moltype = DNA  length = 27
FEATURE                  Location/Qualifiers
source                   1..27
                         mol_type = genomic DNA
                         organism = Homo sapiens
SEQUENCE: 204
tttgattctt ttctatctca ggacaga                                        27

SEQ ID NO: 205           moltype = DNA  length = 27
FEATURE                  Location/Qualifiers
source                   1..27
                         mol_type = genomic DNA
                         organism = Homo sapiens
SEQUENCE: 205
tttatagaca tcccacactg tagttct                                        27
```

```
SEQ ID NO: 206         moltype = DNA  length = 27
FEATURE                Location/Qualifiers
source                 1..27
                       mol_type = genomic DNA
                       organism = Homo sapiens
SEQUENCE: 206
tttattaatt tgagaaccaa cataagg                                  27

SEQ ID NO: 207         moltype = DNA  length = 27
FEATURE                Location/Qualifiers
source                 1..27
                       mol_type = genomic DNA
                       organism = Homo sapiens
SEQUENCE: 207
tttattttct ttttggtaag aaggaac                                  27

SEQ ID NO: 208         moltype = DNA  length = 27
FEATURE                Location/Qualifiers
source                 1..27
                       mol_type = genomic DNA
                       organism = Homo sapiens
SEQUENCE: 208
tttcacacac acacacacac acacaca                                  27

SEQ ID NO: 209         moltype = RNA  length = 43
FEATURE                Location/Qualifiers
misc_feature           1..43
                       note = crRNA for Cpf1 target site of SEQ ID NO: 203
source                 1..43
                       mol_type = other RNA
                       organism = synthetic construct
SEQUENCE: 209
taatttctac tcttgtagat gagctgttgg catcatgttc ctg                43

SEQ ID NO: 210         moltype = DNA  length = 25
FEATURE                Location/Qualifiers
source                 1..25
                       mol_type = genomic DNA
                       organism = Homo sapiens
SEQUENCE: 210
tttatccaaa cctcctaaat gatac                                    25

SEQ ID NO: 211         moltype = RNA  length = 41
FEATURE                Location/Qualifiers
misc_feature           1..41
                       note = crRNA for Cpf1 target site of SEQ ID NO: 210
source                 1..41
                       mol_type = other RNA
                       organism = synthetic construct
SEQUENCE: 211
taatttctac tcttgtagat tccaaacctc ctaaatgata c                  41

SEQ ID NO: 212         moltype = DNA  length = 25
FEATURE                Location/Qualifiers
source                 1..25
                       mol_type = genomic DNA
                       organism = Homo sapiens
SEQUENCE: 212
tttacacccg atccactggg gagca                                    25

SEQ ID NO: 213         moltype = DNA  length = 27
FEATURE                Location/Qualifiers
source                 1..27
                       mol_type = genomic DNA
                       organism = Homo sapiens
SEQUENCE: 213
tttttgattc ttttctatct caggaca                                  27

SEQ ID NO: 214         moltype = DNA  length = 511
FEATURE                Location/Qualifiers
source                 1..511
                       mol_type = genomic DNA
                       organism = Homo sapiens
SEQUENCE: 214
ggggttgggg ttgcgccttt tccaaggcag ccctgggttt gcgcagggac gcggctgctc  60
tgggcgtggt tccgggaaac gcagcggcgc cgaccctggg tctcgcacat tcttcacgtc  120
cgttcgcagc gtcacccgga tcttcgccgc taccettgtg ggcccccegg cgacgcttcc  180
tgctccgccc ctaagtcggg aaggttcctt gcggttcgcg gcgtgccgga cgtgacaaac  240
ggaagccgca cgtctcacta gtaccctcgc agacggacag cgccagggag caatggcagc  300
```

```
gcgccgaccg cgatgggctg tggccaatag cggctgctca gcggggcgcg ccgagagcag  360
cggccgggaa ggggcggtgc gggaggcggg gtgtggggcg gtagtgtggg ccctgttcct  420
gcccgcgcgg tgttccgcat tctgcaagcc tccggagcgc acgtcggcag tcggctccct  480
cgttgaccga atcaccgacc tctctcccca g                                511

SEQ ID NO: 215          moltype = DNA  length = 4107
FEATURE                 Location/Qualifiers
source                  1..4107
                        mol_type = genomic DNA
                        organism = Streptococcus pyogenes
SEQUENCE: 215
atggataaga aatactcaat aggcttagat atcggcacaa atagcgtcgg atgggcggtg  60
atcactgatg aatataaggt tccgtctaaa aagttcaagg ttctgggaaa tacagaccgc  120
cacagtatca aaaaaaatct tataggggct cttttatttg acagtggaga gacagcggaa  180
gcgactcgtc tcaaacggac agctcgtaga aggtatacac gtcggaagaa tcgtatttgt  240
tatctacagg agattttttc aaatgagatg gcgaaagtag atgatagttt ctttcatcga  300
cttgaagagt cttttttggt ggaagaagac aagaagcatg aacgtcatcc tatttttgga  360
aatatagtag atgaagttgc ttatcatgag aaatatccaa ctatctatca tctgcgaaaa  420
aaattggtag attctactga taaagcggat ttgcgcttaa tctatttggc cttagcgcat  480
atgattaagt ttcgtggtca tttttttgatt gagggagatt taaatcctga taatagtgat  540
gtggacaaac tatttatcca gttggtacaa acctacaatc aattatttga agaaaaccct  600
attaacgcaa gtggagtaga tgctaaagcg attctttctg cacgattgag taaatcaaga  660
cgattagaaa atctcattgc tcagctcccc ggtgagaaga aaaatggctt atttgggaat  720
ctcattgctt tgtcattggg tttgacccct aattttaaat caaattttga tttggcagaa  780
gatgctaaat tacagctttc aaaagatact tacgatgatg atttagataa tttattggcg  840
caaattggag atcaatatgc tgatttgttt ttggcagcta agaatttatc agatgctatt  900
ttactttcag atatcctaag agtaaatact gaaataacta aggctcccct atcagcttca  960
atgattaaac gctacgatga acatcatcaa gacttgactc ttttaaaagc tttagttcga  1020
caacaacttc cagaaaagta taaagaaatc ttttttgatc aatcaaaaaa cggatatgca  1080
ggttatattg atgggggagc tagccaagaa gaattttata aatttatcaa accaatttta  1140
gaaaaaatgg atggtactga ggaattattg gtgaaactaa atcgtgaaga tttgctgcgc  1200
aagcaacgga cctttgacaa cggctctatt ccccatcaaa ttcacttggg tgagctgcat  1260
gctattttga gaagacaaga agacttttat ccatttttaa aagacaatcg tgagaagatt  1320
gaaaaaatct tgacttttcg aattccttat tatgttggtc cattggcgcg tggcaatagt  1380
cgttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaaagt actaccaaaa catagtttgc tttatgagta ttttacggtt  1560
tataacgaat tgacaaaggt caaatatgtt actgaaggaa tgcgaaaacc agcatttctt  1620
tcaggtgaac agaagaaagc cattgttgat ttactcttca aaacaaatcg aaaagtaacc  1680
gttaagcaat taaaagaaga ttatttcaaa aaaatagaat gttttgatag tgttgaaatt  1740
tcaggagttg aagatagatt taatgcttca ttaggtacct accatgattt gctaaaaatt  1800
attaaagata aagatttttt ggataatgaa gaaaatgaag atatcttaga ggatattgtt  1860
ttaacattga ccttatttga agatagggag atgattgagg aaagacttaa aacatatgct  1920
cacctctttg atgataaggt gatgaaacag cttaaacgtc gccgttatac tggttgggga  1980
cgtttgtctc gaaaattgat taatggtatt agggataagc aatctggcaa aacaatatta  2040
gatttttttga aatcagatgg ttttgccaat cgcaatttta tgcagctgat ccatgatgat  2100
agtttgacat ttaaagaaga cattcaaaaa gcacaagtgt ctggacaagg cgatagttta  2160
catgaacata ttgcaaattt agctggtagc cctgctatta aaaaaggtat tttacagact  2220
gtaaaagttg ttgatgaatt ggtcaaagta atggggcggc ataagccaga aaatatcgtt  2280
attgaaatgg cacgtgaaaa tcagacaact caaaagggcc agaaaaattc gcgagagcgt  2340
atgaaacgaa tcgaagaagg tatcaaagaa ttaggaagtc agattcttaa agagcatcct  2400
gttgaaaata ctcaattgca aaatgaaaag ctctatctct attatctcca aaatggaaga  2460
gacatgtatg tggaccaaga attagatatt aatcgtttaa gtgattatga tgtcgatcac  2520
attgttccac aaagtttcct taaagacgat tcaatagaca ataaggtctt aacgcgttct  2580
gataaaaatc gtggtaaatc ggataacgtt ccaagtgaag aagtagtcaa aaagatgaaa  2640
aactattgga gacaacttct aaacgccaag ttaatcactc aacgtaagtt tgataattta  2700
acgaaagctg aacgtggagg tttgagtgaa cttgataaag ctggttttat caaacgccaa  2760
ttggttgaaa ctcgccaaat cactaagcat gtggcacaaa ttttggatag tcgcatgaat  2820
actaaatacg atgaaaatga taaacttatt cgagaggtta aagtgattac cttaaaatct  2880
aaattagttt ctgacttccg aaaagatttc caattctata aagtacgtga gattaacaat  2940
taccatcatg cccatgatgc gtatctaaat gccgtcgttg gaactgcttt gattaagaaa  3000
tatccaaaac ttgaatcgga gtttgtctat ggtgattata aagtttatga tgttcgtaaa  3060
atgattgcta agtctgagca agaaataggc aaagcaaccg caaaatattt cttttactct  3120
aatatcatga acttcttcaa aacagaaatt acacttgcaa atggagagat tcgcaaacgc  3180
cctctaatcg aaactaatgg ggaaactgga gaaattgtct gggataaagg gcgagatttt  3240
gccacagtgc gcaaagtatt gtccatgccc caagtcaata ttgtcaagaa aacagaagta  3300
cagacaggcg gattctccaa ggagtcaatt ttaccaaaaa gaaattcgga caagcttatt  3360
gctcgtaaaa aagactggga tccaaaaaaa tatggtggtt ttgatagtcc aacggtagct  3420
tattcagtcc tagtggttgc taaggtggaa aaagggaaat cgaagaagtt aaaatccgtt  3480
aaagagttac tagggatcac aattatggaa agaagttcct ttgaaaaaaa tccgattgac  3540
tttttagaag ctaaaggata taaggaagtt aaaaaagact taatcattaa actacctaaa  3600
tatagtcttt ttgagttaga aaacggtcgt aaacggatgc tggctagtgc cggagaatta  3660
caaaaaggaa atgagctggc tctgccaagc aaatatgtga atttttttata tttagctagt  3720
cattatgaaa agttgaaggg tagtccagaa gataacgaac aaaaacaatt gtttgtggag  3780
cagcataagc attatttaga tgagattatt gagcaaatca gtgaattttc taagcgtgtt  3840
attttagcag atgccaattt agataaagtt cttagtgcat ataacaaaca tagagacaaa  3900
ccaatacgtg aacaagcaga aaatattatt catttattta cgttgacgaa tcttggagct  3960
cccgctgctt ttaaatattt tgatacaaca attgatcgta aacgatatac gtctacaaaa  4020
gaagttttag atgccactct tatccatcaa tccatcactg gtctttatga aacacgcatt  4080
```

```
gatttgagtc agctaggagg tgactga                                       4107

SEQ ID NO: 216          moltype = DNA  length = 3903
FEATURE                 Location/Qualifiers
source                  1..3903
                        mol_type = genomic DNA
                        organism = Francisella tularensis
SEQUENCE: 216
atgtcaattt atcaagaatt tgttaataaa tatagtttaa gtaaaactct aagatttgag  60
ttaatcccac agggtaaaac acttgaaaac ataaaagcaa gaggtttgat tttagatgat  120
gagaaaagag ctaaagacta caaaaaggct aaacaaataa ttgataaata tcatcagttt  180
tttatagagg agatattaag ttcggtttgt attagcgaag atttattaca aaactattct  240
gatgtttatt ttaaacttaa aaagagtgat gatgataatc tacaaaaaga ttttaaaagt  300
gcaaaagata cgataaagaa acaaatatct gaatatataa aggactcaga gaaatttaag  360
aatttgttta atcaaaacct tatcgatgct aaaaaagggc aagagtcaga tttaattcta  420
tggctaaagc aatctaagga taatggtata gaactattta aagccaatag tgatatcaca  480
gatatagatg aggcgttaga aataatcaaa tcttttaaag gttggacaac ttattttaag  540
ggttttcatg aaaatagaaa aaatgtttat agtagcaatg atattcctac atctattatt  600
tataggatag tagatgataa tttgcctaaa tttctagaaa ataaagctaa gtatgagagt  660
ttaaaagaca aagctccaga agctataaac tatgaacaaa ttaaaaaaga tttggcagaa  720
gagctaacct ttgatattga ctacaaaaca tctgaagtta atcaaagagt tttttcactt  780
gatgaagttt ttgagatagc aaactttaat aattatctaa atcaaagtgg tattactaaa  840
tttaatacta ttattggtgg taaatttgta aatggtgaaa atacaaagag aaaaggtata  900
aatgaatata taaatctata ctcacagcaa ataaatgata aaacactcaa aaaatataaa  960
atgagtgttt tatttaagca aattttaagt gatacagaat ctaaatcttt tgtaattgat  1020
aagttagaag atgatagtga tgtagttaca acgatgcaaa gtttttatga gcaaatagca  1080
gcttttaaaa cagtagaaga aaaatctatt aaagaaacac tatctttatt atttgatgat  1140
ttaaaagctc aaaaacttga tttgagtaaa atttatttta aaaatgataa atctcttact  1200
gatctatcac aacaagtttt tgatgattat agtgttattg gtacagcggt actagaatat  1260
ataactcaac aaatagcacc taaaaatctt gataacccta gtaagaaaga gcaagaatta  1320
atagccaaaa aaactgaaaa agcaaaatac ttatctctag aaactataaa gcttgcctta  1380
gaagaattta ataagcatag agatatagat aaacagtgta ggtttgaaga aatacttgca  1440
aactttgcgg ctattccgat gatatttgat gaaatagctc aaaacaaaga caatttggca  1500
cagatatcta tcaaatatca aaatcaaggt aaaaaagacc tacttcaagc tagtgcggaa  1560
gatgatgtta aagctatcaa ggatctttta gatcaaacta ataatctctt acataaacta  1620
aaaatatttc atattagtca gtcagaagat aaggcaaata ttttagacaa ggatgagcat  1680
ttttatctag tatttgagga gtgctacttt gagctagcga atatagtgcc tctttataac  1740
aaaattagaa actatataac tcaaaagcca tatagtgatg agaaatttaa gctcaatttt  1800
gagaactcga ctttggctaa tggttgggat aaaaataaag agcctgacaa tacggcaatt  1860
ttatttatca aagatgataa atattatctg ggtgtgatga ataagaaaaa taacaaaata  1920
tttgatgata aagctatcaa agaaaataaa ggcgagggtt ataaaaaaat tgtttataaa  1980
cttttacctg gcgcaaataa aatgttacct aaggtttttct tttctgctaa atctataaaa  2040
ttttataatc ctagtgaaga tatacttaga ataagaaatc attccacaca tacaaaaaat  2100
ggtagtcctc aaaaaggata tgaaaaattt gagtttaata ttgaagattg ccgaaaattt  2160
atagattttt ataaacagtc tataagtaag catccggagt ggaaagattt tggatttaga  2220
ttttctgata ctcaaagata taattctata gatgaatttt atagagaagt tgaaaatcaa  2280
ggctacaaac taacttttga aaatatatca gagagctata ttgatagcgt agttaatcag  2340
ggtaaattgt acctattcca aatctataat aaagattttt cagcttatag caaagggcga  2400
ccaaatctac atactttata ttggaaagcg ctgtttgatg agagaaatct tcaagatgtg  2460
gtttataagc taaatggtga ggcagagctt ttttatcgta aacaatcaat acctaaaaaa  2520
atcactcacc cagctaaaga ggcaatagct aataaaaaca aagataatcc taaaaaagag  2580
agtgtttttg aatatgattt aatcaaagat aaacgcttta ctgaagataa gtttttcttt  2640
cactgtccta ttacaatcaa ttttaaatct agtggagcta ataagtttaa tgatgaaatc  2700
aatttattgc taaaagaaaa agcaaatgat gttcatatat taagtataga tagaggtgaa  2760
agacatttag cttactatac tttggtagat ggtaaaggca atatcatcaa acaagatact  2820
ttcaacatca ttggtaatga tagaatgaaa acaaactacc atgataagct tgctgcaata  2880
gagaaagata gggattcagc taggaaagac tggaaaaaga taaataacat caaagagatg  2940
aaagagggct atctatctca ggtagttcat gaaatagcta agctagttat agagtataat  3000
gctattgtgg tttttgagga tttaaatttt ggatttaaaa gagggcgttt caaggtagag  3060
aagcaggtct atcaaaagtt agaaaaaatg ctaattgaga aactaaacta tctagttttc  3120
aaagataatg agtttgataa aactggggga gtgcttagag cttatcagct aacagcacct  3180
tttgagactt ttaaaaagat gggtaaacaa acaggtatta tctactatgt accagctggt  3240
tttacttcaa aaatttgtcc tgtaactggt tttgtaaatc agttatatcc taagtatgaa  3300
agtgtcagca aatctcaaga gttctttagt aagtttgaca agatttgtta taaccttgat  3360
aagggctatt ttgagtttag ttttgattat aaaaactttg gtgacaaggc tgccaaaggc  3420
aagtggacta tagctagctt tgggagtaga ttgattaact ttagaaattc agataaaaat  3480
cataattggg atactcgaga agtttatcca actaaagagt tggagaaatt gctaaaagat  3540
tattctatcg aatatgggca tggcgaatgt atcaaagcag ctatttgcgg tgagagcgac  3600
aaaaagtttt ttgctaagct aactagtgtc ctaaatacta tcttacaaat gcgtaactca  3660
aaaacaggta ctgagttaga ttatctaatt tcaccagtag cagatgtaaa tggcaatttc  3720
tttgattcgc gacaggcgcc aaaaaatatg cctcaagatg ctgatgccaa tggtgcttat  3780
catattgggc taaaaggtct gatgctacta ggtaggatca aaaataatca agagggcaaa  3840
aaactcaatt tggttatcaa aaatgaagag tattttgagt tcgtgcagaa taggaataac  3900
taa                                                                 3903

SEQ ID NO: 217          moltype = DNA  length = 3921
FEATURE                 Location/Qualifiers
source                  1..3921
                        mol_type = genomic DNA
```

organism = Acidaminococcus sp.
strain = BV3L6

SEQUENCE: 217

```
atgacacagt tcgagggctt taccaacctg tatcaggtga gcaagacact gcggtttgag  60
ctgatcccac agggcaagac cctgaagcac atccaggagc agggcttcat cgaggaggac  120
aaggcccgca atgatcacta caaggagctg aagcccatca tcgatcggat ctacaagacc  180
tatgccgacc agtgcctgca gctggtgcag ctggattggg agaacctgag cgccgccatc  240
gactcctata gaaaggagaa aaccgaggag acaaggaacg ccctgatcga ggagcaggcc  300
acatatcgca atgccatcca cgactacttc atcggccgga cagacaacct gaccgatgcc  360
atcaataaga gacacgccga gatctacaag ggcctgttca aggccgagct gtttaatggc  420
aaggtgctga agcagctggg caccgtgacc acaaccgagc acgagaacgc cctgctgcgg  480
agcttcgaca agtttacaac ctacttctcc ggcttttatg agaacaggaa gaacgtgttc  540
agcgccgagg atatcagcac agccatccca caccgcatcg tgcaggacaa cttccccaag  600
tttaaggaga attgtcacat cttcacacgc ctgatcaccg ccgtgcccag cctgcgggag  660
cactttgaga acgtgaagaa ggccatcggc atcttcgtga gcacctccat cgaggaggtg  720
ttttccttcc ctttttataa ccagctgctg acacagaccc agatcgacct gtataaccag  780
ctgctgggag gaatctctcg ggaggcaggc accgagaaga tcaagggcct gaacgaggtg  840
ctgaatctgg ccatccagaa gaatgatgag acagcccaca tcatcgcctc cctgccacac  900
agattcatcc ccctgtttaa gcagatcctg tccgatagga acaccctgtc tttcatcctg  960
gaggagttta agagcgacga ggaagtgatc cagtccttct gcaagtacaa gacactgctg  1020
agaaacgaga acgtgctgga gacagccgag gccctgttta acgagctgaa cagcatcgac  1080
ctgacacaca tcttcatcag ccacaagaag ctggagacaa tcagcagcgc cctgtgcgac  1140
cactgggata cactgaggaa tgccctgtat gagcggagaa tctccgagct gacaggcaag  1200
atcaccaagt ctgccaagga gaaggtgcag cgcagcctga agcacgagga tatcaacctg  1260
caggagatca tctctgccgc aggcaaggag ctgagcgagg ccttcaagca gaaaaccagc  1320
gagatcctgt cccacgcaca cgccgccctg gatcagccac tgcctacaac cctgaagaag  1380
caggaggaga aggagatcct gaagtctcag ctggacagcc tgctgggcct gtaccacctg  1440
ctggactggt ttgccgtgga tgagtccaac gaggtggacc ccgagttctc tgcccggctg  1500
accggcatca agctggagat ggagccttct ctgagcttct acaacaaggc cagaaattat  1560
gccaccaaga agccctactc cgtggagaag ttcaagctga actttcagat gcctacactg  1620
gcctctggct gggacgtgaa taaggagaag aacaatggcg ccatcctgtt tgtgaagaac  1680
ggcctgtact atctgggcat catgccaaag cagaagggca ggtataaggc cctgagcttc  1740
gagcccacag agaaaaccag cgagggcttt gataagatgt actatgacta cttccctgat  1800
gccgccaaga tgatcccaaa gtgcagcacc cagctgaagg ccgtgacagc ccactttcag  1860
acccacacaa cccccatcct gctgtccaac aatttcatcg agcctctgga gatcacaaag  1920
gagatctacg acctgaacaa tcctgagaag gagccaaaga agtttcagac agcctacgcc  1980
aagaaaaccg gcgaccagaa gggctacaga gaggccctgt gcaagtggat cgacttcaca  2040
agggatttc tgtccaagta taccaagaca acctctatcg atctgtctag cctgcggcca  2100
tcctctcagt ataaggacct gggcgagtac tatgccgagc tgaatcccct gctgtaccac  2160
atcagcttcc agagaatcgc cgagaaggag atcatggatg ccgtggagac aggcaagctg  2220
tacctgttcc agatctataa caaggacttt gccaagggcc accacggcaa gcctaatctg  2280
cacacactgt attggaccgg cctgttttct ccagagaacc tggccaagac aagcatcaag  2340
ctgaatggcc aggccgagct gttctaccgc cctaagtcca ggatgaagag gatggcacac  2400
cggctgggag agaagatgct gaacaagaag ctgaaggatc agaaaacccc aatccccgac  2460
accctgtacc aggagctgta cgactatgtg aatcacagac tgtcccacga cctgtctgat  2520
gaggccaggg ccctgctgcc caacgtgatc accaaggagg tgtctcacga gatcatcaag  2580
gataggcgct ttaccagcga caagttcttt ttccacgtgc ctatcacact gaactatcag  2640
gccgccaatt ccccatctaa gttcaaccag agggtgaatg cctacctgaa ggagcacccc  2700
gagacaccta tcatcggcat cgatcggggc gagagaaacc tgatctatat cacagtgatc  2760
gactccaccg gcaagatcct ggagcagcgg agcctgaaca ccatccagca gtttgattac  2820
cagaagaagc tggacaacag ggagaaggag agggtggcag caaggcaggc ctggtctgtg  2880
gtgggcacaa tcaaggatct gaagcagggc tatctgagcc aggtcatcca cgagatcgtg  2940
gacctgatga tccactacca ggccgtggtg gtgctggaga acctgaattt cggctttaag  3000
agcaagagga ccggcatcgc cgagaaggcc gtgtaccagc agttcgagaa gatgctgatc  3060
gataagctga attgcctggt gctgaaggac tatccagcag agaaagtggg aggcgtgctg  3120
aacccatacc agctgacaga ccagttcacc tcctttgcca agatgggcac ccagtctggc  3180
ttcctgtttt acgtgcctgc cccatataca tctaagatcg atcccctgac cggcttcgtg  3240
gacccctcg tgtggaaaac catcaagaat cacgagagcc gcaagcactt cctggagggc  3300
ttcgactttc tgcactacga cgtgaaaacc ggcgacttca tcctgcactt taagatgaac  3360
agaaatctgt ccttccagag gggcctgccc ggctttatgc ctgcatggga tatcgtgttc  3420
gagaagaacg agacacagtt tgacgccaag ggcacccctt tcatcgccgg caagagaatc  3480
gtgccagtga tcgagaatca cagattcacc ggcagatacc gggacctgta tcctgccaac  3540
gagctgatcg ccctgctgga ggagaagggc atcgtgttca gggatggctc caacatcctg  3600
ccaaagctgc tggagaatga cgattctcac gccatcgaca ccatggtggc cctgatccgc  3660
agcgtgctgc agatgcggaa ctccaatgcc gccacaggcg aggactatat caacagcccc  3720
gtgcgcgatc tgaatggcgt gtgcttcgac tcccggtttc agaacccaga gtggcccatg  3780
gacgccgatg ccaatggcgc ctaccacatc gccctgaagg gccagctgct gctgaatcac  3840
ctgaaggaga gcaaggatct gaagctgcag aacggcatct ccaatcagga ctggctggcc  3900
tacatccagg agctgcgcaa c                                           3921
```

SEQ ID NO: 218 moltype = DNA length = 3699
FEATURE Location/Qualifiers
source 1..3699
mol_type = genomic DNA
note = Lachnospiraceae bacterium
organism = unidentified
strain = MC2017

SEQUENCE: 218

```
atggattacg gcaacggcca gtttgagcgg agagcccccc tgaccaagac aatcaccctg  60
```

```
cgcctgaagc ctatcggcga gacacgggag acaatccgcg agcagaagct gctggagcag  120
gacgccgcct tcagaaagct ggtggagaca gtgaccccta tcgtggacga ttgtatcagg  180
aagatcgccg ataacgccct gtgccacttt ggcaccgagt atgacttcag ctgtctgggc  240
aacgccatct ctaagaatga cagcaaggcc atcaagaagg agacagagaa ggtggagaag  300
ctgctggcca aggtgctgac cgagaatctg ccagatggcc tgcgcaaggt gaacgacatc  360
aattccgccg cctttatcca ggatacactg acctctttcg tgcaggacga tgccgacaag  420
cgggtgctga tccaggagct gaagggcaag accgtgctga tgcagcggtt cctgaccaca  480
cggatcacag ccctgaccgt gtggctgccc gacagagtgt tcgagaactt taatatcttc  540
atcgagaacg ccgagaagat gagaatcctg ctggactccc ctctgaatga gaagatcatg  600
aagtttgacc cagatgccga gcagtacgcc tctctggagt tctatggcca gtgcctgtct  660
cagaaggaca tcgatagcta caacctgatc atctccggca tctatgccga cgatgaggtg  720
aagaaccctg gcatcaatga gatcgtgaag gagtacaatc agcagatccg gggcgacaag  780
gatgagtccc cactgcccaa gctgaagaag ctgcacaagc agatcctgat gccagtggag  840
aaggccttct ttgtgcgcgt gctgtctaac gacagcgatg cccggagcat cctggagaag  900
atcctgaagg acacagagat gctgccctcc aagatcatcg aggccatgaa ggaggcagat  960
gcaggcgaca tcgccgtgta cggcagccgg ctgcacgagc tgagccacgt gatctacggc  1020
gatcacggca agctgtccca gatcatctat gacaaggagt ccaagaggat ctctgagctg  1080
atggagacac tgtctccaaa ggagcgcaag gagagcaaga agcggctgga gggcctggag  1140
gagcacatca gaaagtctac atacaccttc gacgagctga acaggtatgc cgagaagaat  1200
gtgatggcag catacatcgc agcagtggag gagtcttgtg ccgagatcat gagaaaggag  1260
aaggatctga ggaccctgct gagcaaggag gacgtgaaga tccggggcaa cagacacaat  1320
acactgatcg tgaagaacta ctttaatgcc tggaccgtgt tccggaacct gatcagaatc  1380
ctgaggcgca agtccgaggc cgagatcgac tctgacttct acgatgtgct ggacgattcc  1440
gtggaggtgc tgtctctgac atacaagggc gagaatctgt gccgcagcta tatcaccaag  1500
aagatcggct ccgacctgaa gcccgagatc gccacatacg gcagcgccct gaggcctaac  1560
agccgctggt ggtccccagg agagaagttt aatgtgaagt tccacaccat cgtgcggaga  1620
gatggccggc tgtactattt catcctgccc aagggcgcca agcctgtgga gctggaggac  1680
atggatggcg acatcgagtg tctgcagatg agaaagatcc ctaacccaac aatctttctg  1740
cccaagctgg tgttcaagga ccctgaggcc ttctttaggg ataatccaga ggccgacgag  1800
ttcgtgtttc tgagcggcat gaaggccccc gtgacaatca ccagagagac atacgaggcc  1860
tacaggtata agctgtatac cgtgggcaag ctgcgcgatg gcgaggtgtc cgaagaggag  1920
tacaagcggg ccctgctgca ggtgctgacc gcctacaagg agtttctgga gaacagaatg  1980
atctatgccg acctgaattt cggctttaag gatctggagg agtataagga cagctccgag  2040
tttatcaagc aggtggagac acacaacacc ttcatgtgct gggccaaggt gtctagctcc  2100
cagctggacg atctggtgaa gtctggcaac ggcctgctgt tcgagatctg gagcgagcgc  2160
ctggagtcct actataagta cggcaatgag aaggtgctgc ggggctatga gggcgtgctg  2220
ctgagcatcc tgaaggatga gaacctggtg tccatgcgga ccctgctgaa cagccggccc  2280
atgctggtgt accggccaaa ggagtctagc aagcctatgg tggtgcaccg ggatggcagc  2340
agagtggtgg acaggtttga taaggacggc aagtacatcc cccctgaggt gcacgacgag  2400
ctgtatcgct tctttaacaa tctgctgatc aaggagaagc tgggcgagaa ggcccggaag  2460
atcctggaca acaagaaggt gaaggtgaag gtgctggaga gcgagagagt gaagtggtcc  2520
aagttctacg atgagcagtt tgccgtgacc ttcagcgtga agaagaacgc cgattgtctg  2580
gacaccacaa aggacctgaa tgccgaagtg atggagcagt atagcgagtc caacagactg  2640
atcctgatca ggaataccac agatatcctg tactatctgg tgctggacaa gaatggcaag  2700
gtgctgaagc agagatccct gaacatcatc aatgacggcg ccagggatgt ggactggaag  2760
gagaggttcc gccaggtgac aaaggataga aacgagggct acaatgagtg ggattattcc  2820
aggacctcta acgacctgaa ggaggtgtac ctgaattatg ccctgaagga gatcgccgag  2880
gccgtgatcg agtacaacgc catcctgatc atcgagaaga tgtctaatgc ctttaaggac  2940
aagtatagct tcctggacga cgtgaccttc aagggcttcg agacaaagct gctggccaag  3000
ctgagcgatc tgcactttag gggcatcaag gacggcgagc catgttcctt cacaaacccc  3060
ctgcagctgt gccagaacga ttctaataag atcctgcagg acggcgtgat ctttatggtg  3120
ccaaattcta tgacacggag cctggacccc gacaccggct tcatctttgc catcaacgac  3180
cacaatatca ggaccaagaa ggccaagctg aactttctga gcaagttcga tcagctgaag  3240
gtgtcctctg agggctgcct gatcatgaag tacagcggcg attccctgcc tacacacaac  3300
accgacaatc gcgtgtggaa ctgctgttgc aatcacccaa tcacaaacta tgaccgggag  3360
acaaagaagg tggagttcat cgaggagccc gtggaggagc tgtcccgcgt gctggaggag  3420
aatggcatcg agacagacac cgagctgaac aagctgaatg agcgggagaa cgtgcctggc  3480
aaggtggtgg atgccatcta ctctctggtg ctgaattatc tgcgcggcac agtgagcgga  3540
gtggcaggac agagggccgt gtactatagc cctgtgaccg gcaagaagta cgatatctcc  3600
tttatccagg ccatgaacct gaataggaag tgtgactact ataggatcgg ctccaaggag  3660
aggggagagt ggaccgattt cgtggcccag ctgatcaac                        3699
```

```
SEQ ID NO: 219          moltype = DNA  length = 3684
FEATURE                 Location/Qualifiers
source                  1..3684
                        mol_type = genomic DNA
                        note = Lachnospiraceae bacterium
                        organism = unidentified
                        strain = ND2006
SEQUENCE: 219
atgagcaagc tggagaagtt tacaaactgc tactccctgt ctaagaccct gaggttcaag  60
gccatccctg tgggcaagac ccaggagaac atcgacaata agcggctgct ggtggaggac  120
gagaagagag ccgaggatta taagggcgtg aagaagctgc tggatcgcta ctatctgtct  180
tttatcaacg acgtgctgca cagcatcaag ctgaagaatc tgaacaatta catcagcctg  240
ttccggaaga aaaccagaac cgagaaggag aataaggagc tggagaacct ggagatcaat  300
ctgcggaagg agatcgccaa ggccttcaag ggcaacgagg gctacaagtc cctgtttaag  360
aaggatatca tcgagacaat cctgccagag ttcctggacg ataaggacga gatcgccctg  420
gtgaacagct tcaatggctt taccacagcc ttcaccggct tctttgataa cagagagaat  480
atgttttccg aggaggccaa gagcacatcc atcgccttca ggtgtatcaa cgagaatctg  540
```

```
acccgctaca tctctaatat ggacatcttc gagaaggtgg acgccatctt tgataagcac  600
gaggtgcagg agatcaagga gaagatcctg aacagcgact atgatgtgga ggatttcttt  660
gagggcgagt tctttaactt tgtgctgaca caggagggca tcgacgtgta taacgccatc  720
atcggcggct tcgtgaccga gagcggcgag aagatcaagg gcctgaacga gtacatcaac  780
ctgtataatc agaaaaccaa gcagaagctg cctaagttta agccactgta taagcaggtg  840
ctgagcgatc gggagtctct gagcttctac ggcgagggct atacatccga tgaggaggtg  900
ctggaggtgt ttagaaacac cctgaacaag aacagcgaga tcttcagctc catcaagaag  960
ctggagaagc tgttcaagaa ttttgacgag tactctagcg ccggcatctt tgtgaagaac  1020
ggccccgcca tcagcacaat ctccaaggat atcttcggcg agtggaacgt gatccgggac  1080
aagtggaatg ccgagtatga cgatatccac ctgaagaaga aggccgtggt gaccgagaag  1140
tacgaggacg atcggagaaa gtccttcaag aagatcggct cctttctct ggagcagctg  1200
caggagtacg ccgacgccga tctgtctgtg gtggagaagc tgaaggagat catcatccag  1260
aaggtggatg agatctacaa ggtgtatggc tcctctgaga agctgttcga cgccgatttt  1320
gtgctggaga agagcctgaa gaagaacgac gccgtggtgg ccatcatgaa ggacctgctg  1380
gattctgtga agagcttcga gaattacatc aaggccttct ttggcgaggg caaggagaca  1440
aacagggacg agtccttcta tggcgatttt gtgctggcct acgacatcct gctgaaggtg  1500
gaccacatct acgatgccat ccgcaattat gtgacccaga agccctactc taaggataag  1560
ttcaagctgt attttcagaa ccctcagttc atgggcggct gggacaagga taaggagaca  1620
gactatcggg ccaccatcct gagatacggc tccaagtact atctggccat catggataag  1680
aagtacgcca agtgcctgca gaagatcgac aaggacgatg tgaacggcaa ttacgagaag  1740
atcaactata agctgctgcc cggccctaat aagatgctgc caaaggtgtt cttttctaag  1800
aagtggatgg cctactataa ccccagcgag gacatccaga agatctacaa gaatggcaca  1860
ttcaagaagg gcgatatgtt taacctgaat gactgtcaca agctgatcga cttctttaag  1920
gatagcatct cccggtatcc aaagtggtcc aatgcctacg atttcaactt ttctgagaca  1980
gagaagtata aggacatcgc cggcttttac agagaggtgg aggagcaggg ctataaggtg  2040
agcttcgagt ctgccagcaa gaaggaggtg gataagctgg tggaggaggg caagctgtat  2100
atgttccaga tctataacaa ggacttttcc gataagtctc acggcacacc caatctgcac  2160
accatgtact tcaagctgct gtttgacgag aacaatcacg gacagatcag gctgagcgga  2220
ggagcagagc tgttcatgag gcgcgcctcc ctgaagaagg aggagctggt ggtgcaccca  2280
gccaactccc ctatcgccaa caagaatcca gataatccca agaaaaccac aaccctgtcc  2340
tacgacgtgt ataaggataa gaggttttct gaggaccagt acgagctgca catcccaatc  2400
gccatcaata agtgccccaa gaacatcttc aagatcaata cagaggtgcg cgtgctgctg  2460
aagcacgacg ataacccccta tgtgatcggc atcgataggg gcgagcgcaa tctgctgtat  2520
atcgtggtgg tggacggcaa gggcaacatc gtggagcagt attccctgaa cgagatcatc  2580
aacaacttca acggcatcag gatcaagaca gattaccact ctctgctgga caagaaggag  2640
aaggagaggt tcgaggcccg ccagaactgg acctccatcg agaatatcaa ggagctgaag  2700
gccggctata tctctcaggt ggtgcacaag atctgcgagc tggtggagaa gtacgatgcc  2760
gtgatcgccc tggaggacct gaactctggc tttaagaata gccgcgtgaa ggtggagaag  2820
caggtgtatc agaagttcga gaagatgctg atcgataagc tgaactacat ggtggacaag  2880
aagtctaatc cttgtgcaac aggcggcgcc ctgaagggct atcagatcac caataagttc  2940
gagagcttta agtccatgtc tacccagaac ggcttcatct tttacatccc tgcctggctg  3000
acatccaaga tcgatccatc taccggcttt gtgaacctgc tgaaaaccaa gtataccagc  3060
atcgccgatt ccaagaagtt catcagctcc tttgacagga tcatgtacgt gcccgaggag  3120
gatctgttcg agtttgccct ggactataag aacttctctc gcacagacgc cgattacatc  3180
aagaagtgga agctgtactc ctacggcaac cggatcagaa tcttccggaa tcctaagaag  3240
aacaacgtgt tcgactggga ggaggtgtgc ctgaccagcg cctataagga gctgttcaac  3300
aagtacggca tcaattatca gcagggcgat atcagagccc tgctgtgcga gcagtccgac  3360
aaggccttct actctagctt tatggccctg atgagcctga tgctgcagat gcggaacagc  3420
atcacaggcc gcaccgacgt ggattttctg atcagccctg tgaagaactc cgacggcatc  3480
ttctacgata gccggaacta tgaggcccag gagaatgcca tcctgccaaa gaacgccgac  3540
gccaatggcg cctataacat cgccagaaag gtgctgtggg ccatcggcca gttcaagaag  3600
gccgaggacg agaagctgga taaggtgaag atcgccatct ctaacaagga gtggctggag  3660
tacgcccaga ccagcgtgaa gcac                                        3684

SEQ ID NO: 220         moltype = DNA  length = 3900
FEATURE                Location/Qualifiers
source                 1..3900
                       mol_type = genomic DNA
                       organism = Francisella tularensis
                       strain = U112
                       sub_species = Novicida
SEQUENCE: 220
atgagcatct accaggagtt cgtcaacaag tattcactga gtaagacact gcggttcgag  60
ctgatcccac agggcaagac actggagaac atcaaggccc gaggcctgat tctggacgat  120
gagaagcggg caaaagacta taagaaagcc aagcagatca ttgataaata ccaccagttc  180
tttatcgagg aaattctgag ctccgtgtgc atcagtgagg atctgctgca gaattactca  240
gacgtgtact tcaagctgaa gaagagcgac gatgacaacc tgcagaagga cttcaagtcc  300
gccaaggaca ccatcaagaa acagattagc gagtacatca aggactccga aaagtttaaa  360
aatctgttca accagaatct gatcgatgct aagaaaggcc aggagtccga cctgatcctg  420
tggctgaaac agtctaagga caatgggatt gaactgttca aggctaactc cgatatcact  480
gatattgacg aggcactgga aatcatcaag agcttcaagg gatggaccac atactttaaa  540
ggcttccacg agaaccgcaa gaacgtgtac tccagcaacg acattcctac ctccatcatc  600
taccgaatcg tcgatgacaa tctgccaaag ttcctggaga acaaggccaa atatgaatct  660
ctgaaggaca aagctcccga ggcaattaat tacgaacaga tcaagaaaga tctggctgag  720
gaactgacat tcgatatcga ctataagact agcgaggtga accagagggt cttttccctg  780
gacgaggtgt ttgaaatcgc caatttcaac aattacctga accagtccgg cattactaaa  840
ttcaatacca tcattggcgg gaagtttgtg aacgggggaga ataccaagcg caagggaatt  900
aacgaataca tcaatctgta tagccagcag atcaacgaca aaactctgaa gaaatacaag  960
atgtctgtgc tgttcaaaca gatcctgagt gataccgagt ccaagtcttt tgtcattgat  1020
```

```
aaactggaag atgactcaga cgtggtcact accatgcaga gcttttatga gcagatcgcc  1080
gctttcaaga cagtggagga aaaatctatt aaggaaactc tgagtctgct gttcgatgac  1140
ctgaaagccc agaagctgga cctgagtaag atctacttca aaaacgataa gagtctgaca  1200
gacctgtcac agcaggtgtt tgatgactat tccgtgattg ggaccgccgt cctggagtac  1260
attacacagc agatcgctcc aaagaacctg gataatccct ctaagaaaga gcaggaactg  1320
atcgctaaga aaaccgagaa ggcaaaatat ctgagtctgg aaacaattaa gctggcactg  1380
gaggagttca acaagcacag ggatattgac aaacagtgcc gctttgagga aatcctggcc  1440
aacttcgcag ccatccccat gatttttgat gagatcgccc agaacaaaga caatctggct  1500
cagatcagta ttaagtacca gaaccagggc aagaaagacc tgctgcaggc ttcagcagaa  1560
gatgacgtga aagccatcaa ggatctgctg gaccagacca acaatctgct gcacaagctg  1620
aaaatcttcc atattagtca gtcagaggat aaggctaata tcctggataa agacgaacac  1680
ttctacctgg tgttcgagga atgttacttc gagctggcaa acattgtccc cctgtataac  1740
aagattagga actacatcac acagaagcct tactctgacg agaagtttaa actgaacttc  1800
gaaaatagta ccctggccaa cggtgggat aagaacaagg agcctgacaa cacagctatc  1860
ctgttcatca aggatgacaa gtactatctg ggagtgatga ataagaaaaa caataagatc  1920
ttcgatgaca aagccattaa ggagaacaaa ggggaaggat acaagaaaat cgtgtataag  1980
ctgctgcccg gcgcaaataa gatgctgcct aaggtgttct tcagcgccaa gagtatcaaa  2040
ttctacaacc catccgagga catcctgcgg attagaaatc actcaacaca tactaagaac  2100
gggagccccc agaagggata tgagaaattt gagttcaaca tcgaggattg caggaagttt  2160
attgacttct acaagcagag catctccaaa caccctgaat ggaaggattt tggcttccgg  2220
ttttccgaca cacagagata taactctatc gacgagttct accgcgaggt ggaaaatcag  2280
gggtataagc tgacttttga gaacatttct gaaagttaca tcgacagcgt ggtcaatcag  2340
ggaaagctgt acctgttcca gatctataac aaagattttt cagcatacag caagggcaga  2400
ccaaacctgc atacactgta ctggaaggcc ctgttcgatg agaggaatct gcaggacgtg  2460
gtctataaac tgaacggaga ggccgaactg ttttaccgga agcagtctat tcctaagaaa  2520
atcactcacc cagctaagga ggccatcgct aacaagaaca aggacaatcc taagaaagag  2580
agcgtgttcg aatacgatct gattaaggac aagcggttca ccgaagataa gttcttttc  2640
cattgtccaa tcaccattaa cttcaagtca agcggcgcta acaagttcaa cgacgagatc  2700
aatctgctgc tgaaggaaaa agcaaacgat gtgcacatcc tgagcattga ccgaggagag  2760
cggcatctgg cctactatac cctggtggat ggcaaaggga atatcattaa gcaggataca  2820
ttcaacatca ttggcaatga ccggatgaaa accaactacc acgataaact ggctgcaatc  2880
gagaaggata gagactcagc taggaaggac tggaagaaaa tcaacaacat taaggagatg  2940
aaggaaggct atctgagcca ggtggtccat gagattgcaa agctggtcat cgaatacaat  3000
gccattgtgg tgttcgagga tctgaacttc ggctttaaga gggggcgctt taaggtggaa  3060
aaacaggtct atcagaagct ggagaaaatg ctgatcgaaa agctgaatta cctggtgttt  3120
aaagataacg agttcgacaa gaccggaggc gtcctgagag cctaccagct gacagctccc  3180
tttgaaactt tcaagaaaat gggaaaacag acaggcatca tctactatgt gccagccgga  3240
ttcacttcca agatctgccc cgtgaccggc tttgtcaacc agctgtaccc taaatatgag  3300
tcagtgagca agtcccagga atttttcagc aagttcgata agatctgtta taatctggac  3360
aaggggtact tcgagtttc cttcgattac aagaacttcg gcgacaaggc cgctaagggg  3420
aaatggacca ttgcctcctt cggatctcgc ctgatcaact ttcgaaattc cgataaaaac  3480
cacaattggg acactaggga ggtgtaccca accaaggagc tggaaaagct gctgaaagac  3540
tactctatcg agtatggaca tggcgaatgc atcaaggcag ccatctgtgg cgagagtgat  3600
aagaaatttt tcgccaagct gacctcagtg ctgaatacaa tcctgcagat gcggaactca  3660
aagaccggga cagaactgga ctatctgatt agccccgtgg ctgatgtcaa cggaaacttc  3720
ttcgacagca gacaggcacc caaaaatatg cctcaggatg cagacgccaa cggggcctac  3780
cacatcgggc tgaagggact gatgctgctg ggccggatca agaacaatca ggaggggaag  3840
aagctgaacc tggtcattaa gaacgaggaa tacttcgagt ttgtccagaa tagaaataac  3900
```

```
SEQ ID NO: 221          moltype = DNA  length = 4431
FEATURE                 Location/Qualifiers
source                  1..4431
                        mol_type = genomic DNA
                        note = Peregrinibacteria bacterium
                        organism = unidentified
                        strain = GW2011_GWA_33_10
SEQUENCE: 221
atgtccaact tctttaagaa tttcaccaac ctgtatgagc tgtccaagac actgaggttt  60
gagctgaagc ccgtgggcga caccctgaca aacatgaagg accacctgga gtacgatgag  120
aagctgcaga ccttcctgaa ggatcagaat atcgacgatg cctatcaggc cctgaagcct  180
cagttcgacg agatccacga ggagtttatc acagattctc tggagagcaa gaaggccaag  240
gagatcgact tctccgagta cctggatctg tttcaggaga agaaggagct gaacgactct  300
gagaagaagc tgcgcaacaa gatcggcgag acattcaaca aggccggcga gaagtggaag  360
aaggagaagt accctcagta tgagtggaag aagggctcca agatcgccaa tggcgccgac  420
atcctgtctt gccaggatat gctgcagttt atcaagtata agaacccaga ggatgagaag  480
atcaagaatt acatcgacga tacactgaag ggcttcttta cctatttcgg cggctttaat  540
cagaacaggg ccaactacta tgagacaaag aaggaggcct ccaccgcagt ggcaacaagg  600
atcgtgcacg agaacctgcc aaagttctgt gacaatgtga tccagtttaa gcacatcatc  660
aagcggaaga aggatggcac cgtggagaaa accgagagaa agaccgagta cctgaacgcc  720
taccagtatc tgaagaacaa taacaagatc acacagatca aggacgccga gacagagaag  780
atgatcgagt ctacacccat cgccgagaag atcttcgacg tgtactactt cagcagctgc  840
ctgagccaga agcagatcga ggagtacaac cggatcatcg gccactataa tctgctgatc  900
aacctgtata accaggccaa gagatctgag ggcaagcacc tgagcgccaa cgagaagaag  960
tataaggacc tgcctaagtt caagaccctg tataagcaga tcggctgcgg caagaagaag  1020
gacctgtttt acacaatcaa gtgtgatacc gaggaggagg ccaataagtc ccggaacgag  1080
ggcaaggagt cccactctgt ggaggagatc atcaacaagg cccaggaggc catcaataag  1140
tacttcaagt ctaataacga ctgtgagaat atcaacaccg tgcccgactt catcaactat  1200
atcctgacaa aggagaatta cgagggcgtg tattggagca aggccgccat gaacaccatc  1260
tccgacaagt acttcgccaa ttatcacgac ctgcaggata gactgaagga ggccaaggtg  1320
```

```
tttcagaagg ccgataagaa gtccgaggac gatatcaaga tcccagaggc catcgagctg  1380
tctggcctgt tcggcgtgct ggacagcctg gccgattggc agaccacact gtttaagtct  1440
agcatcctga gcaacgagga caagctgaag atcatcacag attcccagac cccctctgag  1500
gccctgctga agatgatctt caatgacatc gagaagaaca tggagtcctt tctgaaggag  1560
acaaacgata tcatcaccct gaagaagtat aagggcaata aggagggcac cgagaagatc  1620
aagcagtggt tcgactatac actggccatc aaccggatgc tgaagtactt tctggtgaag  1680
gagaataaga tcaagggcaa ctccctggat accaatatct ctgaggccct gaaaaccctg  1740
atctacagcg acgatgccga gtggttcaag tggtacgacg ccctgagaaa ctatctgacc  1800
cagaagcctc aggatgaggc caaggagaat aagctgaagc tgaatttcga caacccatct  1860
ctggccggcg gctgggatgt gaacaaggag tgcagcaatt tttgcgtgat cctgaaggac  1920
aagaacgaga agaagtacct ggccatcatg aagaagggcg agaataccct gttccagaag  1980
gagtggacag agggccgggg caagaacctg acaaagaagt ctaatccact gttcgagatc  2040
aataactgcg agatcctgag caagatggag tatgactttt gggccgacgt gagcaagatg  2100
atccccaagt gtagcaccca gctgaaggcc gtggtgaacc acttcaagca gtccgacaat  2160
gagttcatct ttcctatcgg ctacaaggtg acaagcggcg agaagtttag ggaggagtgc  2220
aagatctcca agcaggactt cgagctgaat aacaaggtgt ttaataagaa cgagctgagc  2280
gtgaccgcca tgcgctacga tctgtcctct acacaggaga agcagtatat caaggccttc  2340
cagaaggagt actgggagct gctgtttaag caggagaagc gggacaccaa gctgacaaat  2400
aacgagatct tcaacgagtg gatcaatttt tgcaacaaga agtatagcga gctgctgtcc  2460
tgggagagaa agtacaagga tgccctgacc aattggatca acttctgtaa gtactttctg  2520
agcaagtatc ccaagaccac actgttcaac tactctttta aggagagcga gaattataac  2580
tccctggacg agttctaccg ggacgtggat atctgttctt acaagctgaa tatcaacacc  2640
acaatcaata agagcatcct ggatagactg gtggaggagg gcaagctgta cctgtttgag  2700
atcaagaatc aggacagcaa cgatggcaag tccatcggcc acaagaataa cctgcacacc  2760
atctactgga acgccatctt cgagaatttt gacaacaggc ctaagctgaa tggcgaggcc  2820
gagatcttct atcgcaaggc catctccaag gataagctgg gcatcgtgaa gggcaagaaa  2880
accaagaacg gcaccgagat catcaagaat tacagattca gcaaggagaa gtttatcctg  2940
cacgtgccaa tcaccctgaa cttctgctcc aataacgagt atgtgaatga catcgtgaac  3000
acaaagttct acaatttttc caacctgcac tttctgggca tcgatagggg cgagaagcac  3060
ctggcctact attctctggt gaataagaac ggcgagatcg tggaccaggg cacactgaac  3120
ctgcctttca ccgacaagga tggcaatcag cgcagcatca agaaggagaa gtacttttat  3180
aacaagcagg aggacaagtg ggaggccaag gaggtggatt gttggaatta taacgacctg  3240
ctggatgcca tggcctctaa ccgggacatg gccagaaaga attggcagag gatcggcacc  3300
atcaaggagg ccaagaacgg ctacgtgagc ctggtcatca ggaagatcgc cgatctggcc  3360
gtgaataacg agcgccccgc cttcatcgtg ctggaggacc tgaatacagg ctttaagcgg  3420
tccagacaga agatcgataa gagcgtgtac cagaagttcg agctggccct ggccaagaag  3480
ctgaactttc tggtggacaa gaatgccaag cgcgatgaga tcggctcccc tacaaaggcc  3540
ctgcagctga cccccccctgt gaataactac ggcgacattg agaacaagaa gcaggccggc  3600
atcatgctgt atacccgggc caattatacc tctcagacag atccagccac aggctggaga  3660
aagaccatct atctgaaggc cggccccgag gagacaacat acaagaagga cggcaagatc  3720
aagaacaaga gcgtgaagga ccagatcatc gagacattca ccgatatcgg ctttgacggc  3780
aaggattact atttcgagta cgacaagggc gagtttgtgg atgagaaaac cggcgagatc  3840
aagcccaaga agtggcggct gtactccggc gagaatggca agtccctgga caggttccgc  3900
ggagagaggg agaaggataa gtatgagtgg aagatcgaca agatcgatat cgtgaagatc  3960
ctggacgatc tgttcgtgaa ttttgacaag aacatcagcc tgctgaagca gctgaaggag  4020
ggcgtggagc tgacccggaa taacgagcac ggcacaggcg agtccctgag attcgccatc  4080
aacctgatcc agcagatccg gaataccggc aataacgaga gagacaacga tttcatcctg  4140
tccccagtga gggacgagaa tggcaagcac tttgactctc gcgagtactg ggataaggag  4200
acaaagggcg agaagatcag catgcccagc tccggcgatg ccaatggcgc cttcaacatc  4260
gcccggaagg gcatcatcat gaacgcccac atcctggcca atagcgactc caaggatctg  4320
tccctgttcg tgtctgacga ggagtgggat ctgcacctga ataacaagac cgagtggaag  4380
aagcagctga acatcttttc tagcaggaag gccatggcca agcgcaagaa g           4431
```

```
SEQ ID NO: 222          moltype = DNA  length = 4056
FEATURE                 Location/Qualifiers
source                  1..4056
                        mol_type = genomic DNA
                        note = Parcubacteria bacterium GWC2011_GWC2_44_17
                        organism = unidentified
SEQUENCE: 222
atggagaaca tcttcgacca gtttatcggc aagtacagcc tgtccaagac cctgagattc  60
gagctgaagc ccgtgggcaa gacagaggac ttcctgaaga tcaacaaggt gtttgagaag  120
gatcagacca tcgacgatag ctacaatcag gccaagttct attttgattc cctgcaccag  180
aagtttatcg acgccgccct ggcctccgat aagacatccg agctgtcttt ccagaacttt  240
gccgacgtgc tggagaagca gaataagatc atcctggata agaagagaga gatgggcgcc  300
ctgaggaagc gcgacaagaa cgccgtgggc atcgataggc tgcagaagga gatcaatgac  360
gccgaggata tcatccagaa ggagaaggag aagatctaca aggacgtgcg caccctgttc  420
gataacgagg ccgagtcttg gaaaacctac tatcaggagc gggaggtgga cggcaagaag  480
atcaccttca gcaaggccga cctgaagcag aagggcgccg attttctgac agccgccggc  540
atcctgaagg tgctgaagta tgagttcccc gaggagaagg agaaggagtt tcaggccaag  600
aaccagccct ccctgttcgt ggaggagaag gagaatcctg gccagaagag gtacatcttc  660
gactcttttg ataagttcgc cggctatctg accaagtttc agcagacaaa gaagaatctg  720
tacgcagcag acggcaccag cacagcagtg gccacccgca tcgccgataa ctttatcatc  780
ttccaccaga ataccaaggt gttccgggac aagtacaaga acaatcacac agacctgggc  840
ttcgatgagg agaacatctt tgagatcgag aggtataaga attgcctgct gcagcgcgag  900
atcgagcaca tcaagaatga gaatagctac aacaagatca tcggccggat caataagaag  960
atcaaggagt atcgggacca gaaggccaag gataccaagc tgacaaagtc cgacttccct  1020
ttctttaaga acctggataa gcagatcctg ggcgaggtgg agaaggagaa gcagctgatc  1080
gagaaaaccc gggagaaaac cgaggaggac gtgctgatcg agcggttcaa ggagttcatc  1140
```

```
gagaacaatg aggagaggtt caccgccgcc aagaagctga tgaatgcctt ctgtaacggc  1200
gagtttgagt ccgagtacga gggcatctat ctgaagaata aggccatcaa cacaatctcc  1260
cggagatggt tcgtgtctga cagagatttt gagctgaagc tgcctcagca gaagtccaag  1320
aacaagtctg agaagaatga gccaaaggtg aagaagttca tctccatcgc cgagatcaag  1380
aacgccgtgg aggagctgga cggcgatatc tttaaggccg tgttctacga caagaagatc  1440
atcgcccagg gcggctctaa gctggagcag ttcctggtca tctggaagta cgagtttgag  1500
tatctgttcc gggacatcga gagagagaac ggcgagaagc tgctgggcta tgatagctgc  1560
ctgaagatcg ccaagcagct gggcatcttc ccacaggaga aggaggcccg cgagaaggca  1620
accgccgtga tcaagaatta cgccgacgcc ggcctgggca tcttccagat gatgaagtat  1680
ttttctctgg acgataagga tcggaagaac acccccggcc agctgagcac aaatttctac  1740
gccgagtatg acggctacta caaggatttc gagtttatca agtactacaa cgagtttagg  1800
aacttcatca ccaagaagcc tttcgacgag gataagatca agctgaactt tgagaatggc  1860
gccctgctga agggctggga cgagaacaag gagtacgatt tcatgggcgt gatcctgaag  1920
aaggagggcc gcctgtatct gggcatcatg cacaagaacc accggaagct gtttcagtcc  1980
atgggcaatg ccaagggcga caacgccaat agataccaga agatgatcta taagcagatc  2040
gccgacgcct ctaaggatgt gcccaggctg ctgctgacca gcaagaaggc catggagaag  2100
ttcaagcctt cccaggagat cctgagaatc aagaaggaga aaaccttcaa gcgggagagc  2160
aagaactttt ccctgagaga tctgcacgcc ctgatcgagt actataggaa ctgcatccct  2220
cagtacagca attggtcctt ttatgacttc cagtttcagg ataccggcaa gtaccagaat  2280
atcaaggagt tcacagacga tgtgcagaag tacggctata agatctcctt tcgcgacatc  2340
gacgatgagt atatcaatca ggccctgaac gagggcaaga tgtacctgtt cgaggtggtg  2400
aacaaggata tctataacac caagaatggc tccaagaatc tgcacacact gtactttgag  2460
cacatcctgt ctgccgagaa cctgaatgac ccagtgttca agctgtctgg catggccgag  2520
atctttcagc ggcagcccag cgtgaacgaa agagagaaga tcaccacaca gaagaatcag  2580
tgtatcctgg acaagggcga tagagcctac aagtataggc gctacaccga gaagaagatc  2640
atgttccaca tgagcctggt gctgaacaca ggcaagggcg agatcaagca ggtgcagttt  2700
aataagatca tcaaccagag gatcagctcc tctgacaacg agatgagggt gaatgtgatc  2760
ggcatcgatc gcggcgagaa gaacctgctg tactatagcg tggtgaagca gaatggcgag  2820
atcatcgagc aggcctccct gaacgagatc aatggcgtga actaccggga caagctgatc  2880
gagagggaga aggagcgcct gaagaaccgg cagagctgga agcctgtggt gaagatcaag  2940
gatctgaaga agggctacat ctcccacgtg atccacaaga tctgccagct gatcgagaag  3000
tattctgcca tcgtggtgct ggaggacctg aatatgagat tcaagcagat caggggagga  3060
atcgagcgga gcgtgtacca gcagttcgag aaggccctga tcgataagct gggctatctg  3120
gtgtttaagg acaacaggga tctgagggca ccaggaggcg tgctgaatgg ctaccagctg  3180
tctgcccccct ttgtgagctt cgagaagatg cgcaagcaga ccggcatcct gttctacaca  3240
caggccgagt ataccagcaa gacagaccca atcaccggct ttcggaagaa cgtgtatatc  3300
tctaatagcg cctccctgga taagatcaag gaggccgtga agaagttcga cgccatcggc  3360
tgggatggca aggagcagtc ttacttcttt aagtacaacc cttacaacct ggccgacgag  3420
aagtataaga actctaccgt gagcaaggag tgggccatct ttgccagcgc cccaagaatc  3480
cggagacaga agggcgagga cggctactgg aagtatgata gggtgaaagt gaatgaggag  3540
ttcgagaagc tgctgaaggt ctggaatttt gtgaacccaa aggccacaga tatcaagcag  3600
gagatcatca agaaggagaa ggcaggcgac ctgcagggag agaaggagct ggatggccgg  3660
ctgagaaact tttggcactc tttcatctac ctgtttaacc tggtgctgga gctgcgcaat  3720
tctttcagcc tgcagatcaa gatcaaggca ggagaagtga tcgcagtgga cgagggcgtg  3780
gacttcatcg ccagcccagt gaagcccttc tttaccacac ccaaccctta catcccctcc  3840
aacctgtgct ggctggccgt ggagaatgca gacgcaaacg gagcctataa tatcgccagg  3900
aagggcgtga tgatcctgaa gaagatccgc gagcacgcca agaaggaccc cgagttcaag  3960
aagctgccaa acctgtttat cagcaatgca gagtgggacg aggcagcccg ggattggggc  4020
aagtacgcag gcaccacagc cctgaacctg gaccac                          4056

SEQ ID NO: 223          moltype = DNA  length = 3618
FEATURE                 Location/Qualifiers
source                  1..3618
                        mol_type = genomic DNA
                        note = Lachnospiraceae bacterium
                        organism = unidentified
                        strain = MA2020
SEQUENCE: 223
atgtactatg agtccctgac caagcagtac cccgtgtcta agacaatccg gaatgagctg  60
atccctatcg gcaagacact ggataacatc cgccagaaca atatcctgga gagcgacgtg  120
aagcggaagc agaactacga gcacgtgaag ggcatcctgg atgagtatca caagcagctg  180
atcaacgagg ccctggacaa ttgcaccctg ccatccctga agatcgccgc cgagatctac  240
ctgaagaatc agaaggaggt gtctgacaga gaggatttca acaagacaca ggacctgctg  300
aggaaggagg tggtggagaa gctgaaggcc cacgagaact ttaccaagat cggcaagaag  360
gacatcctgg atctgctgga gaagctgcct tccatctctg aggacgatta caatgccctg  420
gagagcttcc gcaactttta cacctatttc acatcctaca acaaggtgcg ggagaatctg  480
tattctgata aggagaagag ctcccacagtg gcctacagac tgatcaacga gaatttccca  540
aagtttctgg acaatgtgaa gagctatagg tttgtgaaaa ccgcaggcat cctggcagat  600
ggcctgggag aggaggagca ggactccctg ttcatcgtgg agacattcaa caagaccctg  660
acacaggacg gcatcgatac ctacaattct caagtgggca agatcaactc tagcatcaat  720
ctgtataacc agaagaatca gaaggccaat ggcttcagaa agatccccaa gatgaagatg  780
ctgtataagc agatcctgtc cgatagggag gagtctttca tcgacgagtt tcagagcgat  840
gaggtgctga tcgacaacgt ggagtcttat ggcagcgtgc tgatcgagtc tctgaagtcc  900
tctaaggtga gcgccttctt tgatgccctg agagagtcta agggcaagaa cgtgtacgtg  960
aagaatgacc tggccaagac agccatgagc aacatcgtgt tcgagaattg gaggaccttt  1020
gacgatctgc tgaaccagga gtacgacctg gccaacgaga acaagaagaa ggacgataag  1080
tatttcgaga agcgccagaa ggagctgaag aagaataaga gctactccct ggagcacctg  1140
tgcaacctgt ccgaggattc ttgtaacctg atcgagaatt atatccacca gatctccgac  1200
gatatcgaga atatcatcat caacaatgag acattcctgc gcatcgtgat caatgagcac  1260
```

```
gacaggtccc gcaagctggc caagaaccgg aaggccgtga aggccatcaa ggactttctg  1320
gattctatca aggtgctgga gcgggagctg aagctgatca acagctccgg ccaggagctg  1380
gagaaggatc tgatcgtgta ctctgcccac gaggagctgc tggtggagct gaagcaggtg  1440
gacagcctgt ataacatgac cagaaattat ctgacaaaga agcctttctc taccgagaag  1500
gtgaagctga actttaatcg cagcacactg ctgaacggct gggatcggaa taaggagaca  1560
gacaacctgg gcgtgctgct gctgaaggac ggcaagtact atctgggcat catgaacaca  1620
agcgccaata aggccttcgt gaatccccct gtggccaaga ccgagaaggt gtttaagaag  1680
gtggattaca agctgctgcc agtgcccaac cagatgctgc caaaggtgtt ctttgccaag  1740
agcaatatcg acttctataa cccctctagc gagatctact ccaattataa gaagggcacc  1800
cacaagaagg gcaatatgtt ttccctggag gattgtcaca acctgatcga cttctttaag  1860
gagtctatca gcaagcacga ggactggagc aagttcggct ttaagttcag cgatacagcc  1920
tcctacaacg acatctccga gttctatcgc gaggtggaga agcagggcta caagctgacc  1980
tatacagaca tcgatgagac atacatcaat gatctgatcg agcggaacga gctgtacctg  2040
ttccagatct ataataagga ctttagcatg tactccaagg gcaagctgaa cctgcacaca  2100
ctgtatttca tgatgctgtt tgatcagcgc aatatcgacg acgtggtgta taagctgaac  2160
ggagaggcag aggtgttcta taggccagcc tccatctctg aggacgagct gatcatccac  2220
aaggccggcg aggagatcaa gaacaagaat cctaaccggg ccagaaccaa ggagacaagc  2280
accttcagct acgacatcgt gaaggataag cggtatagca aggataagtt taccctgcac  2340
atccccatca caatgaactt cggcgtggat gaggtgaagc ggttcaacga cgccgtgaac  2400
agcgccatcc ggatcgatga gaatgtgaac gtgatcggca tcgaccgggg cgagagaaat  2460
ctgctgtacg tggtggtcat cgactctaag ggcaacatcc tggagcagat ctccctgaac  2520
tctatcatca ataaggagta cgacatcgag acagattatc acgcactgct ggatgagagg  2580
gagggcggca gagataaggc ccggaaggac tggaacaccg tggagaatat cagggacctg  2640
aaggccggct acctgagcca ggtggtgaac gtggtggcca agctggtgct gaagtataat  2700
gccatcatct gcctggagga cctgaacttt ggcttcaaga ggggccgcca gaaggtggag  2760
aagcaggtgt accagaagtt cgagaagatg ctgatcgata agctgaatta cctggtcatc  2820
gacaagagcc gcgagcagac atcccctaag gagctgggag gcgccctgaa cgcactgcag  2880
ctgacctcta agttcaagag ctttaaggag ctgggcaagc agtccggcgt gatctactat  2940
gtgcctgcct acctgacctc taagatcgat ccaaccacag gcttcgccaa tctgttttat  3000
atgaagtgtg agaacgtgga gaagtccaag agattctttg acggctttga tttcatcagg  3060
ttcaacgccc tggagaacgt gttcgagttc ggctttgact accggagctt cacccagagg  3120
gcctgcggca tcaattccaa gtggaccgtg tgcaccaacg gcgagcgcat catcaagtat  3180
cggaatccag ataagaacaa tatgttcgac gagaaggtgg tggtggtgac cgatgagatg  3240
aagaacctgt ttgagcagta caagatcccc tatgaggatg gcagaaatgt gaaggacatg  3300
atcatcagca acgaggaggc cgagttctac cggagactgt ataggctgct gcagcagacc  3360
ctgcagatga gaaacagcac ctccgacggc acaagggatt acatcatctc ccctgtgaag  3420
aataagagag aggcctactt caacagcgag ctgtccgacg gctctgtgcc aaaggacgcc  3480
gatgccaacg gcgcctacaa tatcgccaga aagggcctgt gggtgctgga gcagatcagg  3540
cagaagagcg agggcgagaa gatcaatctg gccatgacca acgccgagtg gctggagtat  3600
gcccagacac acctgctg                                               3618
```

```
SEQ ID NO: 224         moltype = DNA  length = 3714
FEATURE                Location/Qualifiers
source                 1..3714
                       mol_type = genomic DNA
                       organism = Candidatus Methanoplasma termitum
SEQUENCE: 224
atgaacaatt acgacgagtt caccaagctg tatcctatcc agaaaaccat ccggtttgag  60
ctgaagccac agggcagaac catggagcac ctggagacat tcaacttctt tgaggaggac  120
cgggatagag ccgagaagta taagatcctg aaggaggcca tcgacgagta ccacaagaag  180
tttatcgatg agcacctgac caatatgtcc ctggattgga actctctgaa gcagatcagc  240
gagaagtact ataagagcag ggaggagaag gacaagaagg tgttcctgtc cgagcagaag  300
aggatgcgcc aggagatcgt gtctgagttt aagaaggacg atcgcttcaa ggacctgttt  360
tccaagaagc tgttctctga gctgctgaag gaggagatct acaagaaggg caaccaccag  420
gagatcgacg ccctgaagag cttcgataag ttttccggct atttcatcgg cctgcacgag  480
aataggaaga acatgtactc cgacggcgat gagatcaccg ccatctccaa tcgcatcgtg  540
aatgagaact tccccaagtt tctggataac ctgcagaagt accaggaggc caggaagaag  600
tatcctgagt ggatcatcaa ggccgagagc gccctggtgg cccacaatat caagatggac  660
gaggtgttct ccctggagta ctttaataag gtgctgaacc aggagggcat ccagcggtac  720
aacctggccc tgggcggcta tgtgaccaag agcggcgaga agatgatggg cctgaatgat  780
gccctgaacc tggcccacca gtccgagaag agctccaagg gcagaatcca catgaccccc  840
ctgttcaagc agatcctgtc cgagaaggag tccttctctt acatccccga cgtgtttaca  900
gaggattctc agctgctgcc tagcatcggc ggcttctttg cccagatcga gaatgacaag  960
gatggcaaca tcttcgaccg ggccctggag ctgatctcta gctacgccga gtatgatacc  1020
gagcggatct atatcagaca ggccgacatc aatagagtgt ccaacgtgat ctttggagag  1080
tggggcaccc tgggaggcct gatgagggag tacaaggccg actctatcaa tgatatcaac  1140
ctggagcgca catgcaagaa ggtggacaag tggctggatt ctaaggagtt tgccctgagc  1200
gatgtgctgg aggccatcaa gaggaccggc aacaatgacg ccttcaacga gtatatctcc  1260
aagatgcgga cagccagaga gaagatcgat gccgcccgca aggagatgaa gttcatcagc  1320
gagaagatct ccggcgatga ggagtctatc cacatcatca agaccctgct ggacagcgtg  1380
cagcagttcc tgcacttctt taatctgttt aaggcaaggc aggacatccc actggatgga  1440
gccttctacg ccgagtttga cgaggtgcac agcaagctgt ttgccatcgt gcccctgtat  1500
aacaaggtgc ggaactatct gaccaagaac aatctgaaca caaagaagat caagctgaat  1560
ttcaagaacc ctacactggc caatggctgg gaccagaaca aggtgtacga ttatgcctcc  1620
ctgatctttc tgcgggacgg caattactat ctgggcatca tcaatcctaa gagaaagaag  1680
aacatcaagt tcgagcaggg ctctggcaac ggcccccttct accggaagat ggtgtataag  1740
cagatccccg gccctaataa gaacctgcca agagtgttcc tgacctccac aaagggcaag  1800
aaggagtata agccctctaa ggagatcatc gagggctacg aggccgacaa gcacatcagg  1860
ggcgataagt tcgacctgga tttttgtcac aagctgatcg atttctttaa ggagtccatc  1920
```

```
gagaagcaca aggactggtc taagttcaac ttctacttca gcccaaccga gagctatggc  1980
gacatctctg agttctacct ggatgtggag aagcagggct atcgcatgca ctttgagaat  2040
atcagcgccg agacaatcga cgagtatgtg gagaagggcg atctgtttct gttccagatc  2100
tacaacaagg attttgtgaa ggccgccacc ggcaagaagg acatgcacac aatctactgg  2160
aatgccgcct tcagccccga gaacctgcag gacgtggtgg tgaagctgaa cggcgaggcc  2220
gagctgtttt atagggacaa gtccgatatc aaggagatcg tgcaccgcga gggcgagatc  2280
ctggtgaata ggacctacaa cggccgcaca ccagtgcccg acaagatcca caagaagctg  2340
accgattatc acaatggccg gacaaaggac ctgggcgagg ccaaggagta cctggataag  2400
gtgagatact tcaaggccca ctatgacatc accaaggatc ggagatacct gaacgacaag  2460
atctatttcc acgtgcctct gaccctgaac ttcaaggcca acggcaagaa gaatctgaac  2520
aagatggtca tcgagaagtt cctgtccgat gagaaggccc acatcatcgg catcgacagg  2580
ggcgagcgca atctgctgta ctattccatc atcgacaggt ctggcaagat catcgatcag  2640
cagagcctga atgtgatcga cggctttgat tatcgggaga agctgaacca gagagagatc  2700
gagatgaagg atgcccgcca gtcttggaac gccatcggca agatcaagga cctgaaggag  2760
ggctacctga gcaaggccgt gcacgagatc accaagatgg ccatccagta taatgccatc  2820
gtggtcatgg aggagctgaa ctacggcttc aagcggggcc ggttcaaggt ggagaagcag  2880
atctatcaga agttcgagaa tatgctgatc gataagatga actacctggt gtttaaggac  2940
gcacctgatg agtccccagg aggcgtgctg aatgcctacc agctgacaaa cccactggag  3000
tctttcgcca agctgggcaa gcagaccggc atcctgtttt acgtgccagc cgcctataca  3060
tccaagatcg accccaccac aggcttcgtg aatctgttta acacctcctc taagacaaac  3120
gcccaggagc ggaaggagtt cctgcagaag tttgagagca tctcctattc tgccaaggat  3180
ggcggcatct ttgccttcgc ctttgactac agaaagttcg gcaccagcaa gacagatcac  3240
aagaacgtgt ggaccgccta tacaaacggc gagaggatgc gctacatcaa ggagaagaag  3300
cggaatgagc tgtttgaccc ttctaaggag atcaaggagg ccctgaccag ctccggcatc  3360
aagtacgatg gcggccagaa catcctgcca gacatcctga ggagcaacaa taacggcctg  3420
atctacacaa tgtattctag cttcatcgcc gccatccaga tgcgcgtgta cgacggcaag  3480
gaggattata tcatcagccc catcaagaac tccaagggcg agttctttag gaccgacccc  3540
aagaggcgcg agctgcctat cgacgccgat gccaatggcg cctacaacat cgccctgagg  3600
ggagagctga caatgagggc aatcgcagag aagttcgacc ctgatagcga gaagatggcc  3660
aagctggagc tgaagcacaa ggattggttc gagtttatgc agaccagagg cgac        3714
```

```
SEQ ID NO: 225          moltype = DNA  length = 3846
FEATURE                 Location/Qualifiers
source                  1..3846
                        mol_type = genomic DNA
                        organism = Eubacterium eligens
SEQUENCE: 225
atgaacggca ataggtccat cgtgtaccgc gagttcgtgg gcgtgatccc cgtggccaag  60
accctgagga atgagctgcg ccctgtgggc cacacacagg agcacatcat ccagaacggc  120
ctgatccagg aggacgagct gcggcaggag aagagcaccg agctgaagga catcatggac  180
gattactata gagagtacat cgataagtct ctgagcggcg tgaccgacct ggacttcacc  240
ctgctgttcg agctgatgaa cctggtgcag agctccccct ccaaggacaa taagaaggcc  300
ctggagaagg agcagtctaa gatgagggag cagatctgca cccacctgca gtccgactct  360
aactacaaga atatctttaa cgccaagctg ctgaaggaga tcctgcctga tttcatcaag  420
aactacaatc agtatgacgt gaaggataag gccggcaagc tggagacact ggccctgttt  480
aatggcttca gcacatactt taccgacttc tttgagaaga ggaagaacgt gttcaccaag  540
gaggccgtga gcacatccat cgcctaccgc atcgtgcacg agaactccct gatcttcctg  600
gccaatatga cctcttataa gaagatcagc gagaaggccc tggatgagat cgaagtgatc  660
gagaagaaca atcaggacaa gatgggcgat tgggagctga atcagatctt taaccctgac  720
ttctacaata tggtgctgat ccagtccggc atcgacttct acaacgagat ctgcggcgtg  780
gtgaatgccc acatgaacct gtactgtcag cagaccaaga acaattataa cctgttcaag  840
atgcggaagc tgcacaagca gatcctggcc tacaccagca ccagcttcga ggtgcccaag  900
atgttcgagg acgatatgag cgtgtataac gccgtgaacg ccttcatcga cgagacagag  960
aagggcaaca tcatcggcaa gctgaaggat atcgtgaata agtacgacga gctggatgag  1020
aagagaatct atatcagcaa ggacttttac gagacactga gctgcttcat gtccggcaac  1080
tggaatctga tcacaggctg cgtggagaac ttctacgatg agaacatcca cgccaagggc  1140
aagtccaagg aggagaaggt gaagaaggcc gtgaaggagg acaagtacaa gtctatcaat  1200
gacgtgaacg atctggtgga gaagtatatc gatgagaagg agaggaatga gttcaagaac  1260
agcaatgcca agcagtacat ccgcgagatc tccaacatca tcaccgacac agagacagcc  1320
cacctggagt atgacgatca catctctctg atcgagagcg aggagaaggc cgacgagatg  1380
aagaagcggc tggatatgta tatgaacatg taccactggg ccaaggcctt tatcgtggac  1440
gaggtgctgg acagagatga gatgttctac agcgatatcg acgatatcta taatatcctg  1500
gagaacatcg tgccactgta taatcgggtg agaaactacg tgacccagaa gccctacaac  1560
tctaagaaga tcaagctgaa tttccagagc cctacactgg ccaatggctg gtcccagtct  1620
aaggagttcg acaacaatgc catcatcctg atcagagata acaagtacta tctggccatc  1680
ttcaatgcca agaacaagcc agacaagaag atcatccagg gcaactccga taagaagaac  1740
gacaacgatt acaagaagat ggtgtataac ctgctgccag gcgccaacaa gatgctgccc  1800
aaggtgtttc tgtctaagaa gggcatcgag acattcaagc cctccgacta tatcatctct  1860
ggctacaacg cccacaagca catcaagaca agcgagaatt ttgatatctc cttctgtcgg  1920
gacctgatcg attacttcaa gaacagcatc gagaagcacg ccgagtggag aaagtatgag  1980
ttcaagtttt ccgccaccga cagctactcc gatatctctg agttctatcg ggaggtggag  2040
atgcagggct acagaatcga ctggacatat atcagcgagg ccgacatcaa caagctggat  2100
gaggagggca agatctatct gtttcagatc tacaataagg atttcgccga gaacagcacc  2160
ggcaaggaga atctgcacac aatgtacttt aagaacatct tctccgagga gaatctgaag  2220
gacatcatca tcaagctgaa cggccaggcc gagctgtttt atcggagagc ctctgtgaag  2280
aatcccgtga agcacaagaa ggatagcgtg ctggtgaaca agacctacaa gaatcagctg  2340
gacaacggcg acgtggtgag aatccccatc cctgacgata tctataacga gatctacaag  2400
atgtataatg gctacatcaa ggagtccgac ctgtctgagg ccgccaagga gtacctggat  2460
aaggtggagg tgaggaccgc ccagaaggac atcgtgaagg attaccgcta tacagtggac  2520
```

```
aagtacttca tccacacacc tatcaccatc aactataagg tgaccgcccg caacaatgtg  2580
aatgatatgg tggtgaagta catcgcccag aacgacgata tccacgtgat cggcatcgac  2640
cggggcgaga gaaacctgat ctacatctcc gtgatcgatt ctcacggcaa catcgtgaag  2700
cagaaatcct acaacatcct gaacaactac gactacaaga agaagctggt ggagaaggag  2760
aaaacccggg agtacgccag aaagaactgg aagagcatcg gcaatatcaa ggagctgaag  2820
gagggctata tctccggcgt ggtgcacgag atcgccatgc tgatcgtgga gtacaacgcc  2880
atcatcgcca tggaggacct gaattatggc tttaagaggg gccgcttcaa ggtggagcgg  2940
caggtgtacc agaagtttga gagcatgctg atcaataagc tgaactattt cgccagcaag  3000
gagaagtccg tggacgagcc aggaggcctg ctgaagggct atcagctgac ctacgtgccc  3060
gataatatca agaacctggg caagcagtgc ggcgtgatct tttacgtgcc tgccgccttc  3120
accagcaaga tcgacccatc cacaggcttt atctctgcct tcaactttaa gtctatcagc  3180
acaaatgcct ctcggaagca gttctttatg cagtttgacg agatcagata ctgtgccgag  3240
aaggatatgt tcagctttgg cttcgactac aacaacttcg atacctacaa catcacaatg  3300
ggcaagacac agtggaccgt gtatacaaac ggcgagagac tgcagtctga gttcaacaat  3360
gccaggcgca ccggcaagac aaagagcatc aatctgacag agacaatcaa gctgctgctg  3420
gaggacaatg agatcaacta cgccgacggc cacgatatca ggatcgatat ggagaagatg  3480
gacgaggata agaagagcga gttctttgcc cagctgctga gcctgtataa gctgaccgtg  3540
cagatgcgca attcctatac agaggccgag gagcaggaga acggcatctc ttacgacaag  3600
atcatcagcc ctgtgatcaa tgatgagggc gagttcttg actccgataa ctataaggag  3660
tctgacgata aggagtgcaa gatgccaaag gacgccgatg ccaacggcgc ctactgtatc  3720
gccctgaagg gcctgtatga ggtgctgaag atcaagagcg agtggaccga ggacggcttt  3780
gataggaatt gcctgaagct gccacacgca gagtggctgg acttcatcca gaacaagcgg  3840
tacgag                                                             3846

SEQ ID NO: 226          moltype = DNA  length = 4119
FEATURE                 Location/Qualifiers
source                  1..4119
                        mol_type = genomic DNA
                        organism = Moraxella bovoculi
                        strain = 237
SEQUENCE: 226
atgctgttcc aggactttac ccacctgtat ccactgtcca agacagtgag atttgagctg  60
aagcccatcg ataggaccct ggagcacatc cacgccaaga acttcctgtc tcaggacgag  120
acaatggccg atatgcacca gaaggtgaaa gtgatcctgg acgattacca ccgcgacttc  180
atcgccgata tgatgggcga ggtgaagctg accaagctgg ccgagttcta tgacgtgtac  240
ctgaagtttc ggaagaaccc aaaggacgat gagctgcaga agcagctgaa ggatctgcag  300
gccgtgctga gaaaggagat cgtgaagccc atcggcaatg gcggcaagta taaggccggc  360
tacgacaggc tgttcggcgc caagctgttt aaggacggca aggagctggg cgatctggcc  420
aagttcgtga tcgcacagga gggagagagc tccccaaagc tggcccacct ggcccacttc  480
gagaagtttt ccacctattt cacaggcttt cacgataacc ggaagaatat gtattctgac  540
gaggataagc acaccgccat cgcctaccgc ctgatccacg agaacctgcc ccggtttatc  600
gacaatctgc agatcctgac cacaatcaag cagaagcact ctgccctgta cgatcagatc  660
atcaacgagc tgaccgccag cggcctggac gtgtctctgg ccagccacct ggatggctat  720
cacaagctgc tgacacagga gggcatcacc gcctacaata cactgctggg aggaatctcc  780
ggagaggcag gctctcctaa gatccagggc atcaacgagc tgatcaattc tcaccacaac  840
cagcactgcc acaagagcga gagaatcgcc aagctgaggc cactgcacaa gcagatcctg  900
tccgacggca tgagcgtgtc cttcctgccc tctaagtttg ccgacgatag cgagatgtgc  960
caggccgtga acgagttcta tcgccactac gccgacgtgt tcgccaaggt gcagagcctg  1020
ttcgacggct ttgacgatca ccagaaggat ggcatctacg tggagcacaa gaacctgaat  1080
gagctgtcca agcaggcctt cggcgacttt gcactgctgg gacgcgtgct ggacggatac  1140
tatgtggatg tggtgaatcc agagttcaac gagcggtttg ccaaggccaa gaccgacaat  1200
gccaaggcca agctgacaaa ggagaaggat aagttcatca agggcgtgca ctccctggcc  1260
tctctggagc aggccatcga gcactatacc gcaaggcacg acgatgagag cgtgcaggca  1320
ggcaagctgg gacagtactt caagcacggc ctggccggag tggacaaccc catccagaag  1380
atccacaaca atcacagcac catcaagggc tttctggaga gggagcgccc tgcaggagag  1440
agagccctgc caaagatcaa gtccggcaag aatcctgaga tgacacagct gaggcagctg  1500
aaggagctgc tggataacgc cctgaatgtg gcccacttcg ccaagctgct gaccacaaag  1560
accacactgg acaatcagga tggcaacttc tatggcgagt ttggcgtgct gtacgacgag  1620
ctggccaaga tccccaccct gtataacaag gtgagagatt acctgagcca gaagcctttc  1680
tccaccgaga agtacaagct gaactttggc aatccaacac tgctgaatgg ctgggacctg  1740
aacaaggaga aggataattt cggcgtgatc ctgcagaagg acggctgcta ctatctggcc  1800
ctgctggaca aggcccacaa gaaggtgttt gataacgccc ctaatacagg caagagcatc  1860
tatcagaaga tgatctataa gtacctggag gtgaggaagc agttccccaa ggtgttcttt  1920
tccaaggagg ccatcgccat caactaccac ccttctaagg agctggtgga gatcaaggac  1980
aagggccggc agagatccga cgatgagcgc ctgaagctgt atcggtttat cctggagtgt  2040
ctgaagatcc accctaagta cgataagaag ttcgagggcg ccatcggcga catccagctg  2100
tttaagaagg ataagaaggg cagagaggtg ccaatcagcg agaaggacct gttcgataag  2160
atcaacggca tcttttctag caagcctaag ctggagatgg aggacttctt tatcggcgag  2220
ttcaagaggt ataacccaag ccaggacctg gtggatcagt ataatatcta caagaagatc  2280
gactccaacg ataatcgcaa gaaggagaat ttctacaaca atcaccccaa gtttaagaag  2340
gatctggtgc ggtactatta cgagtctatg tgcaagcacg aggagtggga ggagagcttc  2400
gagttttcca agaagctgca ggacatcggc tgttacgtgg atgtgaacga gctgtttacc  2460
gagatcgaga cacggagact gaattataag atctccttct gcaacatcaa tgccgactac  2520
atcgatgagc tggtggagca gggccagctg tatctgttcc agatctacaa caaggacttt  2580
tccccaaagg cccacggcaa gcccaatctg cacaccctgt acttcaaggc cctgttttct  2640
gaggacaacc tggccgatcc tatctataag ctgaatggcg aggcccagat cttctacaga  2700
aaggcctccc tggacatgaa cgagacaaca atccacaggg ccggcgaggt gctggagaac  2760
aagaatcccg ataatcctaa gaagagacag ttcgtgtacg acatcatcaa ggataagagg  2820
tacacacagg acaagttcat gctgcacgtg ccaatcacca tgaactttgg cgtgcagggc  2880
```

```
atgacaatca aggagttcaa taagaaggtg aaccagtcta tccagcagta tgacgaggtg  2940
aacgtgatcg gcatcgatcg gggcgagaga cacctgctgt acctgaccgt gatcaatagc  3000
aagggcgaga tcctggagca gtgttccctg aacgacatca ccacagcctc tgccaatggc  3060
acacagatga ccacacctta ccacaagatc ctggataaga gggagatcga gcgcctgaac  3120
gcccgggtgg gatggggcga gatcgagaca atcaaggagc tgaagtctgg ctatctgagc  3180
cacgtggtgc accagatcag ccagctgatg ctgaagtaca acgccatcgt ggtgctggag  3240
gacctgaatt tcggctttaa gaggggccgc tttaaggtgg agaagcagat ctatcagaac  3300
ttcgagaatg ccctgatcaa gaagctgaac cacctggtgc tgaaggacaa ggccgacgat  3360
gagatcggct cttacaagaa tgccctgcag ctgaccaaca atttcacaga tctgaagagc  3420
atcggcaagc agaccggctt cctgttttat gtgcccgcct ggaacacctc taagatcgac  3480
cctgagacag gctttgtgga tctgctgaag ccaagatacg agaacatcgc ccagagccag  3540
gccttctttg gcaagttcga caagatctgc tataatgccg acaaggatta cttcgagttt  3600
cacatcgact acgccaagtt taccgataag gccaagaata gccgccagat ctggacaatc  3660
tgttcccacg gcgacaagcg gtacgtgtac gataagacag ccaaccagaa taagggcgcc  3720
gccaagggca tcaacgtgaa tgatgagctg aagtccctgt tcgcccgcca ccacatcaac  3780
gagaagcagc ccaacctggt catggacatc tgccagaaca atgataagga gtttcacaag  3840
tctctgatgt acctgctgaa aaccctgctg gccctgcggt acagcaacgc ctcctctgac  3900
gaggatttca tcctgtcccc cgtggcaaac gacgagggcg tgttctttaa tagcgccctg  3960
gccgacgata cacagcctca gaatgccgat gccaacggcg cctaccacat cgccctgaag  4020
ggcctgtggc tgctgaatga gctgaagaac tccgacgatc tgaacaaggt gaagctggcc  4080
atcgacaatc agacctggct gaatttcgcc cagaacagg                         4119

SEQ ID NO: 227         moltype = DNA  length = 3969
FEATURE                Location/Qualifiers
source                 1..3969
                       mol_type = genomic DNA
                       organism = Prevotella disiens
SEQUENCE: 227
atggagaact atcaggagtt caccaacctg tttcagctga ataagacact gagattcgag  60
ctgaagccca tcggcaagac ctgcgagctg ctggaggagg gcaagatctt cgccagcggc  120
tcctttctgg agaaggacaa ggtgagggcc gataacgtga gctacgtgaa gaaggagatc  180
gacaagaagc acaagatctt tatcgaggag acactgagct ccttctctat cagcaacgat  240
ctgctgaagc agtactttga ctgctataat gagctgaagg ccttcaagaa ggactgtaag  300
agcgatgagg aggaggtgaa gaaaaccgcc ctgcgcaaca agtgtacctc catccagagg  360
gccatgcgcg aggccatctc tcaggccttt ctgaagagcc cccagaagaa gctgctggcc  420
atcaagaacc tgatcgagaa cgtgttcaag gccgacgaga atgtgcagca cttctccgag  480
tttaccagct atttctccgg ctttgagaca aacagagaga atttctactc tgacgaggag  540
aagtccacat ctatcgccta taggctggtg cacgataacc tgcctatctt catcaagaac  600
atctacatct tcgagaagct gaaggagcag ttcgacgcca agaccctgag cgagatcttc  660
gagaactaca agctgtatgt ggccggctct agcctggatg aggtgttctc cctggagtac  720
tttaacaata ccctgacaca gaagggcatc gacaactata atgccgtgat cggcaagatc  780
gtgaaggagg ataagcagga gatccagggc ctgaacgagc acatcaacct gtataatcag  840
aagcacaagg accggagact gcccttcttt atctccctga agaagcagat cctgtccgat  900
cgggaggccc tgtcttggct gcctgacatg ttcaagaatg attctgaagt gatcaaggcc  960
ctgaagggct tctacatcga ggacggcttt gagaacaatg tgctgacacc tctggccacc  1020
ctgctgtcct ctctggataa gtacaacctg aatggcatct ttatccgcaa caatgaggcc  1080
ctgagctccc tgtcccagaa cgtgtatcgg aatttttcta tcgacgaggc catcgatgcc  1140
aacgccgagc tgcagacctt caacaattac gagctgatcg ccaatgccct gcgcgccaag  1200
atcaagaagg agacaaagca gggccggaag tctttcgaga agtacgagga gtatatcgat  1260
aagaaggtga aggccatcga cagcctgtcc atccaggaga tcaacgagct ggtggagaat  1320
tacgtgagcg agtttaactc taatagcggc aacatgccaa gaaaggtgga ggactacttc  1380
agcctgatga ggaagggcga cttcggctcc aacgatctga tcgaaaatat caagaccaag  1440
ctgagcgccg cagagaagct gctgggcaca aagtaccagg agacagccaa ggacatcttc  1500
aagaaggatg agaactccaa gctgatcaag gagctgctgg acgccaccaa gcagttccag  1560
cactttatca agccactgct gggcacaggc gaggaggcag atcgggacct ggtgttctac  1620
ggcgattttc tgcccctgta tgagaagttt gaggagctga ccctgctgta taacaaggtg  1680
cggaatagac tgacacagaa gccctattcc aaggacaaga tccgcctgtg cttcaacaag  1740
cctaagctga tgacaggctg ggtggattcc aagaccgaga agtctgacaa cggcacacag  1800
tacggcggct atctgtttcg gaagaagaat gagatcggcg agtacgatta ttttctgggc  1860
atctctagca aggcccagct gttcagaaag aacgaggccg tgatcggcga ctacgagagg  1920
ctggattact atcagccaaa ggccaatacc atctacggct ctgcctatga gggcgagaac  1980
agctacaagg aggacaagaa gcggctgaac aaagtgatca tcgcctatat cgagcagatc  2040
aagcagacaa acatcaagaa gtctatcatc gagtccatct ctaagtatcc taatatcagc  2100
gacgatgaca aggtgacccc atcctctctg ctggagaaga tcaagaaggt gtctatcgac  2160
agctacaacg gcatcctgtc cttcaagtct tttcagagcg tgaacaagga agtgatcgat  2220
aacctgctga aaaccatcag ccccctgaag aacaaggccg agtttctgga cctgatcaat  2280
aaggattatc agatcttcac cgaggtgcag gccgtgatcg acgagatctg caagcagaaa  2340
accttcatct actttccaat ctccaacgtg gagctggaga aggagatggg cgataaggac  2400
aagcccctgt gcctgttcca gatcagcaat aaggatctgt ccttcgccaa gacctttagc  2460
gccaacctgc ggaagaagag aggcgccgag aatctgcaca caatgctgtt taaggccctg  2520
atggagggca accaggataa tctggacctg ggctctggcg ccatcttcta cagagccaag  2580
agcctggacg gcaacaagcc cacacaccct gccaatgagg ccatcaagtg taggaacgtg  2640
gccaataagg ataaggtgtc cctgttcacc tacgacatct ataagaacag gcgctacatg  2700
gagaataagt tcctgtttca cctgagcatc gtgcagaact ataaggccgc caatgactcc  2760
gcccagctga acagctccgc caccgagtat atcagaaagg ccgatgacct gcacatcatc  2820
ggcatcgata ggggcgagcg caatctgctg tactattccg tgatcgatat gaagggcaac  2880
atcgtggagc aggactctct gaatatcatc aggaacaatg acctggagac agattaccac  2940
gacctgctgg ataagaggga gaaggagcgc aaggccaacc ggcagaattg ggaggccgtg  3000
gagggcatca aggacctgaa gaagggctac ctgagccagg ccgtgcacca gatcgcccag  3060
```

-continued

```
ctgatgctga agtataacgc catcatcgcc ctggaggatc tgggccagat gtttgtgacc  3120
cgcggccaga agatcgagaa ggccgtgtac cagcagttcg agaagagcct ggtggataag  3180
ctgtcctacc tggtggacaa gaagcggcct tataatgagc tgggcggcat cctgaaggcc  3240
taccagctgg cctctagcat caccaagaac aattctgaca agcagaacgg cttcctgttt  3300
tatgtgccag cctggaatac aagcaagatc gatcccgtga ccggctttac agacctgctg  3360
cggcccaagg ccatgaccat caaggaggcc caggacttct ttggcgcctt cgataacatc  3420
tcttacaatg acaagggcta tttcgagttt gagacaaact acgacaagtt taagatcaga  3480
atgaagagcg cccagaccag gtggacaatc tgcaccttcg gcaatcggat caagagaaag  3540
aaggataaga actactggaa ttatgaggag gtggagctga ccgaggagtt caagaagctg  3600
tttaaggaca gcaacatcga ttacgagaac tgtaatctga aggaggagat ccagaacaag  3660
gacaatcgca agttctttga tgacctgatc aagctgctgc agctgacact gcagatgcgg  3720
aactccgatg acaagggcaa tgattatatc atctctcctg tggccaacgc cgagggccag  3780
ttctttgact cccgcaatgg cgataagaag ctgccactgg atgcagacgc aaacggagcc  3840
tacaatatcg cccgcaaggg cctgtggaac atccggcaga tcaagcagac caagaacgac  3900
aagaagctga atctgagcat ctcctctaca gagtggctgg atttcgtgcg ggagaagcct  3960
tacctgaag                                                          3969

SEQ ID NO: 228         moltype = AA  length = 1368
FEATURE                Location/Qualifiers
source                 1..1368
                       mol_type = protein
                       organism = Streptococcus pyogenes
SEQUENCE: 228
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD               1368

SEQ ID NO: 229         moltype = AA  length = 1300
FEATURE                Location/Qualifiers
source                 1..1300
                       mol_type = protein
                       organism = Francisella tularensis
SEQUENCE: 229
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                         1300

SEQ ID NO: 230         moltype = AA  length = 1307
FEATURE                Location/Qualifiers
source                 1..1307
```

```
                        mol_type = protein
                        note = BV3L6
                        organism = Acidaminococcus sp.
SEQUENCE: 230
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN                1307

SEQ ID NO: 231          moltype = AA  length = 1233
FEATURE                 Location/Qualifiers
source                  1..1233
                        mol_type = protein
                        note = Lachnospiraceae bacterium MC2017
                        organism = unidentified
SEQUENCE: 231
MDYGNGQFER RAPLTKTITL RLKPIGETRE TIREQKLLEQ DAAFRKLVET VTPIVDDCIR  60
KIADNALCHF GTEYDFSCLG NAISKNDSKA IKKETEKVEK LLAKVLTENL PDGLRKVNDI  120
NSAAFIQDTL TSFVQDDADK RVLIQELKGK TVLMQRFLTT RITALTVWLP DRVFENFNIF  180
IENAEKMRIL LDSPLNEKIM KFDPDAEQYA SLEFYGQCLS QKDIDSYNLI ISGIYADDEV  240
KNPGINEIVK EYNQQIRGDK DESPLPKLKK LHKQILMPVE KAFFVRVLSN DSDARSILEK  300
ILKDTEMLPS KIIEAMKEAD AGDIAVYGSR LHELSHVIYG DHGKLSQIIY DKESKRISEL  360
METLSPKERK ESKKRLEGLE EHIRKSTYTF DELNRYAEKN VMAAYIAAVE ESCAEIMRKE  420
KDLRTLLSKE DVKIRGNRHN TLIVKNYFNA WTVFRNLIRI LRRKSEAEID SDFYDVLDDS  480
VEVLSLTYKG ENLCRSYITK KIGSDLKPEI ATYGSALRPN SRWWSPGEKF NVKFHTIVRR  540
DGRLYYFILP KGAKPVELED MDGDIECLQM RKIPNPTIFL PKLVFKDPEA FFRDNPEADE  600
FVFLSGMKAP VTITRETYEA YRYKLYTVGK LRDGEVSEEE YKRALLQVLT AYKEFLENRM  660
IYADLNFGFK DLEEYKDSSE FIKQVETHNT FMCWAKVSSS QLDDLVKSGN GLLFEIWSER  720
LESYYKYGNE KVLRGYEGVL LSILKDENLV SMRTLLNSRP MLVYRPKESS KPMVVHRDGS  780
RVVDRFDKDG KYIPPEVHDE LYRFFNNLLI KEKLGEKARK ILDNKKVKVK VLESERVKWS  840
KFYDEQFAVT FSVKKNADCL DTTKDLNAEV MEQYSESNRL ILIRNTTDIL YYLVLDKNGK  900
VLKQRSLNII NDGARDVDWK ERFRQVTKDR NEGYNEWDYS RTSNDLKEVY LNYALKEIAE  960
AVIEYNAILI IEKMSNAFKD KYSFLDDVTF KGFETKLLAK LSDLHFRGIK DGEPCSFTNP  1020
LQLCQNDSNK ILQDGVIFMV PNSMTRSLDP DTGFIFAIND HNIRTKKAKL NFLSKFDQLK  1080
VSSEGCLIMK YSGDSLPTHN TDNRVWNCCC NHPITNYDRE TKKVEFIEEP VEELSRVLEE  1140
NGIETDTELN KLNERENVPG KVVDAIYSLV LNYLRGTVSG VAGQRAVYYS PVTGKKYDIS  1200
FIQAMNLNRK CDYYRIGSKE RGEWTDFVAQ LIN                                1233

SEQ ID NO: 232          moltype = AA  length = 1246
FEATURE                 Location/Qualifiers
source                  1..1246
                        mol_type = protein
                        note = Lachnospiraceae bacterium ND2006
                        organism = unidentified
SEQUENCE: 232
MLKNVGIDRL DVEKGRKNMS KLEKFTNCYS LSKTLRFKAI PVGKTQENID NKRLLVEDEK  60
RAEDYKGVKK LLDRYYLSFI NDVLHSIKLK NLNNYISLFR KKTRTEKENK ELENLEINLR  120
KEIAKAFKGN EGYKSLFKKD IIETILPEFL DDKDEIALVN SFNGFTTAFT GFFDNRENMF  180
SEEAKSTSIA FRCINENLTR YISNMDIFEK VDAIFDKHEV QEIKEKILNS DYDVEDFFEG  240
EFFNFVLTQE GIDVYNAIIG GFVTESGEKI KGLNEYINLY NQKTKQKLPK FKPLYKQVLS  300
DRESLSFYGE GYTSDEEVLE VFRNTLNKNS EIFSSIKKLE KLFKNFDEYS SAGIFVKNGP  360
AISTISKDIF GEWNVIRDKW NAEYDDIHLK KKAVVTEKYE DDRRKSFKKI GSFSLEQLQE  420
YADADLSVVE KLKEIIIQKV DEIYKVYGSS EKLFDADFVL EKSLKKNDAV VAIMKDLLDS  480
VKSFENYIKA FFGEGKETNR DESFYGDFVL AYDILLKVDH IYDAIRNYVT QKPYSKDKFK  540
LYFQNPQFMG GWDKDKETDY RATILRYGSK YYLAIMDKKY AKCLQKIDKD DVNGNYEKIN  600
YKLLPGPNKM LPKVFFSKKW MAYYNPSEDI QKIYKNGTFK KGDMFNLNDC HKLIDFFKDS  660
ISRYPKWSNA YDFNFSETEK YKDIAGFYRE VEEQGYKVSF ESASKKEVDK LVEEGKLYMF  720
QIYNKDFSDK SHGTPNLHTM YFKLLFDENN HGQIRLSGGA ELFMRRASLK KEELVVHPAN  780
SPIANKNPDN PKKTTTLSYD VYKDKRFSED QYELHIPIAI NKCPKNIFKI NTEVRVLLKH  840
DDNPYVIGID RGERNLLYIV VVDGKGNIVE QYSLNEIINN FNGIRIKTDY HSLLDKKEKE  900
RFEARQNWTS IENIKELKAG YISQVVHKIC ELVEKYDAVI ALEDLNSGFK NSRVKVEKQV  960
```

-continued

```
YQKFEKMLID KLNYMVDKKS NPCATGGALK GYQITNKFES FKSMSTQNGF IFYIPAWLTS  1020
KIDPSTGFVN LLKTKYTSIA DSKKFISSFD RIMYVPEEDL FEFALDYKNF SRTDADYIKK  1080
WKLYSYGNRI RIFRNPKKNN VFDWEEVCLT SAYKELFNKY GINYQQGDIR ALLCEQSDKA  1140
FYSSFMALMS LMLQMRNSIT GRTDVDFLIS PVKNSDGIFY DSRNYEAQEN AILPKNADAN  1200
GAYNIARKVL WAIGQFKKAE DEKLDKVKIA ISNKEWLEYA QTSVKH                 1246

SEQ ID NO: 233         moltype = AA  length = 1228
FEATURE                Location/Qualifiers
source                 1..1228
                       mol_type = protein
                       note = Lachnospiraceae bacterium ND2006
                       organism = unidentified
SEQUENCE: 233
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                      1228

SEQ ID NO: 234         moltype = AA  length = 1300
FEATURE                Location/Qualifiers
source                 1..1300
                       mol_type = protein
                       note = Novicida U112
                       organism = Francisella tularensis
SEQUENCE: 234
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                         1300

SEQ ID NO: 235         moltype = AA  length = 1477
FEATURE                Location/Qualifiers
source                 1..1477
                       mol_type = protein
                       note = Peregrinibacteria bacterium GW2011_GWA_33_10
                       organism = unidentified
SEQUENCE: 235
MSNFFKNFTN LYELSKTLRF ELKPVGDTLT NMKDHLEYDE KLQTFLKDQN IDDAYQALKP  60
QFDEIHEEFI TDSLESKKAK EIDFSEYLDL FQEKKELNDS EKKLRNKIGE TFNKAGEKWK  120
KEKYPQYEWK KGSKIANGAD ILSCQDMLQF IKYKNPEDEK IKNYIDDTLK GFFTYFGGFN  180
QNRANYYETK KEASTAVATR IVHENLPKFC DNVIQFKHII KRKKDGTVEK TERKTEYLNA  240
YQYLKNNNKI TQIKDAETEK MIESTPIAEK IFDVYYFSSC LSQKQIEEYN RIIGHYNLLI  300
NLYNQAKRSE GKHLSANEKK YKDLPKFKTL YKQIGCGKKK DLFYTIKCDT EEEANKSRNE  360
GKESHSVEEI INKAQEAINK YFKSNNDCEN INTVPDFINY ILTKENYEGV YWSKAAMNTI  420
```

```
SDKYFANYHD LQDRLKEAKV FQKADKKSED DIKIPEAIEL SGLFGVLDSL ADWQTTLFKS  480
SILSNEDKLK IITDSQTPSE ALLKMIFNDI EKNMESFLKE TNDIITLKKY KGNKEGTEKI  540
KQWFDYTLAI NRMLKYFLVK ENKIKGNSLD TNISEALKTL IYSDDAEWFK WYDALRNYLT  600
QKPQDEAKEN KLKLNFDNPS LAGGWDVNKE CSNFCVILKD KNEKKYLAIM KKGENTLFQK  660
EWTEGRGKNL TKKSNPLFEI NNCEILSKME YDFWADVSKM IPKCSTQLKA VVNHFKQSDN  720
EFIFPIGYKV TSGEKFREEC KISKQDFELN NKVFNKNELS VTAMRYDLSS TQEKQYIKAF  780
QKEYWELLFK QEKRDTKLTN NEIFNEWINF CNKKYSELLS WERKYKDALT NWINFCKYFL  840
SKYPKTTLFN YSFKESENYN SLDEFYRDVD ICSYKLNINT TINKSILDRL VEEGKLYLFE  900
IKNQDSNDGK SIGHKNNLHT IYWNAIFENF DNRPKLNGEA EIFYRKAISK DKLGIVKGKK  960
TKNGTEIIKN YRFSKEKFIL HVPITLNFCS NNEYVNDIVN TKFYNFSNLH FLGIDRGEKH  1020
LAYYSLVNKN GEIVDQGTLN LPFTDKDGNQ RSIKKEKYFY NKQEDKWEAK EVDCWNYNDL  1080
LDAMASNRDM ARKNWQRIGT IKEAKNGYVS LVIRKIADLA VNNERPAFIV LEDLNTGFKR  1140
SRQKIDKSVY QKFELALAKK LNFLVDKNAK RDEIGSPTKA LQLTPPVNNY GDIENKKQAG  1200
IMLYTRANYT SQTDPATGWR KTIYLKAGPE ETTYKKDGKI KNKSVKDQII ETFTDIGFDG  1260
KDYYFEYDKG EFVDEKTGEI KPKKWRLYSG ENGKSLDRFR GEREKDKYEW KIDKIDIVKI  1320
LDDLFVNFDK NISLLKQLKE GVELTRNNEH GTGESLRFAI NLIQQIRNTG NNERDNDFIL  1380
SPVRDENGKH FDSREYWDKE TKGEKISMPS SGDANGAFNI ARKGIIMNAH ILANSDSKDL  1440
SLFVSDEEWD LHLNNKTEWK KQLNIFSSRK AMAKRKK                           1477

SEQ ID NO: 236         moltype = AA  length = 1352
FEATURE                Location/Qualifiers
source                 1..1352
                       mol_type = protein
                       note = Parcubacteria bacterium GWC2011_GWC2_44_17
                       organism = unidentified
SEQUENCE: 236
MENIFDQFIG KYSLSKTLRF ELKPVGKTED FLKINKVFEK DQTIDDSYNQ AKFYFDSLHQ  60
KFIDAALASD KTSELSFQNF ADVLEKQNKI ILDKKREMGA LRKRDKNAVG IDRLQKEIND  120
AEDIIQKEKE KIYKDVRTLF DNEAESWKTY YQEREVDGKK ITFSKADLKQ KGADFLTAAG  180
ILKVLKYEFP EEKEKEFQAK NQPSLFVEEK ENPGQKRYIF DSFDKFAGYL TKFQQTKKNL  240
YAADGTSTAV ATRIADNFII FHQNTKVFRD KYKNNHTDLG FDEENIFEIE RYKNCLLQRE  300
IEHIKNENSY NKIIGRINKK IKEYRDQKAK DTKLTKSDFP FFKNLDKQIL GEVEKEKQLI  360
EKTREKTEED VLIERFKEFI ENNEERFTAA KKLMNAFCNG EFESEYEGIY LKNKAINTIS  420
RRWFVSDRDF ELKLPQQKSK NKSEKNEPKV KKFISIAEIK NAVEELDGDI FKAVFYDKKI  480
IAQGGSKLEQ FLVIWKYEFE YLFRDIEREN GEKLLGYDSC LKIAKQLGIF PQEKEAREKA  540
TAVIKNYADA GLGIFQMMKY FSLDDKDRKN TPGQLSTNFY AEYDGYYKDF EFIKYYNEFR  600
NFITKKPFDE DKIKLNFENG ALLKGWDENK EYDFMGVILK KEGRLYLGIM HKNHRKLFQS  660
MGNAKGDNAN RYQKMIYKQI ADASKDVPRL LLTSKKAMEK FKPSQEILRI KKEKTFKRES  720
KNFSLRDLHA LIEYYRNCIP QYSNWSFYDF QFQDTGKYQN IKEFTDDVQK YGYKISFRDI  780
DDEYINQALN EGKMYLFEVV NKDIYNTKNG SKNLHTLYFE HILSAENLND PVFKLSGMAE  840
IFQRQPSVNE REKITTQKNQ CILDKGDRAY KYRRYTEKKI MFHMSLVLNT GKGEIKQVQF  900
NKIINQRISS SDNEMRVNVI GIDRGEKNLL YYSVVKQNGE IIEQASLNEI NGVNYRDKLI  960
EREKERLKNR QSWKPVVKIK DLKKGYISHV IHKICQLIEK YSAIVVLEDL NMRFKQIRGG  1020
IERSVYQQFE KALIDKLGYL VFKDNRDLRA PGGVLNGYQL SAPFVSFEKM RKQTGILFYT  1080
QAEYTSKTDP ITGFRKNVYI SNSASLDKIK EAVKKFDAIG WDGKEQSYFF KYNPYNLADE  1140
KYKNSTVSKE WAIFASAPRI RRQKGEDGYW KYDRVKVNEE FEKLLKVWNF VNPKATDIKQ  1200
EIIKKEKAGD LQGEKELDGR LRNFWHSFIY LFNLVLELRN SFSLQIKIKA GEVIAVDEGV  1260
DFIASPVKPF FTTPNPYIPS NLCWLAVENA DANGAYNIAR KGVMILKKIR EHAKKDPEFK  1320
KLPNLFISNA EWDEAARDWG KYAGTTALNL DH                                1352

SEQ ID NO: 237         moltype = AA  length = 1206
FEATURE                Location/Qualifiers
source                 1..1206
                       mol_type = protein
                       note = Lachnospiraceae bacterium MA2020
                       organism = unidentified
SEQUENCE: 237
MYYESLTKQY PVSKTIRNEL IPIGKTLDNI RQNNILESDV KRKQNYEHVK GILDEYHKQL  60
INEALDNCTL PSLKIAAEIY LKNQKEVSDR EDFNKTQDLL RKEVVEKLKA HENFTKIGKK  120
DILDLLEKLP SISEDDYNAL ESFRNFYTYF TSYNKVRENL YSDKEKSSTV AYRLINENFP  180
KFLDNVKSYR FVKTAGILAD GLGEEEQDSL FIVETFNKTL TQDGIDTYNS QVGKINSSIN  240
LYNQKNQKAN GFRKIPKMKM LYKQILSDRE ESFIDEFQSD EVLIDNVESY GSVLIESLKS  300
SKVSAFFDAL RESKGKNVYV KNDLAKTAMS NIVFENWRTF DDLLNQEYDL ANENKKKDDK  360
YFEKRQKELK KNKSYSLEHL CNLSEDSCNL IENYIHQISD DIENIIINNE TFLRIVINEH  420
DRSRKLAKNR KAVKAIKDFL DSIKVLEREL KLINSSGQEL EKDLIVYSAH EELLVELKQV  480
DSLYNMTRNY LTKKPFSTEK VKLNFNRSTL LNGWDRNKET DNLGVLLLKD GKYYLGIMNT  540
SANKAFVNPP VAKTEKVFKK VDYKLLPVPN QMLPKVFFAK SNIDFYNPSS EIYSNYKKGT  600
HKKGNMFSLE DCHNLIDFFK ESISKHEDWS KFGFKFSDTA SYNDISEFYR EVEKQGYKLT  660
YTDIDETYIN DLIERNELYL FQIYNKDFSM YSKGKLNLHT LYFMMLFDQR NIDDVVYKLN  720
GEAEVFYRPA SISEDELIIH KAGEEIKNKN PNRARTKETS TFSYDIVKDK RYSKDKFTLH  780
IPITMNFGVD EVKRFNDAVN SAIRIDENVN VIGIDRGERN LLYVVVIDSK GNILEQISLN  840
SIINKEYDIE TDYHALLDER EGGRDKARKD WNTVENIRDL KAGYLSQVVN VVAKLVLKYN  900
AIICLEDLNF GFKRGRQKVE KQVYQKFEKM LIDKLNYLVI DKSREQTSPK ELGGALNALQ  960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTSDG TRDYIISPVK  1140
NKREAYFNSE LSDGSVPKDA DANGAYNIAR KGLWVLEQIR QKSEGEKINL AMTNAEWLEY  1200
AQTHLL                                                             1206
```

-continued

```
SEQ ID NO: 238          moltype = AA  length = 1238
FEATURE                 Location/Qualifiers
source                  1..1238
                        mol_type = protein
                        organism = Candidatus Methanoplasma termitum
SEQUENCE: 238
MNNYDEFTKL YPIQKTIRFE LKPQGRTMEH LETFNFFEED RDRAEKYKIL KEAIDEYHKK  60
FIDEHLTNMS LDWNSLKQIS EKYYKSREEK DKKVFLSEQK RMRQEIVSEF KKDDRFKDLF  120
SKKLFSELLK EEIYKKGNHQ EIDALKSFDK FSGYFIGLHE NRKNMYSDGD EITAISNRIV  180
NENFPKFLDN LQKYQEARKK YPEWIIKAES ALVAHNIKMD EVFSLEYFNK VLNQEGIQRY  240
NLALGGYVTK SGEKMMGLND ALNLAHQSEK SSKGRIHMTP LFKQILSEKE SFSYIPDVFT  300
EDSQLLPSIG GFFAQIENDK DGNIFDRALE LISSYAEYDT ERIYIRQADI NRVSNVIFGE  360
WGTLGGLMRE YKADSINDIN LERTCKKVDK WLDSKEFALS DVLEAIKRTG NNDAFNEYIS  420
KMRTAREKID AARKEMKFIS EKISGDEESI HIIKTLLDSV QQFLHFFNLF KARQDIPLDG  480
AFYAEFDEVH SKLFAIVPLY NKVRNYLTKN NLNTKKIKLN FKNPTLANGW DQNKVYDYAS  540
LIFLRDGNYY LGIINPKRKK NIKFEQGSGN GPFYRKMVYK QIPGPNKNLP RVFLTSTKGK  600
KEYKPSKEII EGYEADKHIR GDKFDLDFCH KLIDFFKESI EKHKDWSKFN FYFSPTESYG  660
DISEFYLDVE KQGYRMHFEN ISAETIDEYV EKGDLFLFQI YNKDFVKAAT GKKDMHTIYW  720
NAAFSPENLQ DVVVKLNGEA ELFYRDKSDI KEIVHREGEI LVNRTYNGRT PVPDKIHKKL  780
TDYHNGRTKD LGEAKEYLDK VRYFKAHYDI TKDRRYLNDK IYFHVPLTLN FKANGKKNLN  840
KMVIEKFLSD EKAHIIGIDR GERNLLYYSI IDRSGKIIDQ QSLNVIDGFD YREKLNQREI  900
EMKDARQSWN AIGKIKDLKE GYLSKAVHEI TKMAIQYNAI VVMEELNYGF KRGRFKVEKQ  960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                          1238

SEQ ID NO: 239          moltype = AA  length = 1282
FEATURE                 Location/Qualifiers
source                  1..1282
                        mol_type = protein
                        organism = Eubacterium eligens
SEQUENCE: 239
MNGNRSIVYR EFVGVIPVAK TLRNELRPVG HTQEHIIQNG LIQEDELRQE KSTELKNIMD  60
DYYREYIDKS LSGVTDLDFT LLFELMNLVQ SSPSKDNKKA LEKEQSKMRE QICTHLQSDS  120
NYKNIFNAKL LKEILPDFIK NYNQYDVKDK AGKLETLALF NGFSTYFTDF FEKRKNVFTK  180
EAVSTSIAYR IVHENSLIFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDDHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYS DISEFYREVE MQGYRIDWTY ISEADINKLD EEGKIYLFQI YNKDFAENST  720
GKENLHTMYF KNIFSEENLK DIIIKLNGQA ELFYRRASVK NPVKHKKDSV LVNKTYKNQL  780
DNGDVVRIPI PDDIYNEIYK MYNGYIKESD LSEAAKEYLD KVEVRTAQKD IVKDYRYTVD  840
KYFIHTPITI NYKVTARNNV NDMVVKYIAQ NDDIHVIGID RGERNLIYIS VIDSHGNIVK  900
QKSYNILNNY DYKKKLVEKE KTREYARKNW KSIGNIKELK EGYISGVVHE IAMLIVEYNA  960
IIAMEDLNYG FKRGRFKVER QVYQKFESML INKLNYFASK EKSVDEPGGL LKGYQLTYVP  1020
DNIKNLGKQC GVIFYVPAAF TSKIDPSTGF ISAFNFKSIS TNASRKQFFM QFDEIRYCAE  1080
KDMFSFGFDY NNFDTYNITM GKTQWTVYTN GERLQSEFNN ARRTGKTKSI NLTETIKLLL  1140
EDNEINYADG HDIRIDMEKM DEDKKSEFFA QLLSLYKLTV QMRNSYTEAE EQENGISYDK  1200
IISPVINDEG EFFDSDNYKE SDDKECKMPK DADANGAYCI ALKGLYEVLK IKSEWTEDGF  1260
DRNCLKLPHA EWLDFIQNKR YE                                           1282

SEQ ID NO: 240          moltype = AA  length = 1373
FEATURE                 Location/Qualifiers
source                  1..1373
                        mol_type = protein
                        note = 237
                        organism = Moraxella bovoculi
SEQUENCE: 240
MLFQDFTHLY PLSKTVRFEL KPIDRTLEHI HAKNFLSQDE TMADMHQKVK VILDDYHRDF  60
IADMMGEVKL TKLAEFYDVY LKFRKNPKDD ELQKQLKDLQ AVLRKEIVKP IGNGGKYKAG  120
YDRLFGAKLF KDGKELGDLA KFVIAQEGES SPKLAHLAHF EKFSTYFTGF HDNRKNMYSD  180
EDKHTAIAYR LIHENLPRFI DNLQILTTIK QKHSALYDQI INELTASGLD VSLASHLDGY  240
HKLLTQEGIT AYNTLLGGIS GEAGSPKIQG INELINSHHN QHCHKSERIA KLRPLHKQIL  300
SDGMSVSFLP SKFADDSEMC QAVNEFYRHY ADVFAKVQSL FDGFDDHQKD GIYVEHKNLN  360
ELSKQAFGDF ALLGRVLDGY YVDVVNPEFN ERFAKAKTDN AKAKLTKEKD KFIKGVHSLA  420
SLEQAIEHYT ARHDDESVQA GKLGQYFKHG LAGVDNPIQK IHNNHSTIKG FLERERPAGE  480
RALPKIKSGK NPEMTQLRQL KELLDNALNV AHFAKLLTTK TTLDNQDGNF YGEFGVLYDE  540
LAKIPTLYNK VRDYLSQKPF STEKYKLNFG NPTLLNGWDL NKEKDNFGVI LQKDGCYYLA  600
LLDKAHKKVF DNAPNTGKSI YQKMIYKYLE VRKQFPKVFF SKEAIAINYH PSKELVEIKD  660
KGRQRSDDER LKLYRFILEC LKIHPKYDKK FEGAIGDIQL FKKDKKGREV PISEKDLFDK  720
INGIFSSKPK LEMEDFFIGE FKRYNPSQDL VDQYNIYKKI DSNDNRKKEN FYNNHPKFKK  780
DLVRYYYESM CKHEEWEESF EFSKKLQDIG CYVDVNELFT EIETRRLNYK ISFCNINADY  840
IDELVEQGQL YLFQIYNKDF SPKAHGKPNL HTLYFKALFS EDNLADPIYK LNGEAQIFYR  900
```

```
KASLDMNETT IHRAGEVLEN KNPDNPKKRQ FVYDIIKDKR YTQDKFMLHV PITMNFGVQG  960
MTIKEFNKKV NQSIQQYDEV NVIGIDRGER HLLYLTVINS KGEILEQCSL NDITTASANG  1020
TQMTTPYHKI LDKREIERLN ARVGWGEIET IKELKSGYLS HVVHQISQLM LKYNAIVVLE  1080
DLNFGFKRGR FKVEKQIYQN FENALIKKLN HLVLKDKADD EIGSYKNALQ LTNNFTDLKS  1140
IGKQTGFLFY VPAWNTSKID PETGFVDLLK PRYENIAQSQ AFFGKFDKIC YNADKDYFEF  1200
HIDYAKFTDK AKNSRQIWTI CSHGDKRYVY DKTANQNKGA AKGINVNDEL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR         1373

SEQ ID NO: 241         moltype = AA  length = 1323
FEATURE                Location/Qualifiers
source                 1..1323
                       mol_type = protein
                       organism = Prevotella disiens
SEQUENCE: 241
MENYQEFTNL FQLNKTLRFE LKPIGKTCEL LEEGKIFASG SFLEKDKVRA DNVSYVKKEI  60
DKKHKIFIEE TLSSFSISND LLKQYFDCYN ELKAFKKDCK SDEEEVKKTA LRNKCTSIQR  120
AMREAISQAF LKSPQKKLLA IKNLIENVFK ADENVQHFSE FTSYFSGFET NRENFYSDEE  180
KSTSIAYRLV HDNLPIFIKN IYIFEKLKEQ FDAKTLSEIF ENYKLYVAGS SLDEVFSLEY  240
FNNTLTQKGI DNYNAVIGKI VKEDKQEIQG LNEHINLYNQ KHKDRRLPFF ISLKKQILSD  300
REALSWLPDM FKNDSEVIKA LKGFYIEDGF ENNVLTPLAT LLSSLDKYNL NGIFIRNNEA  360
LSSLSQNVYR NFSIDEAIDA NAELQTFNNY ELIANALRAK IKKETKQGRK SFEKYEEYID  420
KKVKAIDSLS IQEINELVEN YVSEFNSNSG NMPRKVEDYF SLMRKGDFGS NDLIENIKTK  480
LSAAEKLLGT KYQETAKDIF KKDENSKLIK ELLDATKQFQ HFIKPLLGTG EEADRDLVFY  540
GDFLPLYEKF EELTLLYNKV RNRLTQKPYS KDKIRLCFNK PKLMTGWVDS KTEKSDNGTQ  600
YGGYLFRKKN EIGEYDYFLG ISSKAQLFRK NEAVIGDYER LDYYQPKANT IYGSAYEGEN  660
SYKEDKKRLN KVIIAYIEQI KQTNIKKSII ESISKYPNIS DDDKVTPSSL LEKIKKVSID  720
SYNGILSFKS FQSVNKEVID NLLKTISPLK NKAEFLDLIN KDYQIFTEVQ AVIDEICKQK  780
TFIYFPISNV ELEKEMGDKD KPLCLFQISN KDLSFAKTFS ANLRKKRGAE NLHTMLFKAL  840
MEGNQDNLDL GSGAIFYRAK SLDGNKPTHP ANEAIKCRNV ANKDKVSLFT YDIYKNRRYM  900
ENKFLFHLSI VQNYKAANDS AQLNSSATEY IRKADDLHII GIDRGERNLL YYSVIDMKGN  960
IVEQDSLNII RNNDLETDYH DLLDKREKER KANRQNWEAV EGIKDLKKGY LSQAVHQIAQ  1020
LMLKYNAIIA LEDLGQMFVT RGQKIEKAVY QQFEKSLVDK LSYLVDKKRP YNELGGILKA  1080
YQLASSITKN NSDKQNGFLF YVPAWNTSKI DPVTGFTDLL RPKAMTIKEA QDFFGAFDNI  1140
SYNDKGYFEF ETNYDKFKIR MKSAQTRWTI CTFGNRIKRK KDKNYWNYEE VELTEEFKKL  1200
FKDSNIDYEN CNLKEEIQNK DNRKFFDDLI KLLQLTLQMR NSDDKGNDYI ISPVANAEGQ  1260
FFDSRNGDKK LPLDADANGA YNIARKGLWN IRQIKQTKND KKLNLSISST EWLDFVREKP  1320
YLK                                                                1323

SEQ ID NO: 242         moltype = DNA  length = 39
FEATURE                Location/Qualifiers
source                 1..39
                       mol_type = genomic DNA
                       organism = Homo sapiens
SEQUENCE: 242
tatctgtttg gagctgttgg catcatgttc ctggggctc                         39

SEQ ID NO: 243         moltype = DNA  length = 39
FEATURE                Location/Qualifiers
source                 1..39
                       mol_type = genomic DNA
                       organism = Homo sapiens
SEQUENCE: 243
gagccccagg aacatgatgc caacagctcc aaacagata                         39

SEQ ID NO: 244         moltype = RNA  length = 43
FEATURE                Location/Qualifiers
misc_feature           1..43
                       note = crRNA sequence for genomic safe harbor locus shown
                        in FIG. 1. The crRNA can be modified at the 3' end with an
                        18 atom oligoethylene glycol spacer and a 3' terminal
                        thiol.
source                 1..43
                       mol_type = other RNA
                       organism = synthetic construct
SEQUENCE: 244
taatttctac tcttgtagat gagctgttgg catcatgttc ctg                    43

SEQ ID NO: 245         moltype = DNA  length = 92
FEATURE                Location/Qualifiers
source                 1..92
                       mol_type = genomic DNA
                       organism = Homo sapiens
SEQUENCE: 245
gagggattcc ctacctcccg tgctatctgt ttggagctgt tggcatcatg ttcctggggc  60
tccgaagctg ctgggaaaca ggagtgttct gc                                92

SEQ ID NO: 246         moltype = DNA  length = 92
FEATURE                Location/Qualifiers
```

```
source                  1..92
                        mol_type = genomic DNA
                        organism = Homo sapiens
SEQUENCE: 246
gcagaacact cctgtttccc agcagcttcg gagccccagg aacatgatgc caacagctcc  60
aaacagatag cacgggaggt agggaatccc tc                                92

SEQ ID NO: 247          moltype = DNA  length = 100
FEATURE                 Location/Qualifiers
misc_feature            1..100
                        note = Synthetic homology template for target sequence of
                         GSH locus shown in FIG. 1 with PAM mutation
source                  1..100
                        mol_type = other DNA
                        organism = synthetic construct
SEQUENCE: 247
gagggattcc ctacctcccg tgctatctgt tcggagctgt tggcatcatg gcggccgctt  60
cctggggctc cgaagctgct gggaaacagg agtgttctgc                        100

SEQ ID NO: 248          moltype = DNA  length = 100
FEATURE                 Location/Qualifiers
misc_feature            1..100
                        note = Synthetic homology template for non-target sequence
                         of GSH locus shown in FIG. 1 with PAM mutation. The
                         synthetic homology template can be modified at the 3' end
                         with an 18 atom oligoethylene glycol spacer and a 3'
                         terminal thiol.
source                  1..100
                        mol_type = other DNA
                        organism = synthetic construct
SEQUENCE: 248
gcagaacact cctgtttccc agcagcttcg gagccccagg aagcggccgc catgatgcca  60
acagctccga acagatagca cgggaggtag ggaatccctc                        100

SEQ ID NO: 249          moltype = DNA  length = 27
FEATURE                 Location/Qualifiers
source                  1..27
                        mol_type = genomic DNA
                        organism = Homo sapiens
SEQUENCE: 249
tttggagctg ttggcatcat gttcctg                                      27

SEQ ID NO: 250          moltype = DNA  length = 27
FEATURE                 Location/Qualifiers
source                  1..27
                        mol_type = genomic DNA
                        organism = Homo sapiens
SEQUENCE: 250
tttggagctg ttggcatctt gttcctg                                      27

SEQ ID NO: 251          moltype = DNA  length = 37
FEATURE                 Location/Qualifiers
source                  1..37
                        mol_type = genomic DNA
                        organism = Homo sapiens
SEQUENCE: 251
ttgttgttta tccaaacctc ctaaatgata cgtgttt                           37

SEQ ID NO: 252          moltype = DNA  length = 37
FEATURE                 Location/Qualifiers
source                  1..37
                        mol_type = genomic DNA
                        organism = Homo sapiens
SEQUENCE: 252
aaacacgtat catttaggag gtttggataa acaacaa                           37

SEQ ID NO: 253          moltype = RNA  length = 41
FEATURE                 Location/Qualifiers
misc_feature            1..41
                        note = crRNA sequence for GSH locus shown in FIG. 3. The
                         crRNA can be modified at the 3' end with an 18 atom
                         oligoethylene glycol spacer and a 3' terminal thiol.
source                  1..41
                        mol_type = other RNA
                        organism = synthetic construct
SEQUENCE: 253
taatttctac tcttgtagat tccaaacctc ctaaatgata c                      41

SEQ ID NO: 254          moltype = DNA  length = 92
```

```
FEATURE                Location/Qualifiers
source                 1..92
                       mol_type = genomic DNA
                       organism = Homo sapiens
SEQUENCE: 254
gcttagtgct tatttatttt aggttgttgt ttatccaaac ctcctaaatg atacgtgttt  60
ggaacaagta acagcattgt tccttgatgt tg                                92

SEQ ID NO: 255         moltype = DNA  length = 92
FEATURE                Location/Qualifiers
source                 1..92
                       mol_type = genomic DNA
                       organism = Homo sapiens
SEQUENCE: 255
caacatcaag gaacaatgct gttacttgtt ccaaacacgt atcatttagg aggtttggat  60
aaacaacaac ctaaaataaa taagcactaa gc                                92

SEQ ID NO: 256         moltype = DNA  length = 100
FEATURE                Location/Qualifiers
misc_feature           1..100
                       note = Synthetic homology template for target sequence of
                        GSH locus shown in FIG. 3 with PAM mutation
source                 1..100
                       mol_type = other DNA
                       organism = synthetic construct
SEQUENCE: 256
gcttagtgct tatttatttt aggttgttgt tcatccaaac ctcctaaatg gcggccgcat  60
acgtgtttgg aacaagtaac agcattgttc cttgatgttg                        100

SEQ ID NO: 257         moltype = DNA  length = 100
FEATURE                Location/Qualifiers
misc_feature           1..100
                       note = Synthetic homology template for non-target sequence
                        of GSH locus shown in FIG. 3 with PAM mutation. The
                        synthetic homology template can be modified at the 3' end
                        with an 18 atom oligoethylene glycol spacer and a 3'
                        terminal thiol.
source                 1..100
                       mol_type = other DNA
                       organism = synthetic construct
SEQUENCE: 257
caacatcaag gaacaatgct gttacttgtt ccaaacacgt atgcggccgc catttaggag  60
gtttggatga acaacaacct aaaataaata agcactaagc                        100

SEQ ID NO: 258         moltype = DNA  length = 53
FEATURE                Location/Qualifiers
source                 1..53
                       mol_type = genomic DNA
                       organism = Homo sapiens
SEQUENCE: 258
gcgagcaagc tcagtttaca cccgatccac tggggagcag gaaatatctg tgg         53

SEQ ID NO: 259         moltype = DNA  length = 53
FEATURE                Location/Qualifiers
source                 1..53
                       mol_type = genomic DNA
                       organism = Homo sapiens
SEQUENCE: 259
ccacagatat ttcctgctcc ccagtggatc gggtgtaaac tgagcttgct cgc         53

SEQ ID NO: 260         moltype = RNA  length = 41
FEATURE                Location/Qualifiers
misc_feature           1..41
                       note = crRNA sequence for GSH locus shown in FIG. 4. The
                        crRNA can be modified at the 3' end with an 18 atom
                        oligoethylene glycol spacer and a 3' terminal thiol.
source                 1..41
                       mol_type = other RNA
                       organism = synthetic construct
SEQUENCE: 260
taatttctac tcttgtagat cacccgatcc actggggagc a                      41

SEQ ID NO: 261         moltype = DNA  length = 88
FEATURE                Location/Qualifiers
misc_feature           1..88
                       note = Synthetic homology template for non-target sequence
                        of GSH locus shown in FIG. 4
source                 1..88
                       mol_type = other DNA
```

-continued

```
                         organism = synthetic construct
SEQUENCE: 261
ccacttgagt ccgtgtcaca agcccacaga tatttcctgc gcggccgctc cccagtggat  60
cgggtgtaaa ctgagcttgc tcgctcgg                                      88

SEQ ID NO: 262           moltype = DNA  length = 88
FEATURE                  Location/Qualifiers
misc_feature             1..88
                         note = Synthetic homology template for target sequence of
                          GSH locus shown in FIG. 4
source                   1..88
                         mol_type = other DNA
                         organism = synthetic construct
SEQUENCE: 262
cgagcaagct cagttcacac ccgatccact ggggagcagg gcggccgcaa atatctgtgg  60
gcttgtgaca cggactcaag tgggctgg                                      88

SEQ ID NO: 263           moltype = DNA  length = 43
FEATURE                  Location/Qualifiers
source                   1..43
                         mol_type = genomic DNA
                         organism = Homo sapiens
SEQUENCE: 263
aagctcagtt tacacccgat ccactgggga gcaggaaata tct                     43

SEQ ID NO: 264           moltype = RNA  length = 36
FEATURE                  Location/Qualifiers
misc_feature             1..36
                         note = crRNA to use with Cas9 described in Example 1. The
                          crRNA can be modified at the 5' end with an 18 atom
                          oligoethylene glycol spacer and a 5' terminal thiol.
source                   1..36
                         mol_type = other RNA
                         organism = synthetic construct
SEQUENCE: 264
cacccgatcc actggggagc gttttagagc tatgct                             36
```